United States Patent
Ueda et al.

(10) Patent No.: US 10,622,570 B2
(45) Date of Patent: Apr. 14, 2020

(54) ORGANIC ELECTROLUMINESCENT ELEMENT

(71) Applicant: NIPPON STEEL & SUMIKIN CHEMICAL CO., LTD., Tokyo (JP)

(72) Inventors: Tokiko Ueda, Tokyo (JP); Junya Ogawa, Tokyo (JP); Masashi Tada, Tokyo (JP); Yuichi Sawada, Tokyo (JP)

(73) Assignee: NIPPON STEEL CHEMICAL & MATERIAL CO., LTD., Tokyo (JP)

(*) Notice: Subject to any disclaimer, the term of this patent is extended or adjusted under 35 U.S.C. 154(b) by 0 days.

(21) Appl. No.: 16/078,499

(22) PCT Filed: Feb. 23, 2017

(86) PCT No.: PCT/JP2017/006780
§ 371 (c)(1),
(2) Date: Aug. 21, 2018

(87) PCT Pub. No.: WO2017/169355
PCT Pub. Date: Oct. 5, 2017

(65) Prior Publication Data
US 2019/0088883 A1    Mar. 21, 2019

(30) Foreign Application Priority Data
Mar. 28, 2016  (JP) ................ 2016-064230

(51) Int. Cl.
*H01L 51/00* (2006.01)
*H01L 51/50* (2006.01)
(Continued)

(52) U.S. Cl.
CPC ........ *H01L 51/0072* (2013.01); *H01L 51/008* (2013.01); *H01L 51/0052* (2013.01);
(Continued)

(58) Field of Classification Search
CPC ..................................................... H01L 51/50
See application file for complete search history.

(56) References Cited

U.S. PATENT DOCUMENTS 10,497,885 B2 * 12/2019 Sasada ............. H01L 51/50
2012/0112173 A1 * 5/2012 Matsumoto ......... H01L 27/3211
257/40
(Continued)

FOREIGN PATENT DOCUMENTS

JP     2005166574 A   * 6/2005 .......... C09K 11/06
JP     2005166574-AE  * 6/2005 .......... C09K 11/06
(Continued)

OTHER PUBLICATIONS

English translation of International Preliminary Report on Patentability dated Oct. 4, 2018, in PCT/JP2017/006780 (Forms PCT/IB/338 and PCT/IPEA/409).
(Continued)

*Primary Examiner* — Moazzam Hossain
(74) *Attorney, Agent, or Firm* — Birch, Stewart, Kolasch & Birch, LLP

(57) ABSTRACT

Provided is an organic EL device that exhibits high luminous efficiency and has high stability when driven despite having low voltage. The organic electroluminescent device is obtained by laminating an anode, organic layers and a cathode on a substrate, wherein at least one of the organic layers contains (i) a compound represented by chemical formula (1) below, and (ii) a carborane compound having one or more divalent carborane groups and an aromatic group substituted for the carborane group. In the formulas, $X^1$ and $X^2$ represent $NR^1$, $PR^2$, O, S, Se, $CR^3R^4$ or $SiR^5R^6$ and Y represents a single bond or aromatic group.

19 Claims, 1 Drawing Sheet

(51) Int. Cl.
*H01L 51/52* (2006.01)
*C07D 405/10* (2006.01)
*C07D 409/04* (2006.01)
*C07D 409/14* (2006.01)
*C07D 209/86* (2006.01)
*C07D 405/14* (2006.01)

(52) U.S. Cl.
CPC ...... *H01L 51/0067* (2013.01); *H01L 51/0073* (2013.01); *H01L 51/0074* (2013.01); *H01L 51/5012* (2013.01); *H01L 51/5092* (2013.01); *H01L 51/5096* (2013.01); *H01L 51/5206* (2013.01); *H01L 51/5221* (2013.01); *C07D 209/86* (2013.01); *C07D 405/10* (2013.01); *C07D 405/14* (2013.01); *C07D 409/04* (2013.01); *C07D 409/14* (2013.01); *H01L 51/5016* (2013.01); *H01L 51/5056* (2013.01); *H01L 51/5072* (2013.01); *H01L 2251/5384* (2013.01)

(56) References Cited

U.S. PATENT DOCUMENTS

| | | | |
|---|---|---|---|
| 2012/0241732 A1 | 9/2012 | Endo et al. | |
| 2012/0319088 A1* | 12/2012 | Lee | H01L 51/008 257/E51.024 |
| 2014/0306207 A1 | 10/2014 | Nishimura et al. | |
| 2014/0332792 A1* | 11/2014 | Tada | H01L 51/0067 257/40 |
| 2015/0158844 A1* | 6/2015 | Saruta | C07D 401/14 514/235.8 |
| 2016/0072064 A1* | 3/2016 | Tada | H01L 51/0072 252/301.16 |
| 2016/0190451 A1* | 6/2016 | Ogawa | H01L 51/0072 257/40 |
| 2016/0315262 A1 | 10/2016 | Ogawa et al. | |
| 2017/0213974 A1 | 7/2017 | Adachi et al. | |
| 2018/0006229 A1* | 1/2018 | Kitamura | H01L 51/0043 |
| 2018/0114908 A1* | 4/2018 | Ogawa | H01L 51/50 |

FOREIGN PATENT DOCUMENTS

| | | |
|---|---|---|
| JP | 2015-207657 A | 11/2015 |
| JP | 2016-9824 A | 1/2016 |

OTHER PUBLICATIONS

English translation of International Search Report dated May 16, 2017, in PCT/JP2017/006780).

\* cited by examiner

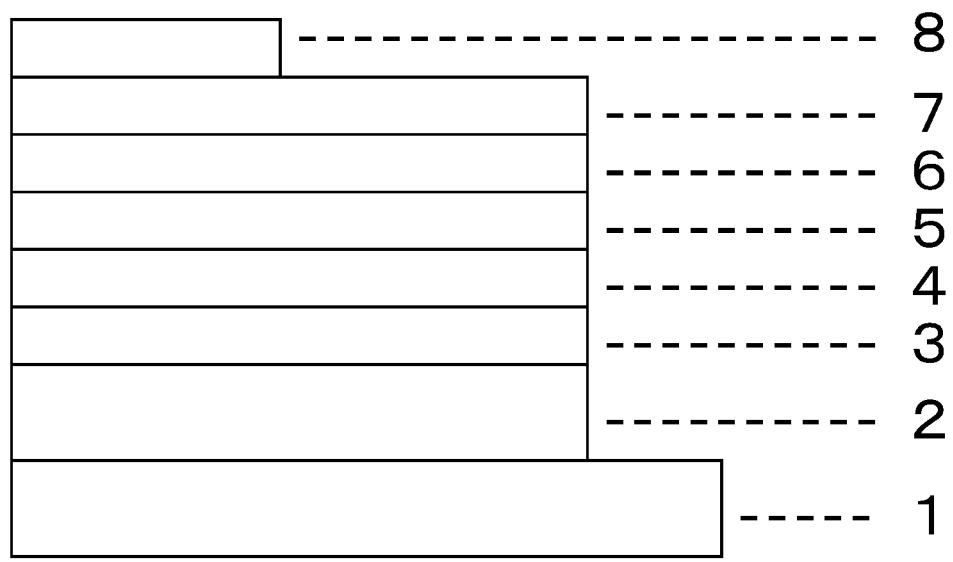

ORGANIC ELECTROLUMINESCENT ELEMENT

TECHNICAL FIELD

The present invention relates to an organic electroluminescent device or element (or hereinafter referred to as an "organic EL device"), and more particularly, to an organic EL device having organic layers containing a plurality of compounds.

BACKGROUND ART

In general, organic EL devices, when employing their simplest structure, are composed of a light emitting layer and a pair of opposing electrodes interposing that layer. Namely, organic EL devices utilize a phenomenon by which, when an electric field is applied between both electrodes, electrons are injected from the cathode and holes are injected from the anode and energy is released in the form of light when the electrons and holes are recombined in the light emitting layer.

Excitons generated during this recombination are formed at a ratio of singlet excitons to triplet excitons of 1:3 in accordance with the statistics of electron spin. Organic EL devices of the fluorescence emission type that utilize emission of light by singlet excitons are said to have a limit of internal quantum efficiency of 25%. On the other hand, organic EL devices of the phosphorescence emission type that utilize emission of light by triplet excitons using an iridium complex are said to theoretically enhance internal quantum efficiency up to 100% in the case of having efficiently carried out intersystem crossing from singlet excitons.

More recently, highly efficient organic EL devices have been developed that utilize delayed fluorescence. For example, PTL 1 discloses an organic EL device that utilizes a thermally activated delayed fluorescence (TADF) mechanism. Although this method enhances internal quantum efficiency, further improvement of service life characteristics is required in the same manner as devices of the phosphorescence emission type.

In order to improve the characteristics of organic EL devices, devices are being studied that contain bis-carbazoles or carborane compounds in an organic layer in the manner of the devices disclosed in PTL 2 to PTL 8.

CITATION LIST

Patent Literature

[PTL 1] WO 2011/070693 A1
[PTL 2] JP 2003-133075 A
[PTL 3] JP 2007-288035 A
[PTL 4] JP 2005-166574 A
[PTL 5] US 2012/0319088 A1
[PTL 6] WO 2015/137202 A1
[PTL 7] WO 2013/062075 A1
[PTL 8] US 2014/0374728 A1

PTL 2 discloses the use of a bis-carbazole compound as a host material. PTL 3 discloses the use of bis-carbazoles as host materials. PTL 4 to PTL 6 disclose the use of a carborane compound as a host material. In addition, PTL 7 and PTL 8 disclose the use of a bis-carbazole compound as a mixed host material. Although PTL 6 discloses the use of a specific carborane compound as a delayed fluorescence material or the use of a bis-carbazole compound as a delayed fluorescence material and the use of a carborane compound as a host material in a light emitting layer, PTL 6 does not teach the use of an organic layer other than a light emitting layer or light emitting layer as a host material by mixing a specific bis-carbazole compound and a carborane compound.

SUMMARY OF INVENTION

Technical Problem

In order to apply organic EL devices to such applications as the display elements of flat panel displays, it is necessary to improve the luminous efficiency of the device while at the same time ensuring adequate stability when driven. With the foregoing in view, an object of the present invention is to provide an organic EL device that is useful in terms of practical use by having high efficiency and high stability when driven despite being driven at a low voltage.

Solution to Problem

The present invention relates to an organic electroluminescent device obtained by laminating an anode, organic layers and a cathode on a substrate, wherein (i) a compound represented by chemical formula (1) below and (ii) a compound represented by general formula (2) below are contained in at least one of the organic layers.

[C1]

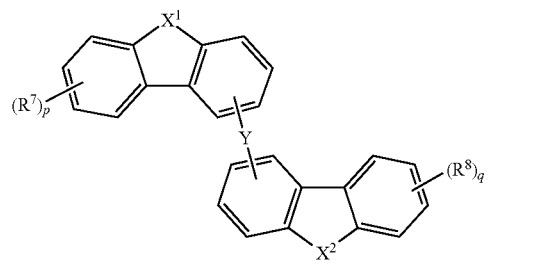

(1)

Here, $X^1$ and $X^2$ represent $NR^1$, $PR^2$, O, S, Se, $CR^3R^4$ or $SiR^5R^6$ and may mutually be the same or different.

Y represents a single bond or divalent group, and the divalent group is a substituted or unsubstituted aromatic hydrocarbon group having 6 to 30 carbons, a substituted or unsubstituted aromatic heterocyclic group having 3 to 30 carbon atoms (excluding a carbazole group), or a substituted or unsubstituted linked aromatic group obtained by linking 2 to 6 of the aromatic rings thereof (referring to an aromatic ring of the substituted or unsubstituted aromatic hydrocarbon group or substituted or unsubstituted aromatic heterocyclic group). Here, a carbazole group in the case of excluding a carbazole group is understood to be a group that contains a carbazole ring.

$R^1$ to $R^6$ independently represent a substituted or unsubstituted aromatic hydrocarbon group having 6 to 30 carbon atoms, a substituted or unsubstituted aromatic heterocyclic group having 3 to 30 carbon atoms, or a substituted or unsubstituted linked aromatic group obtained by linking 2 to 6 of the aromatic rings thereof.

$R^7$ and $R^8$ independently represent a substituted or unsubstituted aromatic hydrocarbon group having 6 to 30 carbon atoms, a substituted or unsubstituted aromatic heterocyclic group having 3 to 30 carbon atoms, a substituted or unsubstituted linked aromatic group obtained by linking 2 to 6 of the aromatic rings thereof, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a diaralkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, a cyano group, a nitro group, a fluoro group or a tosyl group.

p and q indicate the numbers of substituents and independently represent an integer of 0 to 7.

[C2]

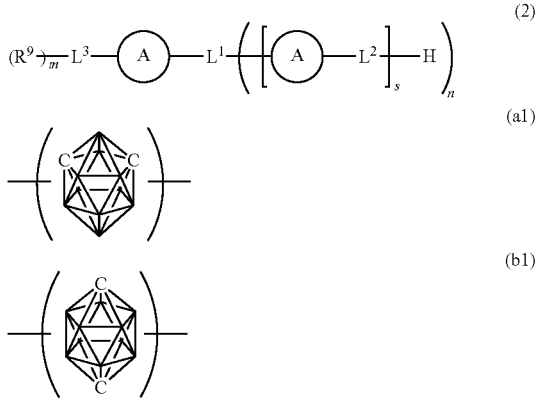

Here, ring A represents a $C_2B_{10}H_{10}$ divalent carborane group represented by formula (a1) or formula (b1), and may be the same or different in the case a plurality of ring A are present within a molecule. s indicates the number of repeats and is an integer of 0 to 2, n and m indicate the number of substituents, n represents an integer of 1 or 2 and m represents an integer of 0 to 4.

$L^1$ represents a single bond or group having a valence of n+1. The group having a valence of n+1 represents a substituted or unsubstituted aromatic hydrocarbon group having 6 to 30 carbon atoms, a substituted or unsubstituted aromatic heterocyclic group having 3 to 30 carbon atoms, or a substituted or unsubstituted linked aromatic group obtained by linking 2 to 6 of the aromatic rings thereof. However, in the case n=1 and s=1, $L^1$ represents a single bond, aromatic heterocyclic group or linked aromatic group containing at least one aromatic heterocyclic group.

$L^2$ independently represents a single bond or divalent group. The divalent group represents a substituted or unsubstituted aromatic hydrocarbon group having 6 to 30 carbon atoms, a substituted or unsubstituted aromatic heterocyclic group having 3 to 30 carbon atoms, or a substituted or unsubstituted linked aromatic group composed by linking 2 to 6 of the aromatic rings thereof.

$L^3$ represents a group having a valence of m+1, and represents an unsubstituted aromatic hydrocarbon group having 6 to 30 carbon atoms or unsubstituted aromatic heterocyclic group having 3 to 30 carbon atoms.

$R^9$ independently represents a group selected from a substituted or unsubstituted aromatic hydrocarbon group having 6 to 30 carbon atoms, a substituted or unsubstituted aromatic heterocyclic group having 3 to 30 carbon atoms, a substituted or unsubstituted linked aromatic group obtained by linking 2 to 6 of the substituted or unsubstituted aromatic rings thereof, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a diaralkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, a cyano group, nitro group, fluoro group or tosyl group, and may further have substituents in the case of being a group other than a cyano group, nitro group, fluoro group or tosyl group.

In general formula (1), $X^1$ and $X^2$ are preferably $NR^1$, O or S, and p and q are preferably integers of 0 to 3. Here, $R^1$ has the same meaning as defined in general formula (1).

The formulas (3) to (7) below indicate preferable aspects of general formula (1).

[C3]

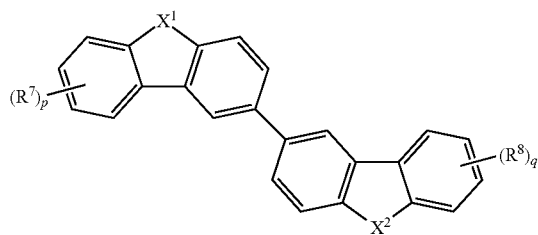

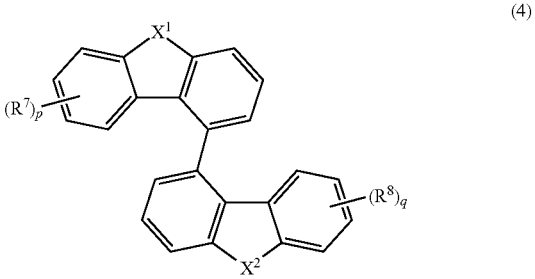

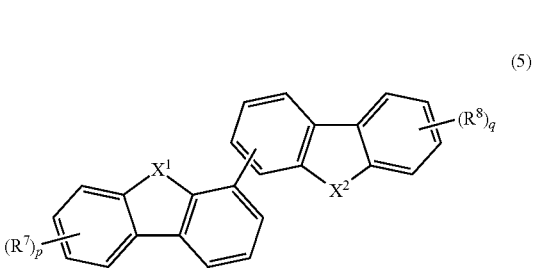

[C4]

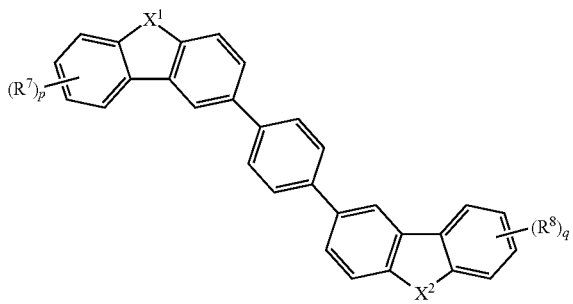

(6)

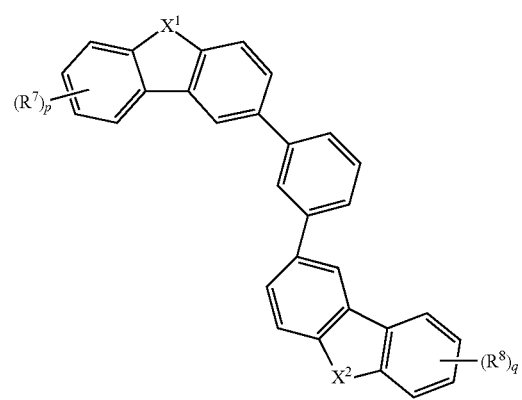

(7)

Here, $X^1$, $X^2$, $R^7$, $R^8$, p and q have the same meanings as $X^1$, $X^2$, $R^7$, $R^8$, p and q defined in general formula (1).

The formula (8) below indicates a preferable aspect of general formula (2).

[C5]

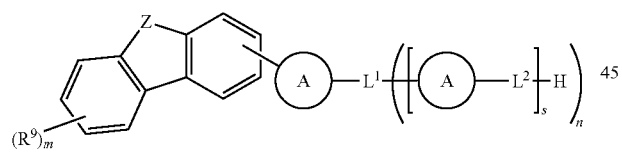

(8)

Here, Z represents $NR^{10}$, $PR^{11}$, O, Se, $CR^{12}R^{13}$ or $SiR^{14}R^{15}$, and $R^{10}$ to $R^{15}$ have the same meaning as $R^1$ to $R^6$ defined in general formula (1). Ring A, $R^9$, $L^1$, $L^2$, s, m and n have the same meaning as defined in general formula (2).

In general formula (2), ring A is preferably a $C_2B_{10}H_{10}$ divalent carborane group represented by formula (1a) and aromatic groups directly bonded to ring A of $L^1$ and $L^3$ may be the same.

In addition, the organic layers containing a compound represented by general formula (1) and at least two types of compounds represented by general formula (2) are preferably at least one layer selected from the group consisting of a light emitting layer containing a luminescent dopant, electron blocking layer and hole blocking layer, or the organic layers preferably contain the above-mentioned two types or two or more types of compounds as host materials.

Moreover, the luminescent dopant is preferably a delayed fluorescence dopant or an organic metal complex containing at least one metal selected from ruthenium, rhodium, palladium, silver, rhenium, osmium, iridium, platinum and gold.

The material used in the organic layers is required to have durability with respect to a charge in order to improve device characteristics, and it is important to inhibit escape of excitons and charge into the surrounding layers in the light emitting layer in particular. Improvement of deviations in the light emitting region of the light emitting layer is effect for inhibiting this escape of charge/excitons, and in order to accomplish this, it is necessary to control the injected amounts of both charges (electrons/holes) to preferable ranges.

Here, although a bis-carbazole compound represented by general formula (1) has high skeletal stability and is able to control electron/hole injection and transport to a certain degree with isomers and substituents, when used alone, it is difficult to control the injected amounts of both charges to preferable ranges as described above. On the other hand, a carborane compound represented by general formula (2) is able to control electron injection and transport of the device at a high level since the lowest unoccupied molecular orbital (LUMO), which has an effect on electron injection and transport, is widely distributed throughout the entire molecule, and since this compound also demonstrates high skeletal stability in the same manner as bis-carbazole compounds, the use of a mixture of a carborane compound and bis-carbazole compound makes it possible to precisely adjust the amount of charge injected into the organic layers. In the case of using in a light emitting layer in particular, the balanced between the injected amounts of both charges can be adjusted, and in the case of a delayed fluorescence EL device or phosphorescent EL device, there is no escape of energy from the light emitting layer and high efficiency at low voltage as well as a long service life can be achieved since the minimum excitation triplet energy is sufficiently high for trapping excitation energy generated in the light emitting layer.

BRIEF DESCRIPTION OF DRAWINGS

FIG. 1 is a schematic cross-sectional diagram showing one example of an organic EL device.

DESCRIPTION OF EMBODIMENTS

The organic electroluminescent device of the present invention is obtained by laminating an anode, organic layers and a cathode on a substrate, wherein (i) a compound represented by general formula (1) and (ii) a compound represented by general formula (2) are contained in at least one of the organic layers. Furthermore, the compounds represented by general formula (1) and general formula (2) may each be one type of compound or two or more types of compounds. The ratio of the compound represented by general formula (1) (also referred to as a bis-carbazole compound) to the total amount of the compound represented by general formula (1) and the compound represented by general formula (2) (also referred to as a carborane compound) is preferably 30% by weight or more, more preferably 35% by weight to 95% by weight, and even more preferably 40% by weight to 90% by weight.

The following provides an explanation of the above-mentioned general formula (1) and formulas (3) to (7). The reference symbols used in general formula (1) and formulas (3) to (7) have the same meanings in each formula.

$X^1$ and $X^2$ represent $NR^1$, $PR^2$, O, S, Se, $CR^3R^4$ or $SiR^5R^6$ and may mutually be the same or different. Among these, $X^1$ and $X^2$ preferably represent $NR^1$, O or S.

p and q indicate the number of substituents and independently represent an integer of 0 to 7, preferably an integer of 0 to 5, and more preferably an integer of 0 to 3.

In general formula (1), Y represents a single bond or divalent group, and the divalent group is a substituted or unsubstituted aromatic hydrocarbon group having 6 to 30 carbons, a substituted or unsubstituted aromatic heterocyclic group having 3 to 30 carbon atoms other than a carbazole group, or a substituted or unsubstituted linked aromatic group obtained by linking 2 to 6 of the substituted or unsubstituted aromatic rings thereof. Y preferably represents a single bond, substituted or unsubstituted aromatic hydrocarbon group having 6 to 18 carbon atoms, substituted or unsubstituted aromatic heterocyclic group having 3 to 17 carbon atoms other than a carbazole group, or a substituted or unsubstituted linked aromatic group obtained by linking two to five of the aromatic rings thereof, and more preferably represents a single bond or phenyl group. Here, a carbazole group in the case of excluding a carbazole group from aromatic heterocyclic groups may have a substituent added to a carbazole group.

A linked aromatic group is a group that is composed by linking 2 to 6 aromatic rings of the above-mentioned aromatic hydrocarbon group or aromatic heterocyclic group by direct bonding, and may have substituents similar to those possessed by the above-mentioned aromatic hydrocarbon group or aromatic heterocyclic group.

An aromatic hydrocarbon group, aromatic heterocyclic group and linked aromatic group are collectively referred to as aromatic groups.

In general formula (1) and formulas (3) to (7), $R^1$ to $R^6$ independently represent a substituted or unsubstituted aromatic hydrocarbon group having 6 to 30 carbon atoms, a substituted or unsubstituted aromatic heterocyclic group having 3 to 30 carbon atoms, or a linked aromatic group obtained by linking 2 to 6 of the substituted or unsubstituted aromatic rings thereof. $R^1$ to $R^6$ preferably represent a substituted or unsubstituted aromatic hydrocarbon group having 6 to 18 carbon atoms, a substituted or unsubstituted aromatic heterocyclic group having 3 to 17 carbon atoms, or a linked aromatic group obtained by linking two to five of the substituted or unsubstituted aromatic rings thereof.

Specific examples of the case in which Y and $R^1$ to $R^6$ are unsubstituted aromatic hydrocarbon groups, aromatic heterocyclic groups or linked aromatic groups include aromatic hydrocarbon compounds such as benzene, pentalene, indene, naphthalene, fluorene, azulene, heptalene, octalene, indacene, acenaphthylene, phenalene, phenanthrene, anthracene, trindene, fluoranthene, acephenanthrilene, aceanthrylene, triphenylene, pyrene, chrysene, tetraphene, tetracene, pleiadene, picene, perylene, pentaphene, pentacene, tetraphenylene, cholanthrylene, helicene, hexaphene, rubicene, coronene, trinaphthylene, heptaphene or pyranthrene, aromatic heterocyclic compounds such as furan, benzofuran, isobenzofuran, xanthene, oxathrene, dibenzofuran, peri-xanthenoxanthene, thiophene, thioxanthene, thianthrene, phenoxathiin, thionaphthene, isothianaphthene, thiophthene, thiophanthrene, dibenzothiophene, pyrrole, pyrazole, tellurazole, selenazole, thiazole, isothiazole, oxazole, furazan, pyridine, pyrazine, pyrimidine, pyridazine, triazine, indolizine, indole, isoindole, indazole, purine, quinolidine, isoquinoline, carbazole, imidazole, naphthyridine, phthalazine, quinazoline, azepine, benzodiazepine, tribenzoazepine, quinoxaline, cinnoline, quinoline, pteridine, phenanthridine, acridine, perymidine, phenanthroline, phenazine, carboline, phenotellurazine, phenoselenazine, phenothiazine, phenoxazine, anthyridine, benzothiazole, benzoimidazole, benzoxazole, benzoisoxazole, benzoisothiazole, dibenzophosphole or dibenzoborole, and linked aromatic groups formed by removing a hydrogen atom from aromatic compounds in which a plurality of aromatic rings of these aromatic compounds are linked.

Preferable examples include groups formed by removing a hydrogen atom from benzene, naphthalene, anthracene, fluorene, phenanthrene, triphenylene, pyridine, pyrimidine, triazine, dibenzofuran, dibenzothiophene or carbazole, and linked aromatic groups formed by removing a hydrogen atom from aromatic compounds in which a plurality of aromatic rings of these aromatic compounds are linked. However, Y does not include a carbazole group.

Substituents in the case these aromatic groups have a substituent consist of an alkyl group having 1 to 20 carbon atoms, aralkyl group having 7 to 38 carbon atoms, alkenyl group having 2 to 20 carbon atoms, alkynyl group having 2 to 20 carbon atoms, dialkylamino group having 2 to 40 carbon atoms, diarylamino group having 12 to 44 carbon atoms, diaralkylamino group having 14 to 76 carbon atoms, acyl group having 2 to 20 carbon atoms, acyloxy group having 2 to 20 carbon atoms, alkoxy group having 1 to 20 carbon atoms, alkoxycarbonyl group having 2 to 20 carbon atoms, alkoxycarbonyloxy group having 2 to 20 carbon atoms, alkylsulfonyl group having 1 to 20 carbon atoms, cyano group, nitro group, fluoro group or tosyl group, and preferably consist of an alkyl group having 1 to 12 carbon atoms, aralkyl group having 7 to 20 carbon atoms, diarylamino group having 12 to 30 carbon atoms, alkoxy group having 1 to 10 carbon atoms, cyano group, fluoro group or tosyl group. Furthermore, the alkyl group may be linear, branched or cyclical.

Specific examples of the above-mentioned substituents include alkyl groups such as a methyl, ethyl, propyl, butyl, pentyl, cyclopentyl, hexyl, cyclohexyl, heptyl, octyl, nonyl, decyl, undecyl, dodecyl, tridecyl, tetradecyl, pentadecyl, hexadecyl, heptadecyl, octadecyl, nonadecyl or eicosyl group, aralkyl groups such as a phenylmethyl, phenylethyl, phenylicosyl, naphthylmethyl, anthranylmethyl, phenanthrenylmethyl or pyrenylmethyl group, alkenyl groups such as a vinyl, propenyl, butenyl, pentenyl, decenyl or icocenyl group, alkynyl groups such as an ethynyl, propargyl, butynyl, pentynyl, decynyl or icosynyl group, dialkylamino groups such as a dimethylamino, ethylmethylamino, diethylamino dipropylamino, dibutylamino, dipentynylamino, didecylamino or diicosylamino group, diarylamino groups such as a diphenylamino, napthylphenylamino, dinaphthylamino, dianthranylamino, diphenanthrenylamino or dipyrenylamino group, diaralkylamino groups such as a diphenylmethylamino, diphenylethylamino, phenylmethylphenylethylamino, dinaphthylmethylamino, dianthranylmethylamino or diphenanthrenylmethylamino group, acyl groups such as an acetyl, propionyl, butyryl, valeryl or benzoyl group, acyloxy groups such as an acetyloxy, propionyloxy, butyryloxy, valeryloxy or benzoyloxy group, alkoxy groups such as a methoxy, ethoxy, propoxy, butoxy, pentoxy, hexoxy, heptoxy, octoxy, nonyloxy or decanyloxy group, alkoxycarbonyl groups such as a methoxycarbonyl, ethoxycarbonyl, propoxycarbonyl, butoxycarbonyl or pentoxycarbonyl group, alkoxycarbonyloxy groups such as a methoxycarbonyloxy, ethoxycarbonyloxy, propoxycarbonyloxy, butoxycarbonyloxy or pentoxycarbonyloxy group, alkylsulfonyl groups such as a methylsulfonyl, ethylsulfonyl, propylsulfonyl, butylsulfonyl or pentylsulfonyl group, and a cyano group, nitro group, fluoro group and tosyl group. Preferable examples include alkyl groups having 1 to 12 carbon atoms such as a methyl, ethyl, propyl, butyl, pentyl, hexyl, heptyl, octyl, nonyl or decyl group, aralkyl groups having 7 to 20 carbon atoms such as a phenylmethyl, phenylethyl, naphthylmethyl, anthranylmethyl, phenanthrenylmethyl or pyrenylmethyl group, alkoxy groups having 1 to 10 carbon atoms such as a methoxy, ethoxy, propoxy, butoxy, pentoxy, hexoxy, heptoxy, octoxy, nonyloxy or decanyloxy group, diarylamino groups having two aromatic hydrocarbon groups having 6 to 15 carbon atoms such as a diphenylamino, naphthylphenylamino, dinaphthylamino, dianthranylamino or diphenanthrenylamino group, and a cyano group, fluoro group and tosyl group.

A linked aromatic group as referred to in the present description is a group in which a plurality of aromatic rings of aromatic compounds having a monocyclic or condensed ring structure (referred to as an aromatic heterocyclic compound, aromatic heterocyclic ring or both) have been linked. Linking of aromatic rings refers to the aromatic rings of aromatic groups being linked by bonding with direct bonds. In the case the aromatic rings are substituted aromatic rings, the substituents are not aromatic rings.

The linked aromatic groups may be linear or branched, the linked aromatic rings may be the same or different, may have one or both an aromatic hydrocarbon ring or aromatic heterocyclic ring, and may have substituents.

In the case the linked aromatic group is a monovalent group, examples of linking modes include those indicated below.

[C6]

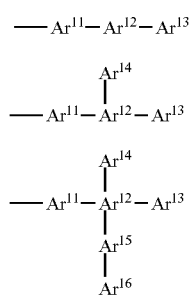

In the case the linked aromatic group is a divalent group, examples of linking modes include those indicated below. Cases of the linked aromatic group being a at least trivalent group can be understood from the above.

[C7]

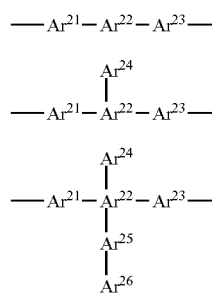

In formulas (9) to (14), $Ar^{11}$ to $Ar^{16}$ and $Ar^{21}$ to $Ar^{26}$ represent substituted or unsubstituted aromatic rings (aromatic groups) and the atoms that compose the aromatic rings are bonded by direct bonding. In addition, bonds extend from atoms composing the aromatic rings. Aromatic rings (aromatic groups) refer to aromatic hydrocarbon groups or aromatic heterocyclic groups, and can be groups having a valence of one or more.

Although the bonds extend from $Ar^{11}$, $Ar^{21}$ or $Ar^{23}$ in formulas (9) to (14), they can also extend from other aromatic rings. In addition, in the case of groups having a valence of two or more, two or more bonds may extend from a single aromatic ring.

Specific examples of linked aromatic groups include groups formed by removing one or more hydrogen atoms from an aromatic compound such as biphenyl, terphenyl, bipyridine, bipyrimidine, bitriazine, terpyridine, phenylterphenyl, binaphthalene, phenylpyridine, diphenylpyridine, phenylpyrimidine, diphenylpyrimidine, phenyltriazine, diphenyltriazine, phenylnaphthalene, diphenylnaphthalene, carbazolylbenzene, bis-carbazolylbenzene, bis-carbazolyltriazine, dibenzofuranylbenzene, bis-dibenzofuranylbenzene, dibenzothiophenylbenzene or bis-dibenzothiophenylbenzene.

The explanation relating to the above-mentioned linked aromatic group is in common with that of linked aromatic groups explained for general formulas (1) and (2) and formulas (3) to (8).

$R^7$ and $R^8$ independently represent a substituted or unsubstituted aromatic hydrocarbon group having 6 to 30 carbon atoms, a substituted or unsubstituted aromatic heterocyclic group having 3 to 30 carbon atoms, a substituted or unsubstituted linked aromatic group obtained by linking 2 to 6 of the aromatic rings thereof, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a diaralkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, a cyano group, a nitro group, a fluoro group or a tosyl group. $R^7$ and $R^8$ preferably represent a substituted or unsubstituted aromatic hydrocarbon group having 6 to 18 carbon atoms, a substituted or unsubstituted aromatic heterocyclic group having 3 to 17 carbon atoms, a substituted or unsubstituted linked aromatic group obtained by linking two to five of the aromatic rings thereof, an alkyl group having 1 to 12 carbon atoms, an aralkyl group having 7 to 20 carbon atoms, a diarylamino group having 12 to 30 carbon atoms, an alkoxy group having 1 to 10 carbon atoms, a cyano group, a fluoro group or a tosyl group.

In the case $R^7$ and $R^8$ represent the above-mentioned aromatic hydrocarbon groups, aromatic heterocyclic groups or linked aromatic groups, these groups are the same as in the explanation of aromatic hydrocarbon groups, aromatic heterocyclic groups and linked aromatic groups previously explained for $R^1$ to $R^6$. However, aromatic heterocyclic groups include a carbazole group.

In the case $R^7$ and $R^8$ represent alkyl groups having 1 to 20 carbon atoms, aralkyl groups having 7 to 38 carbon atoms, alkenyl groups having 2 to 20 carbon atoms, alkynyl groups having 2 to 20 carbon atoms, dialkylamino groups having 2 to 40 carbon atoms, diarylamino groups having 12 to 44 carbon atoms, diaralkylamino groups having 14 to 76 carbon atoms, acyl groups having 2 to 20 carbon atoms, acyloxy groups having 2 to 20 carbon atoms, alkoxy groups having 1 to 20 carbon atoms, alkoxycarbonyl groups having 2 to 20 carbon atoms, alkoxycarbonyloxy groups having 2 to 20 carbon atoms, alkylsulfonyl groups having 1 to 20 carbon atoms, cyano groups, nitro groups, fluoro groups or tosyl groups, these groups are the same as those explained for substituents of aromatic groups as explained for the above-mentioned $R^1$ to $R^6$.

In the case $R^7$ and $R^8$ represent groups other than cyano groups, nitro groups, fluoro groups or tosyl groups, those groups may have additional substituents, and those substituents are the same as those explained for substituents of aromatic groups as explained for the above-mentioned $R^1$ to $R^6$. Furthermore, the number of substituents is 0 to 5 and preferably 0 to 2.

In the present description, calculation of the number of carbon atoms is understood to not include the number of carbon atoms of substituents. However, the total number of carbon atoms, including the number of carbon atoms of substituents, can be said to preferably within the range of the above-mentioned numbers of carbon atoms. The number of carbon atoms of linked aromatic groups is understood to be the total of the number of carbon atoms possessed by the linked aromatic hydrocarbon groups or aromatic heterocyclic groups.

Although the following indicates preferable specific examples of compounds represented by general formula (1), these compounds are not limited thereto.

[C8]

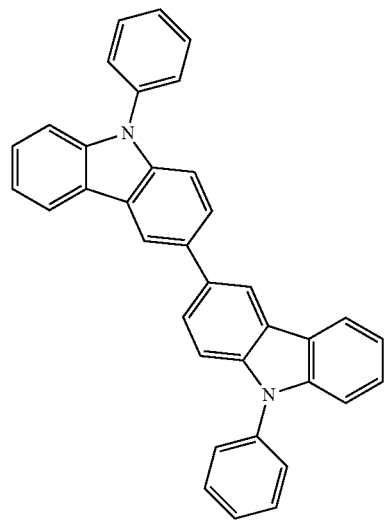

1-1

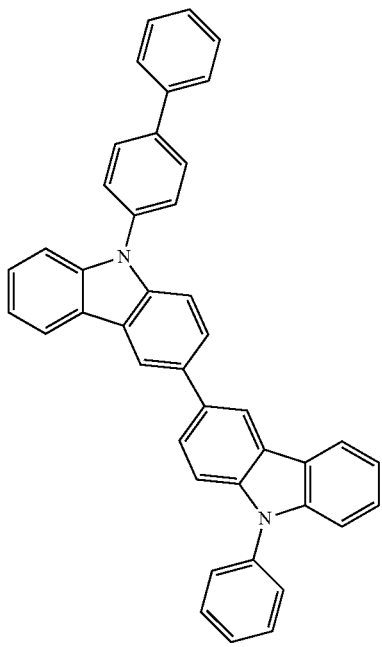

1-2

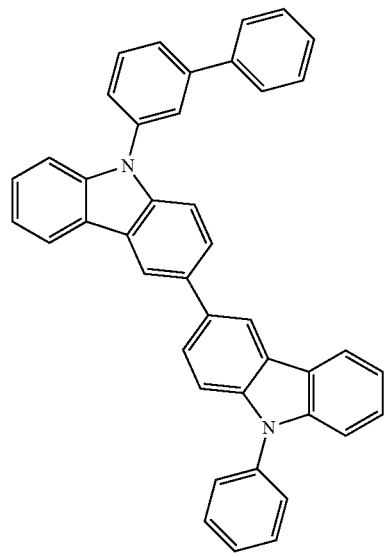

1-3

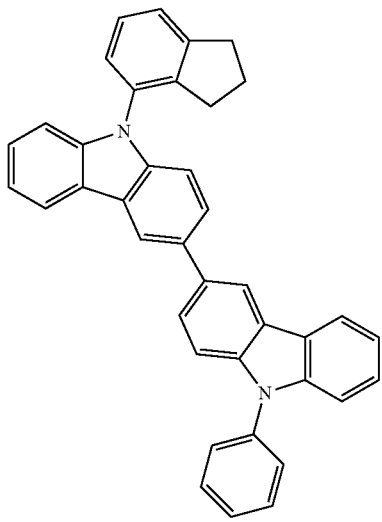

1-4

-continued
1-5
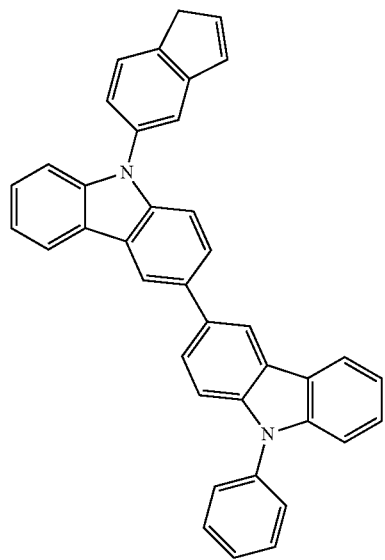
1-6
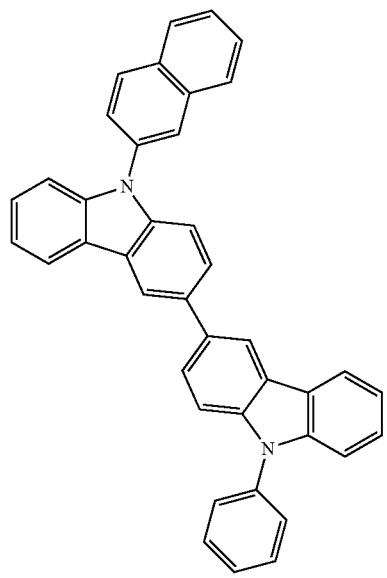
1-7
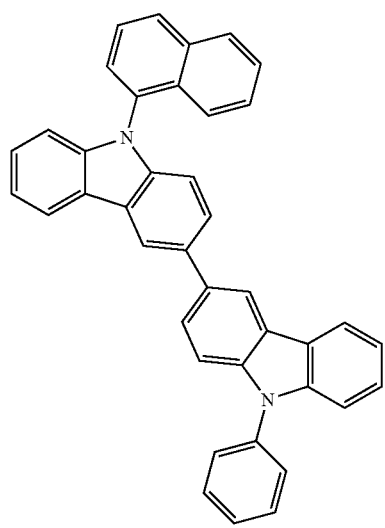
1-8
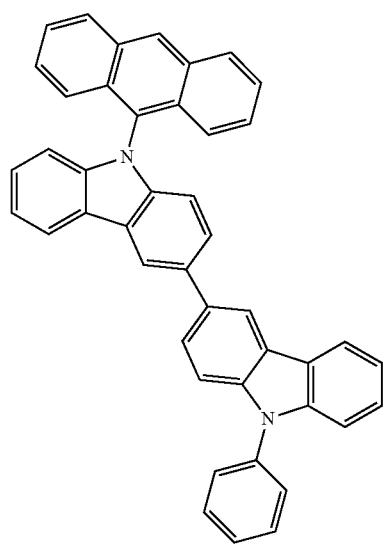

-continued
1-9
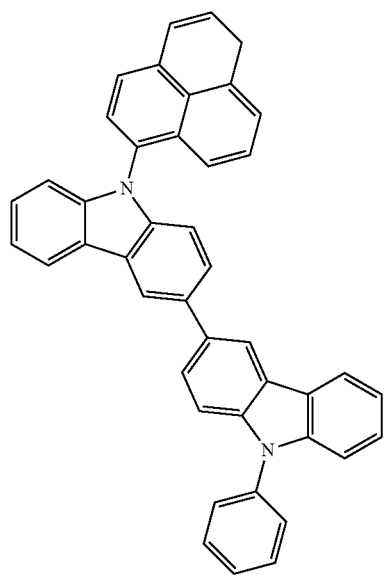
1-10
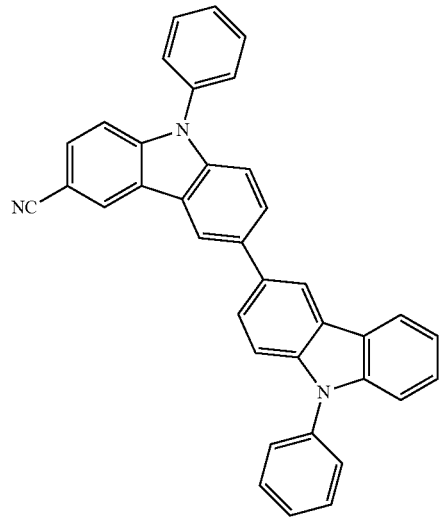
1-11
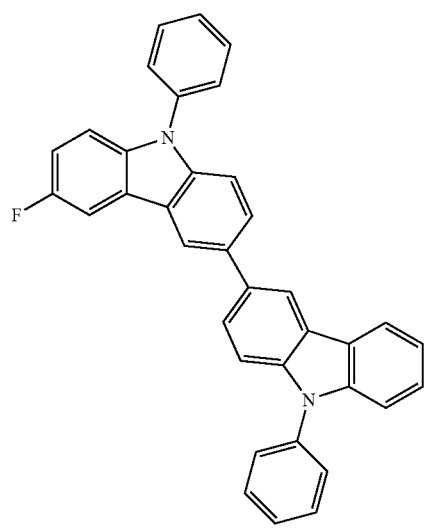
1-12
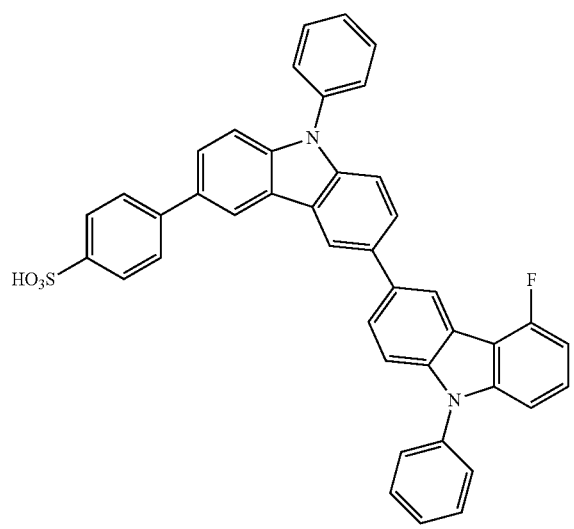

1-13
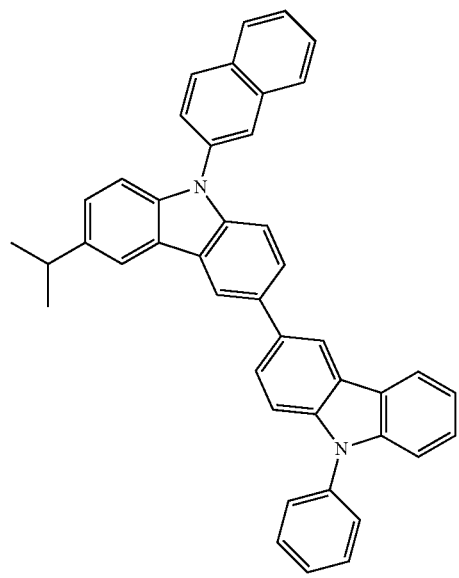
1-14
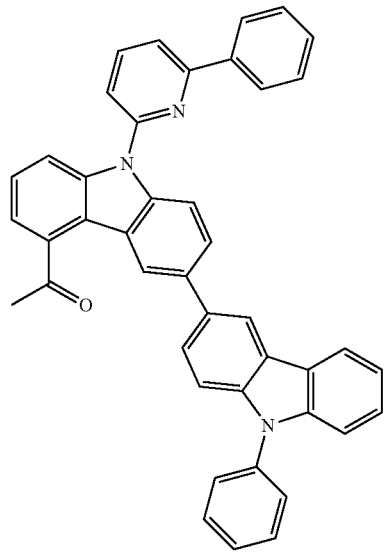
1-15
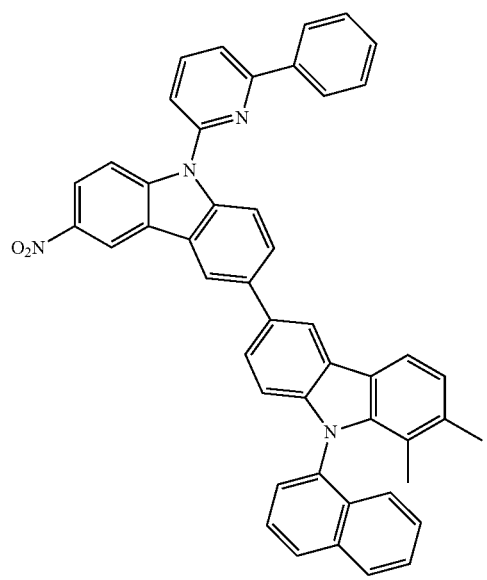

[C9]
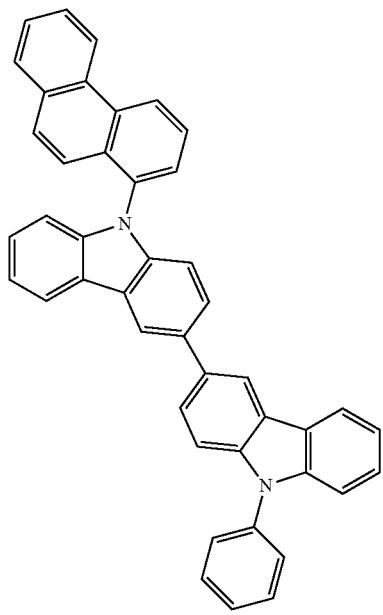
1-16
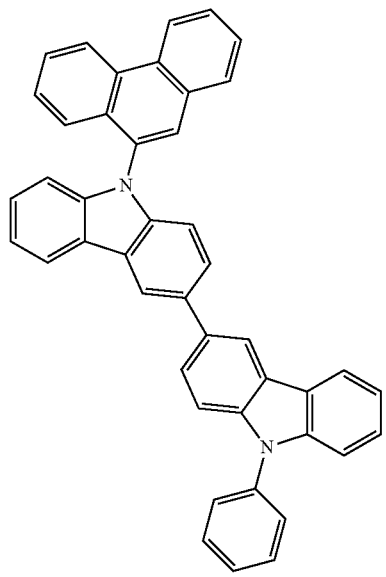
1-17
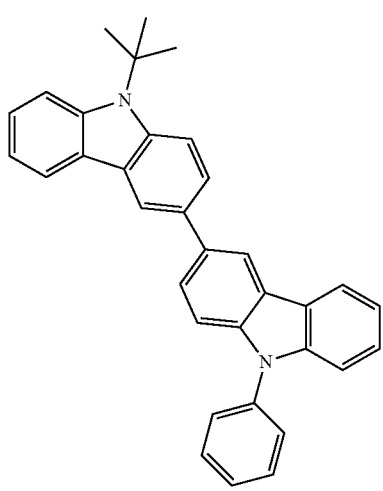
1-18
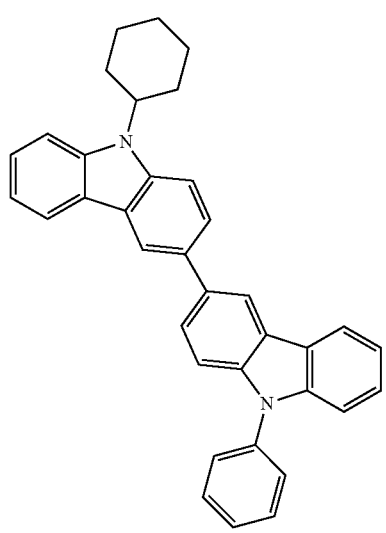
1-19

-continued
1-20
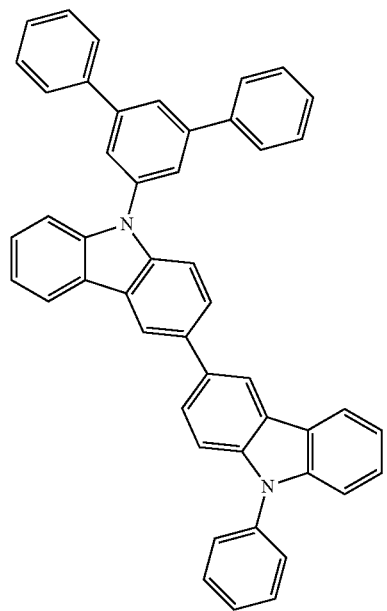
1-21
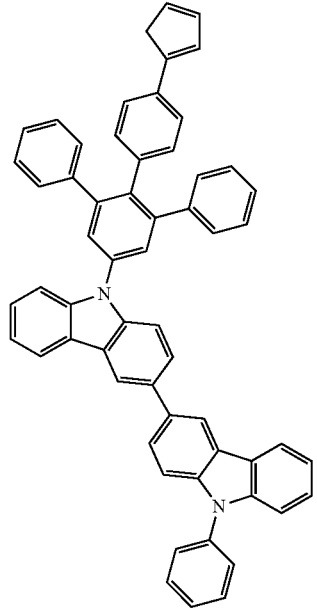
1-23
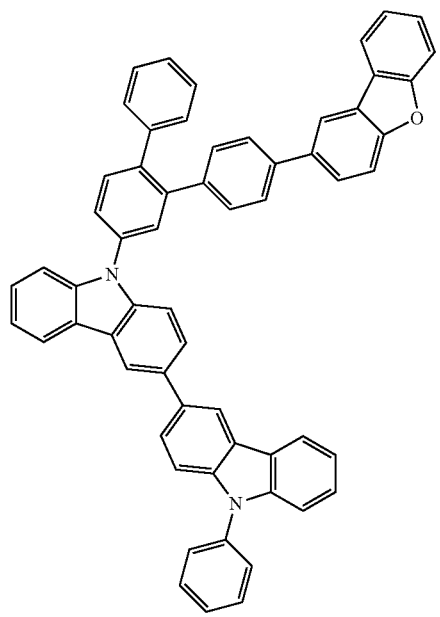
1-24
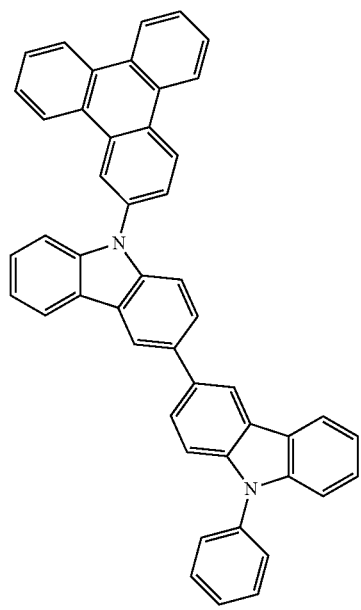

-continued
1-25
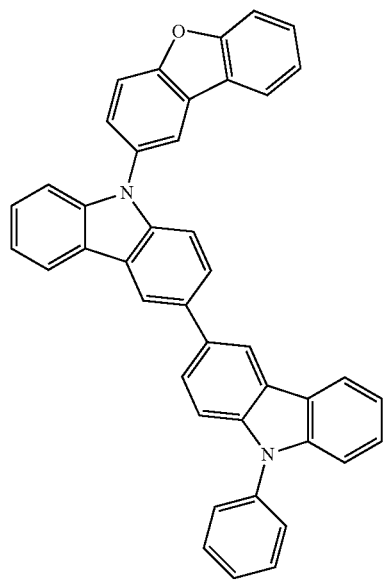
1-26
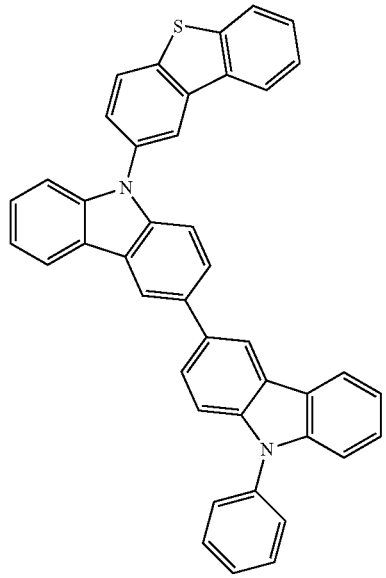
1-27
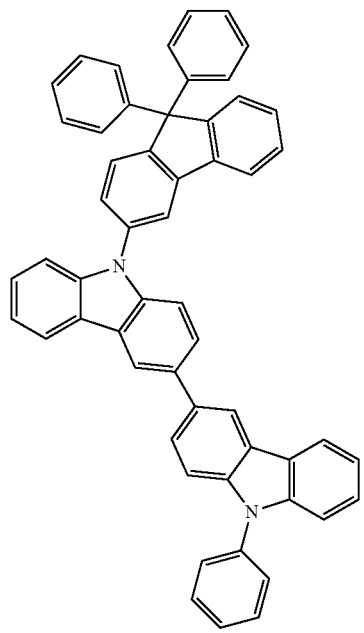
1-28
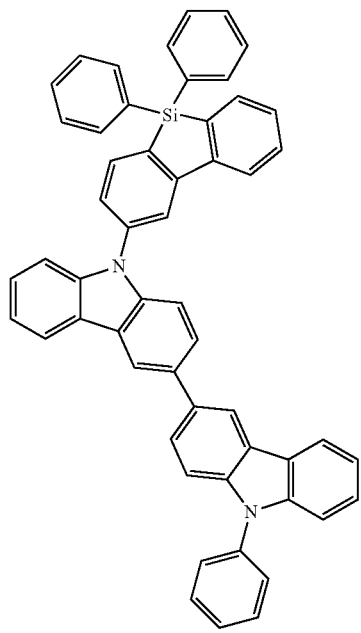

1-29
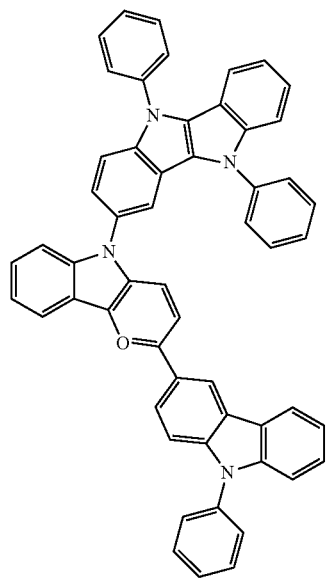
1-30
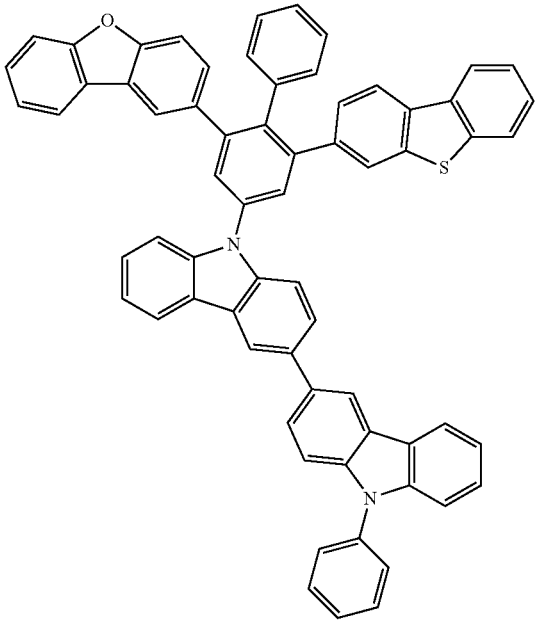
[C10]
1-31
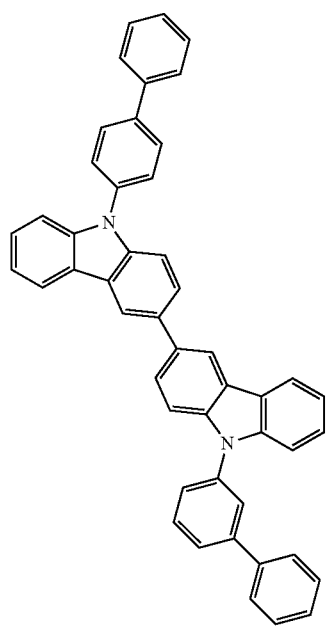
1-32
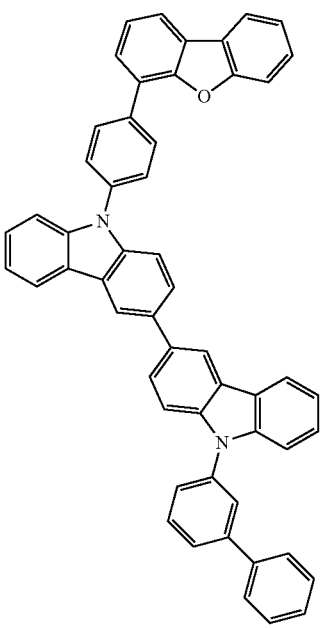

-continued
1-33
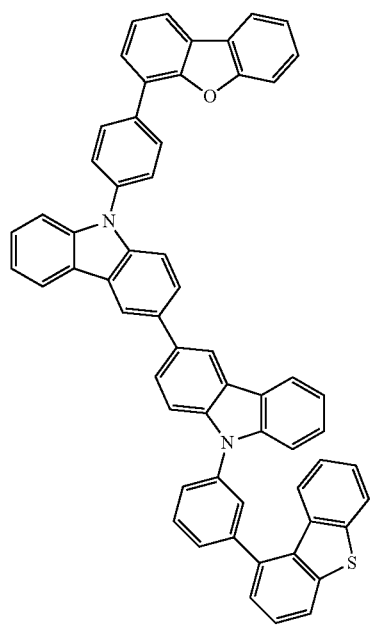
1-34
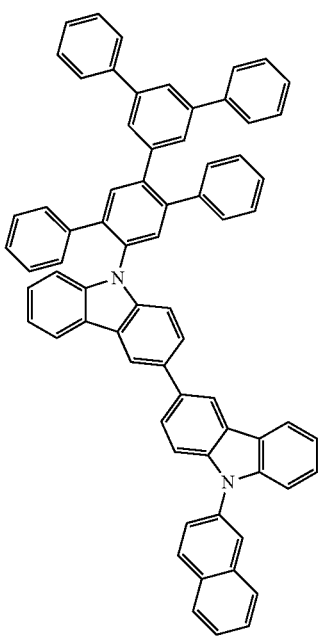
1-35
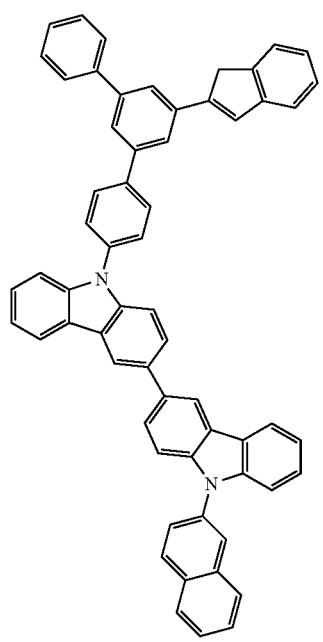
1-36
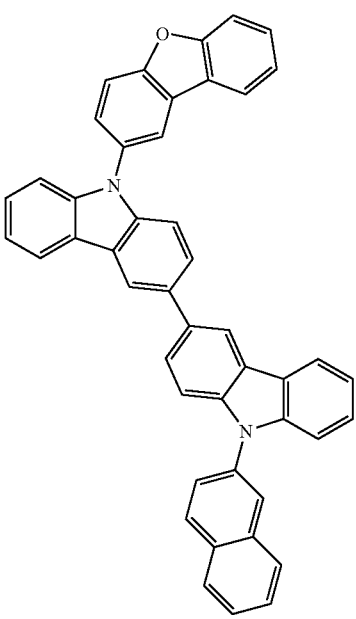

-continued
1-37
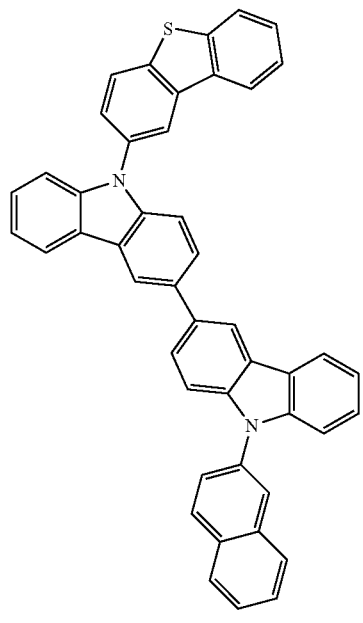
1-38
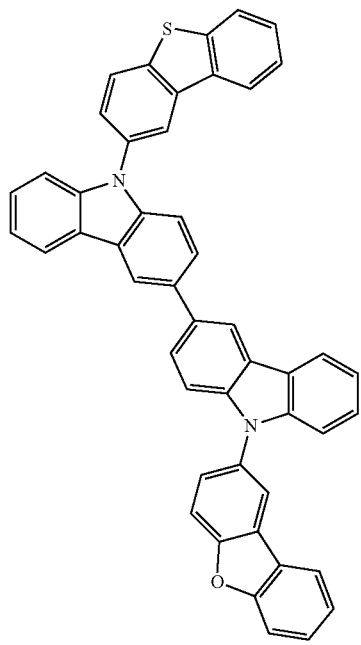
1-39
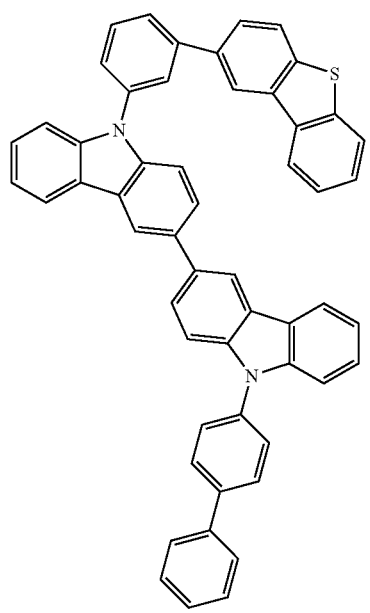
1-40
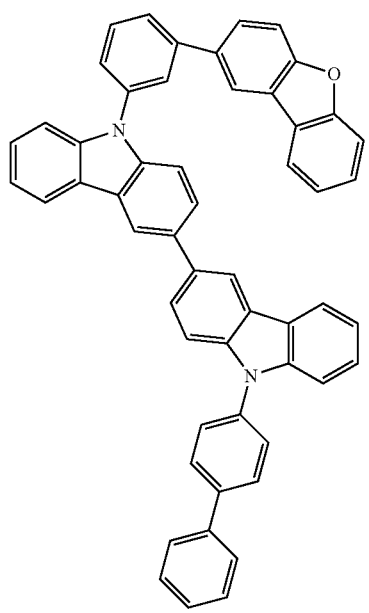

-continued
| 1-41 | 1-42 |
|---|---|
| 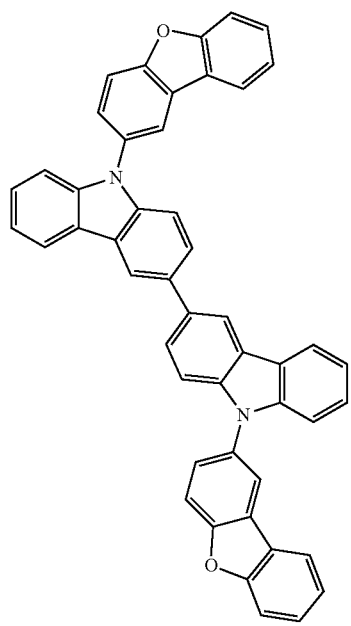 | 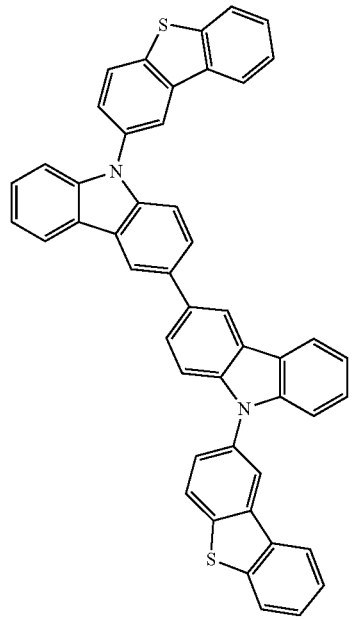 |
| 1-43 | 1-44 |
|---|---|
| 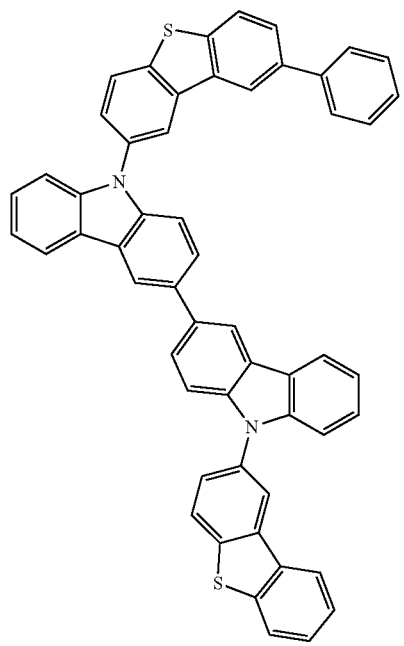 | 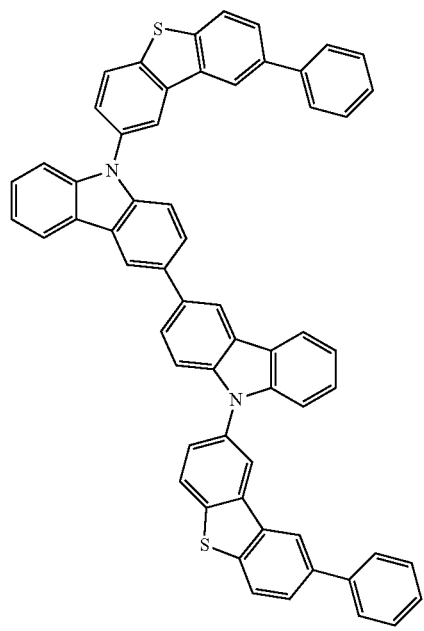 |

1-45
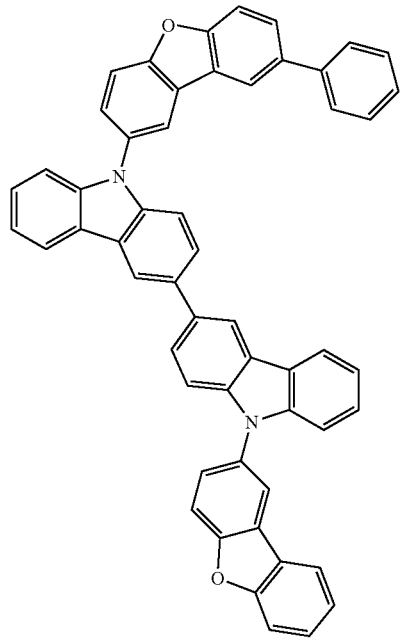
[C11]
1-46
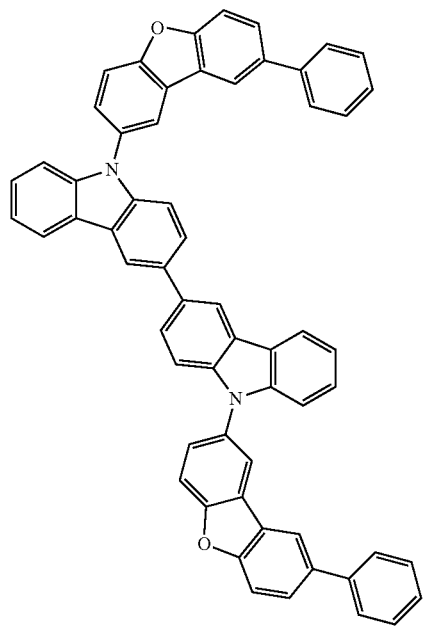
1-47
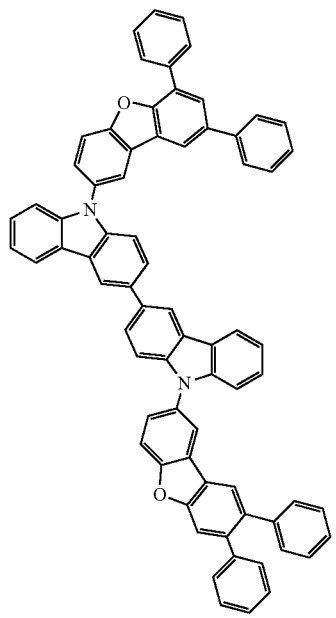

1-48
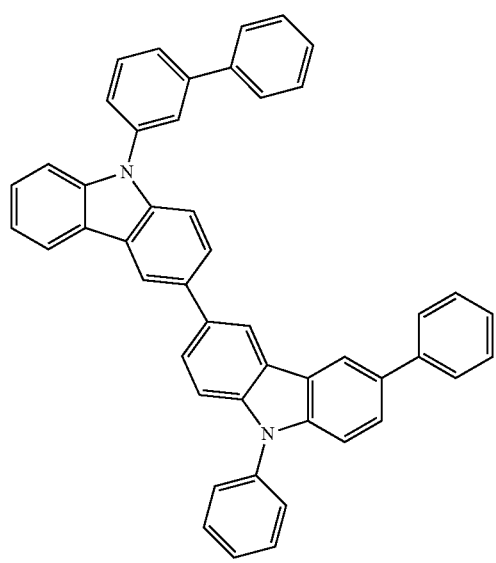
1-49
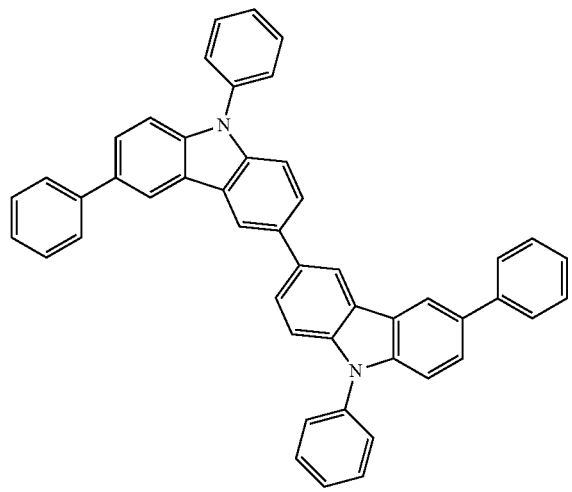
1-50
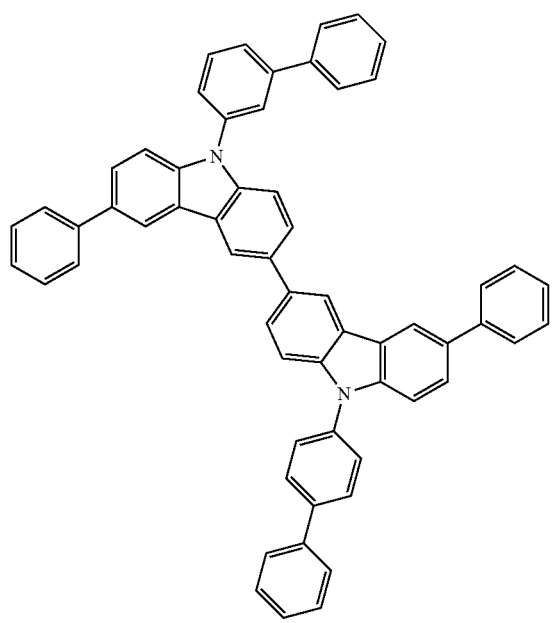
1-51
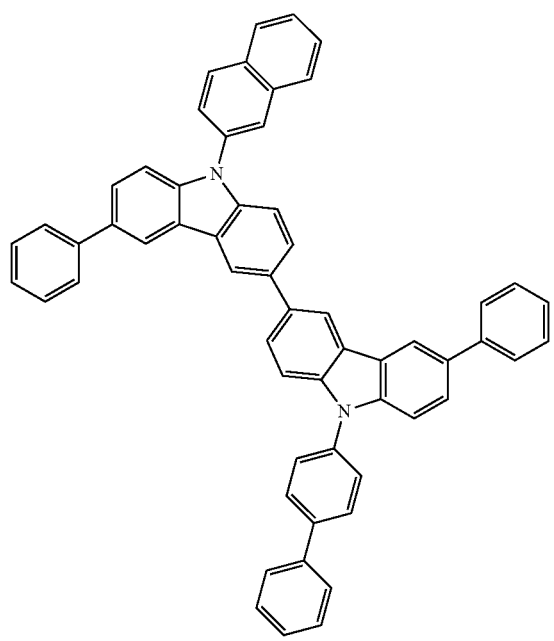

1-52
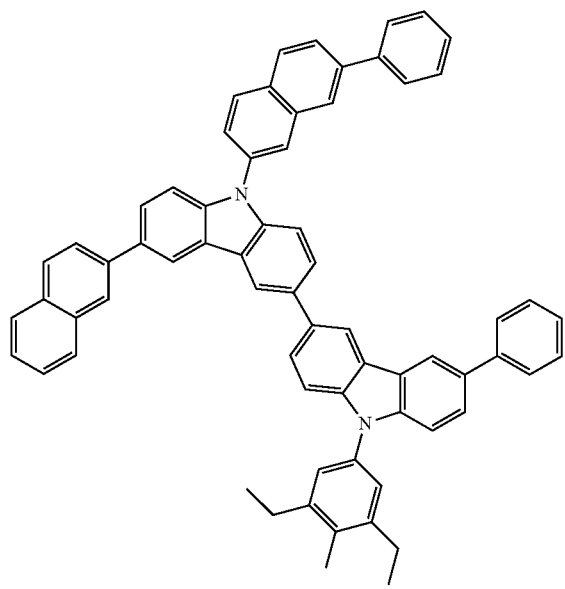
1-53
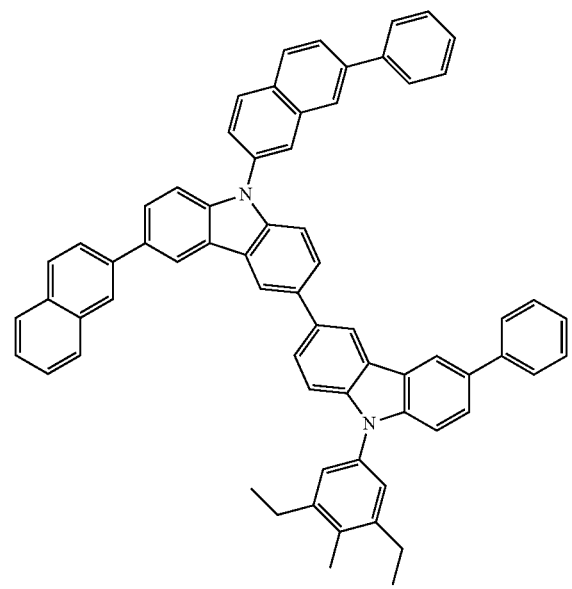
1-54
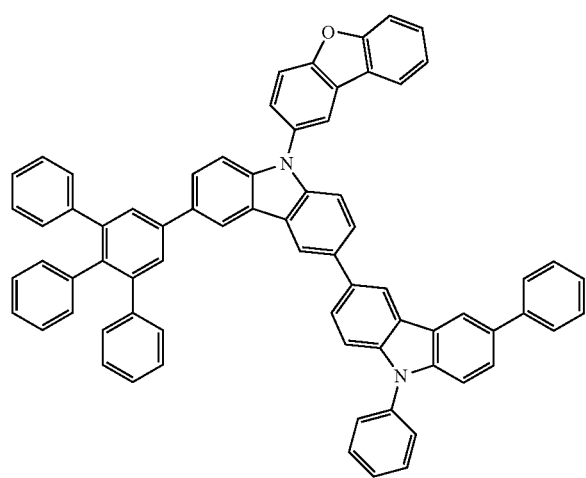

[C12]
1-55
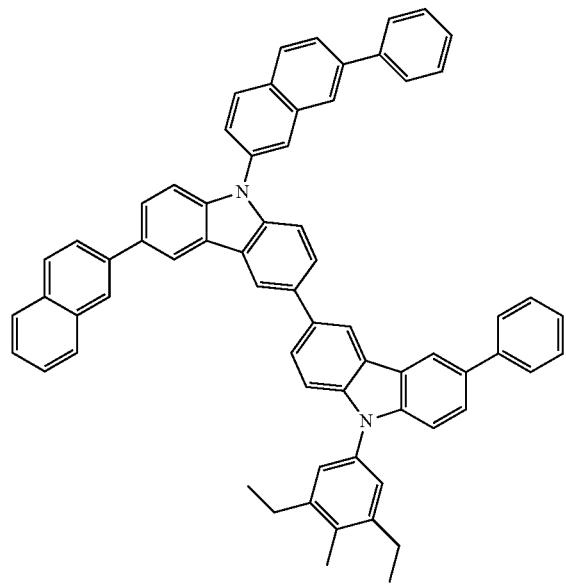
1-56
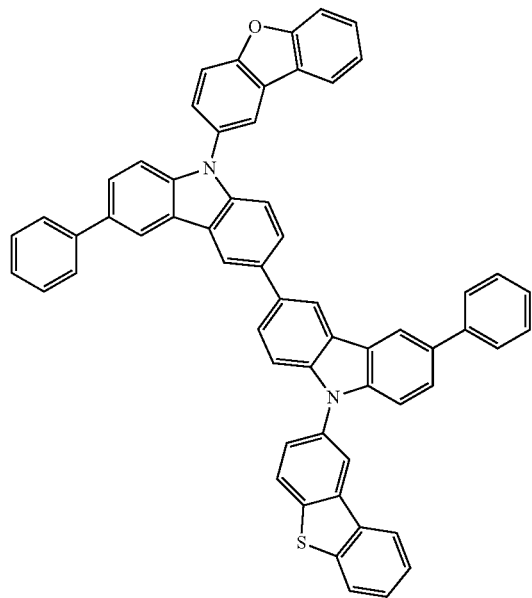
1-57
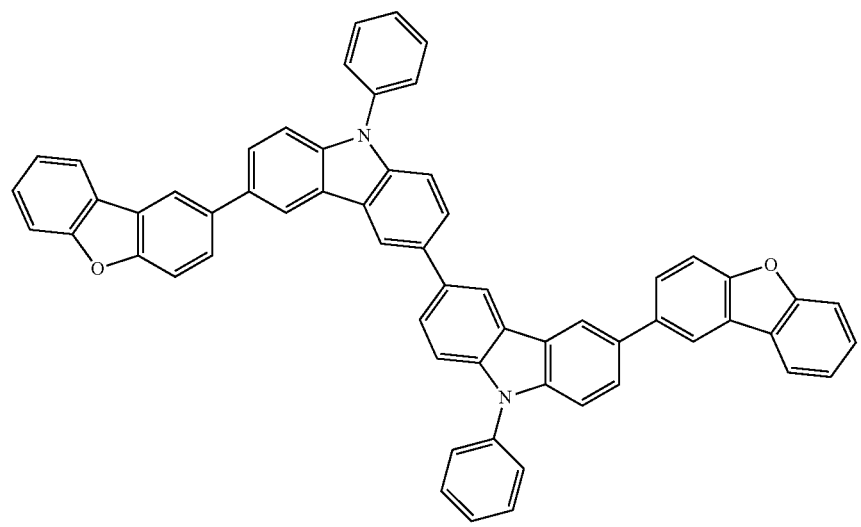

1-58
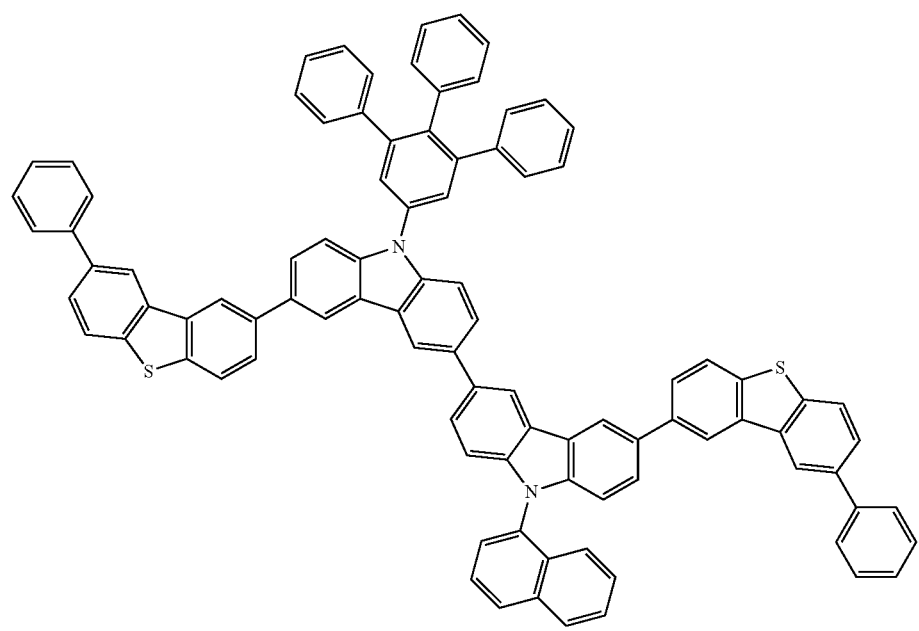
1-59
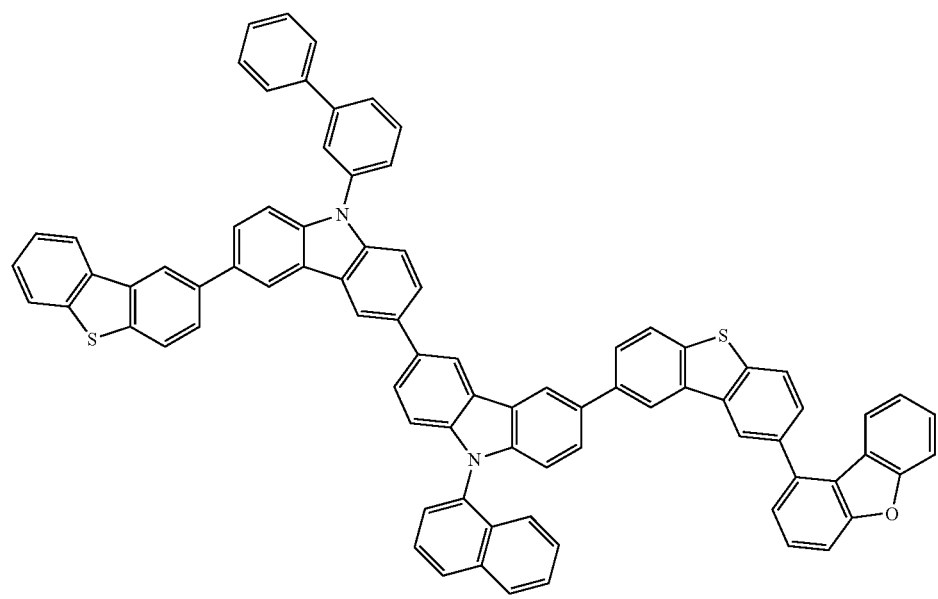

1-60
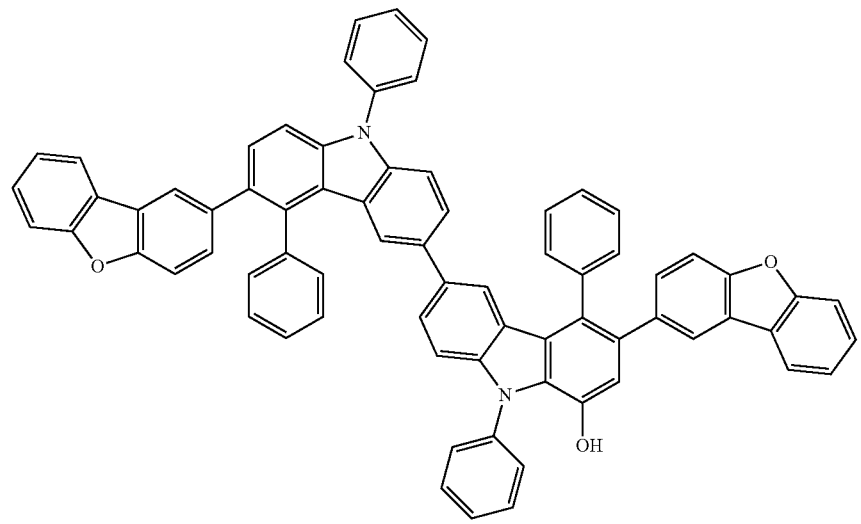
1-61
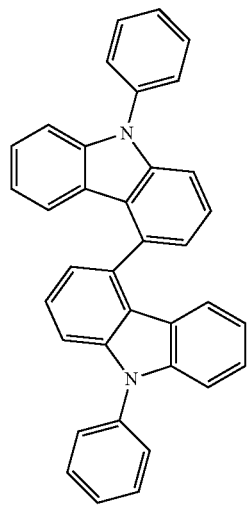
1-62
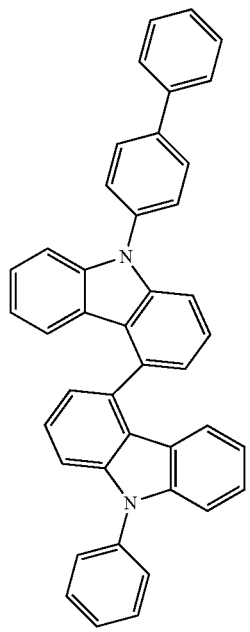

1-63
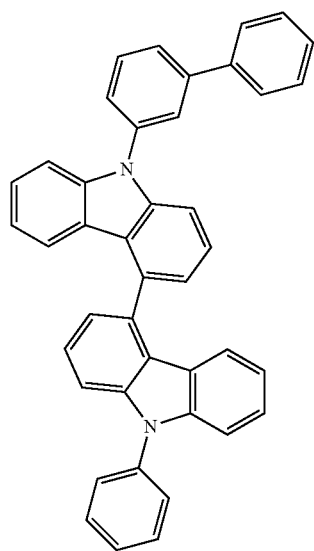
1-64
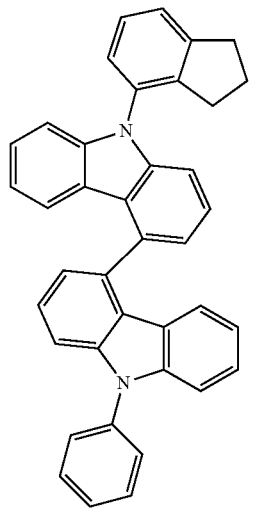
1-65
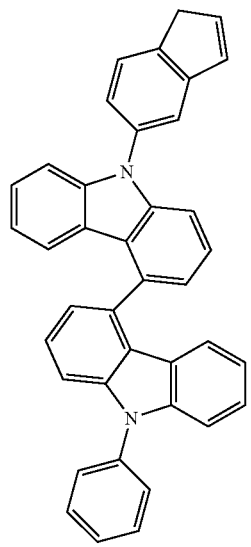
1-66
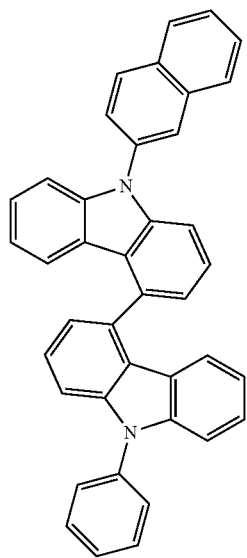

[C13]
1-67
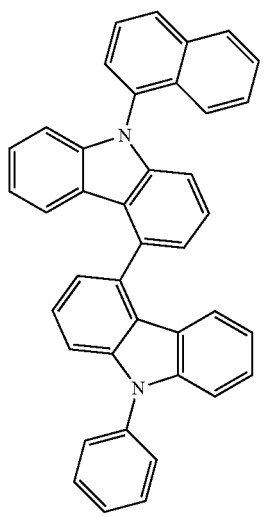
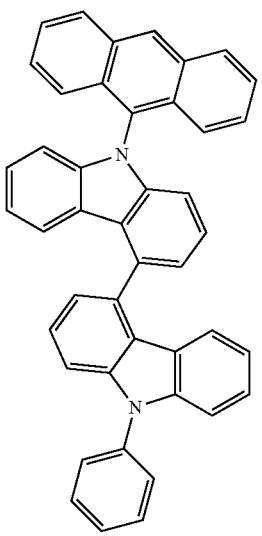
1-68
1-69
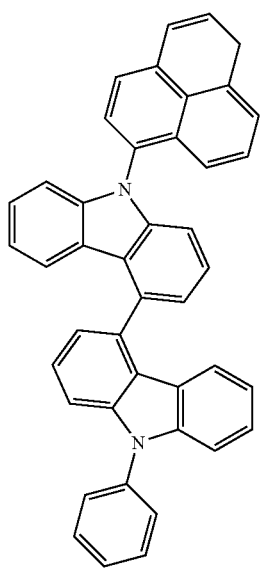
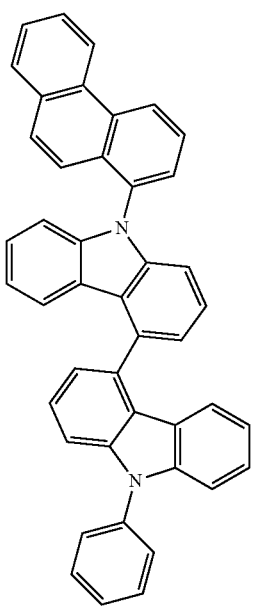
1-70

1-71
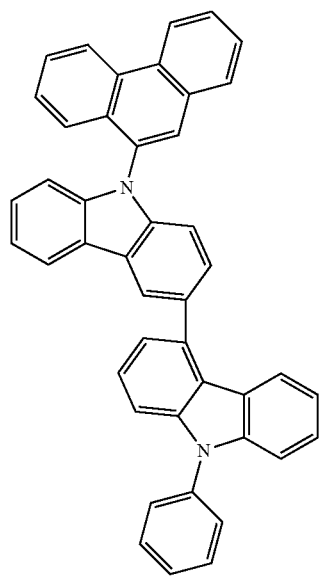
1-72
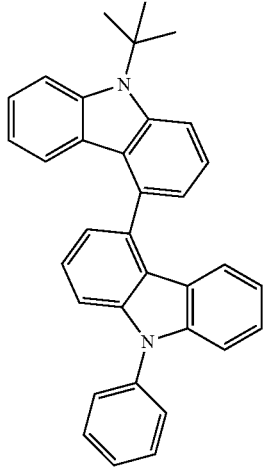
1-73
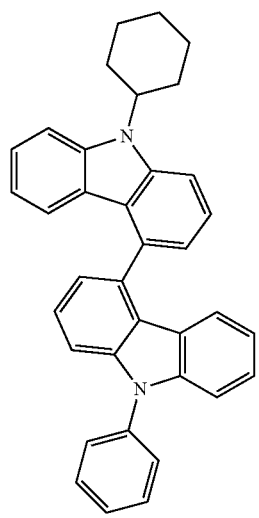
1-74
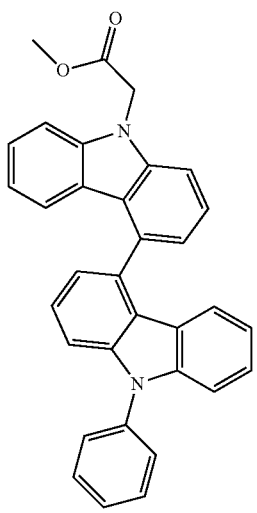

1-75
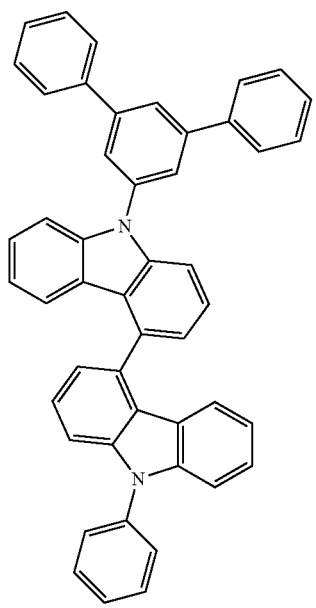
1-76
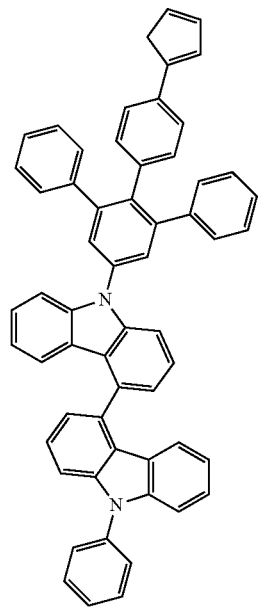
1-77
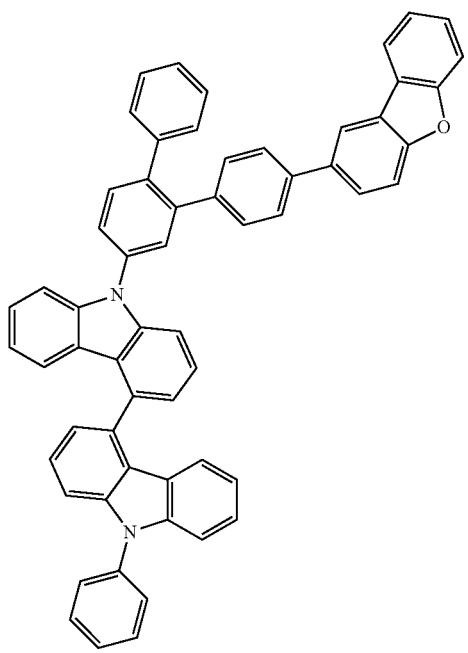
1-78
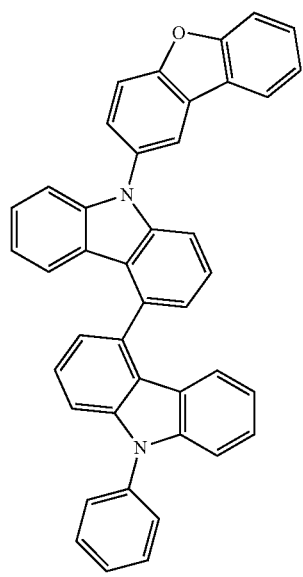

-continued
1-79
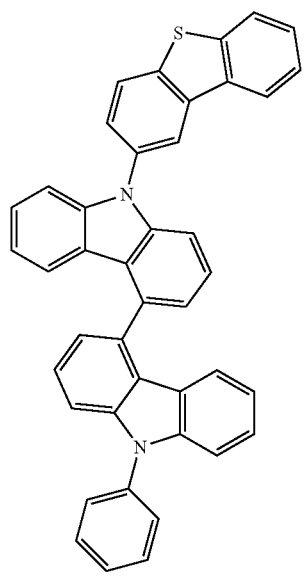
1-80
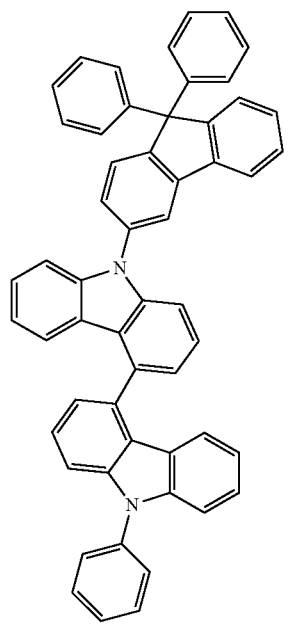
1-81
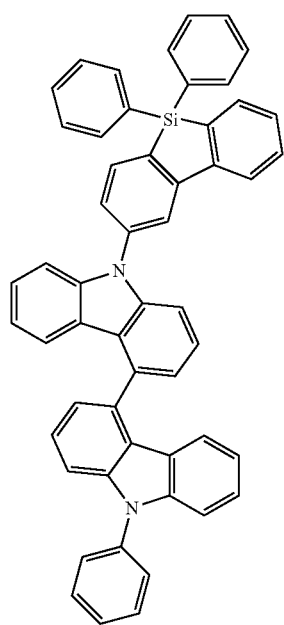
1-82
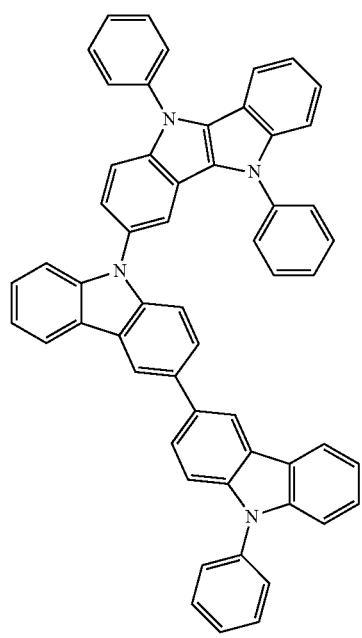

1-83
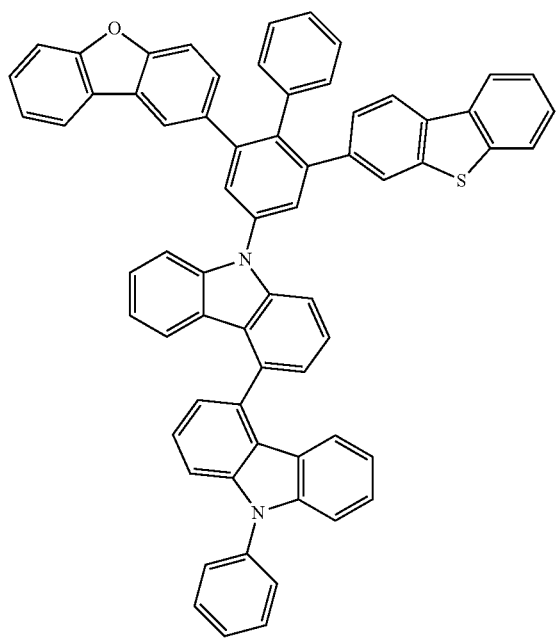
1-84
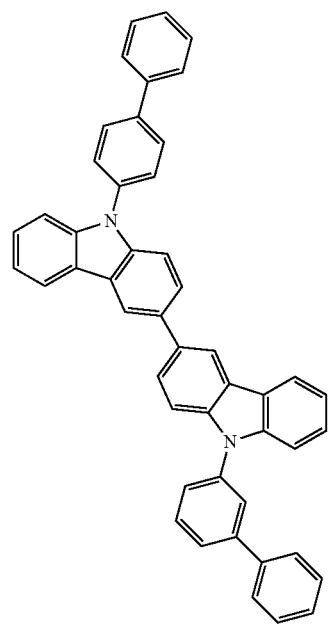
[C14]
1-85
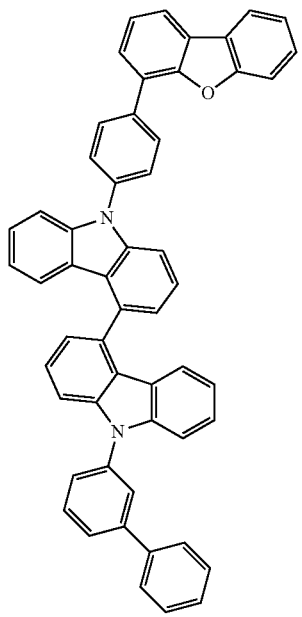
1-86
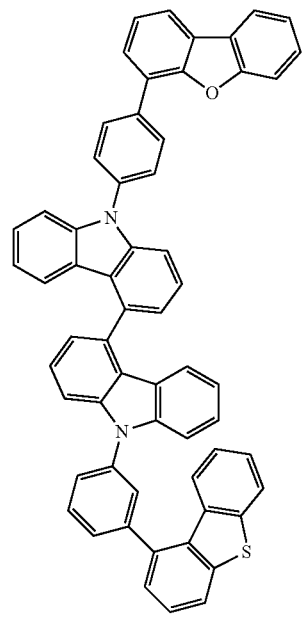

-continued
1-87
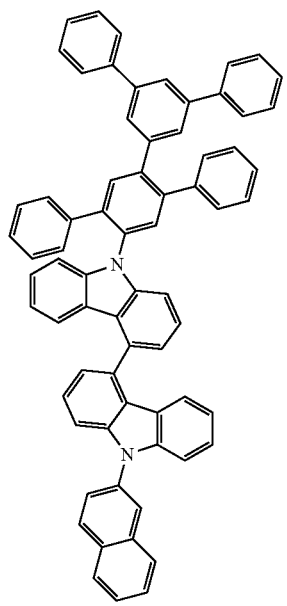
1-88
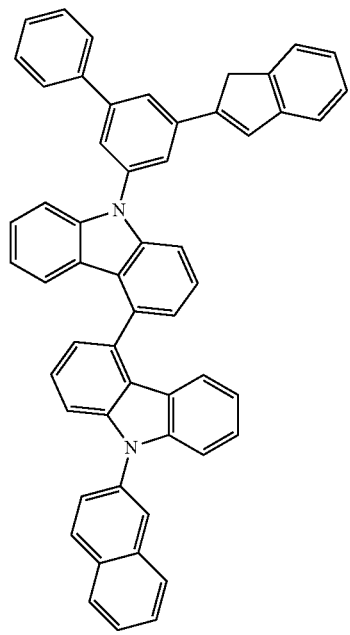
1-89
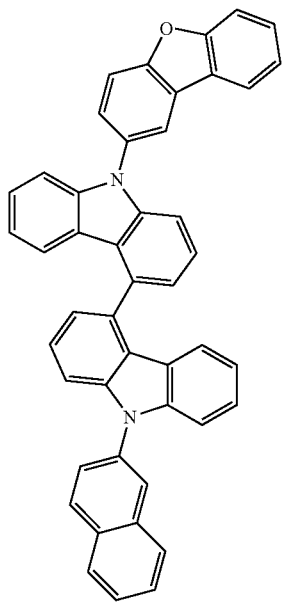
1-89b
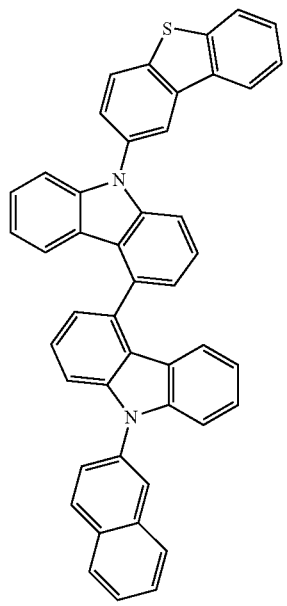

-continued
1-90
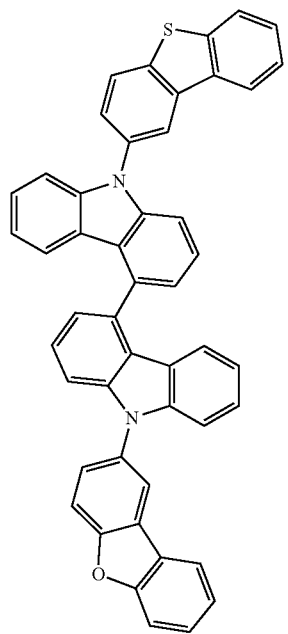
1-91
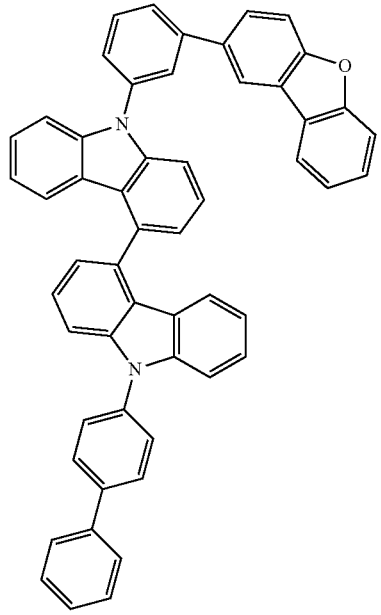
1-92
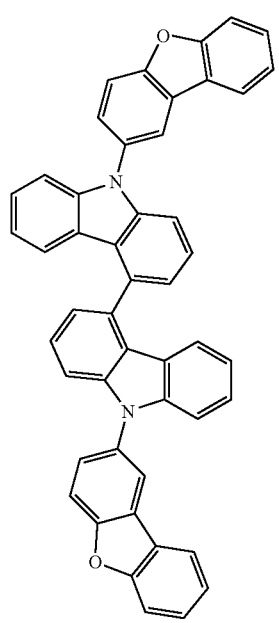
1-93
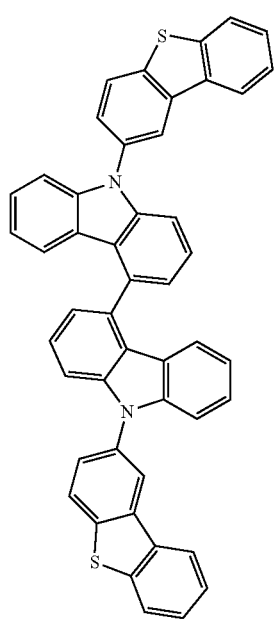

-continued
1-94
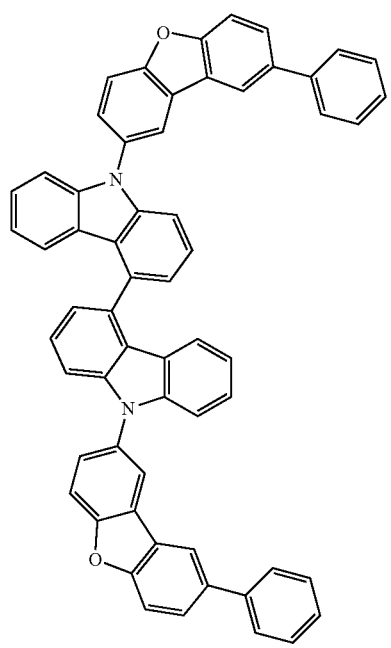
1-95
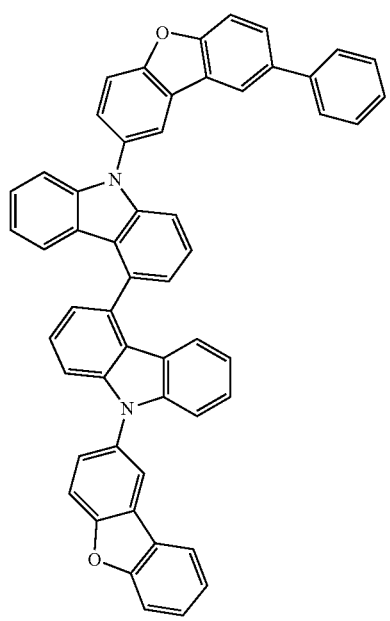
1-96
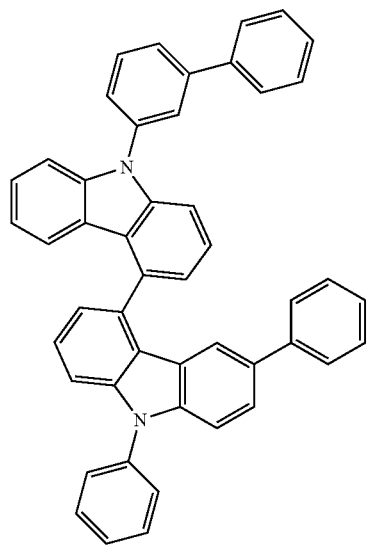
1-97
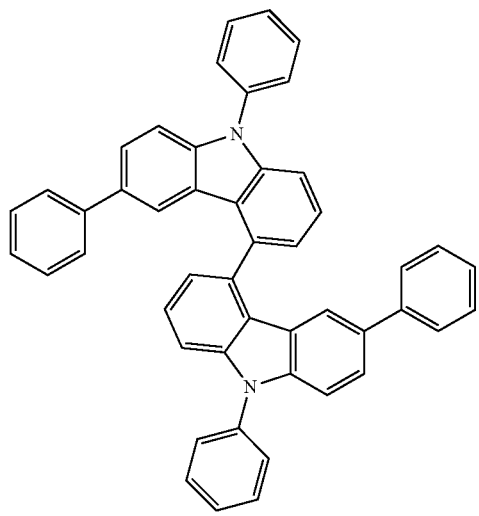

[C-15]
1-98
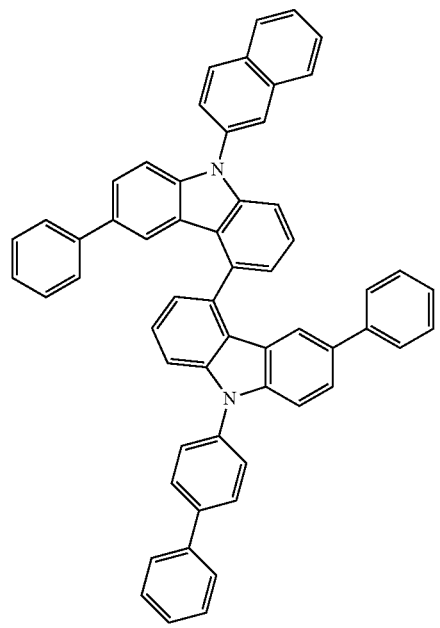
1-99
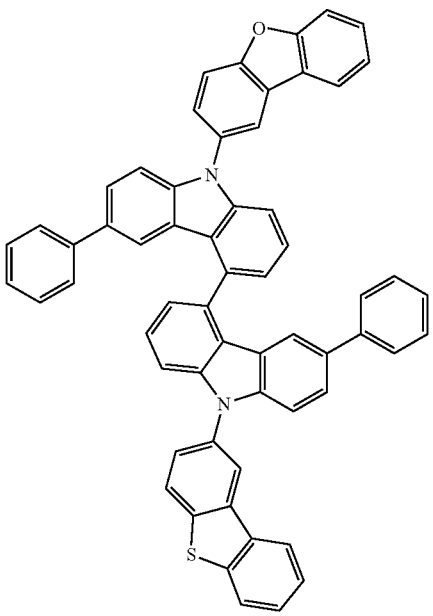
1-100
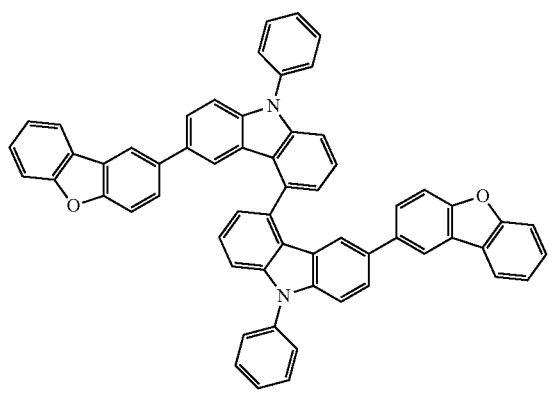
1-101
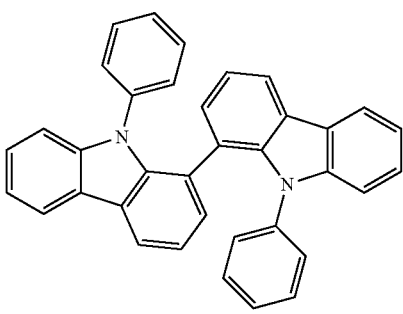
1-102
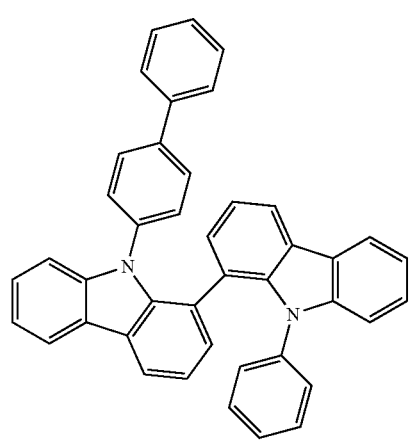
1-103
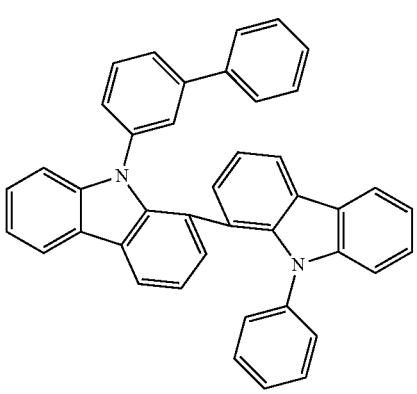

-continued
1-104
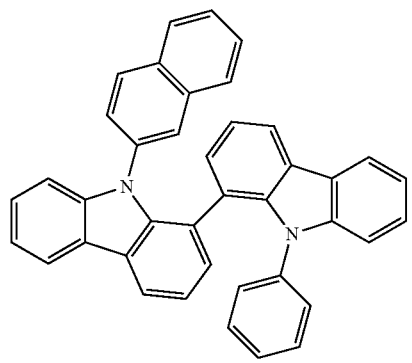
1-105
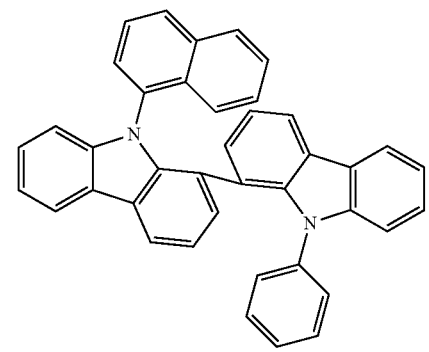
1-106
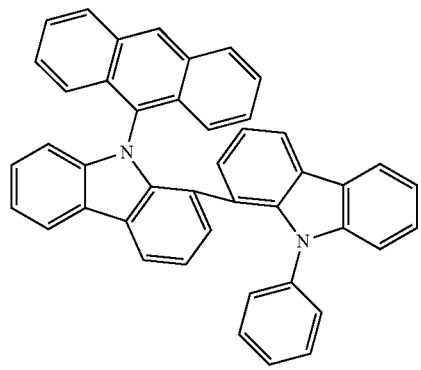
1-107
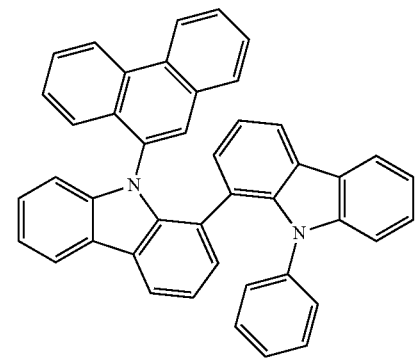
1-108
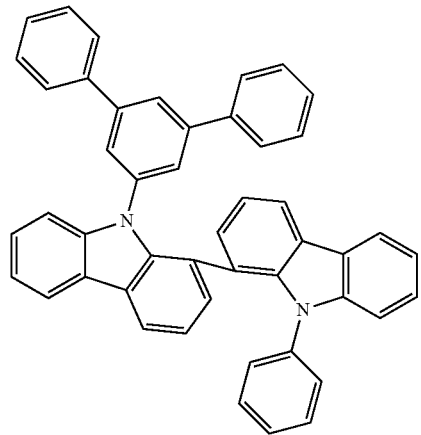
1-109
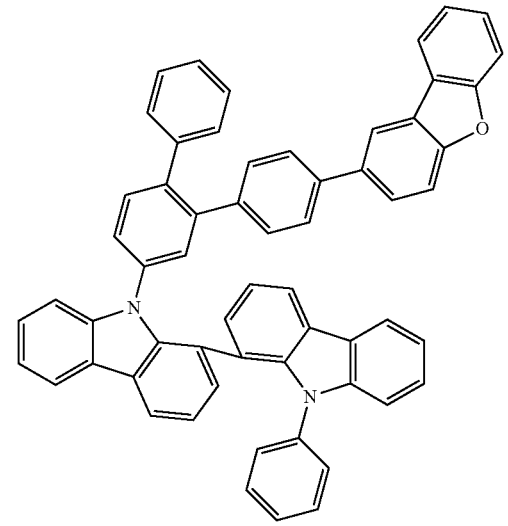
1-110
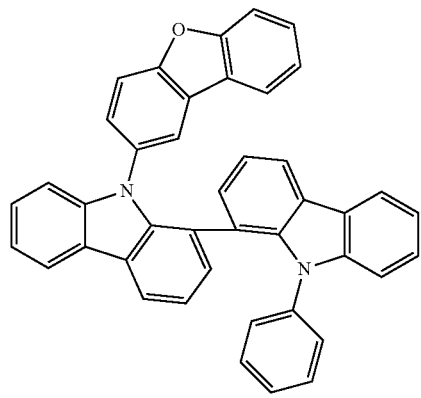
1-111
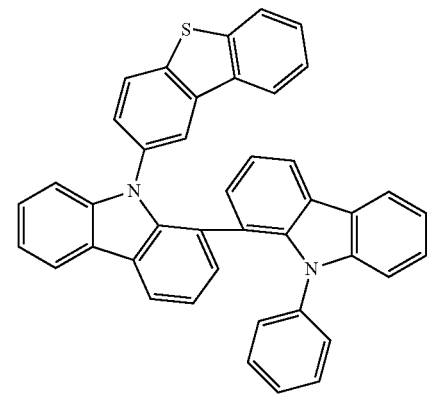

1-112
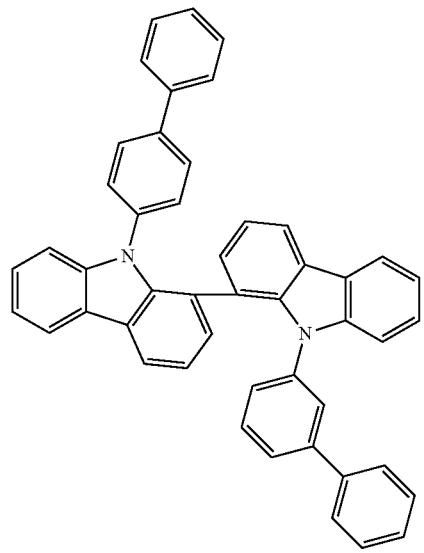
[C16]
1-113
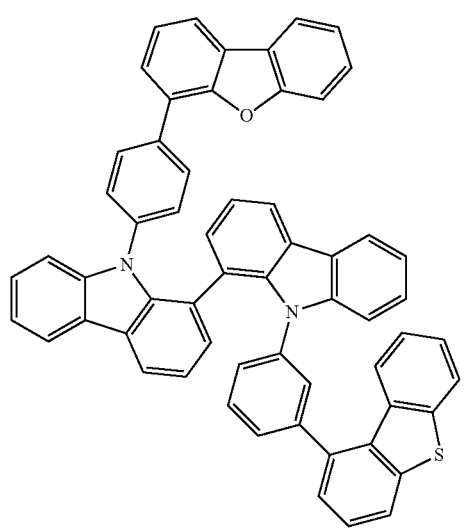
1-114
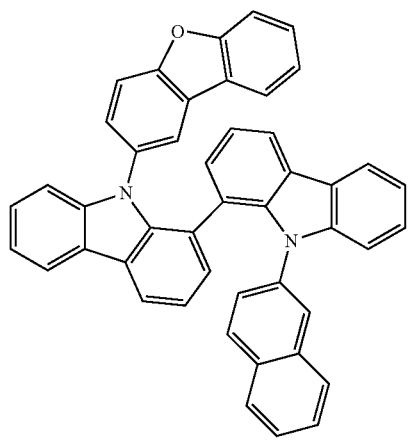
1-115
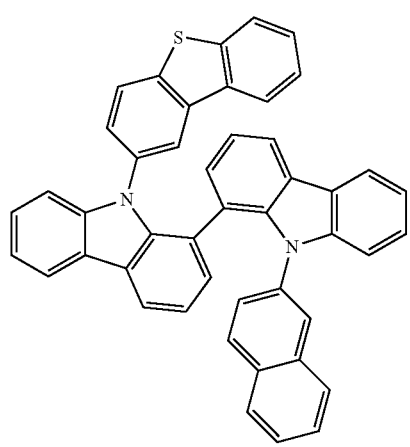
1-116
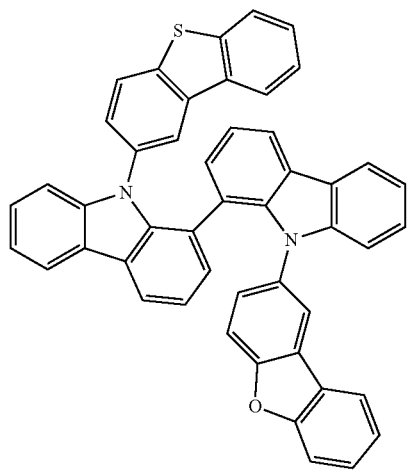

-continued
1-117
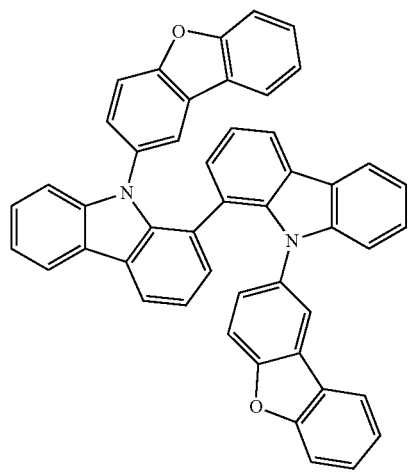
1-118
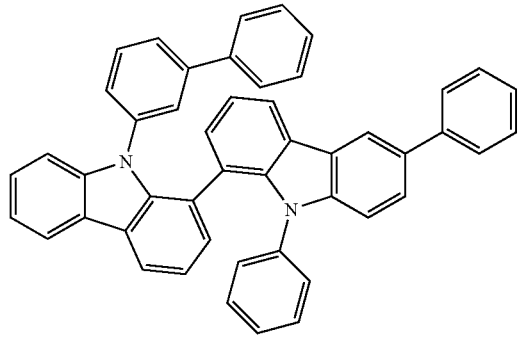
1-119
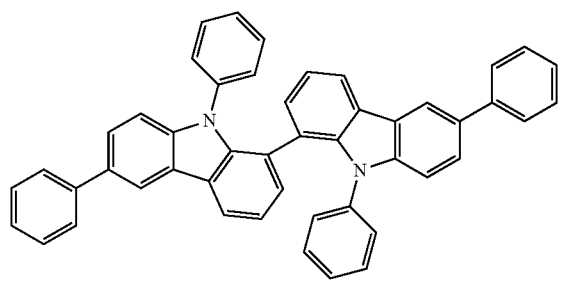
1-120
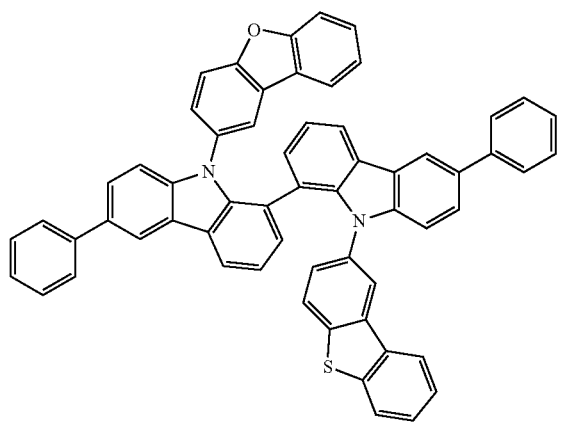
1-121
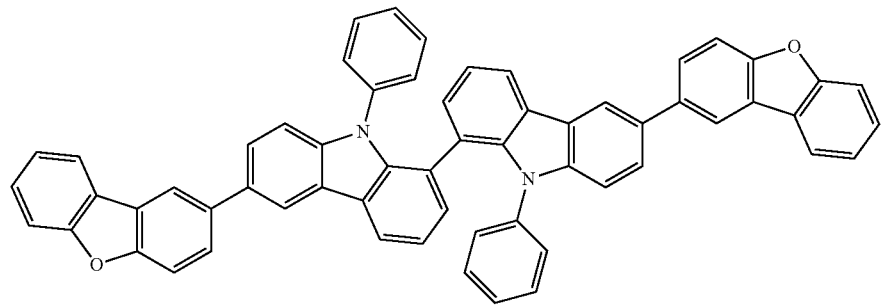

1-122
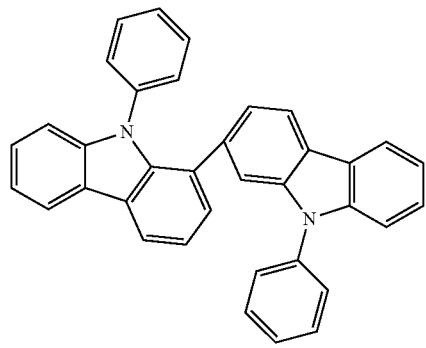
1-123
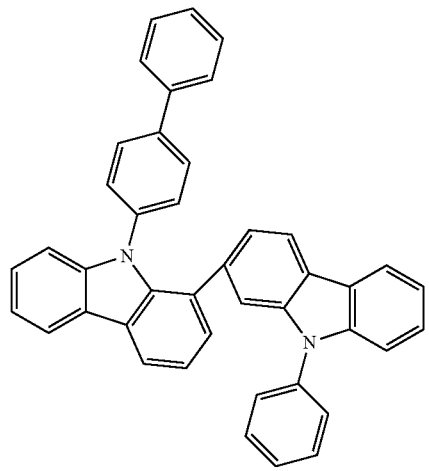
1-124
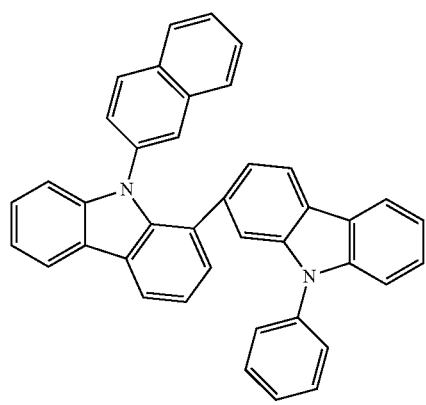
[C17]
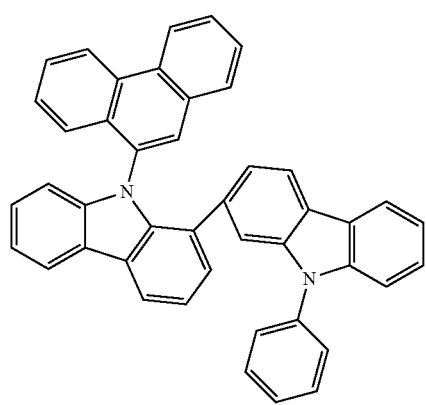
1-125
1-126
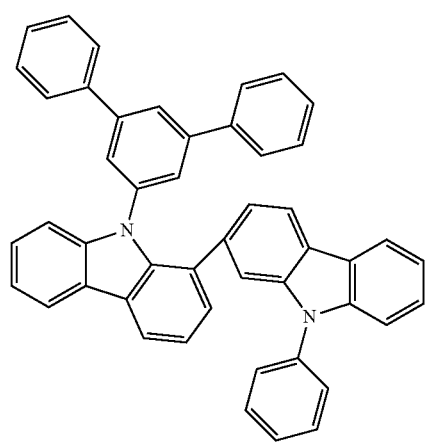

-continued
1-127
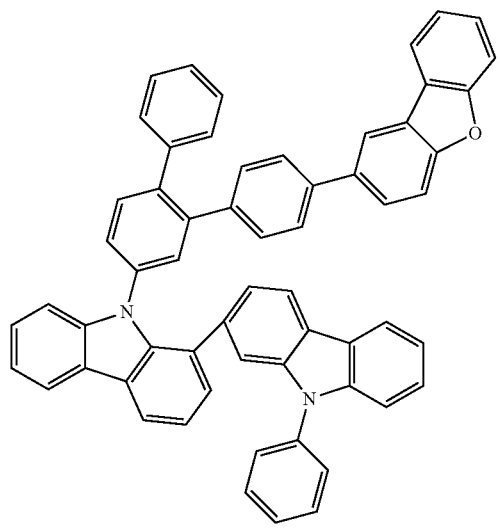
1-128
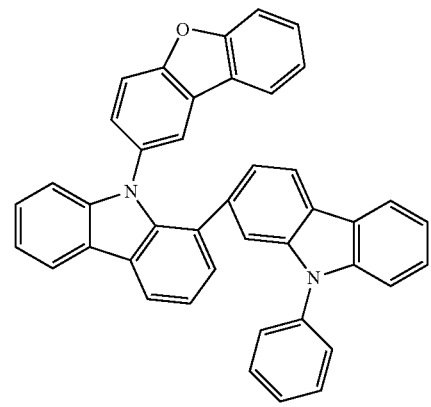
1-129
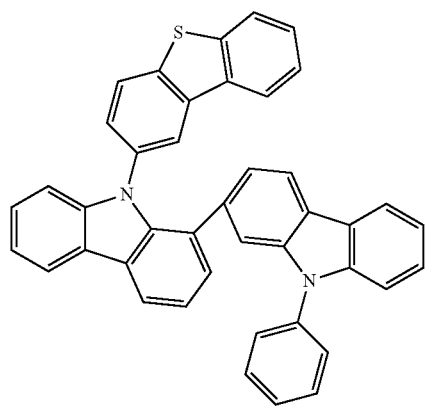
1-130
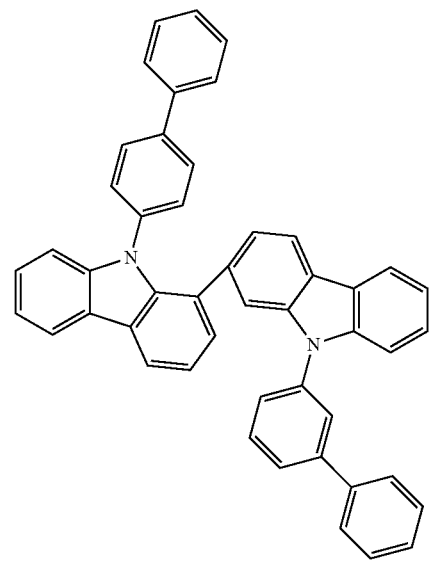
1-131
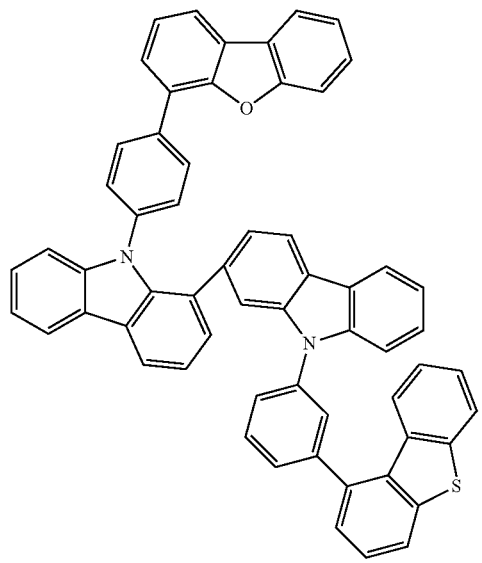
1-132
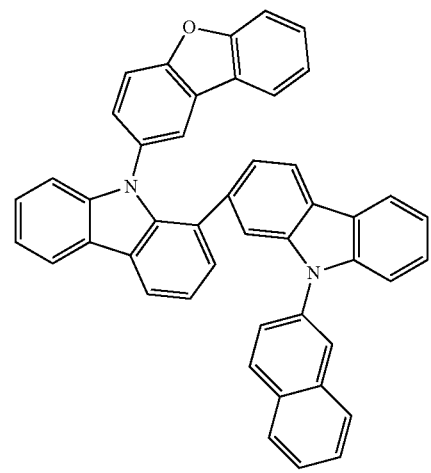

-continued
1-133
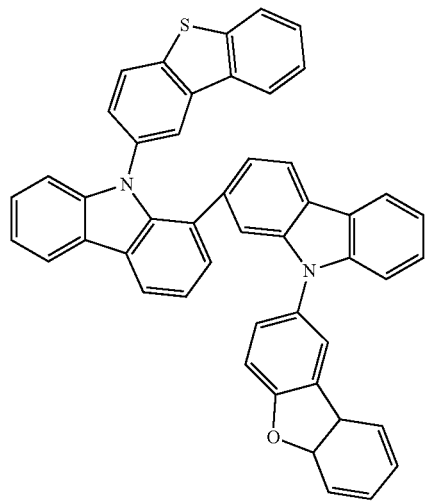
1-134
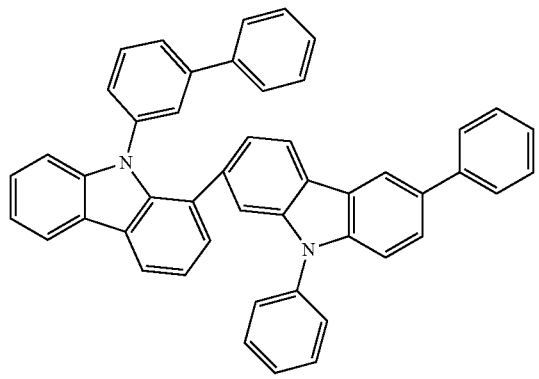
1-135
1-136
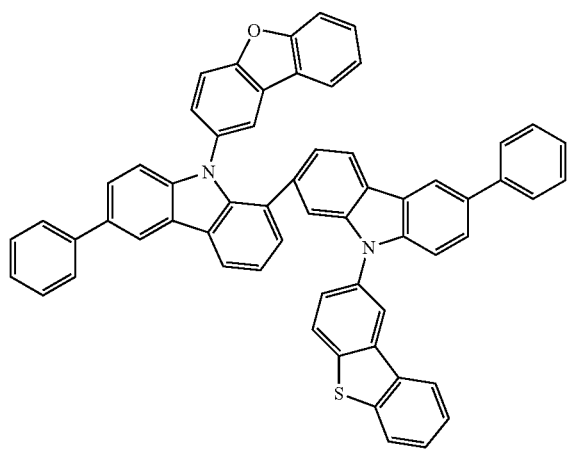
1-137
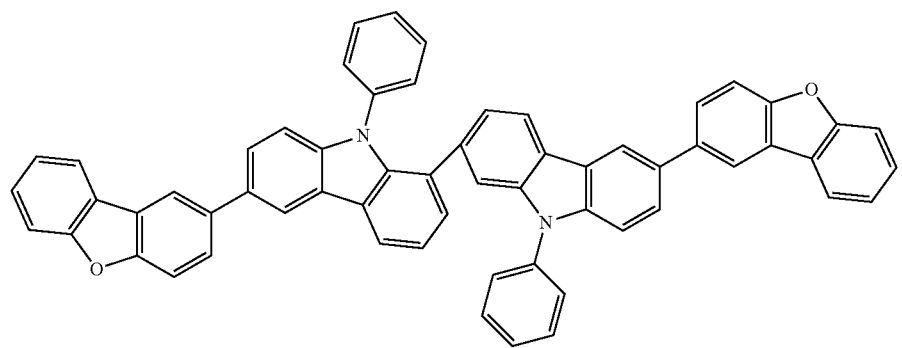

[C18]
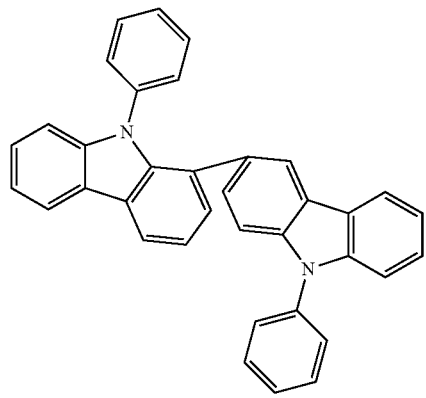
1-138
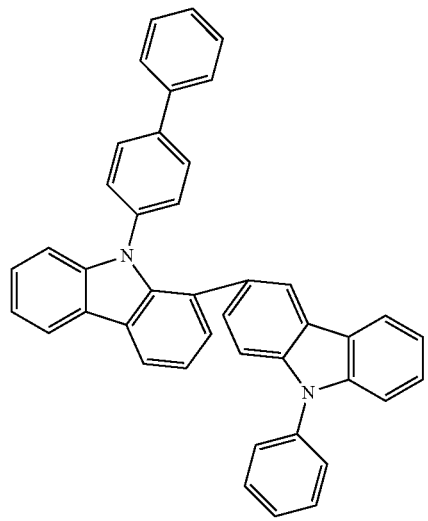
1-139
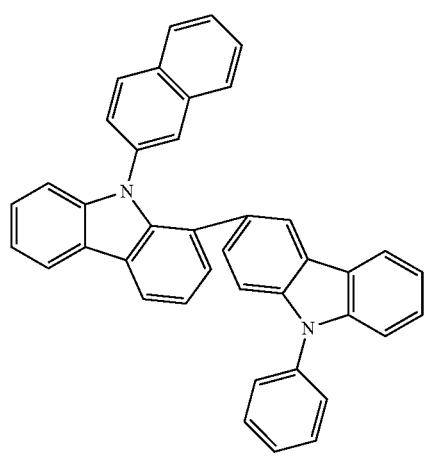
1-140
1-141
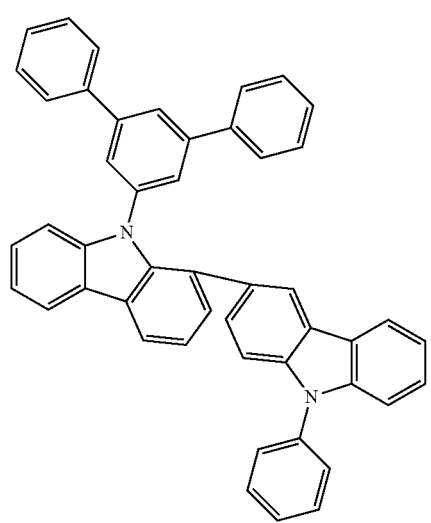
1-142
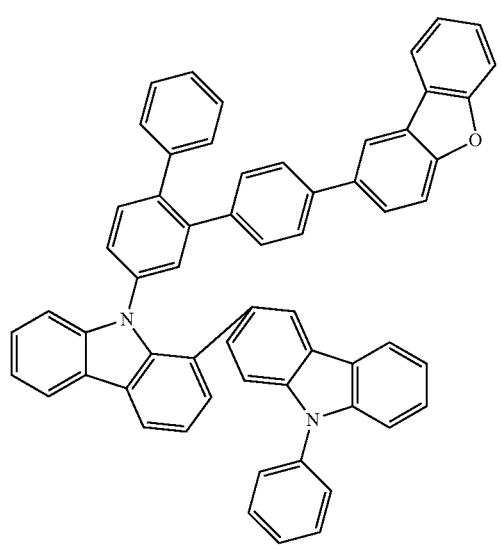
1-143

-continued
1-144
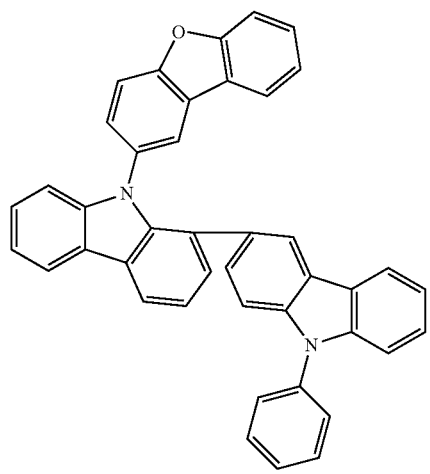
1-145
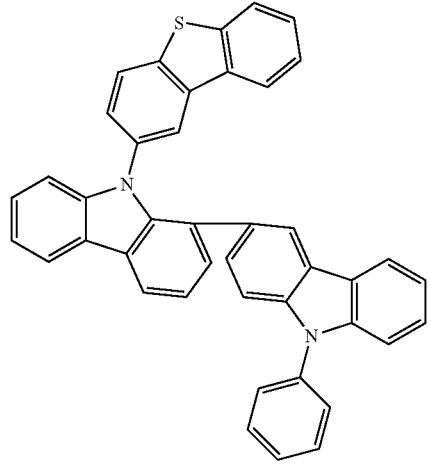
1-146
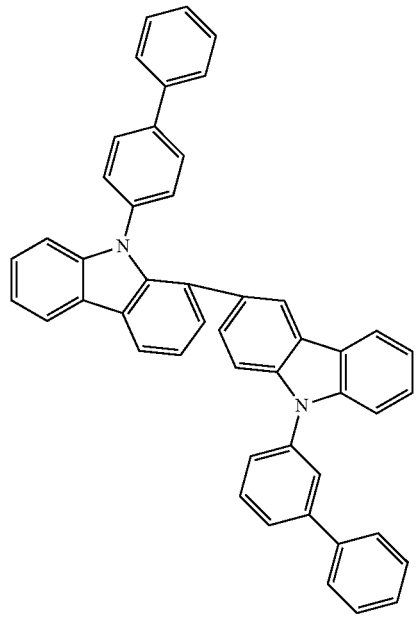
1-147
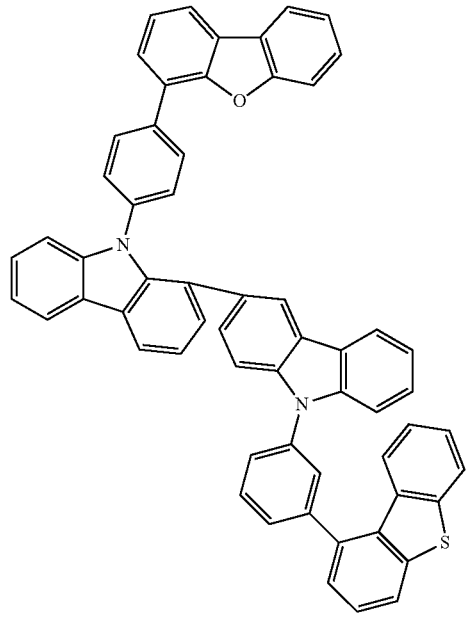

-continued
1-148
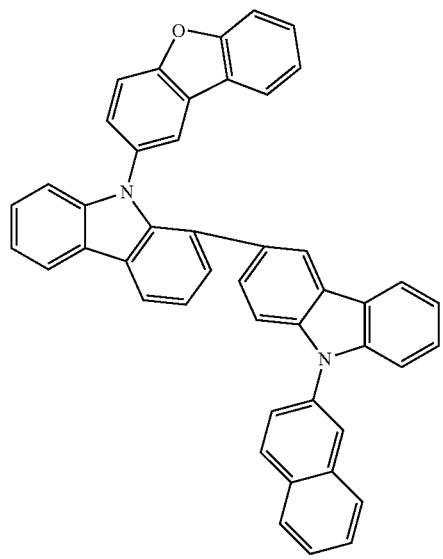
1-149
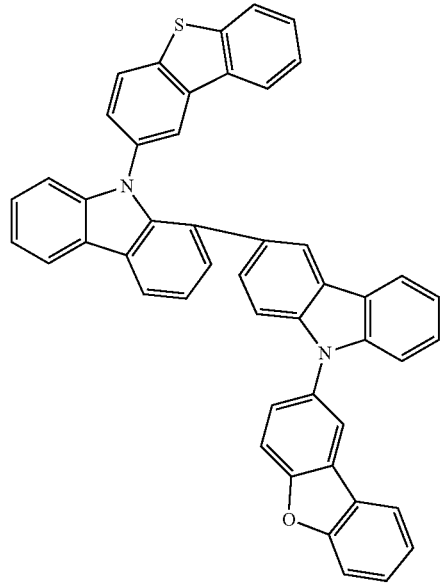
[C19]
1-150
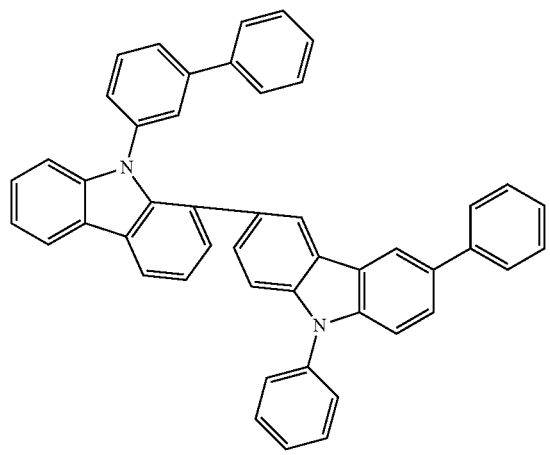
1-151
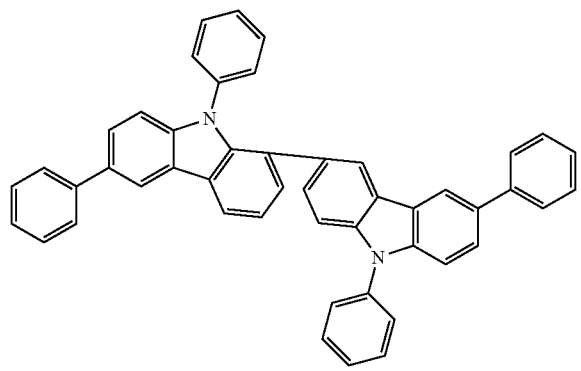

1-152
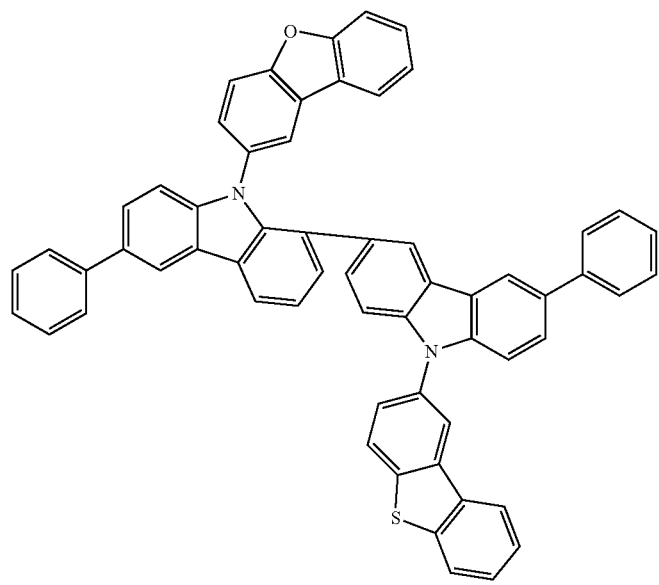
1-153
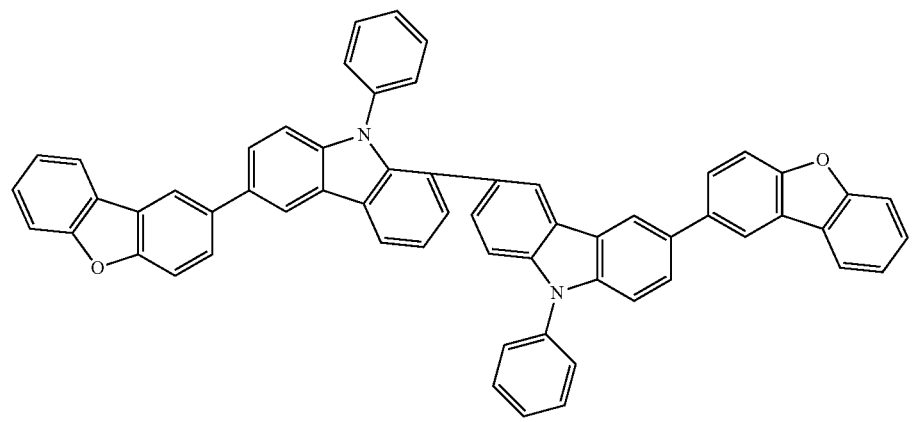
1-154
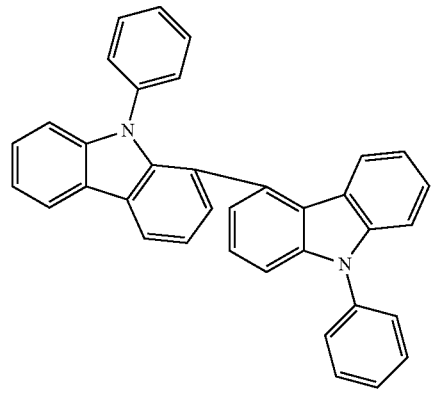
1-155
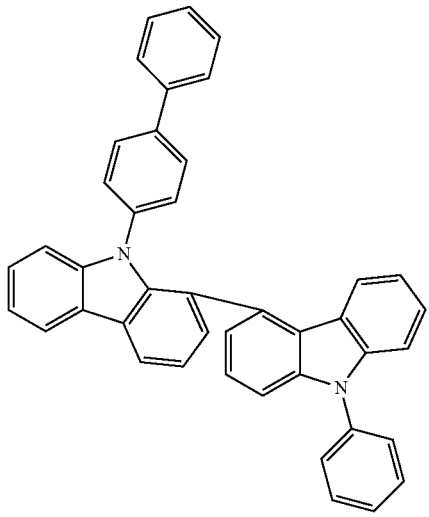

-continued
1-156
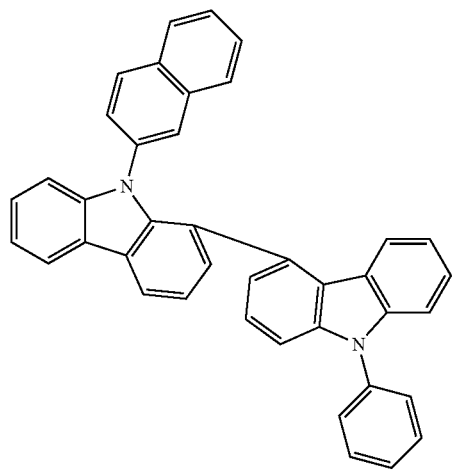
1-157
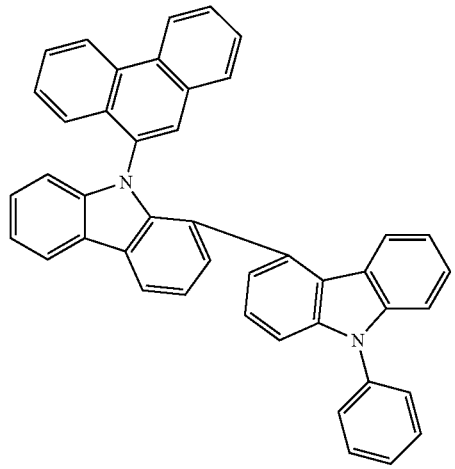
1-158
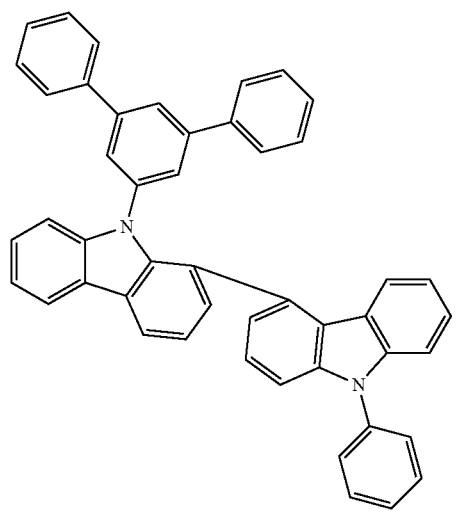
1-159
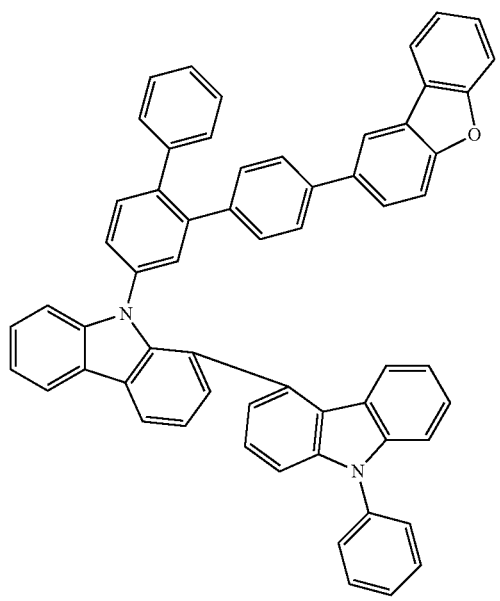
1-160
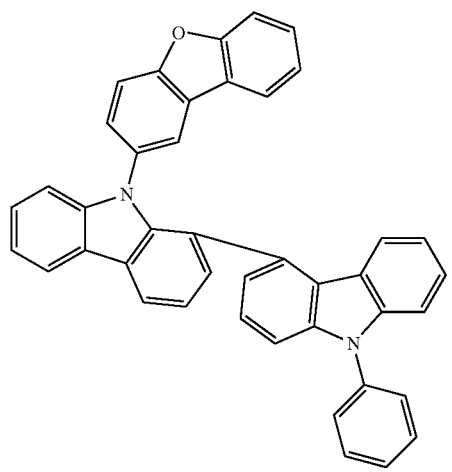
1-161
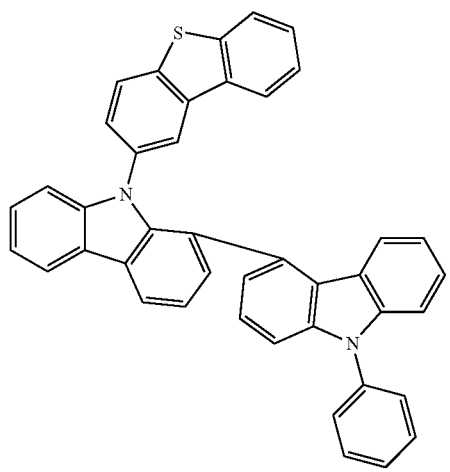

[C20]
1-162
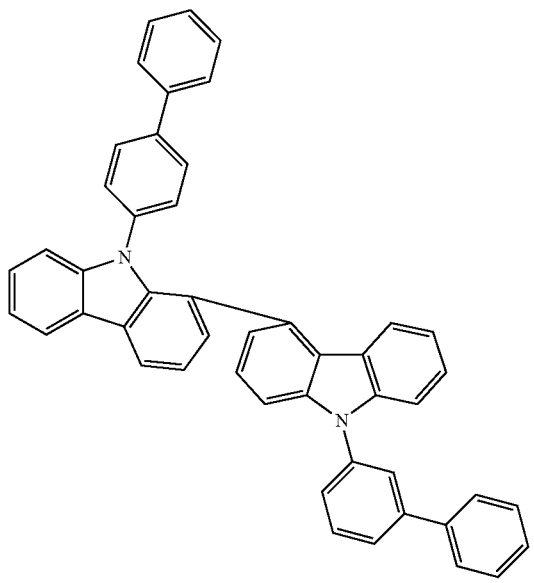
1-163
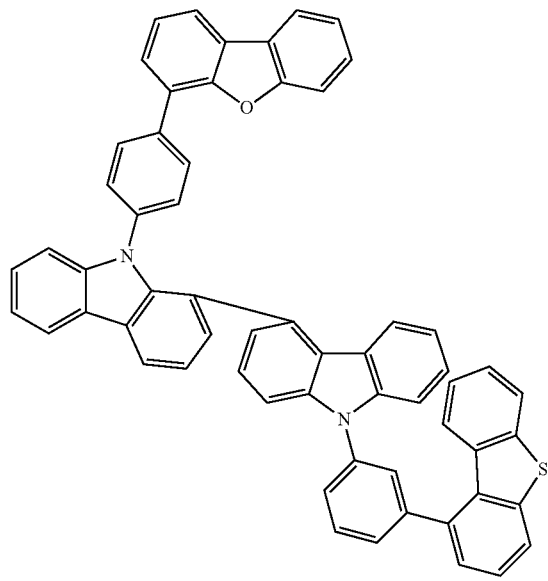
1-164
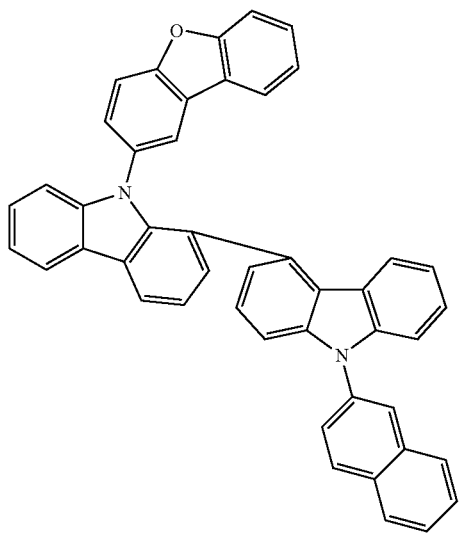
1-165
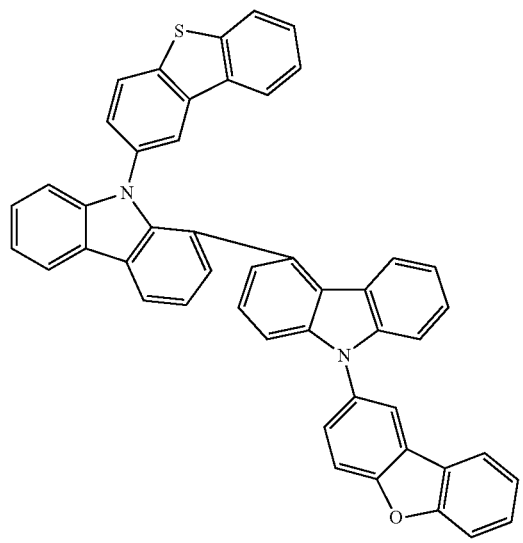
1-166
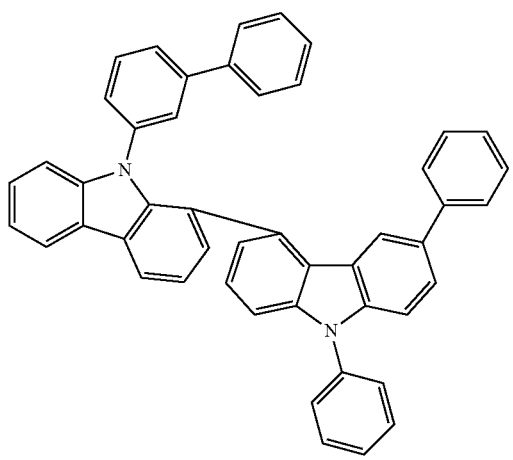
1-167
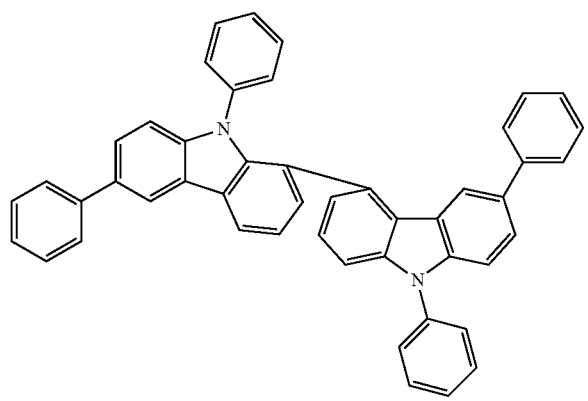

-continued
1-168
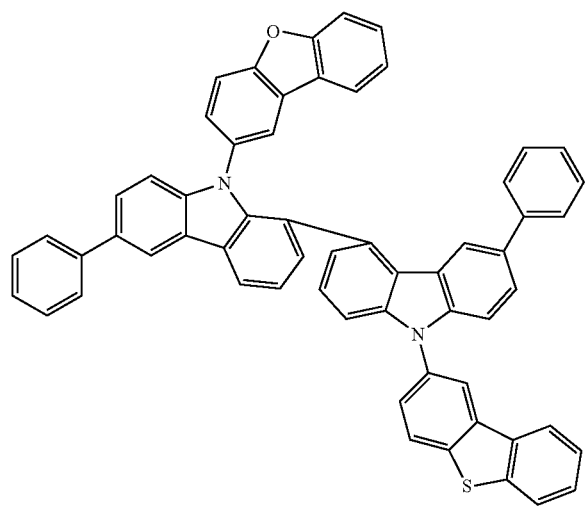
1-169
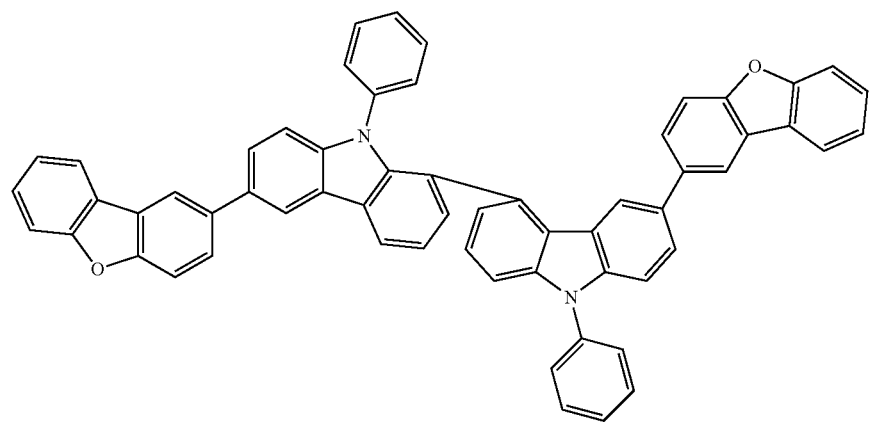
1-170
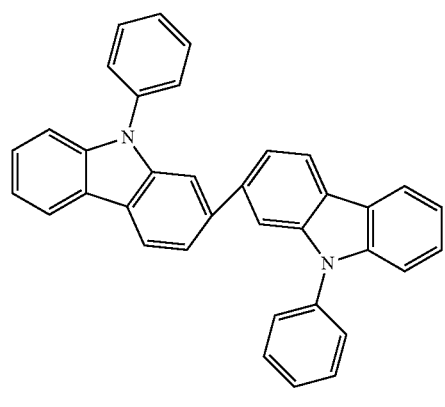
1-171
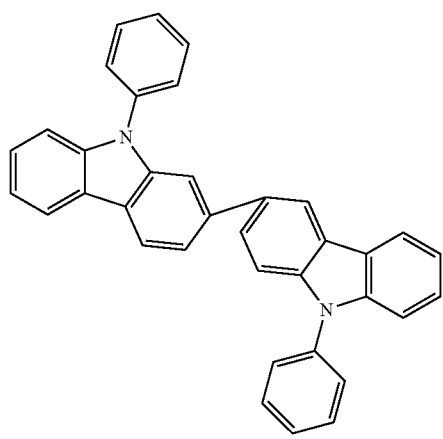

-continued
1-172
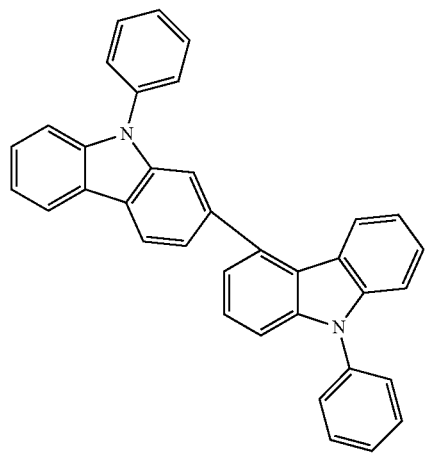
[C21]
1-173
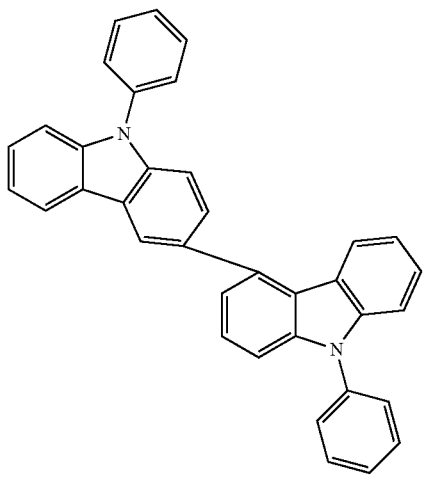
1-174
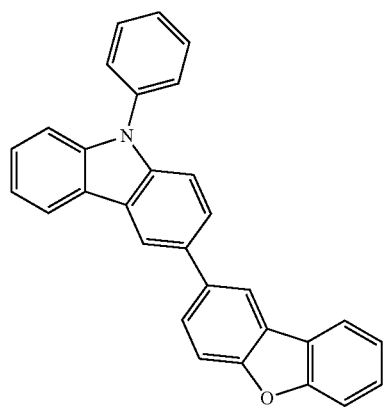
1-175
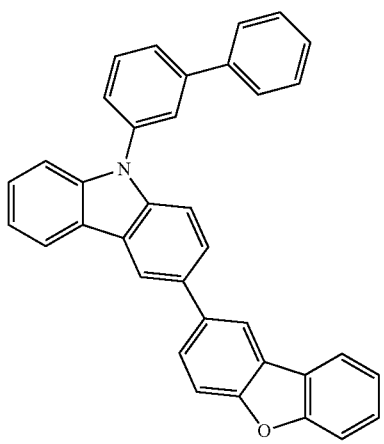
1-176
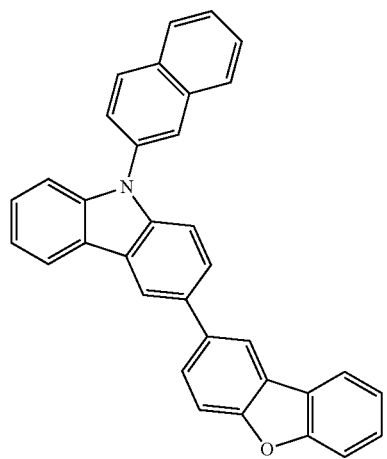
1-177
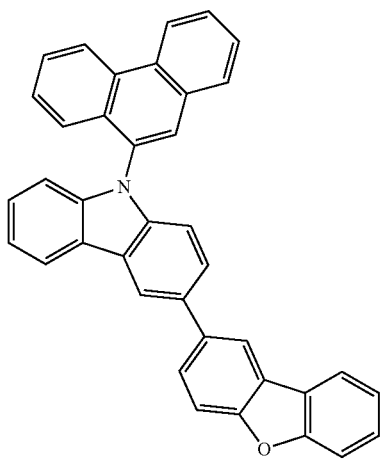

-continued
1-179
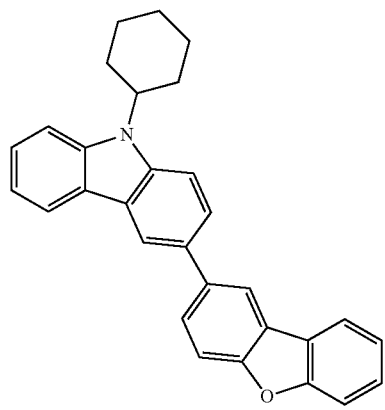
1-179
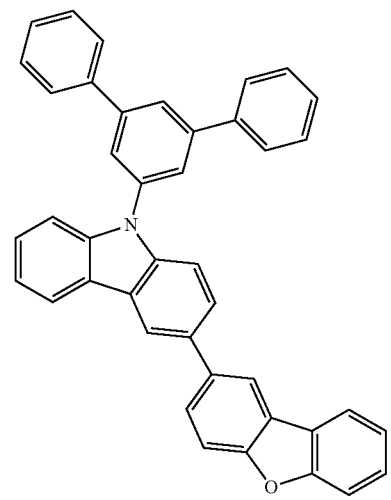
1-180
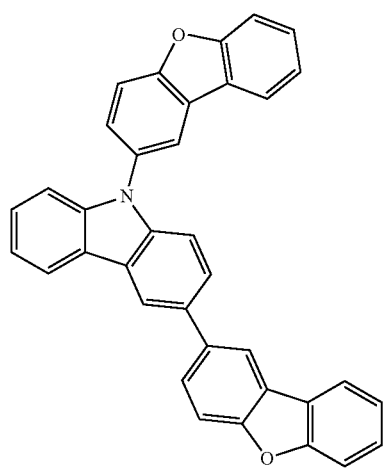
1-181
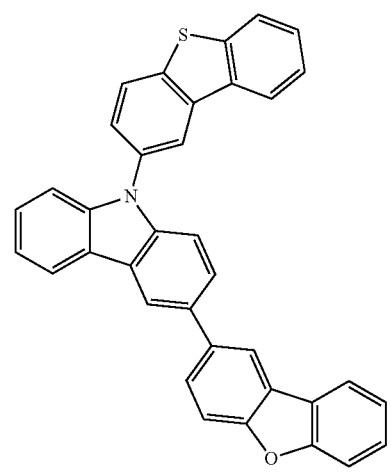
1-182
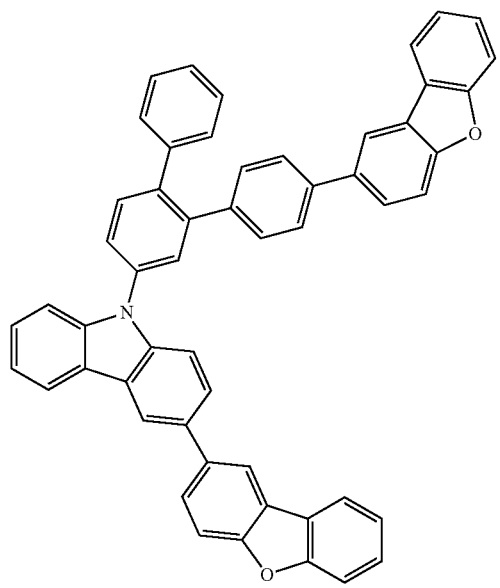
1-183
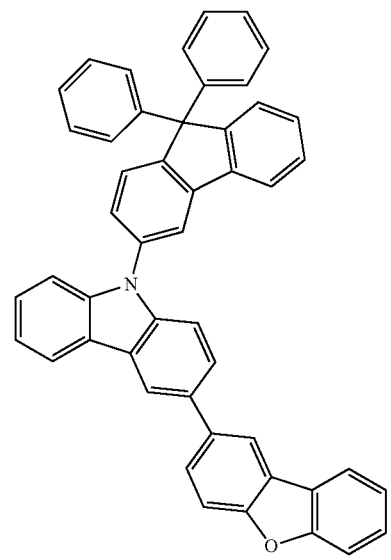

-continued
1-184
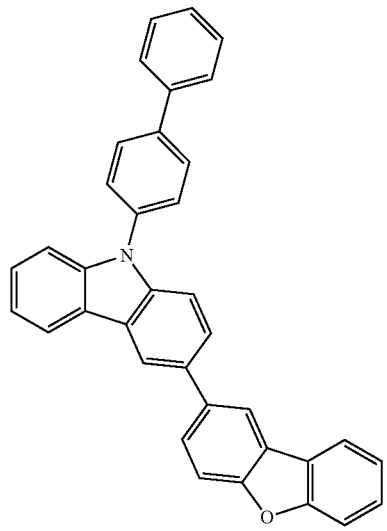
1-185
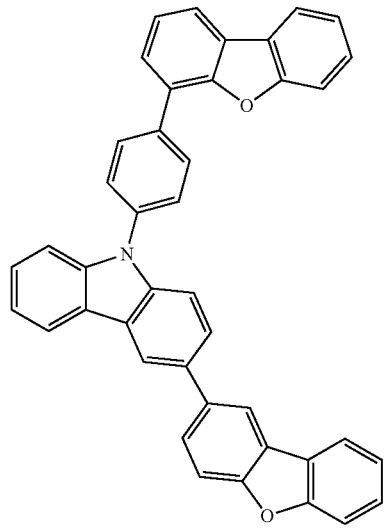
1-186
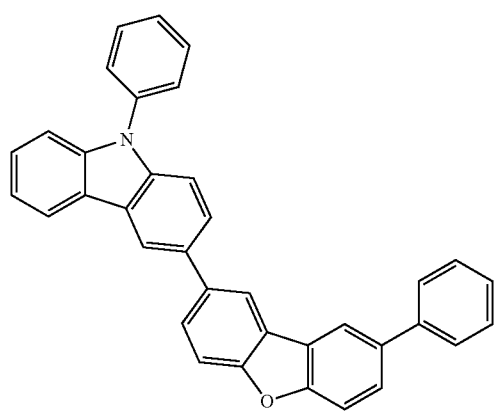
1-187
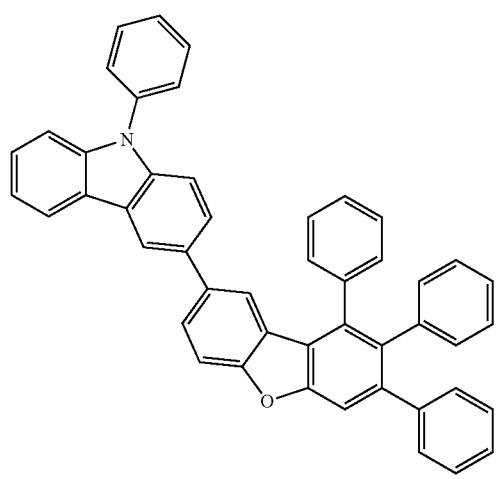
1-188
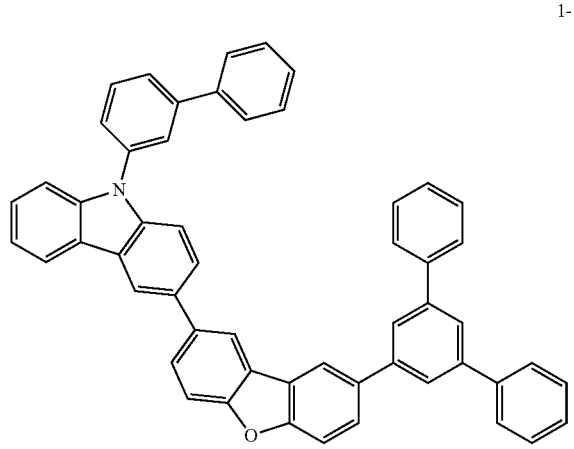
1-189
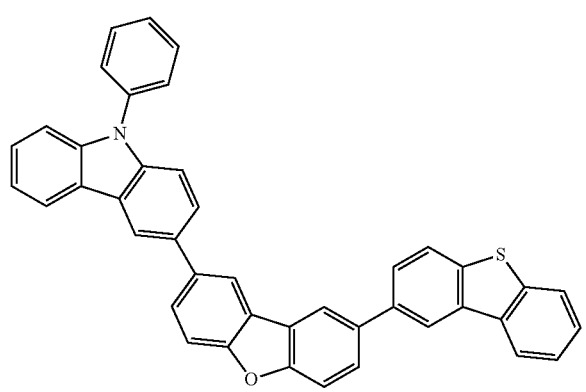

[C22]
1-190
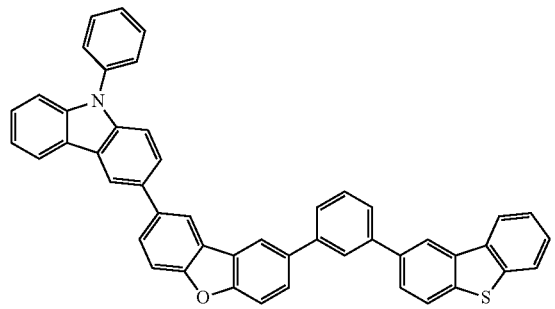
1-191
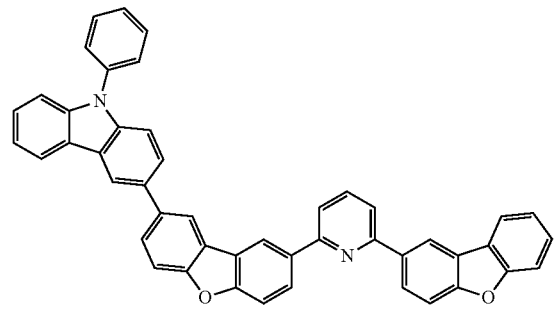
1-192
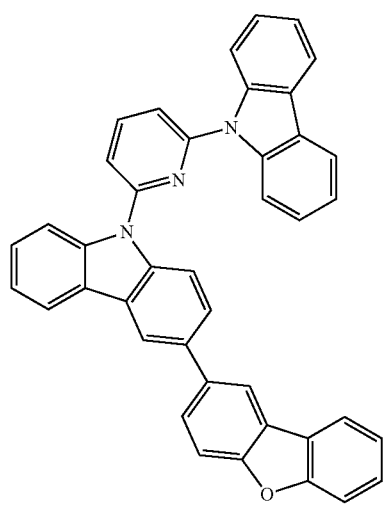
1-193
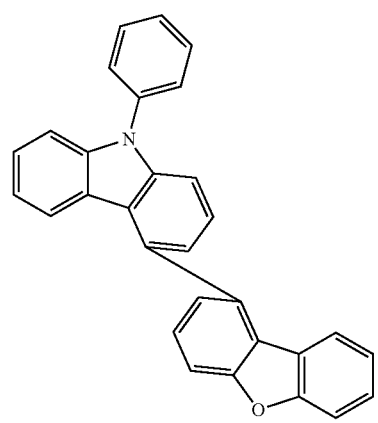
1-194
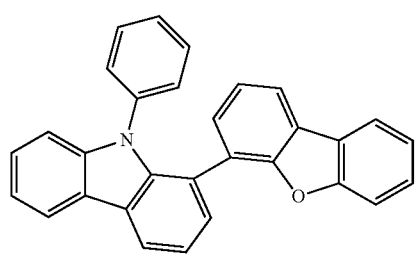
1-195
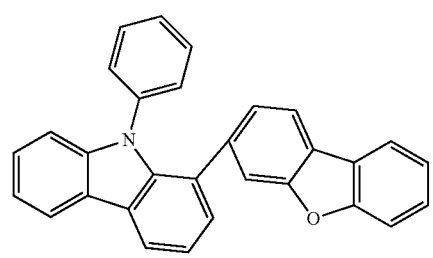
1-196
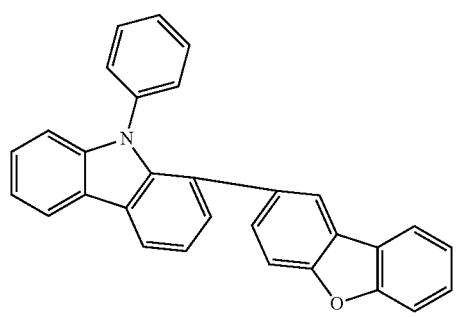
1-197
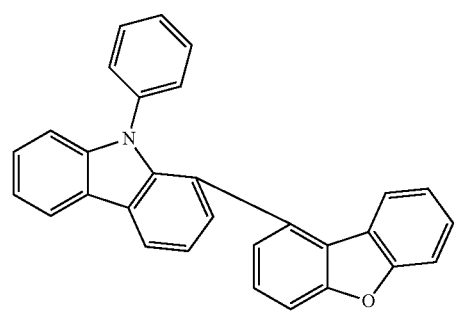

-continued
1-198
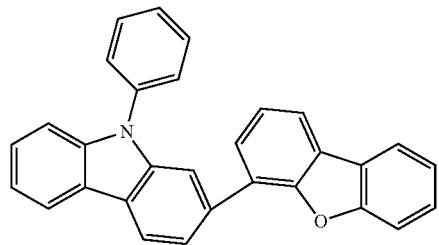
1-199
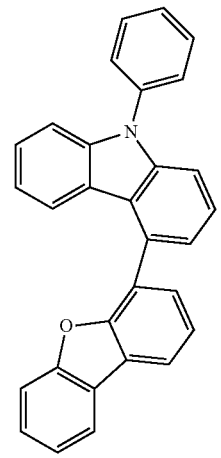
1-200
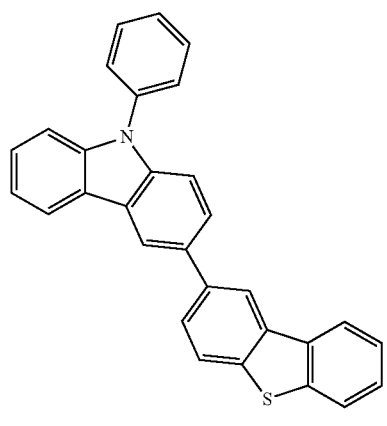
1-201
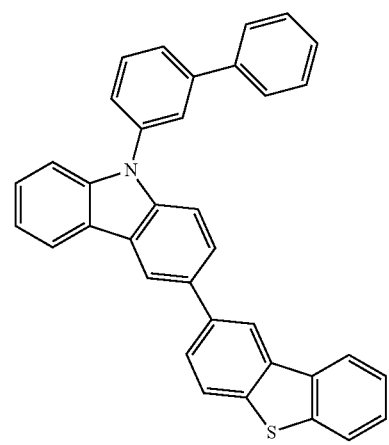
1-202
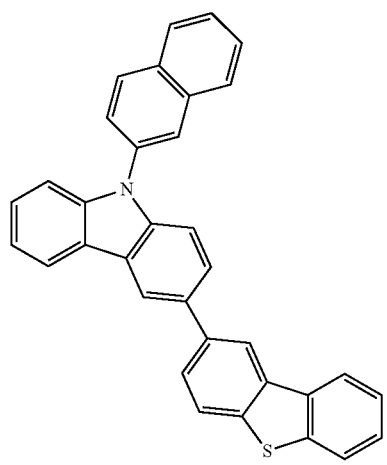
1-203
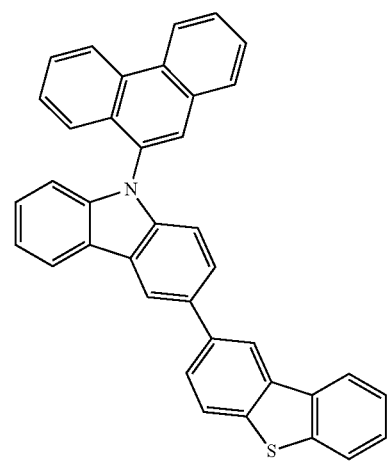

-continued
1-204
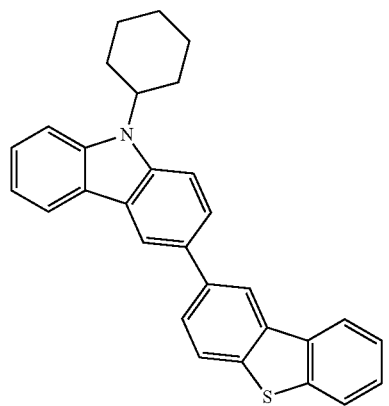
1-205
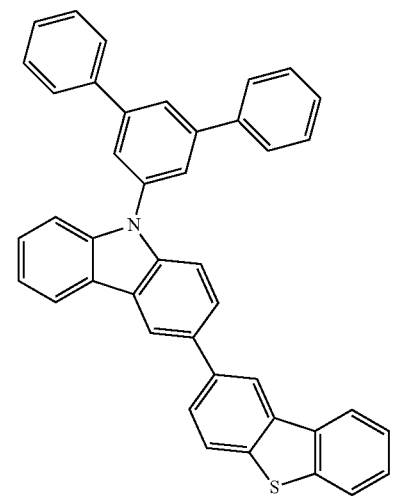
1-206
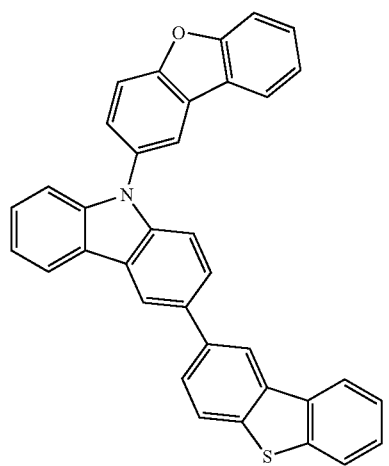
1-207
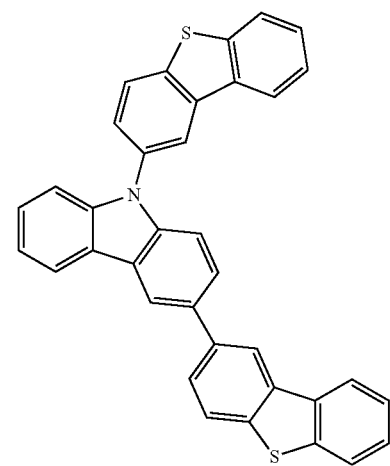
1-208
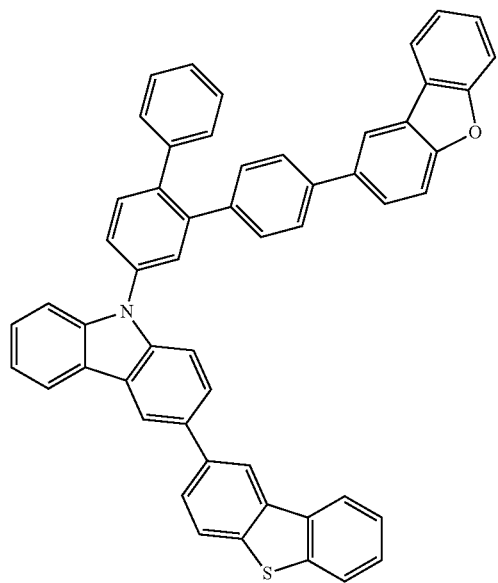

[C23]
1-209
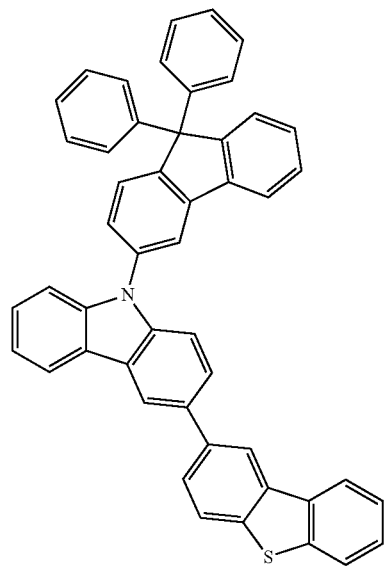
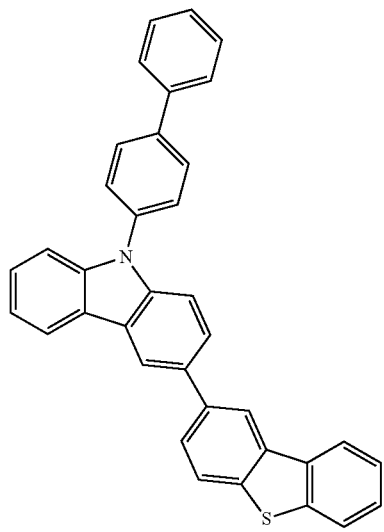
1-210
1-211
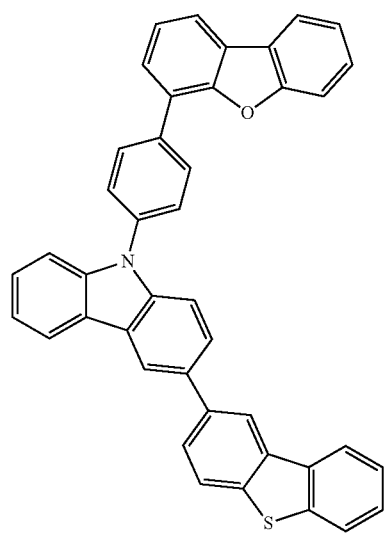
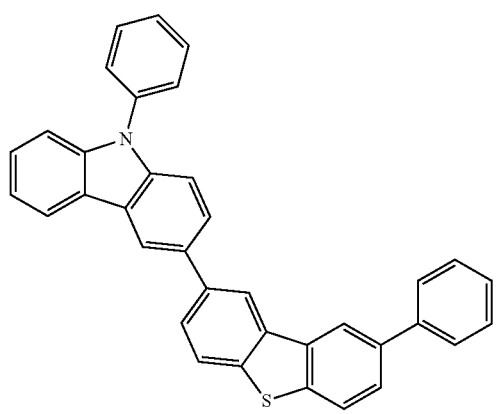
1-212
1-213
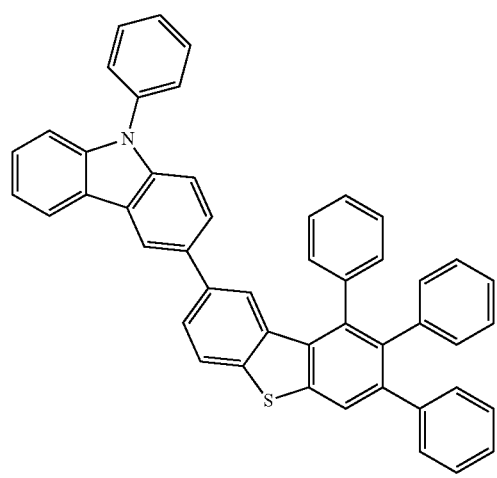
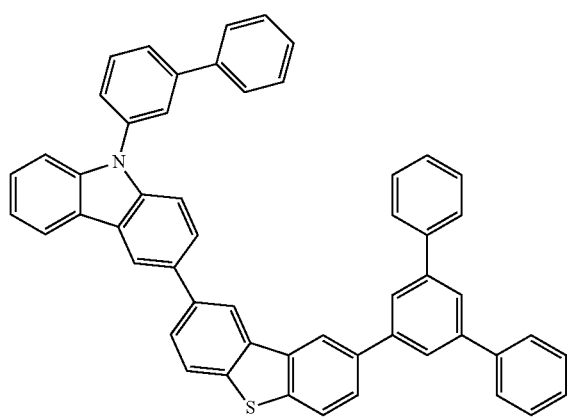
1-214

-continued
1-215
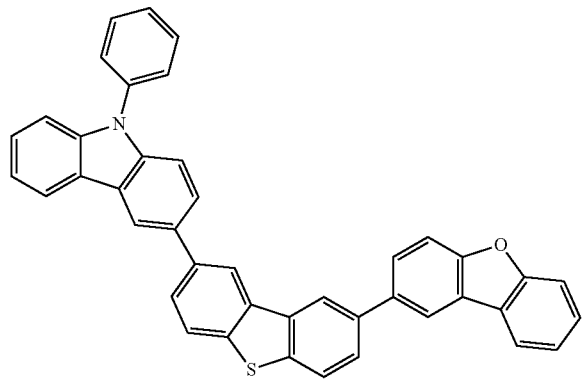
1-216
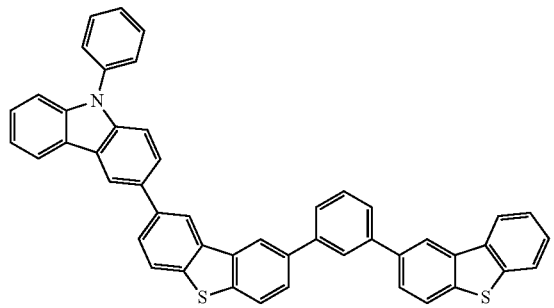
1-217
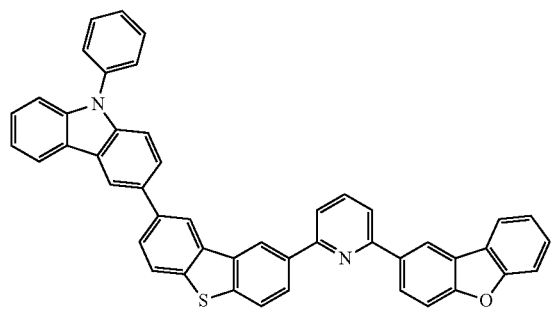
1-218
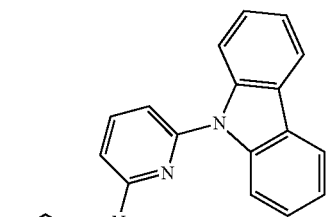
1-219
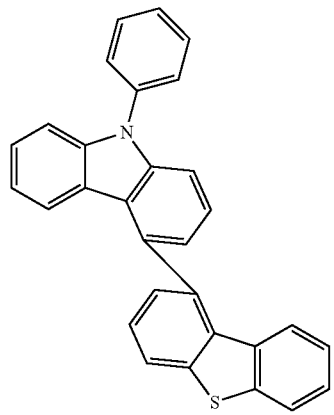
1-220
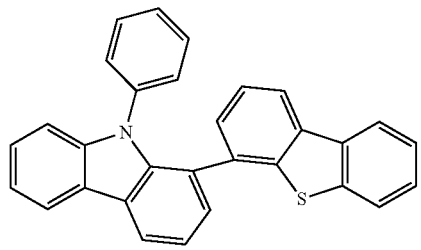
1-221
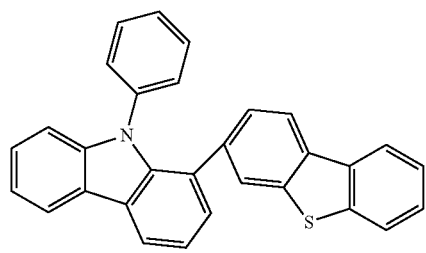
1-222
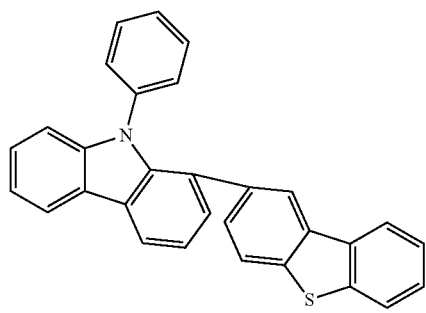

-continued
[C24]
1-223
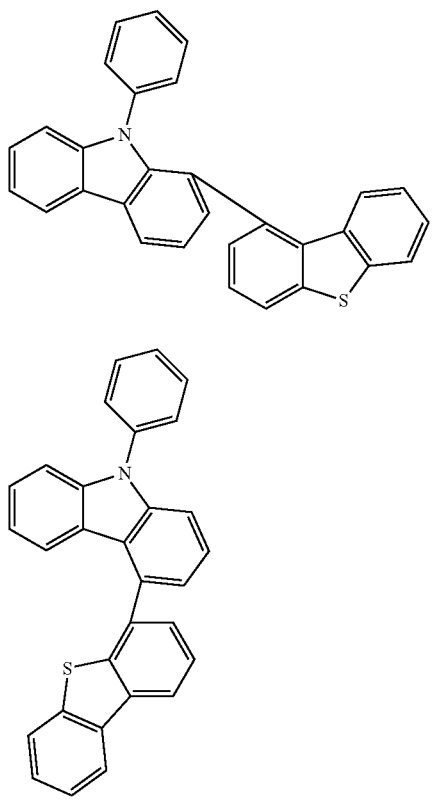
1-224
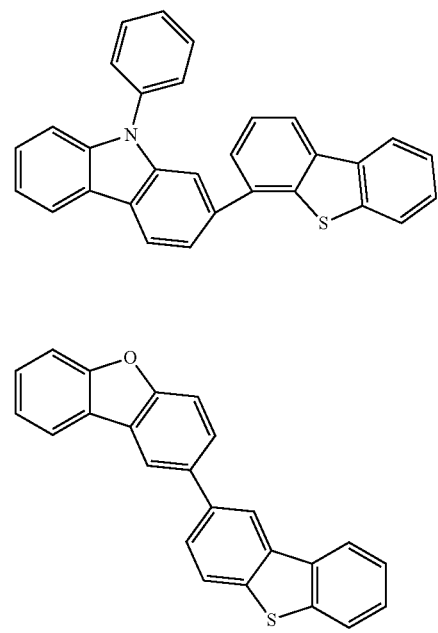
1-225
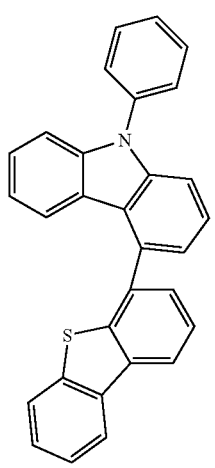
1-226
1-227
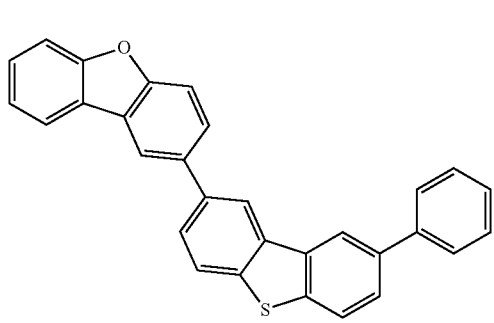
1-228
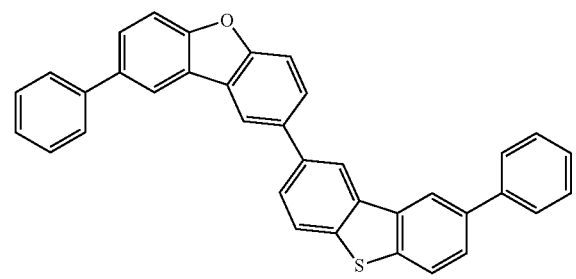
1-229
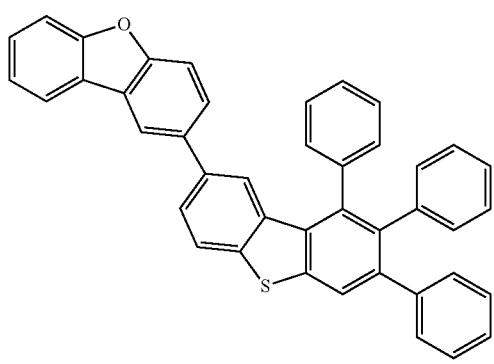
1-230
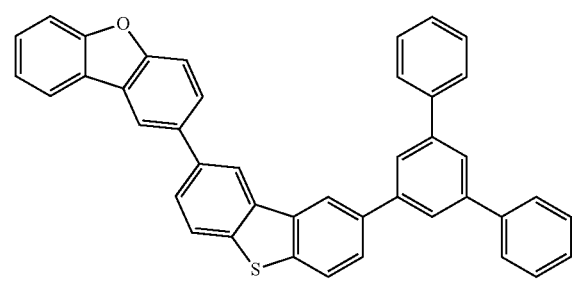

-continued
1-231
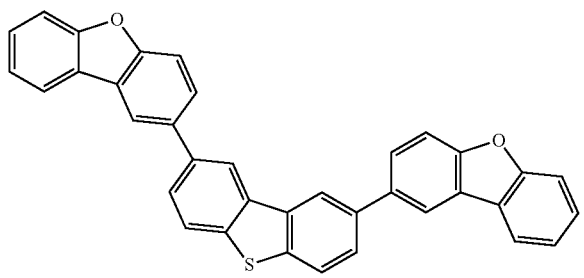
1-232
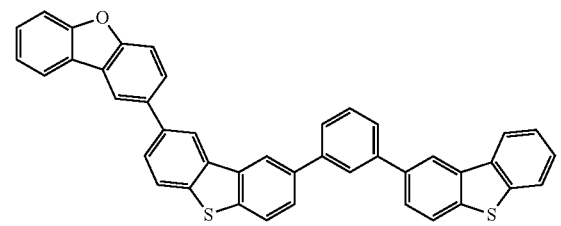
1-233
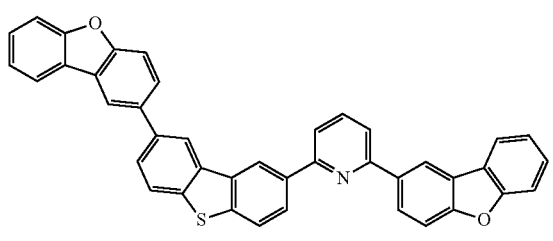
1-234
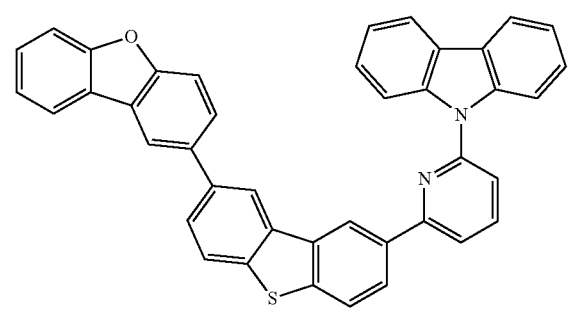
1-235
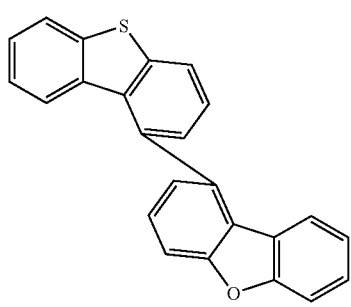
1-236
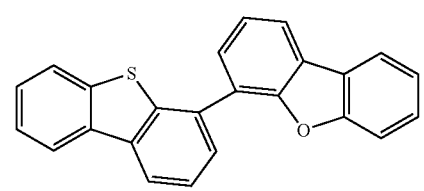
1-237
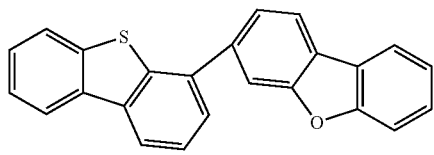
1-238
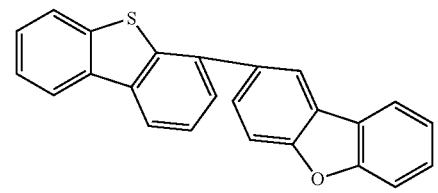
1-239
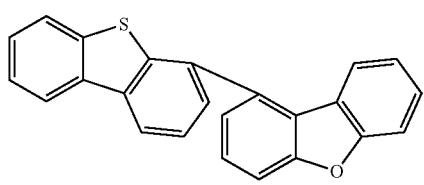
1-240
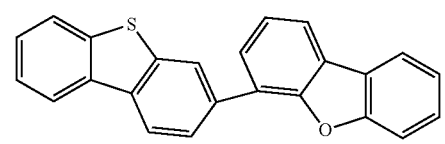

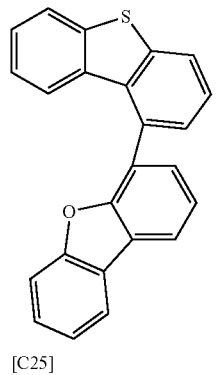
[C25]
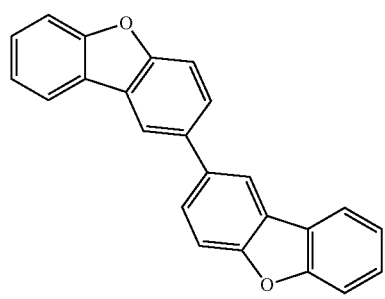
1-242
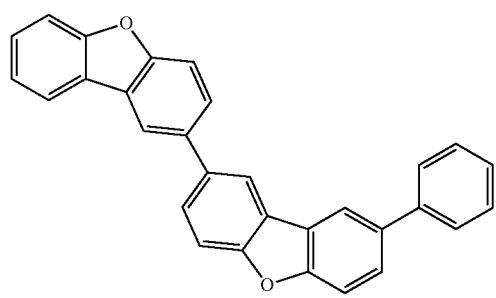
1-243
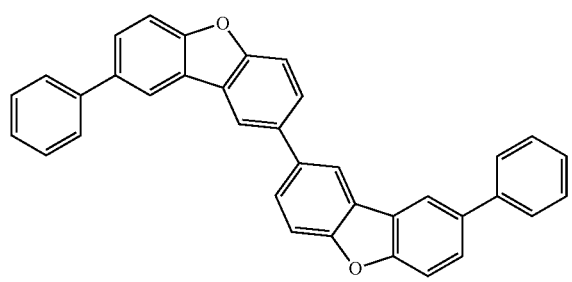
1-244
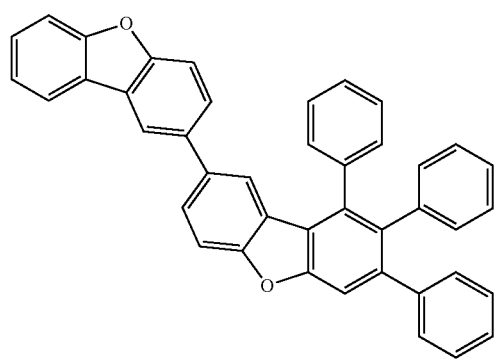
1-245
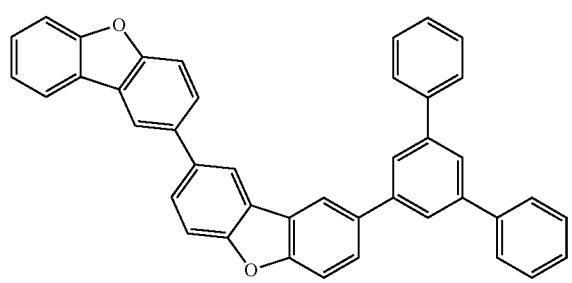
1-246
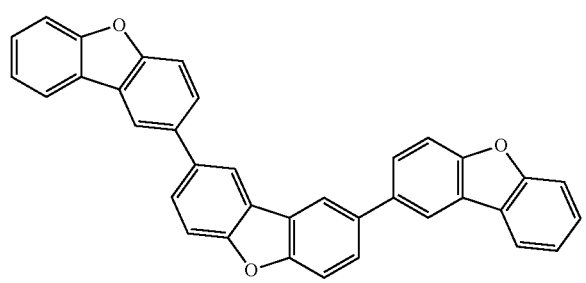
1-247

1-248
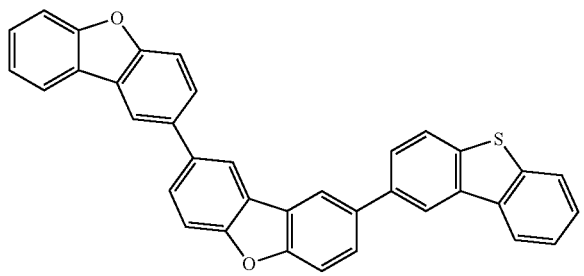
1-249
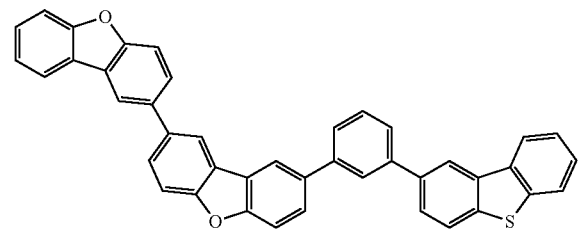
1-250
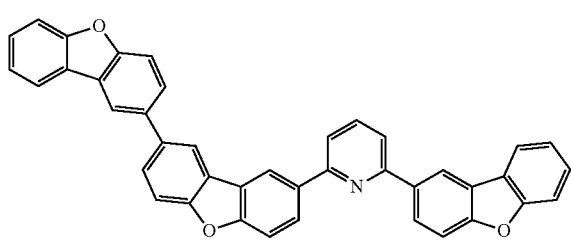
1-251
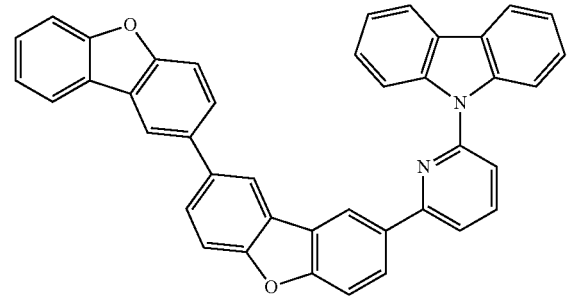
1-252
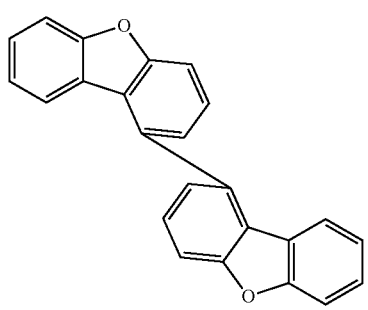
1-253
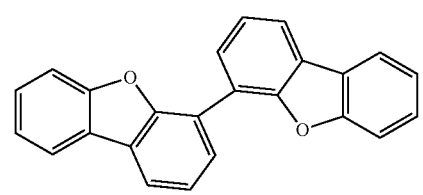
1-254
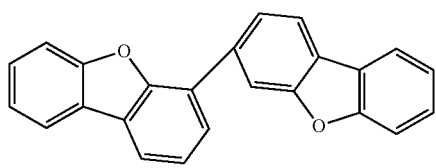
1-255
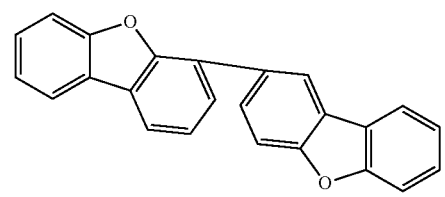
1-256
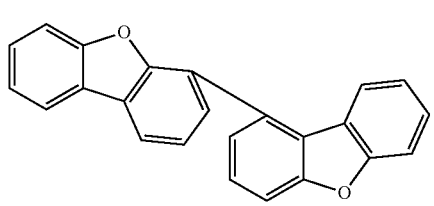
1-257
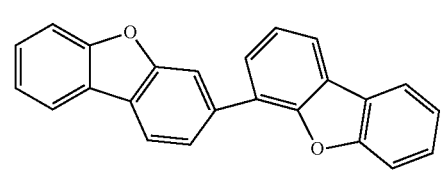

-continued
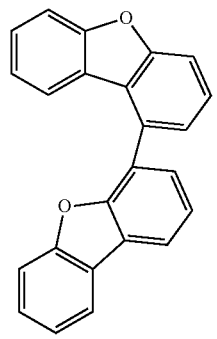
[C26]
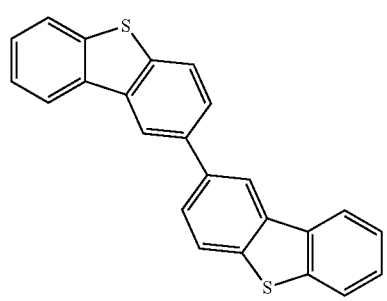
1-259
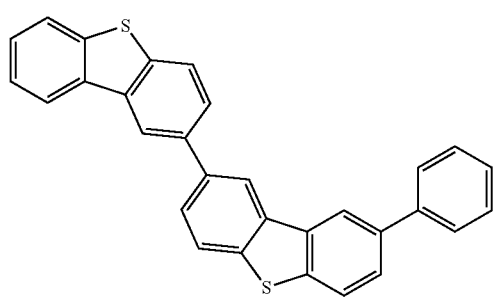
1-260
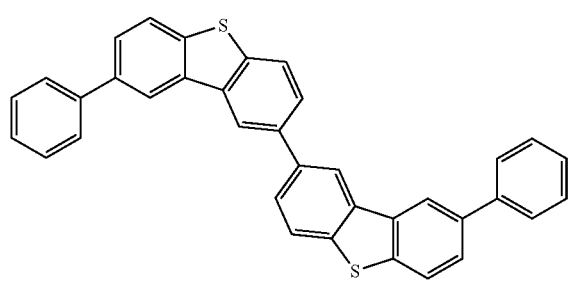
1-261
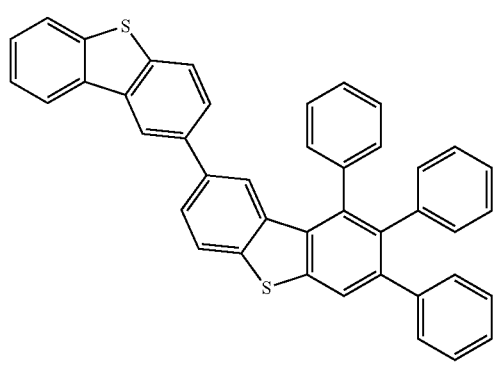
1-262
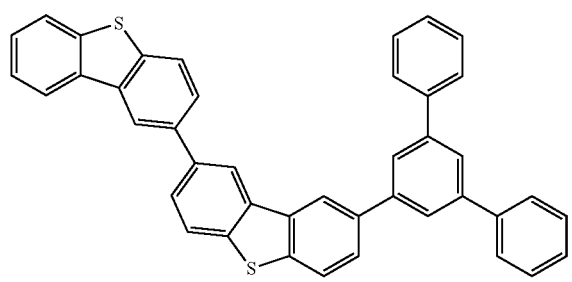
1-263
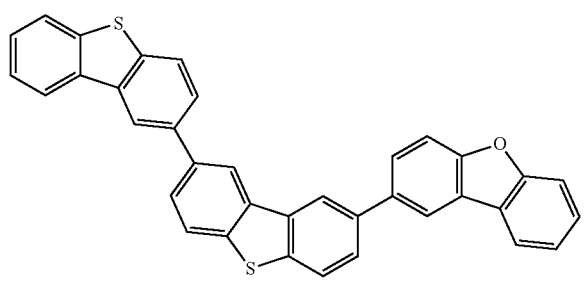
1-264
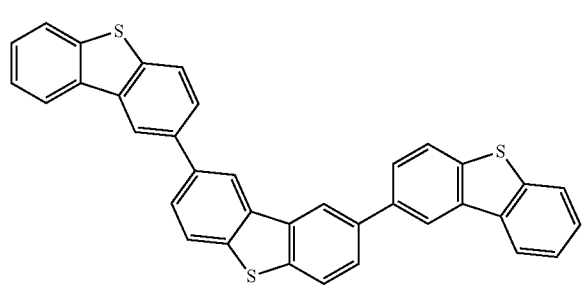
1-265
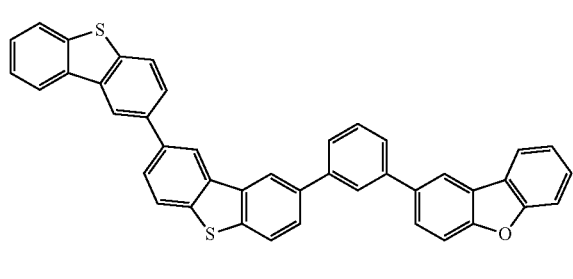
1-266

-continued
1-267
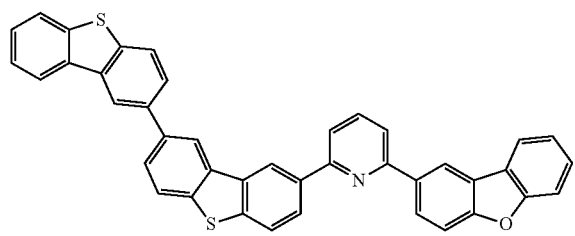
1-268
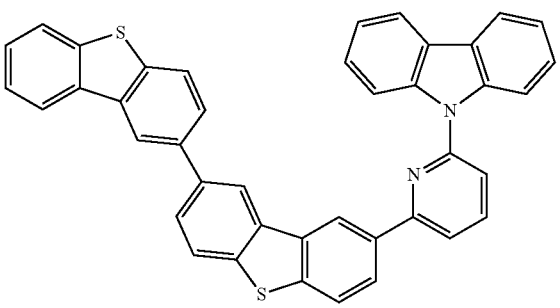
1-269
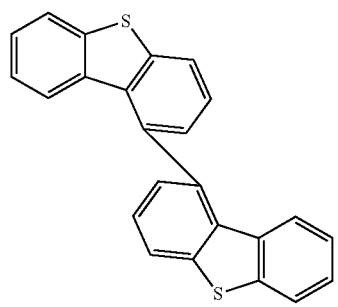
1-270
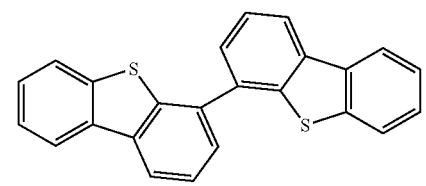
1-271
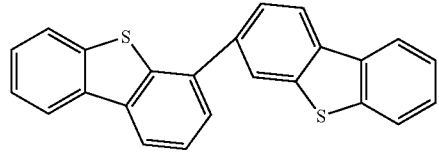
1-272
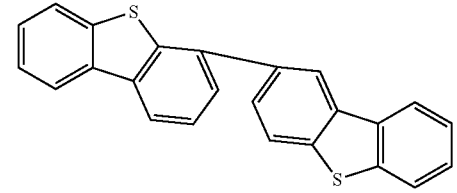
1-273
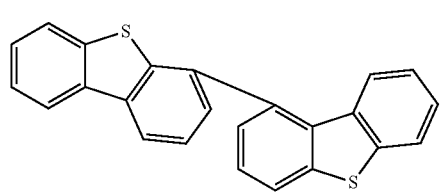
1-274
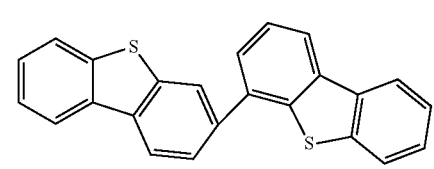
1-275
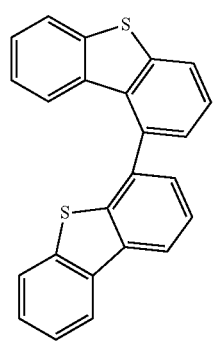

[C27]
1-276
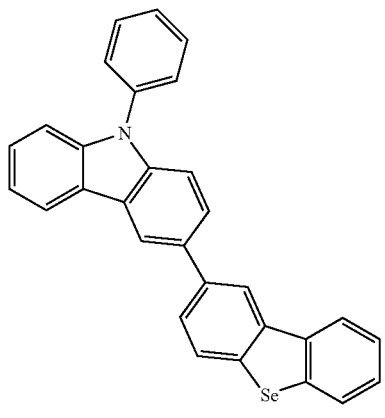
1-277
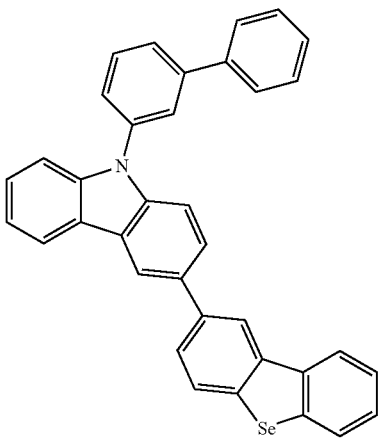
1-278
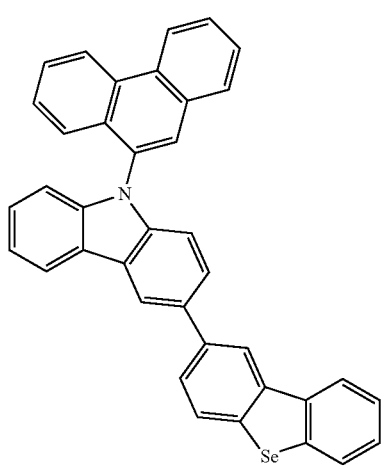
1-279
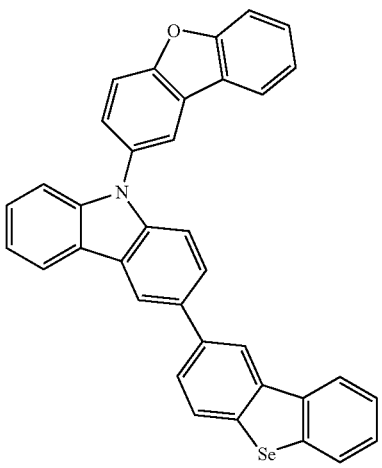
1-280
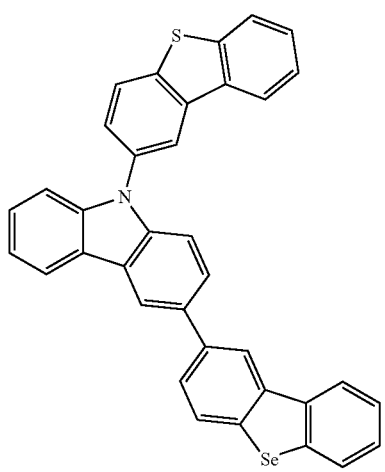
1-281
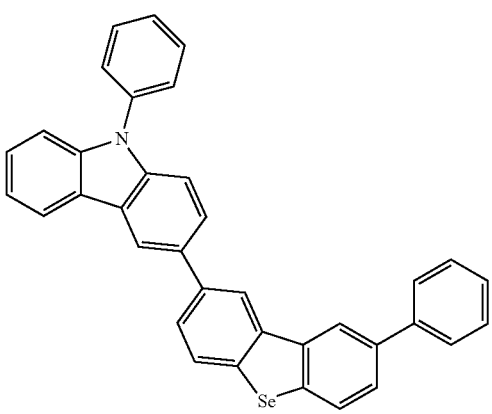

-continued
1-282
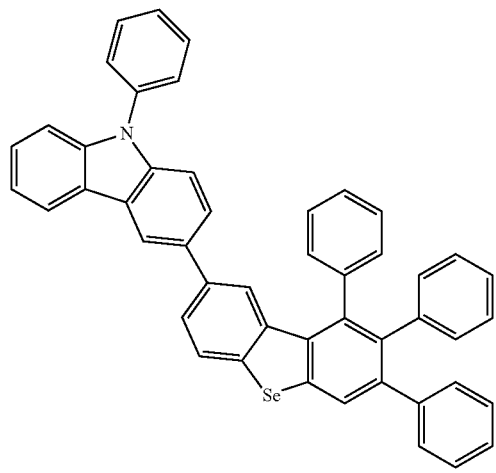
1-283
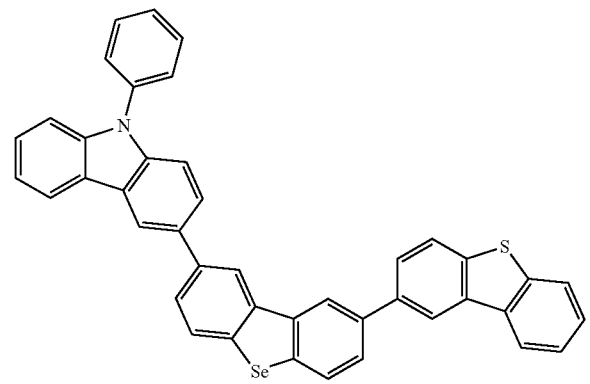
1-284
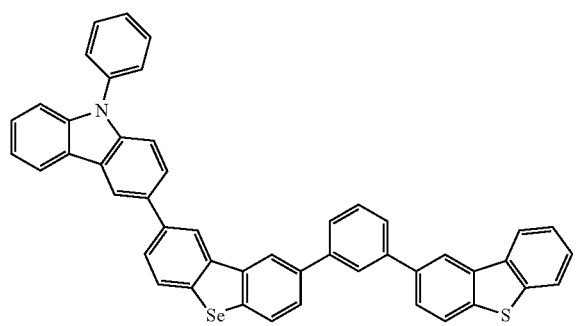
1-285
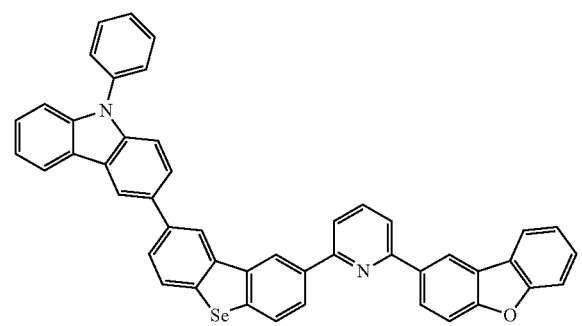
1-286
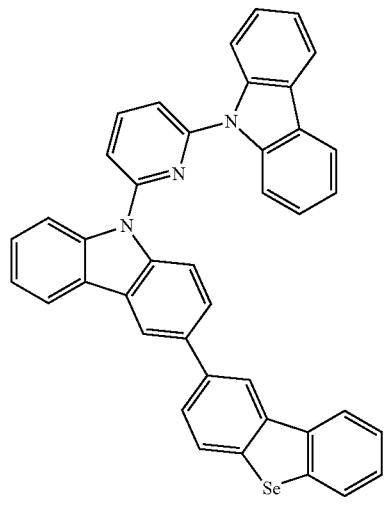
1-287
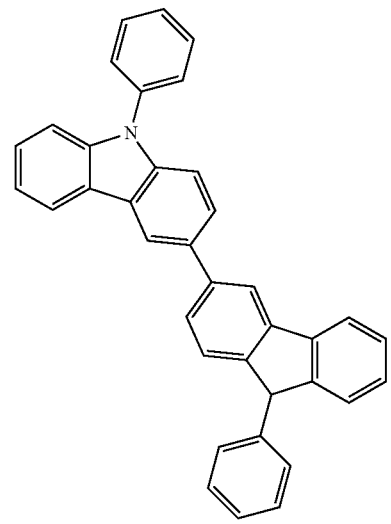

-continued
1-288
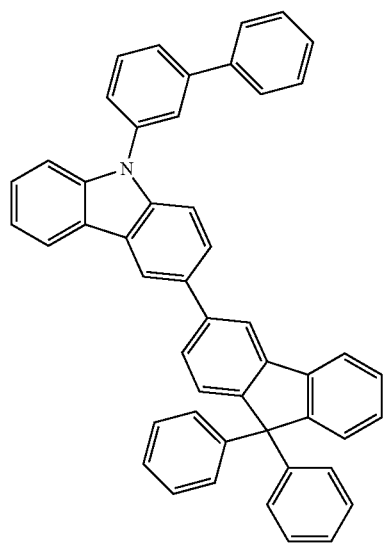
1-289
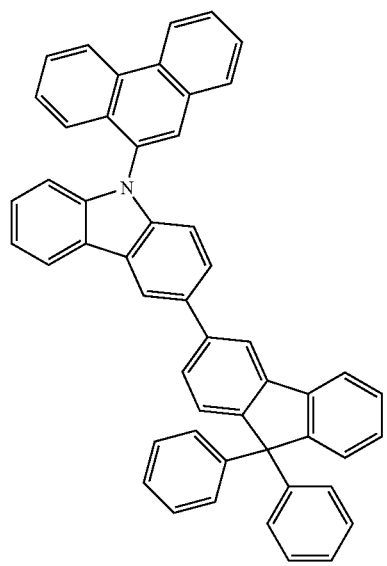
1-290
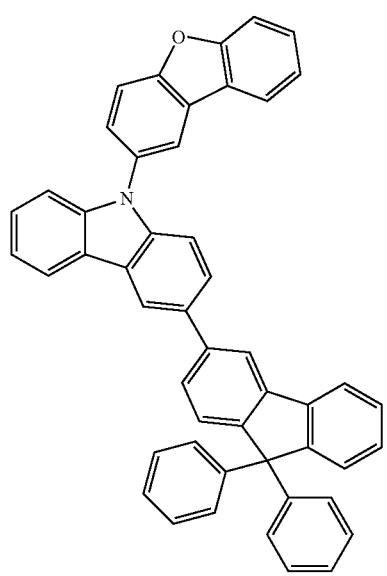
1-291
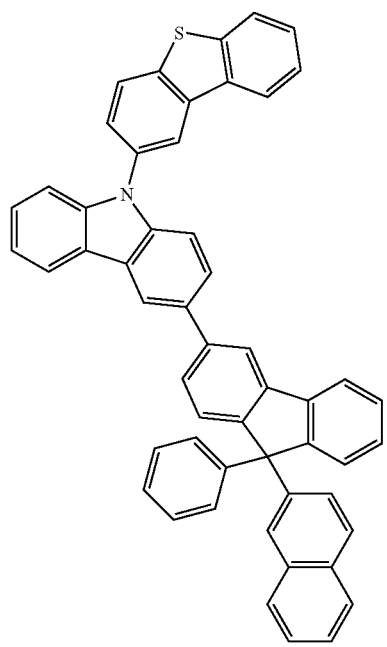

-continued
[C28]
1-292
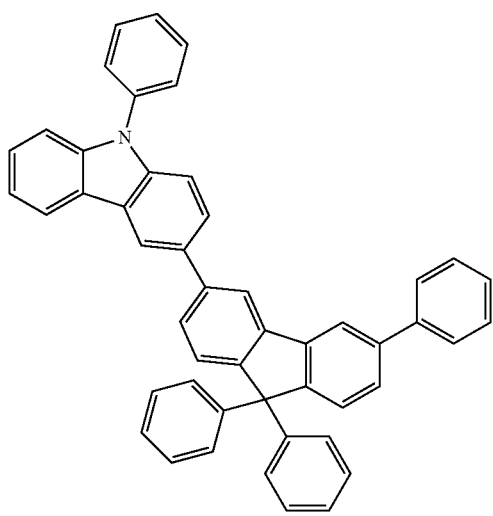
1-293
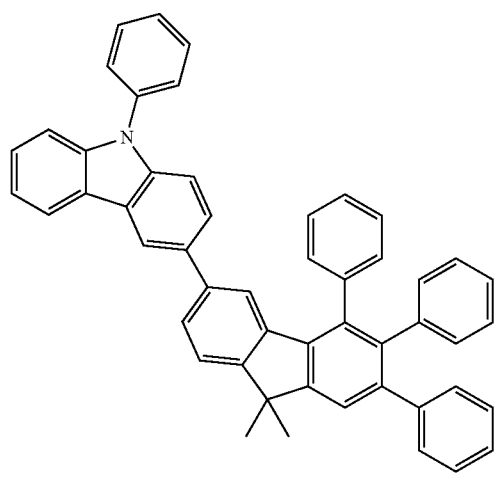
1-294
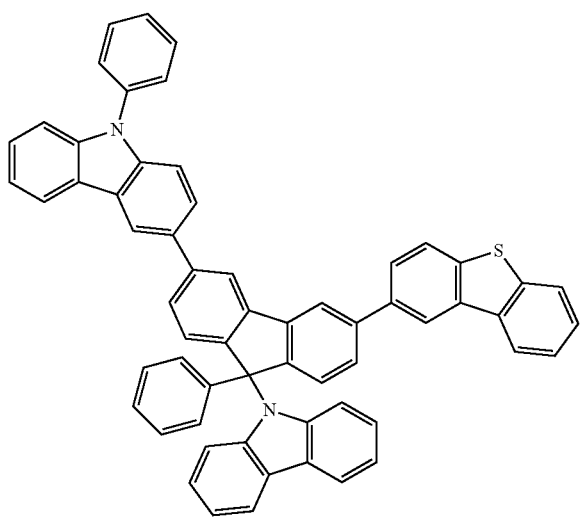
1-295
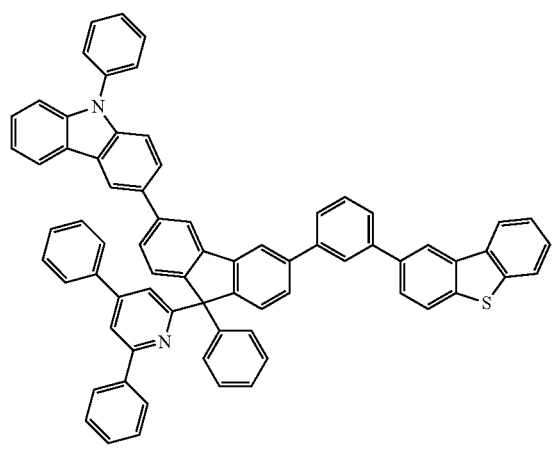
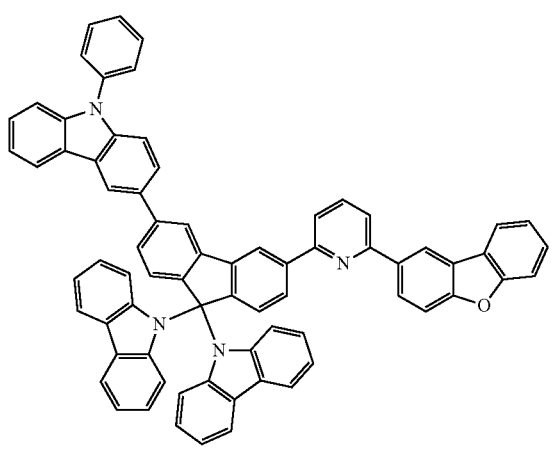
1-297
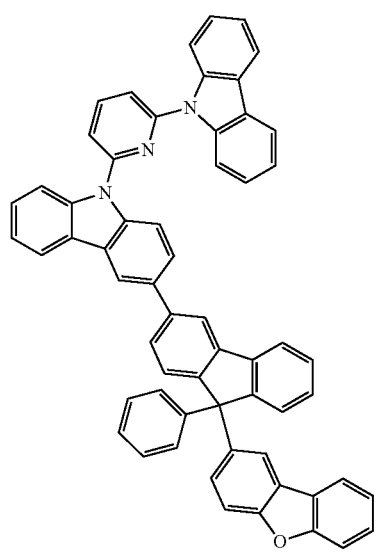

-continued
1-298
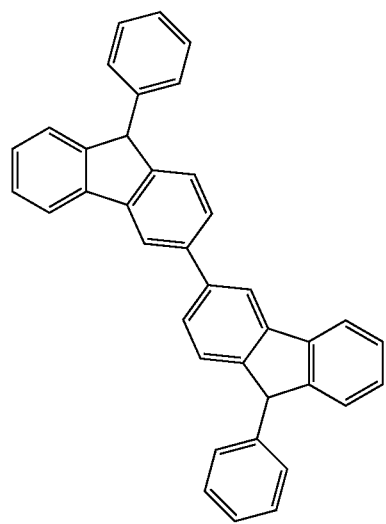
1-299
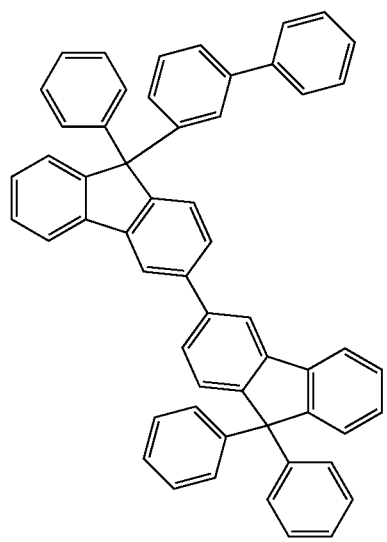
1-300
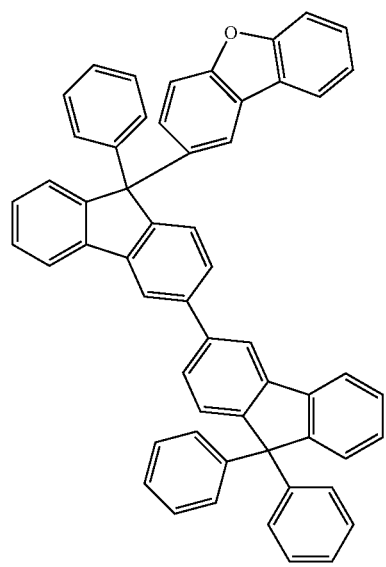
1-301
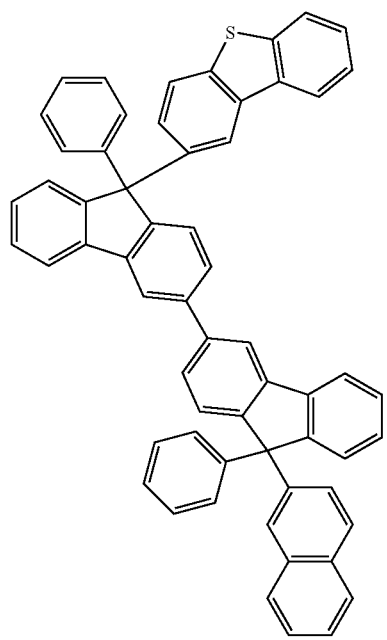

1-302
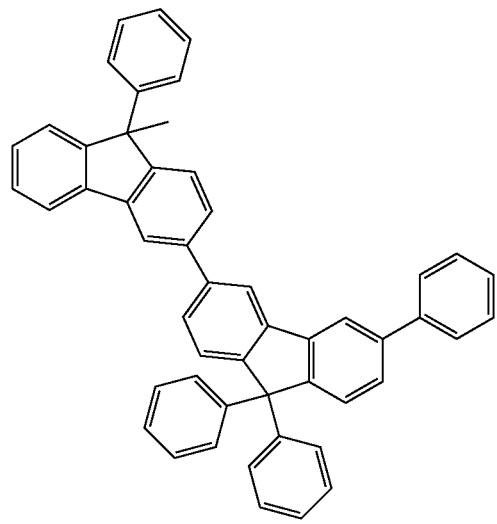
1-303
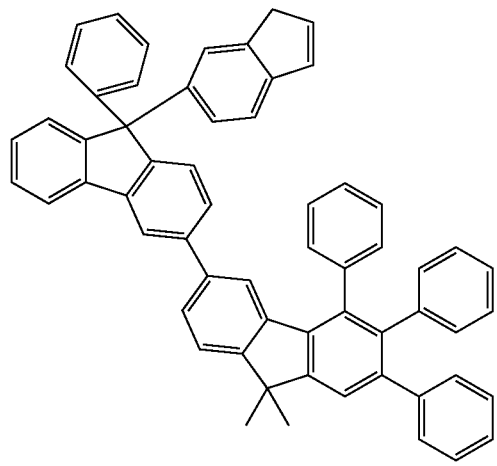
1-304
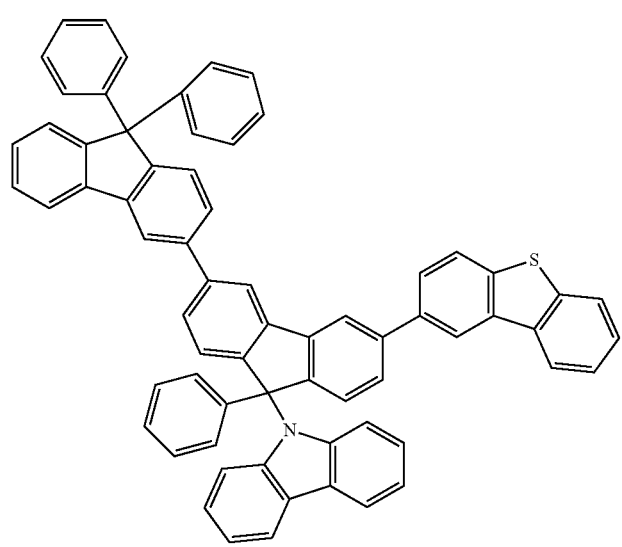

[C29]
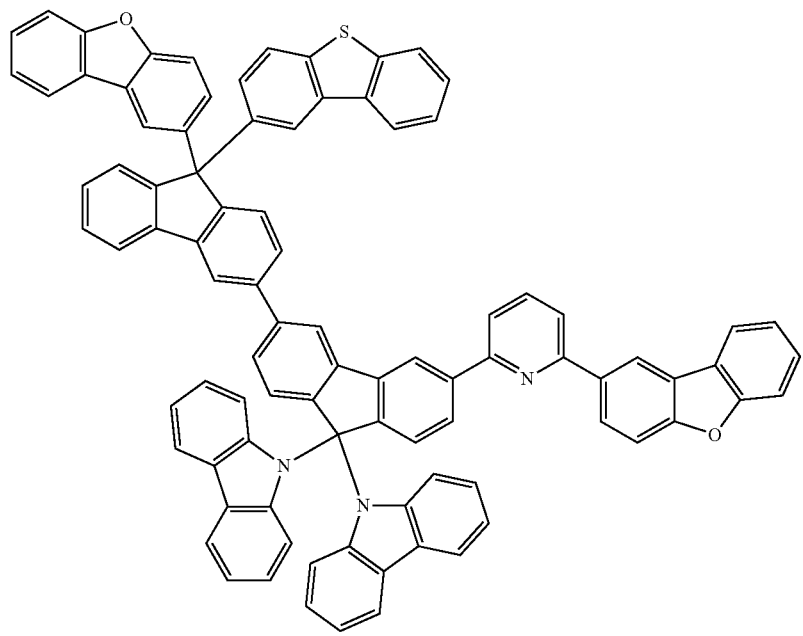
1-305
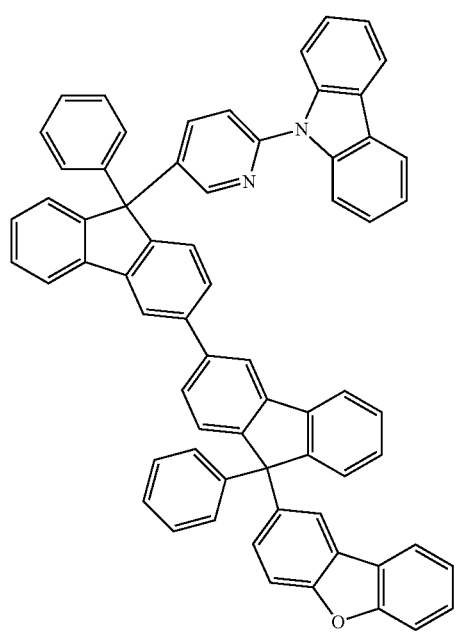
1-306
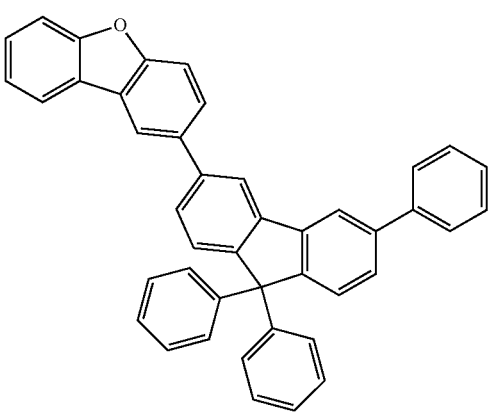
1-307

1-308
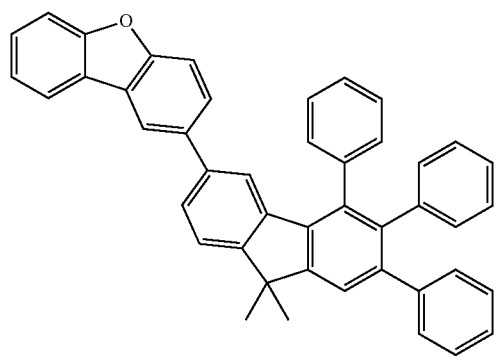
1-309
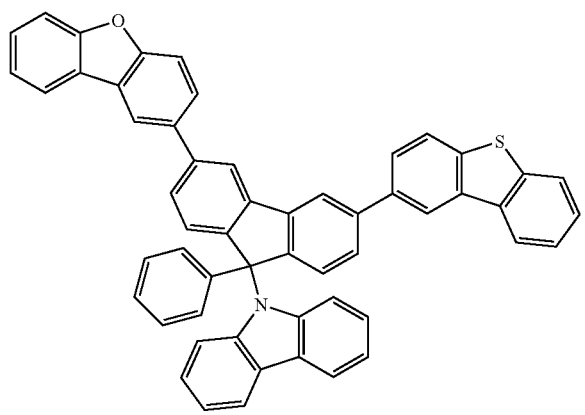
1-310
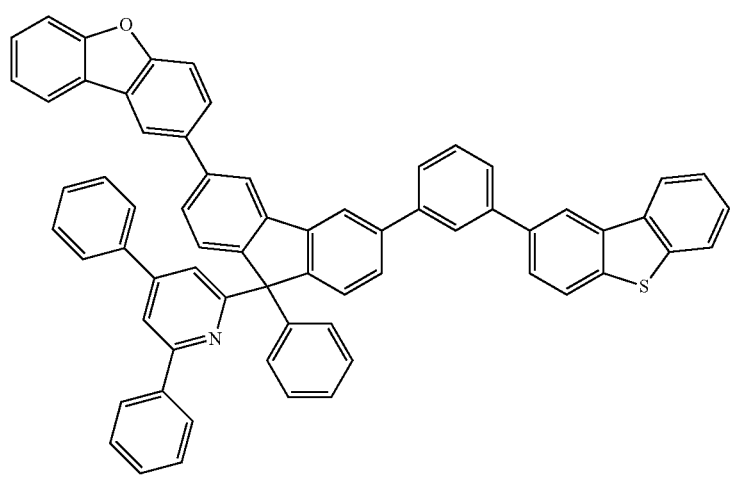
1-311
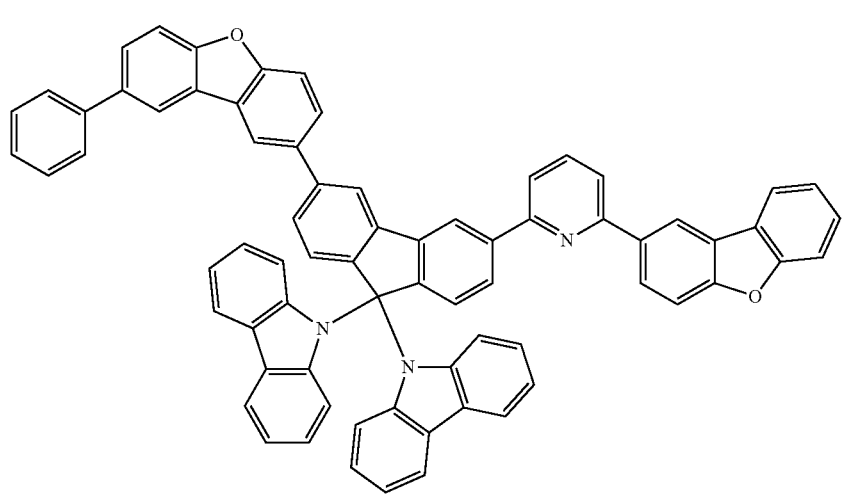

1-312
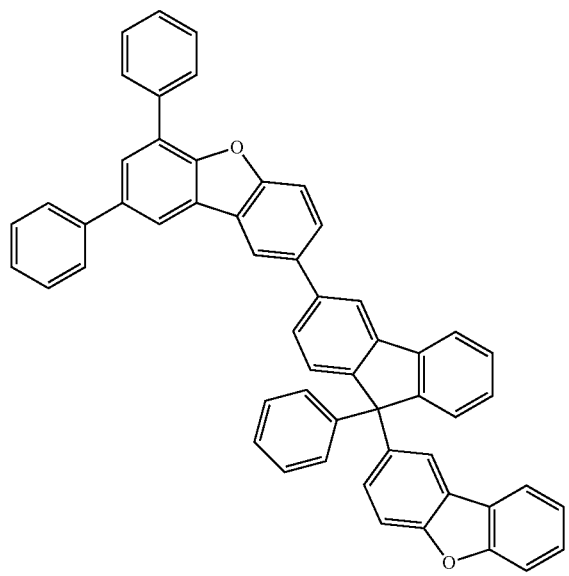
[C30]
1-313
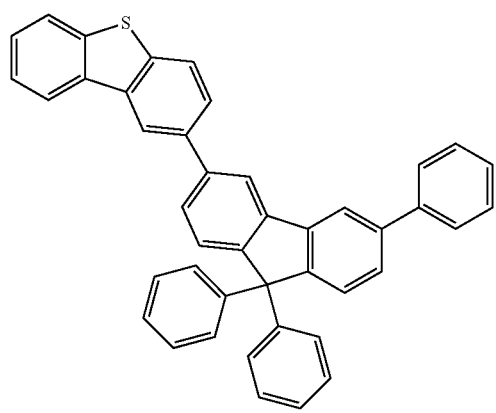
1-314
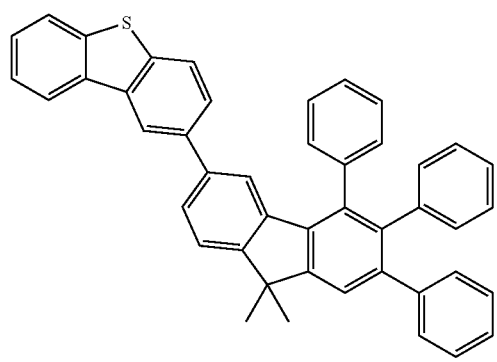
1-315
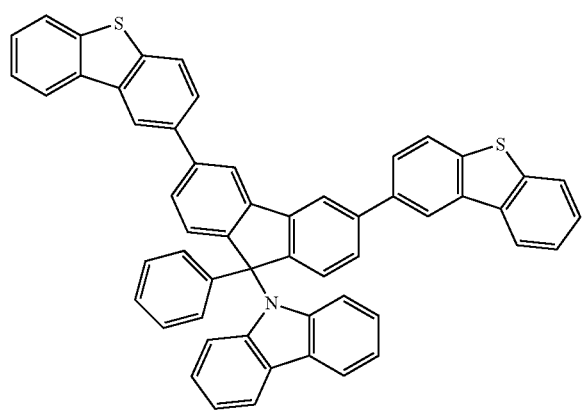
1-316
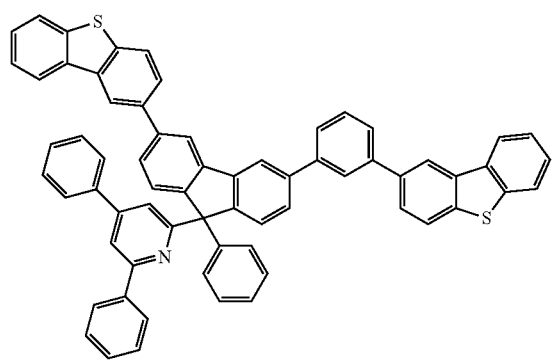

1-317
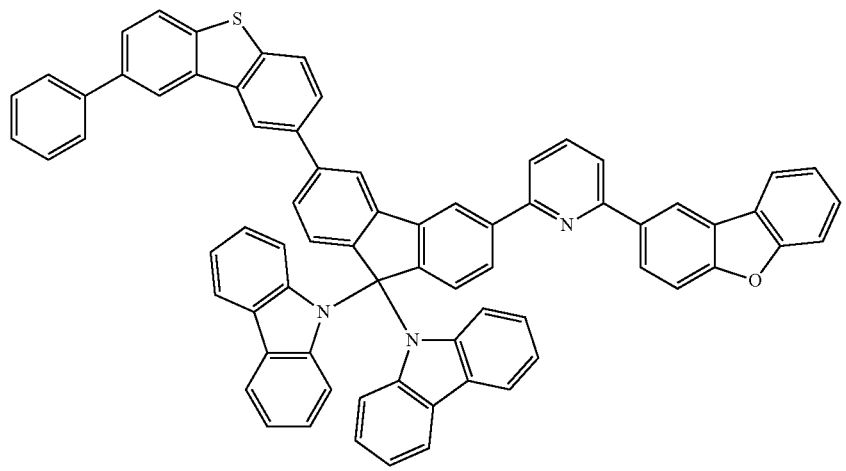
1-318
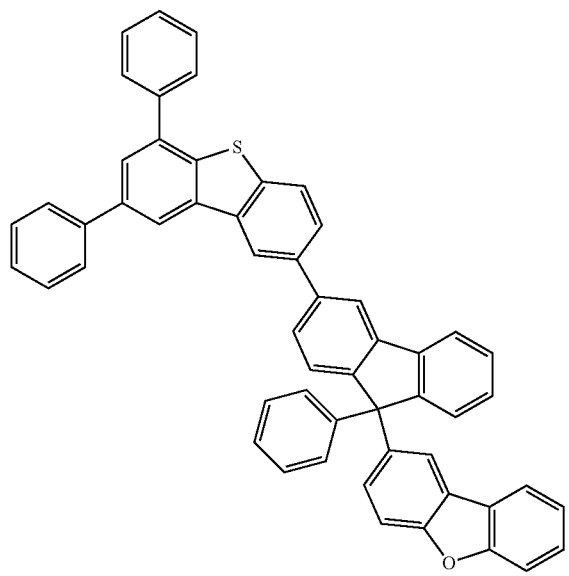
1-319
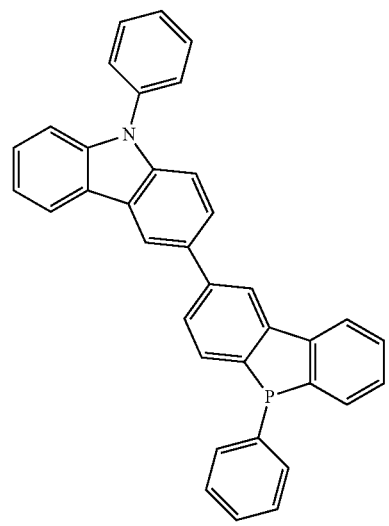
1-320
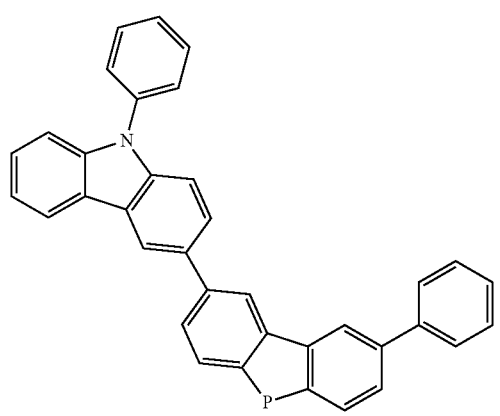
1-321
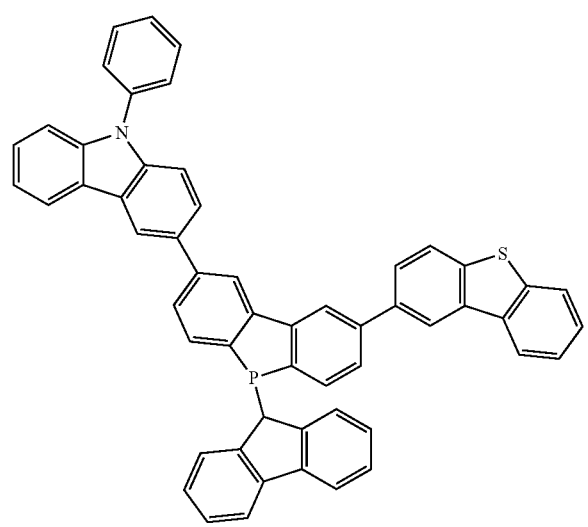

1-322
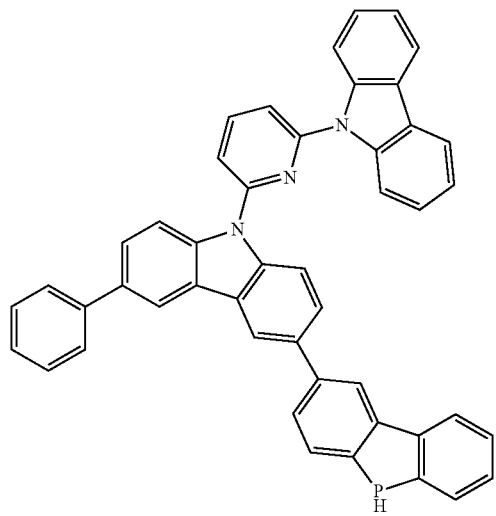
[C31]
1-323
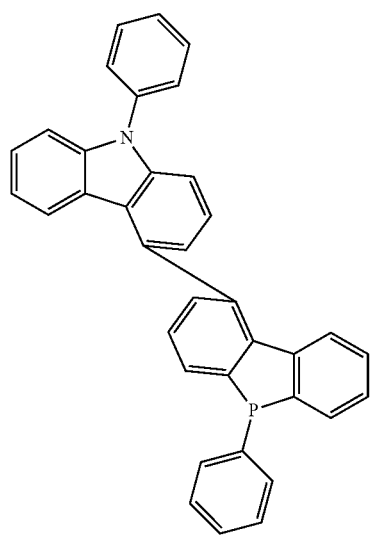
1-324
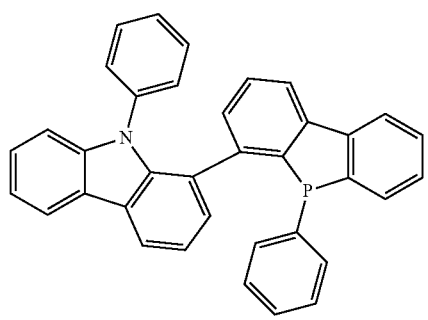
1-325
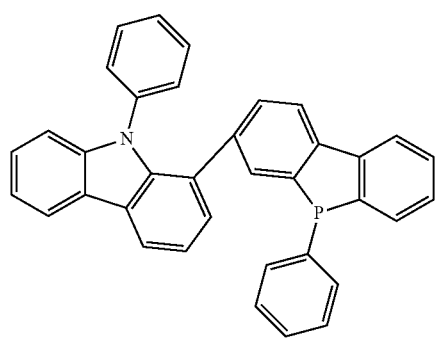
1-326
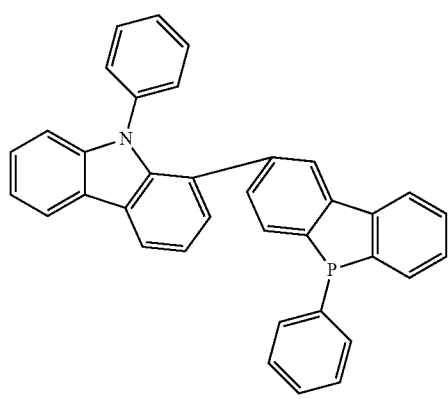

-continued
1-327
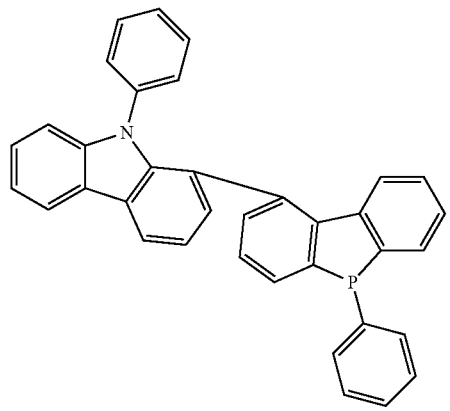
1-328
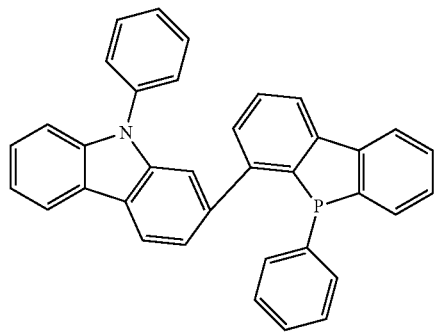
1-329
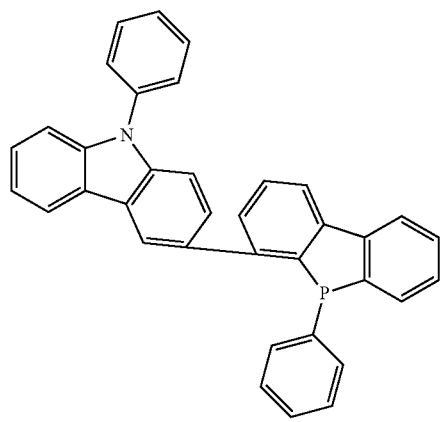
1-330
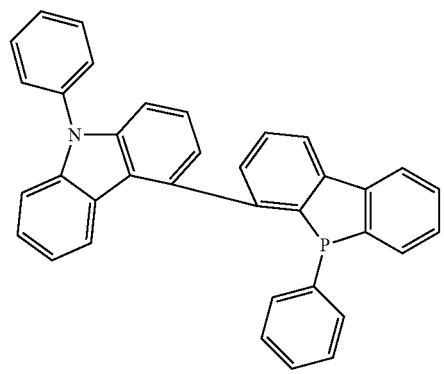
1-331
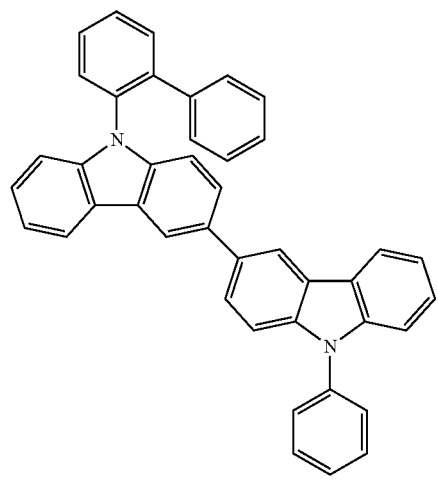
1-332
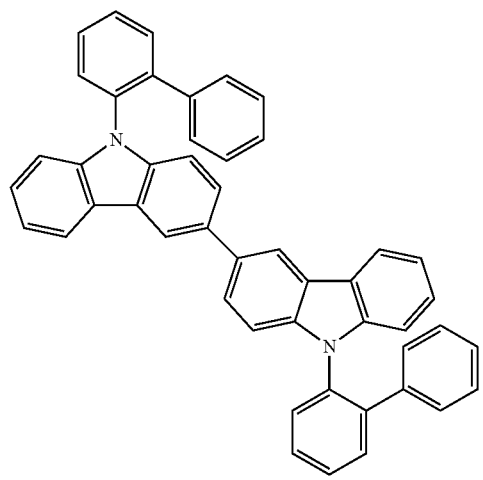

1-333
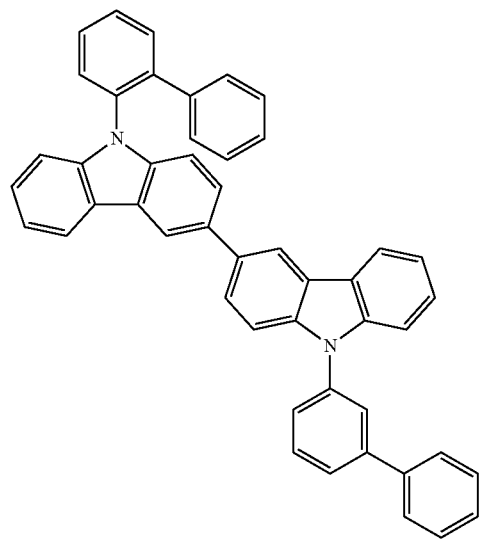
1-334
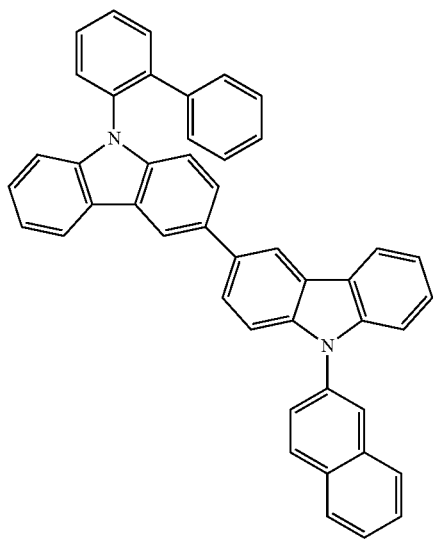
1-335
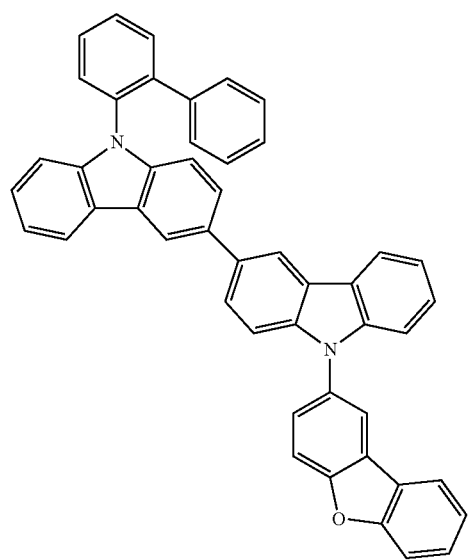
1-336

-continued
1-337
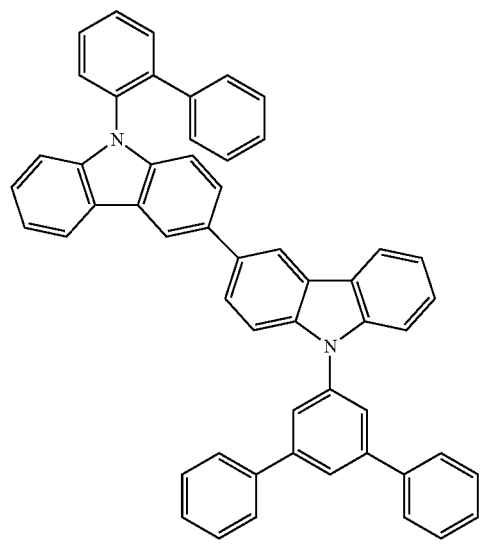
1-338
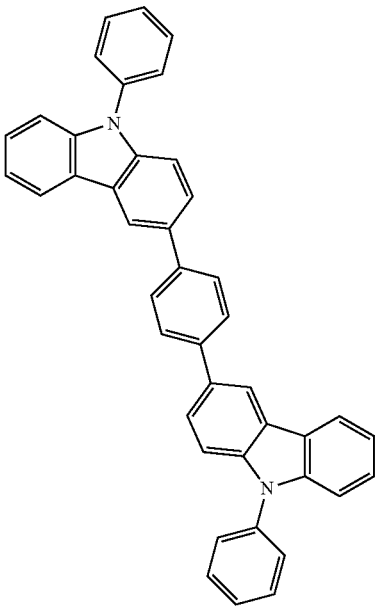
[C32]
1-339
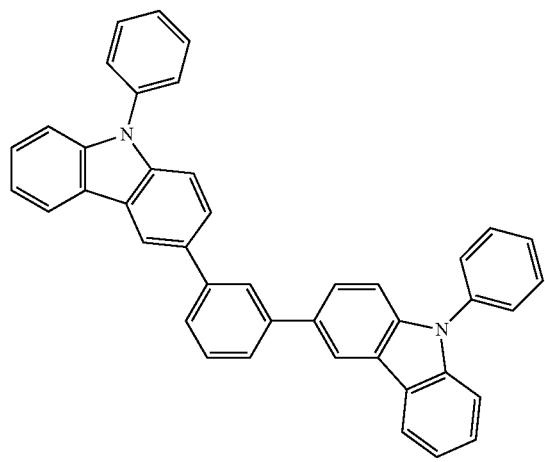
1-340
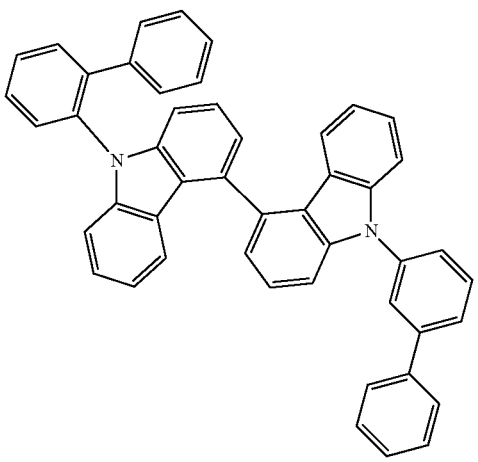
1-341
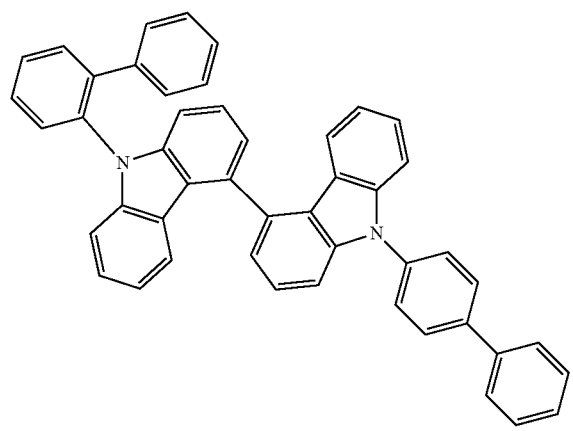
1-342
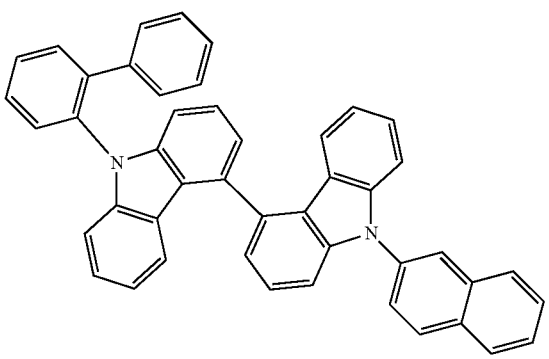

-continued
1-343
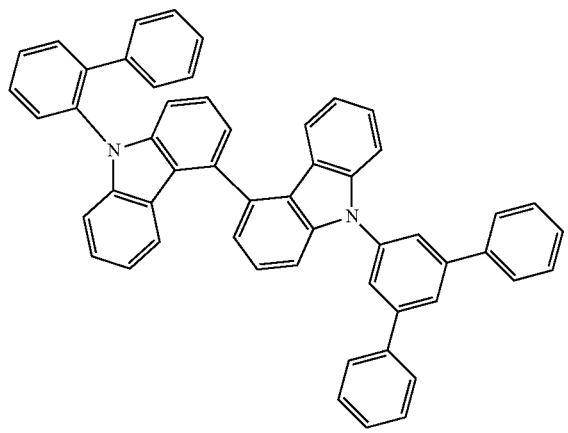
1-344
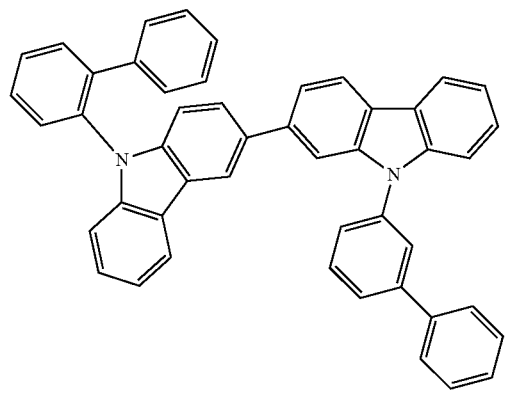
1-345
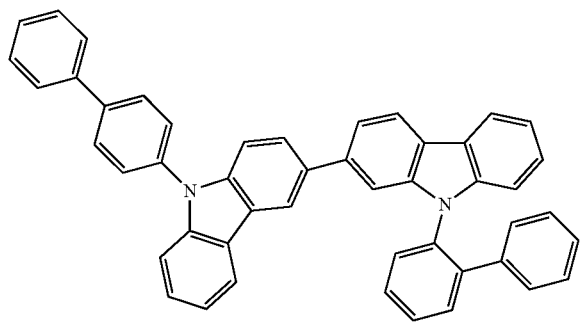
1-346
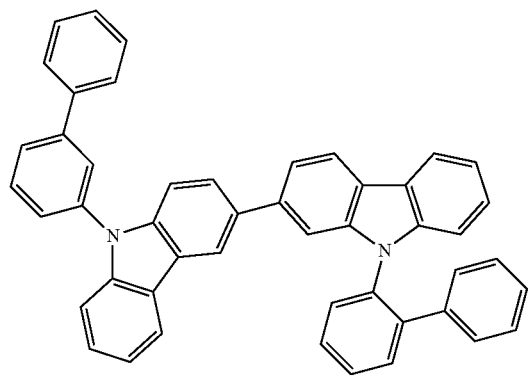
1-347
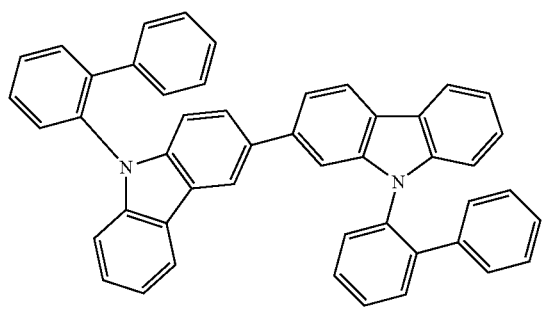
1-348
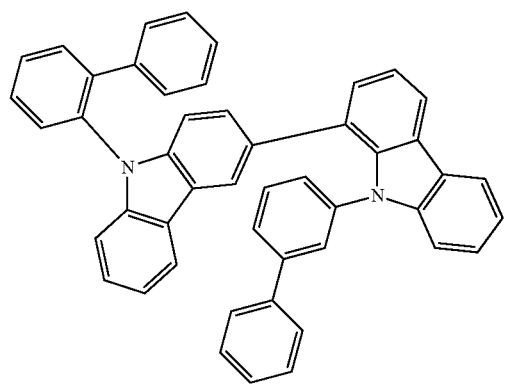
1-349
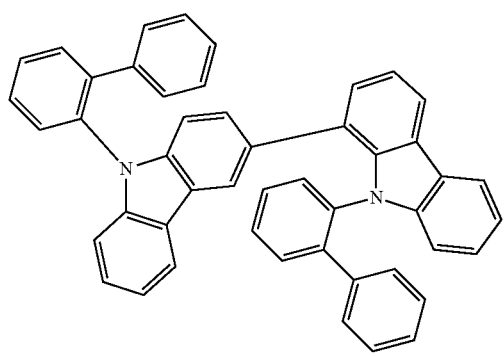

[C33]
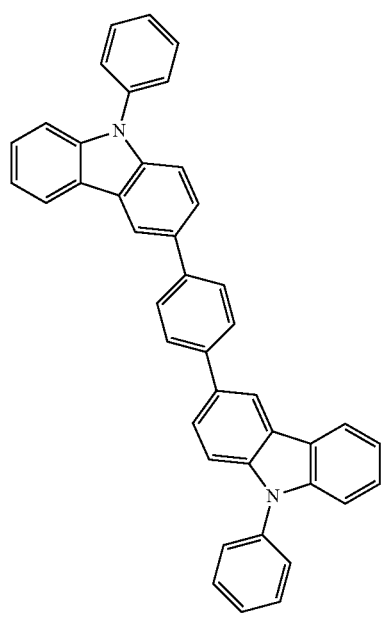
2-1
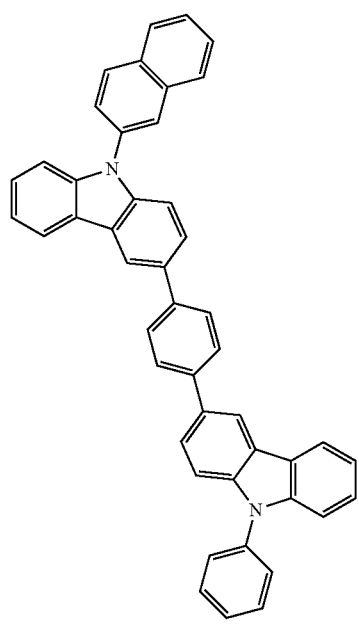
2-2
2-3
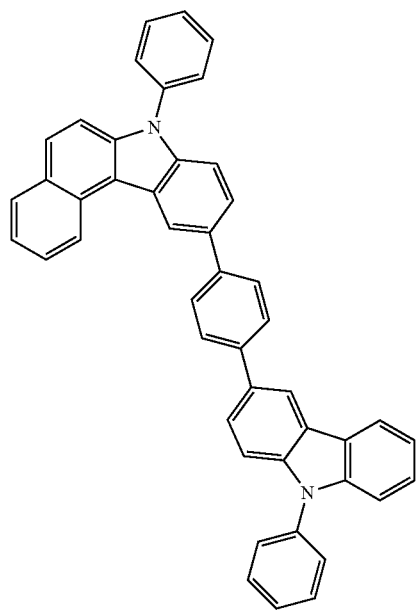
2-4
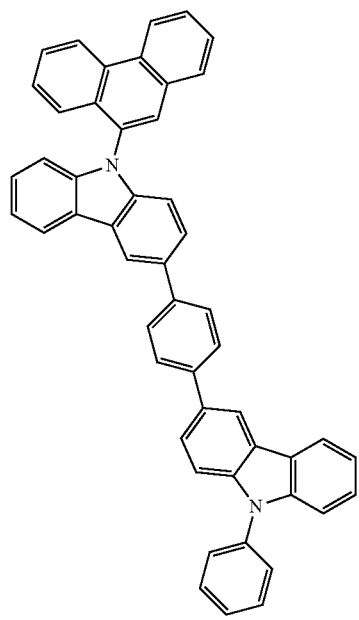

-continued
2-5
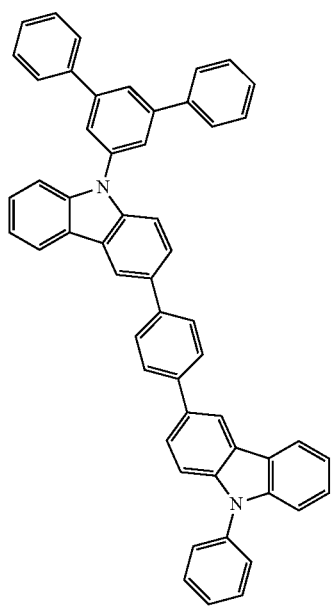
2-6
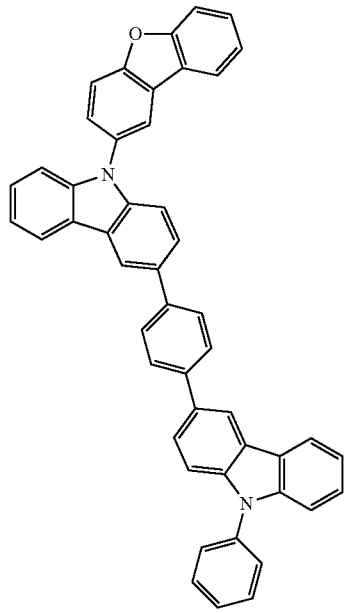
27
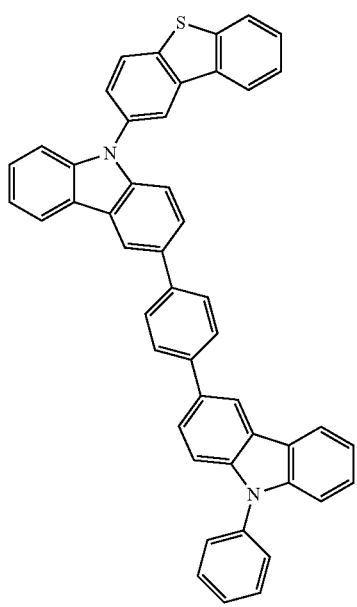
2-8
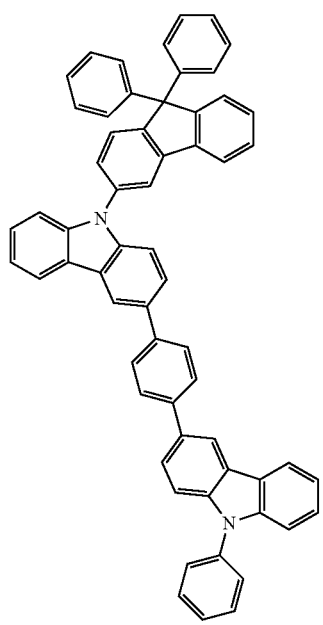

-continued
2-9
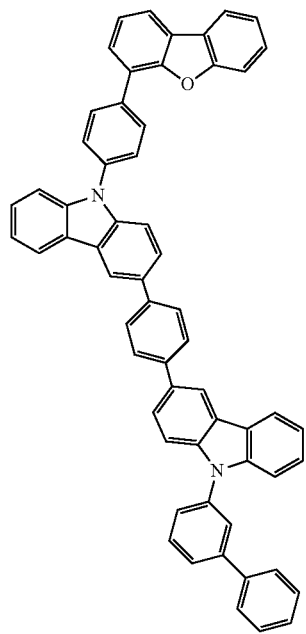
2-10
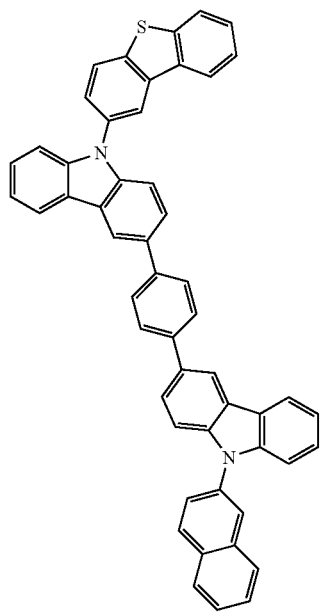
2-11
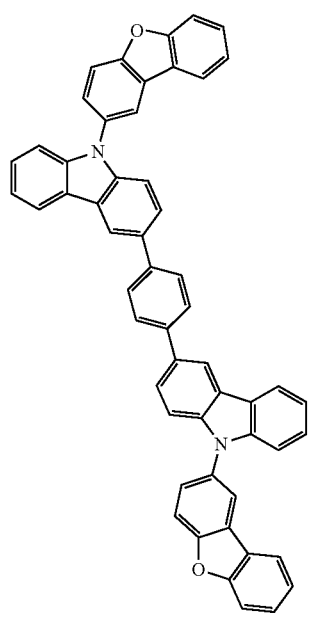
2-12
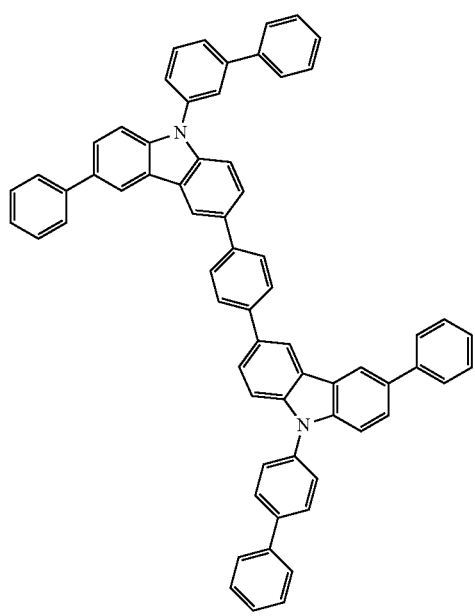

[C34]
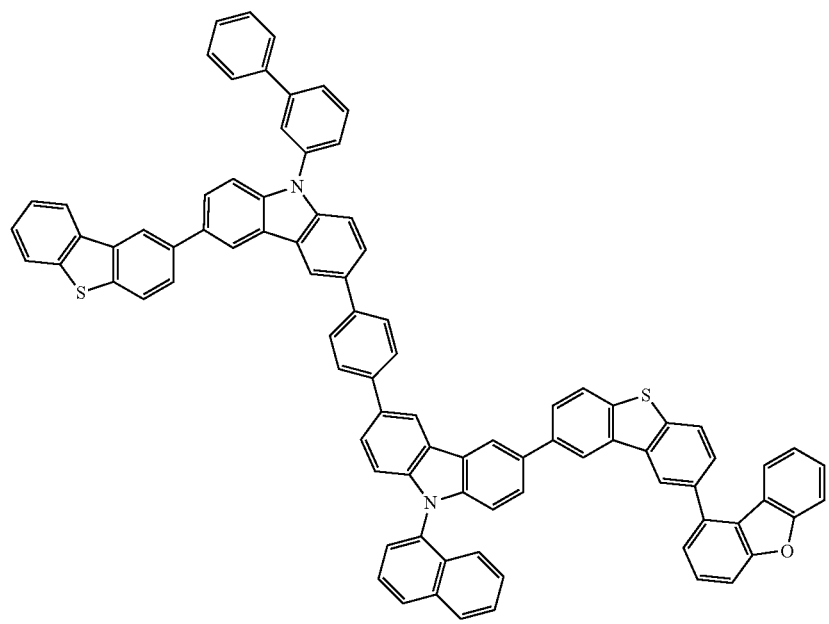
2-13
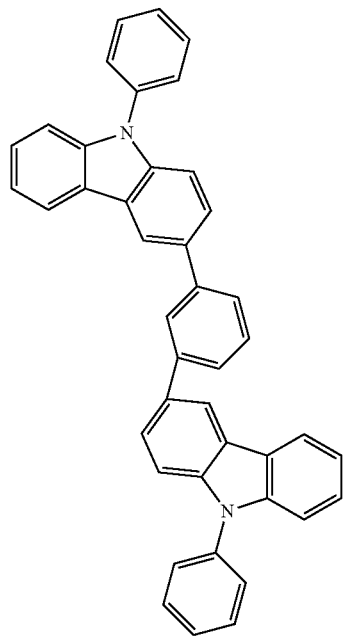
2-14
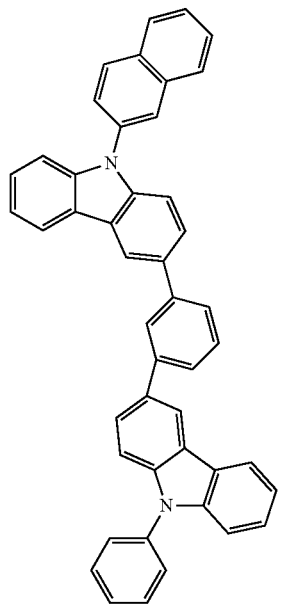
2-15

-continued
2-16
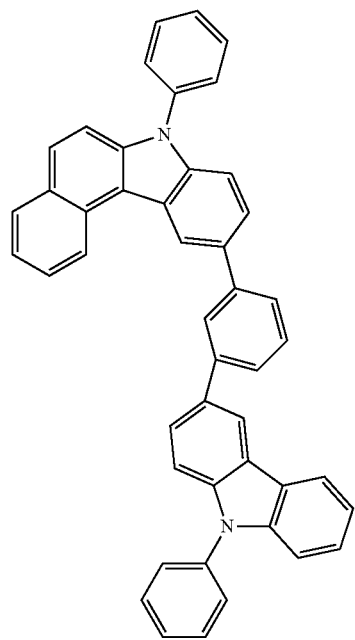
2-17
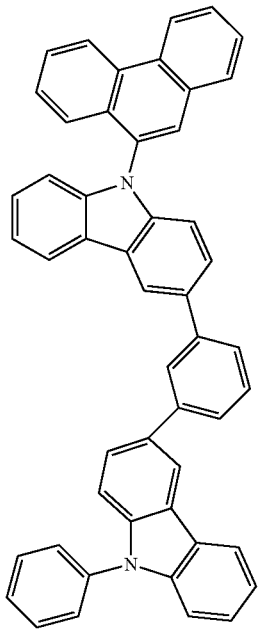
2-18
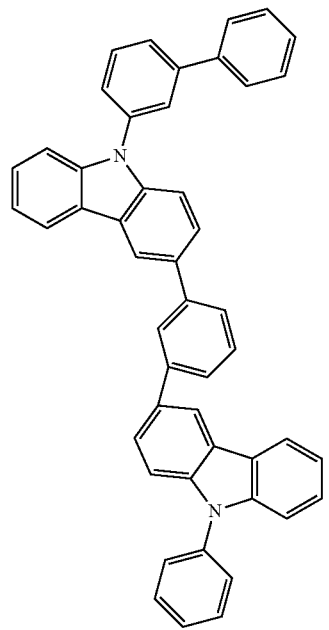
2-19
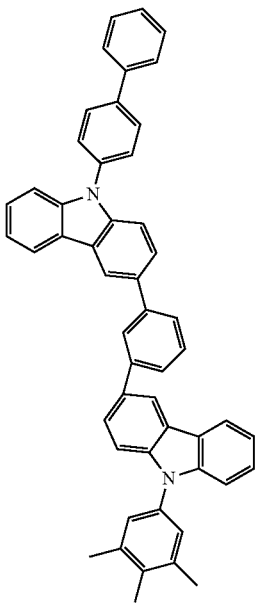

-continued
2-20
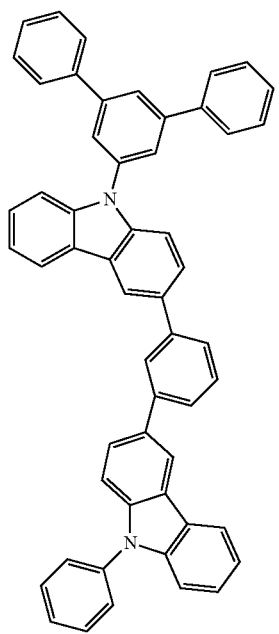
2-21
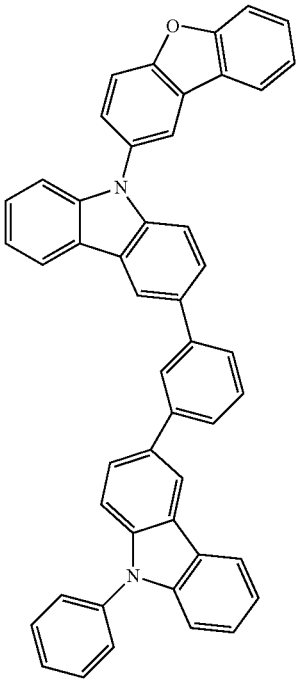
2-22
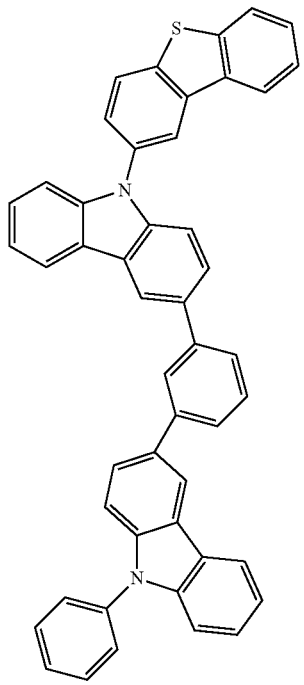
2-23
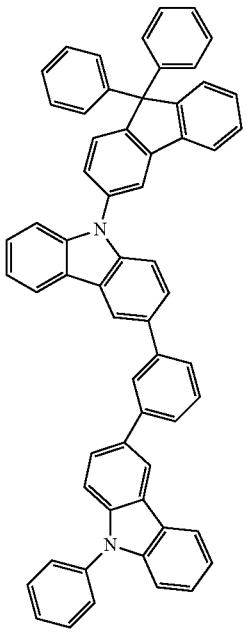

-continued
2-24
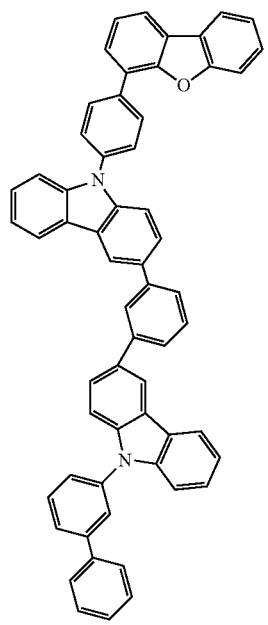
2-25
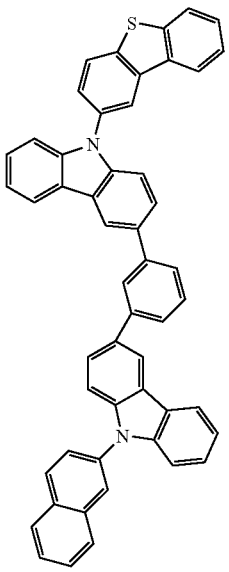
[C35]
2-26
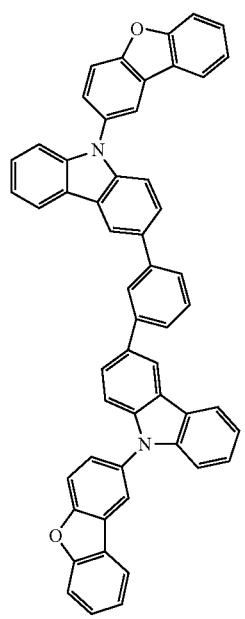
2-27
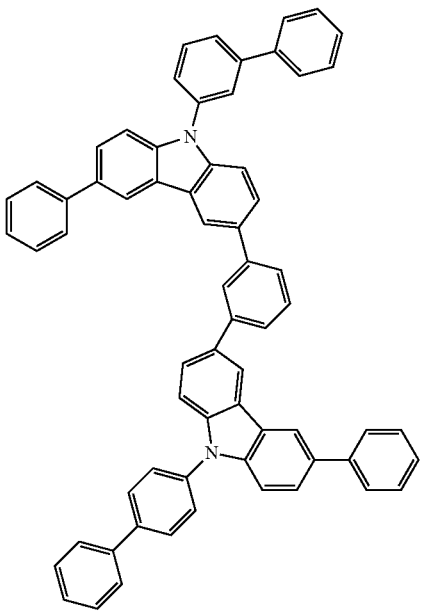

2-28
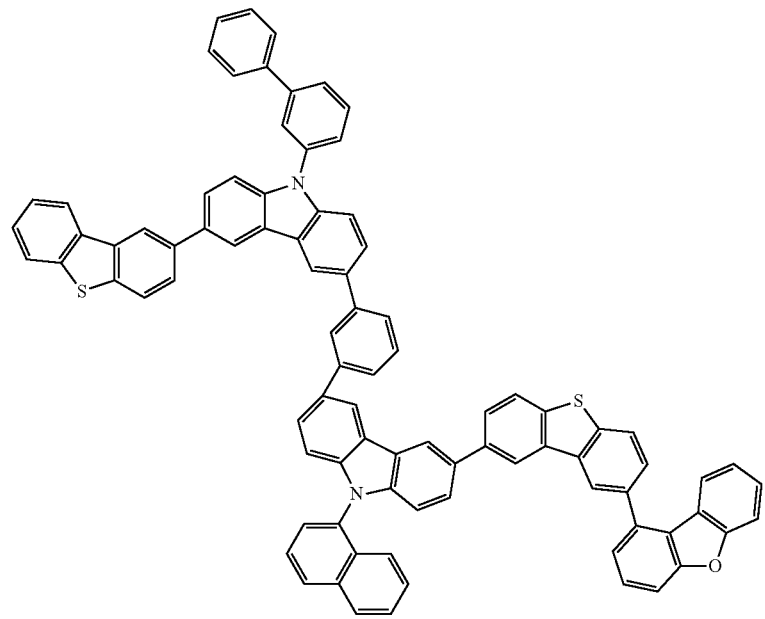
2-29
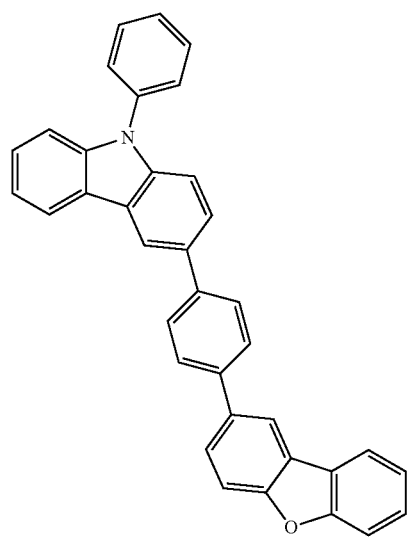
2-30
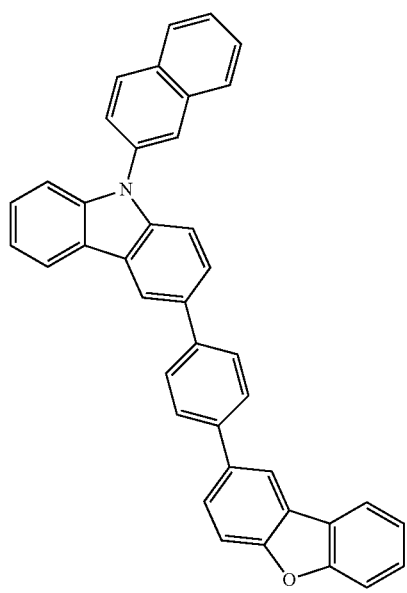

-continued
2-31
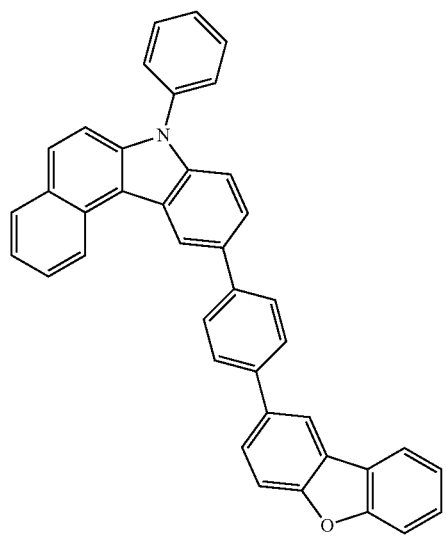
2-32
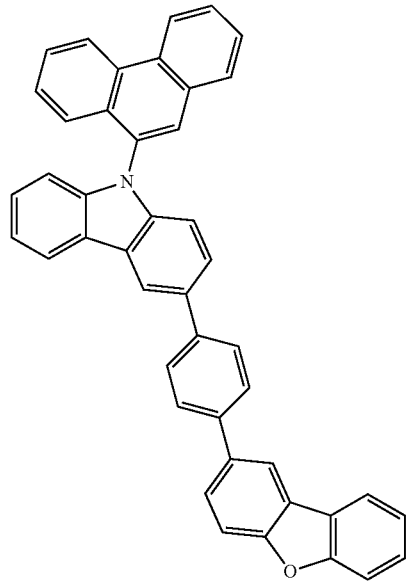
2-33
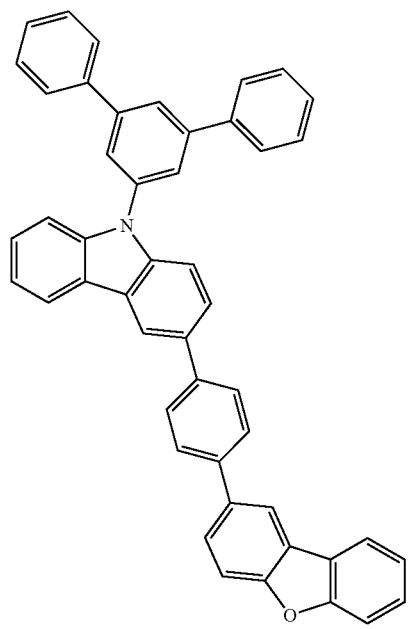
2-34
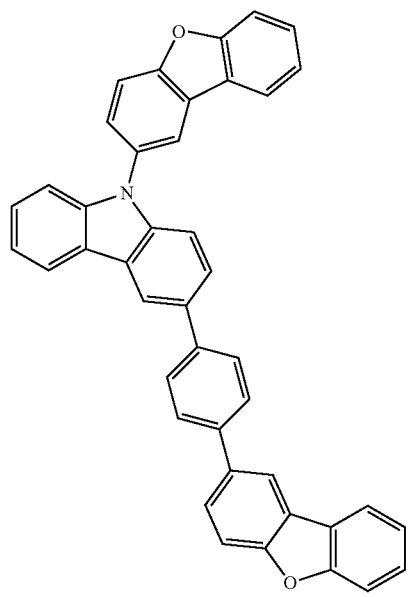

-continued
2-35
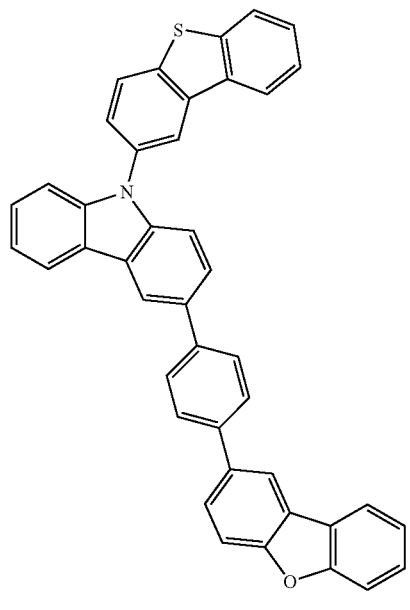
2-36
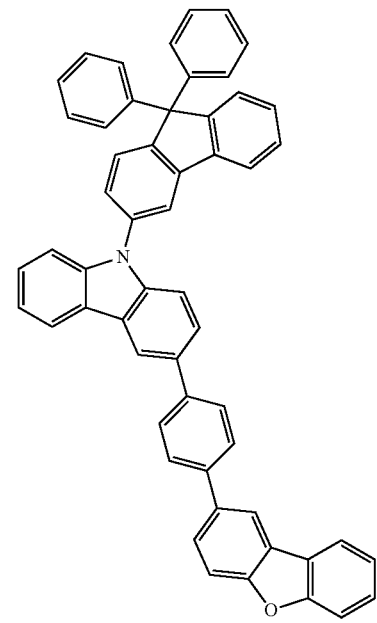
[C36]
2-37
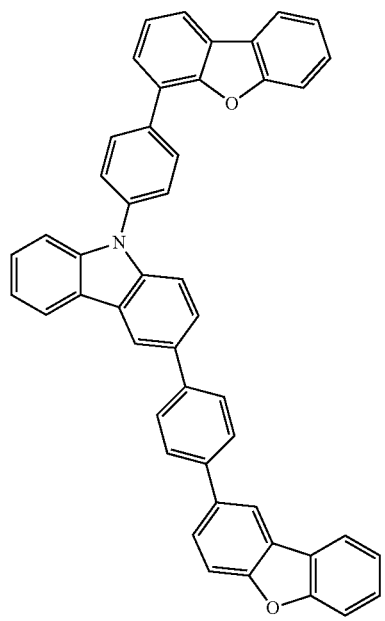
2-38
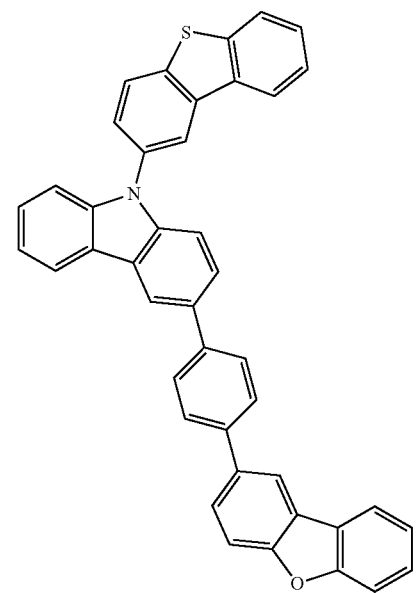

2-39
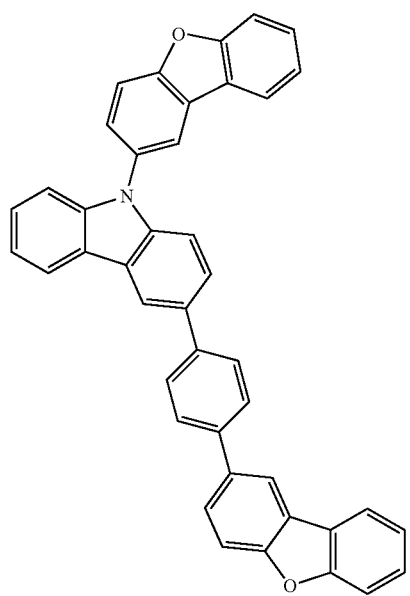
2-40
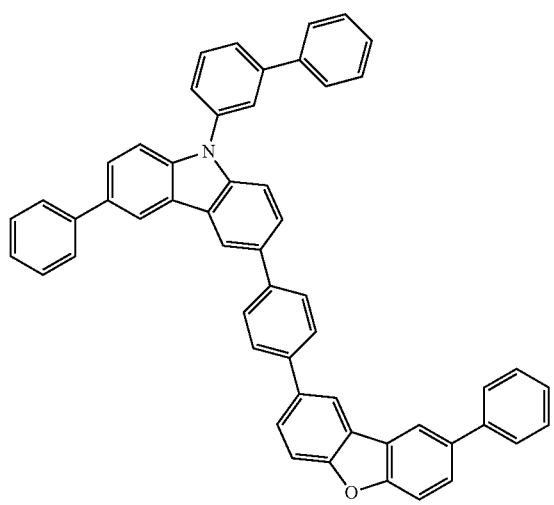
2-41
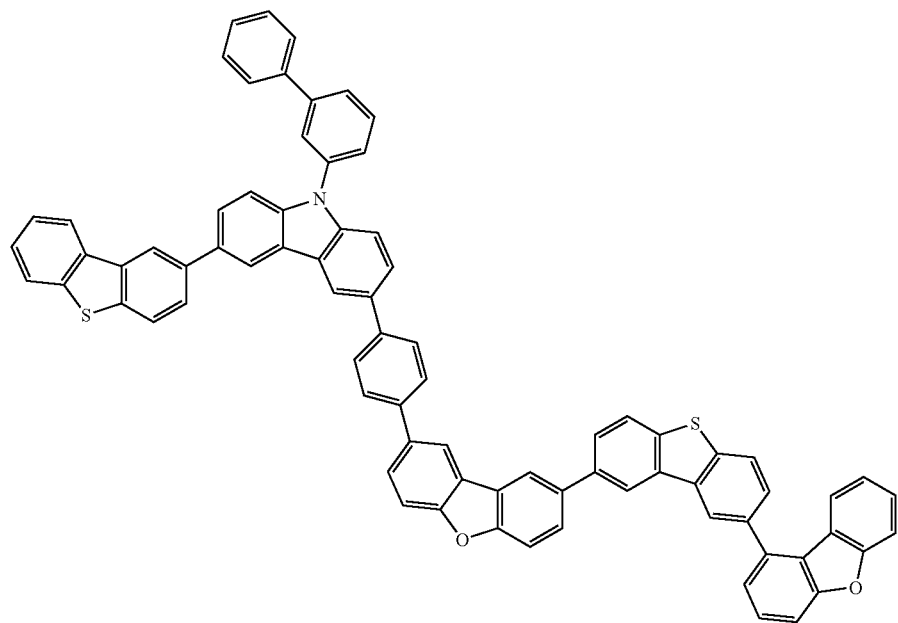

-continued
2-42
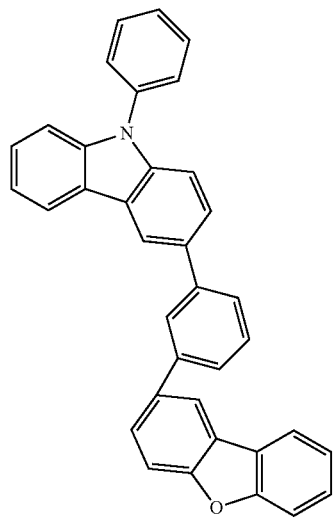
2-43
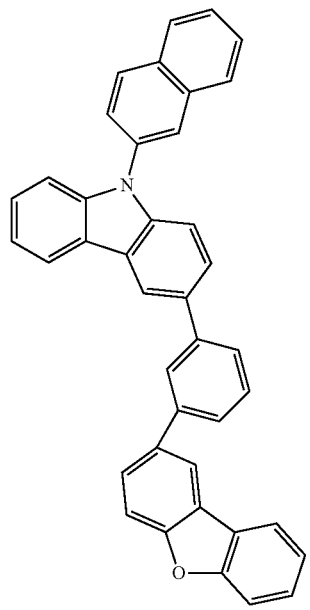
2-44
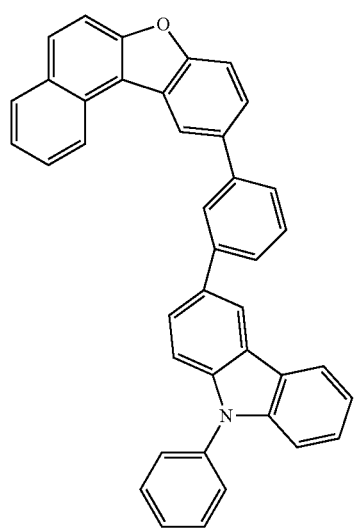
2-45
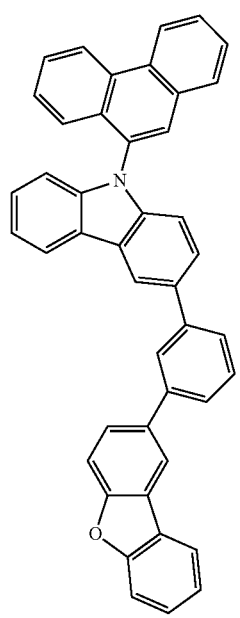

-continued
2-46
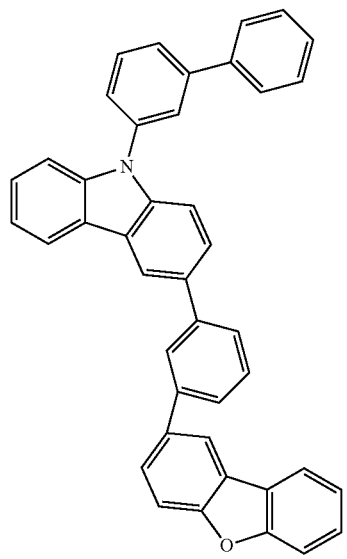
2-47
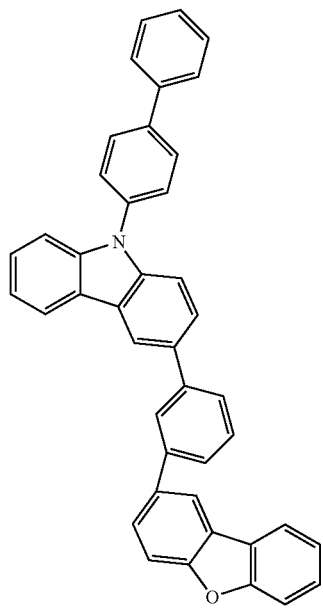
[C37]
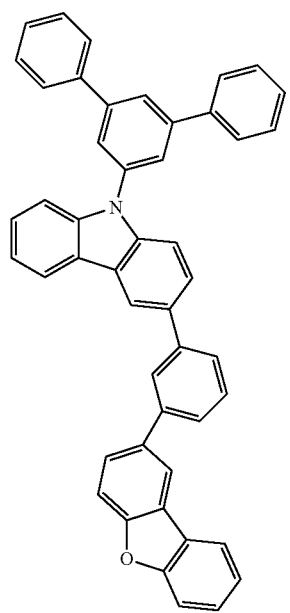
2-48
2-49
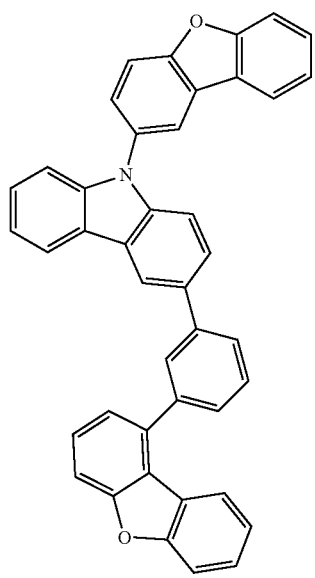

-continued
2-50
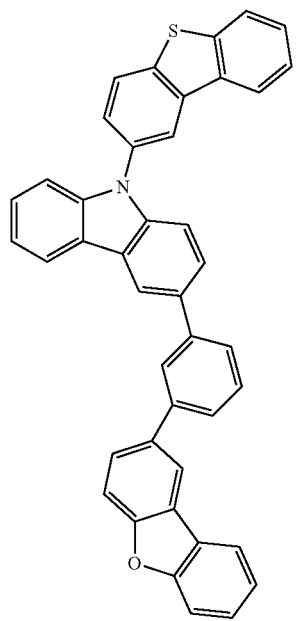
2-51
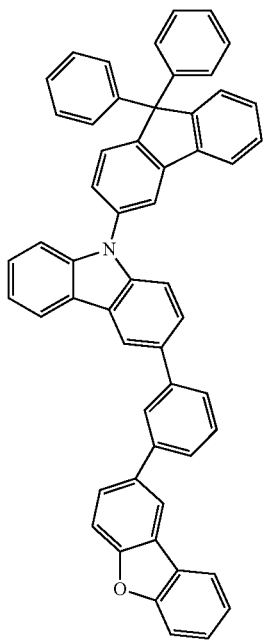
2-52
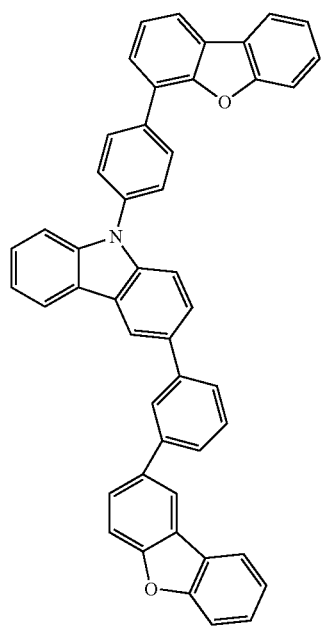
2-53
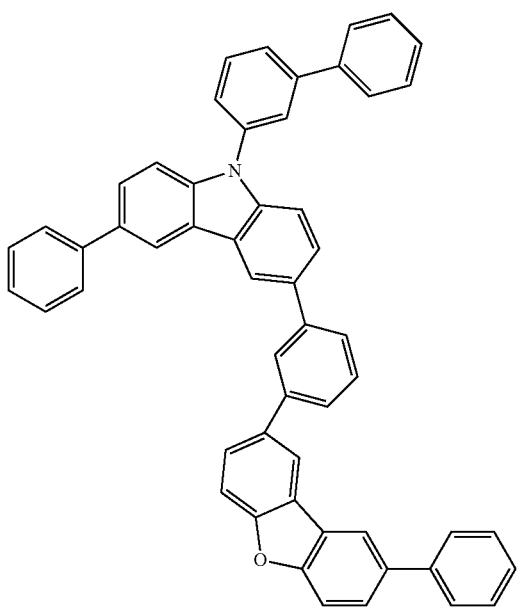

2-54
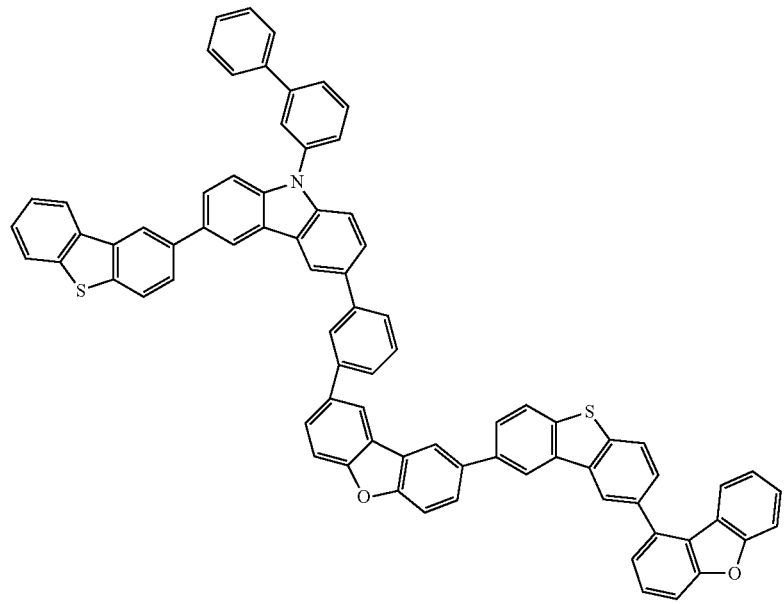
2-55
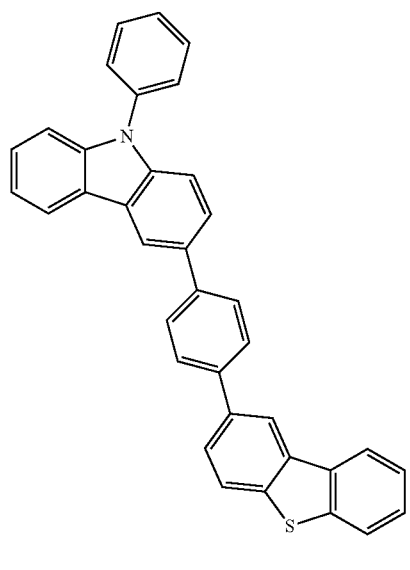
2-56
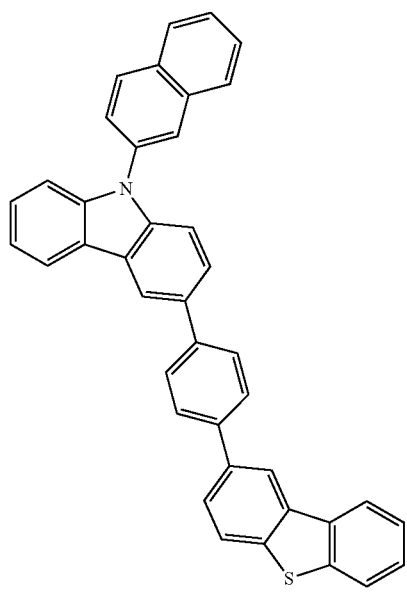

2-57
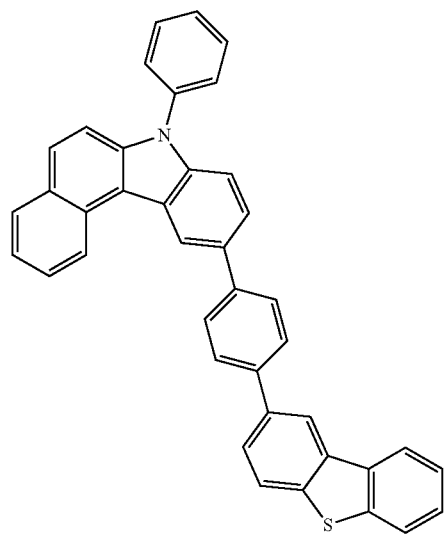
2-58
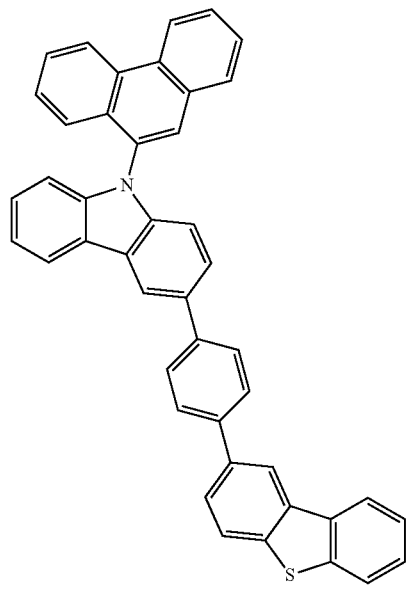
[C38]
2-59
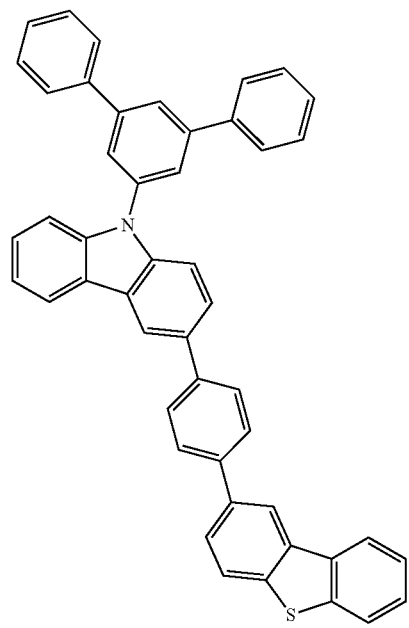
2-60
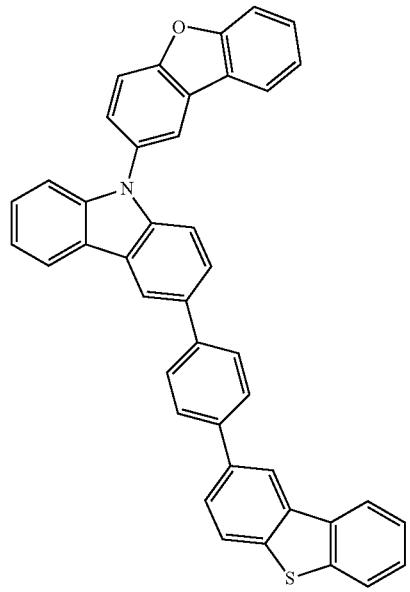

-continued
2-61
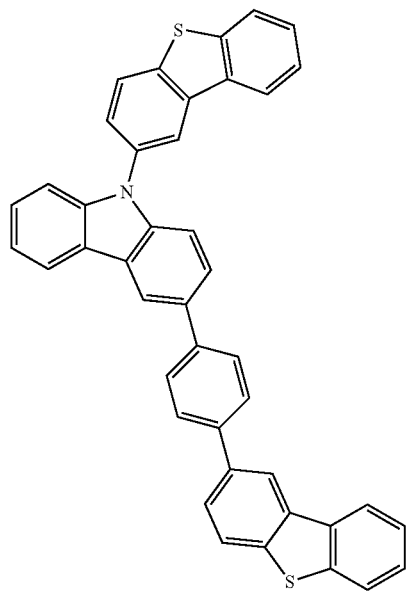
2-62
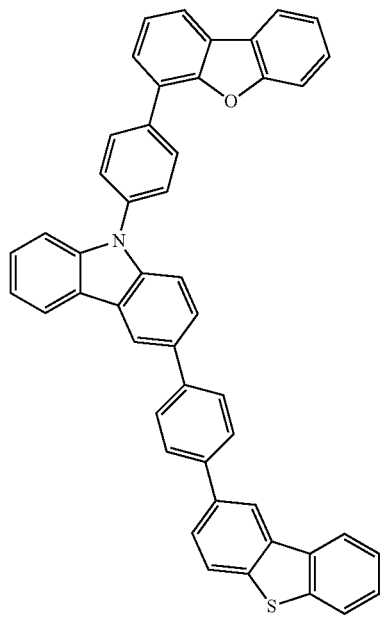
2-63
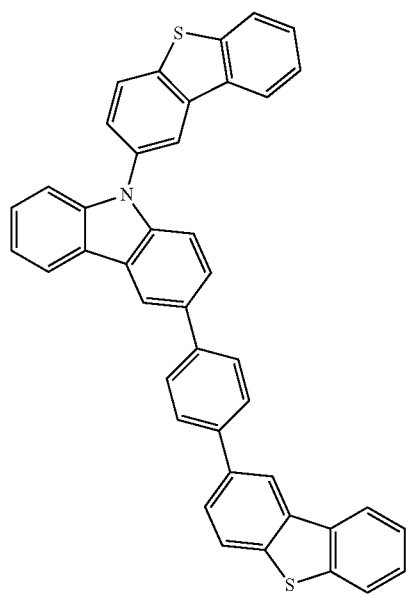
2-64
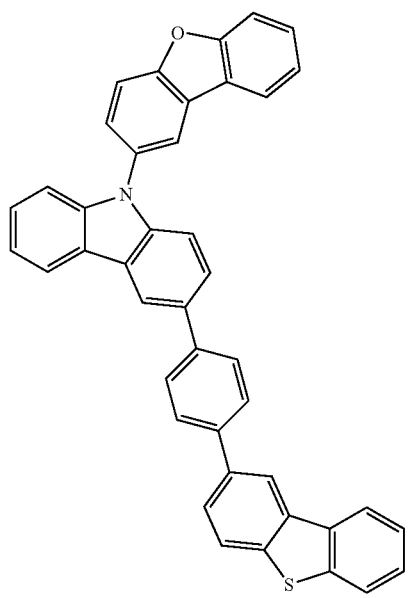

2-65
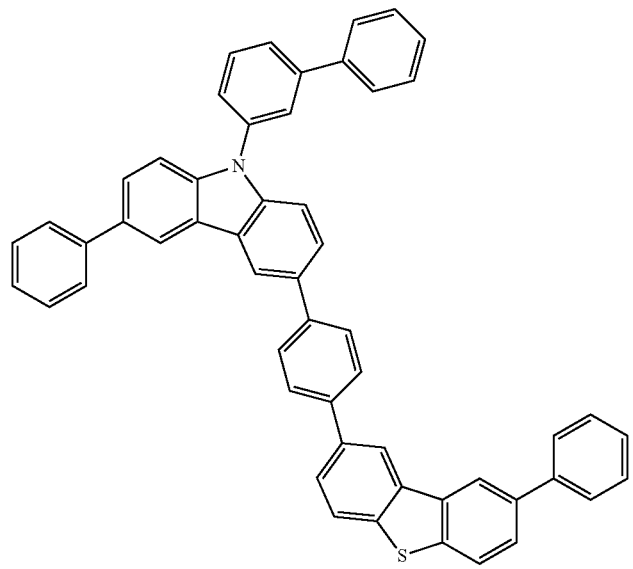
2-66
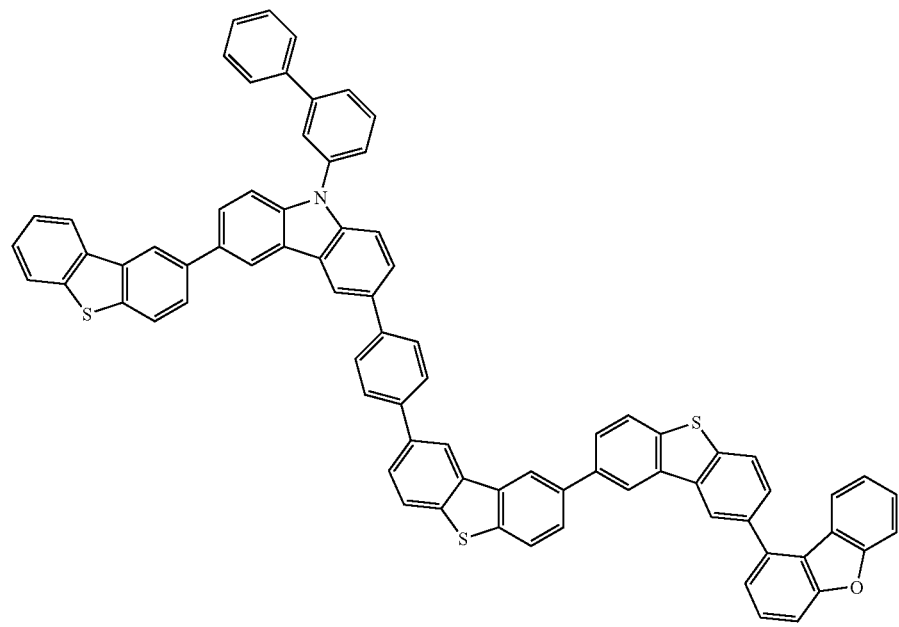

185 186
-continued
2-67
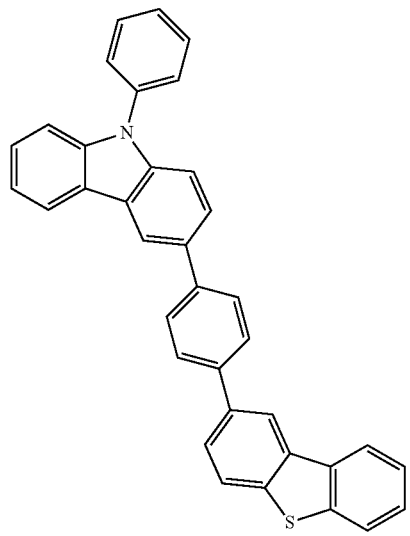
2-68
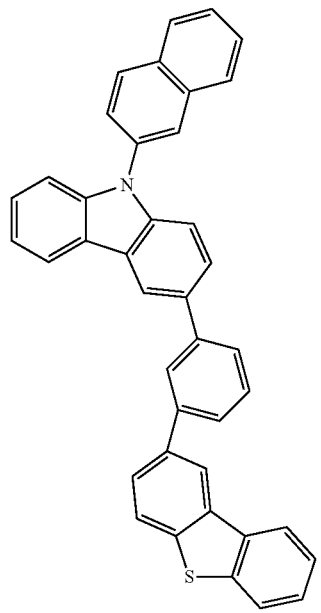
2-69
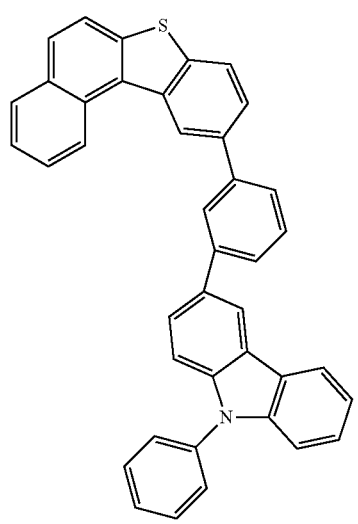
2-70
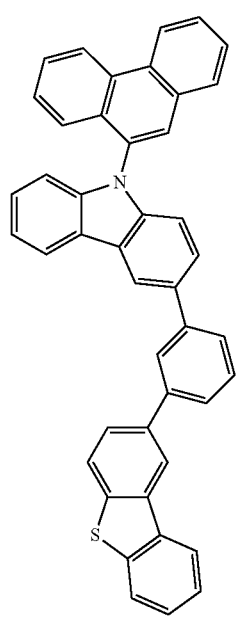

2-71
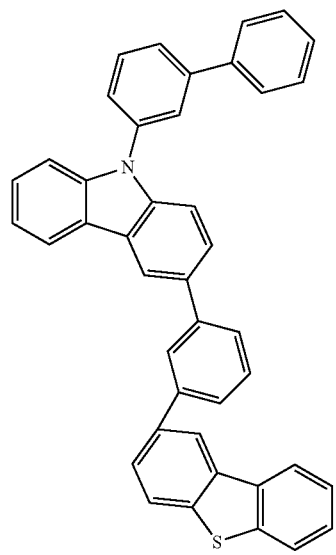
2-72
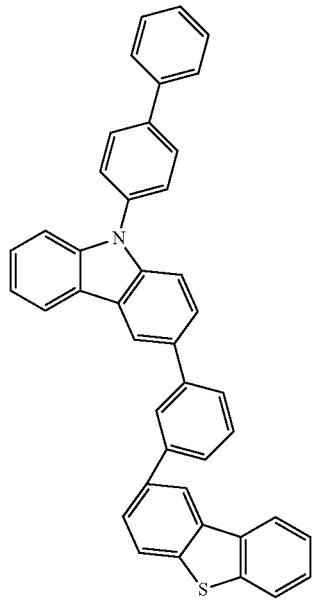
[C39]
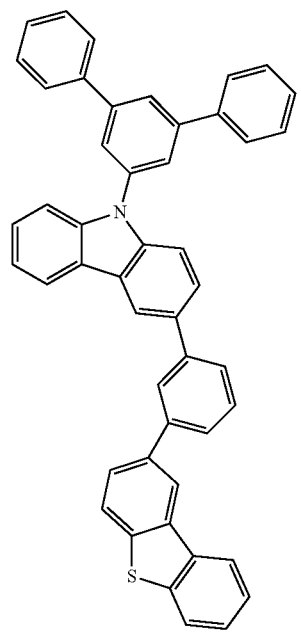
2-73
2-74
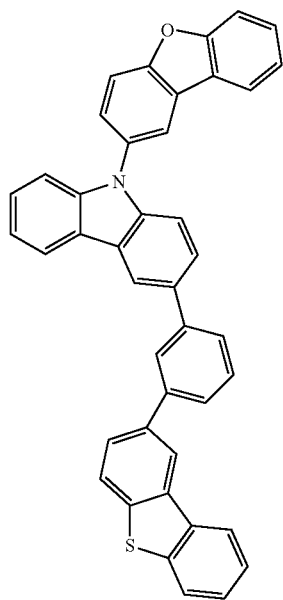

-continued
2-75
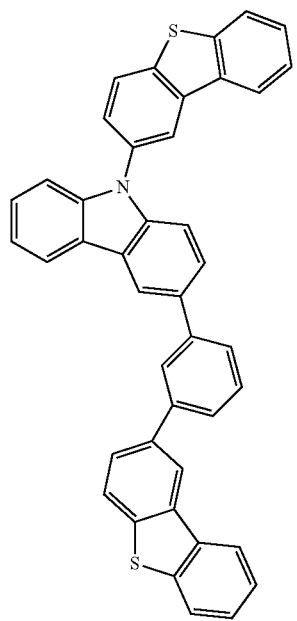
2-76
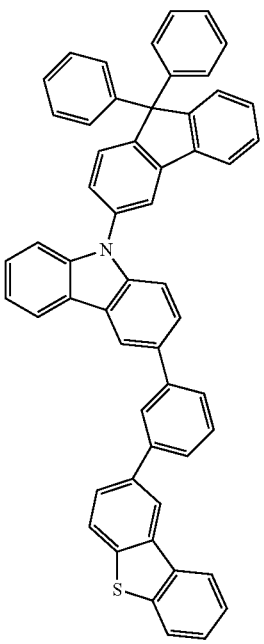
2-77
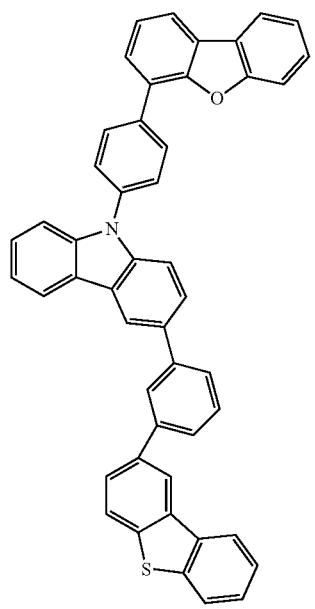
2-78
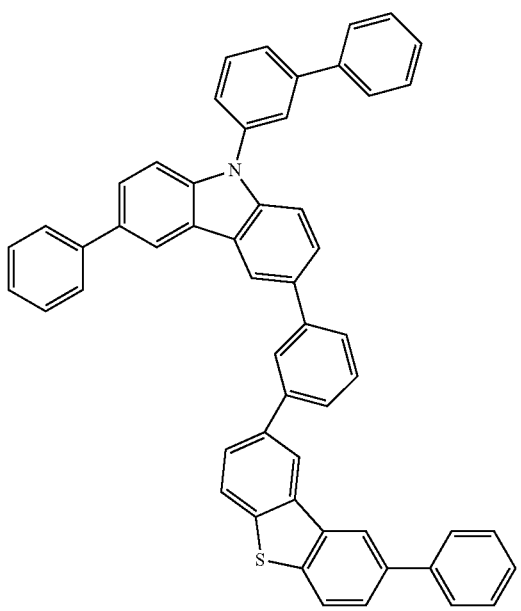

2-79
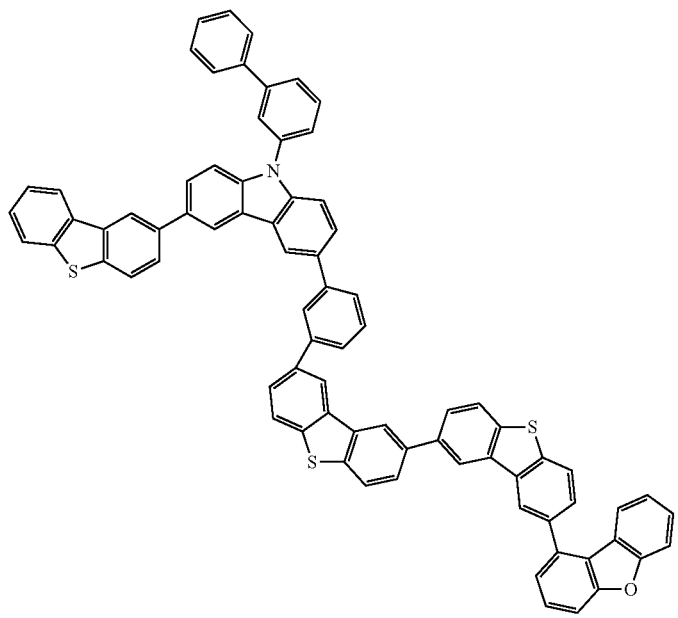
2-80
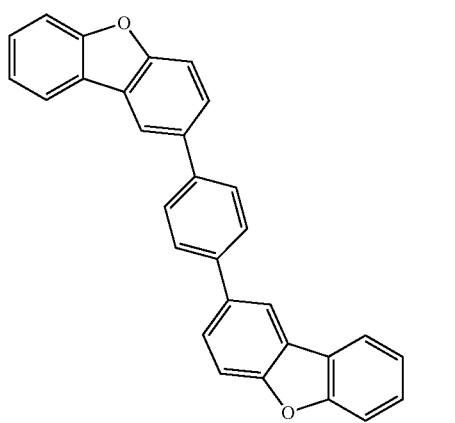
2-81
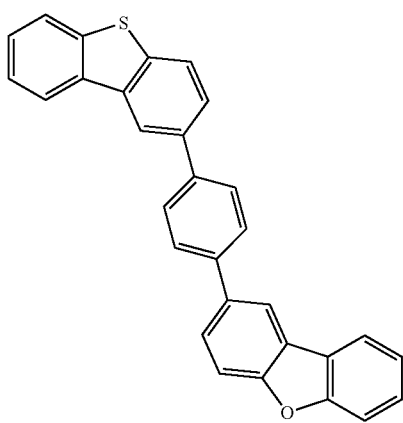
2-82
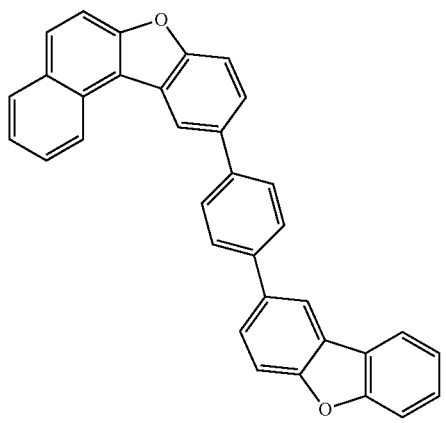
2-83
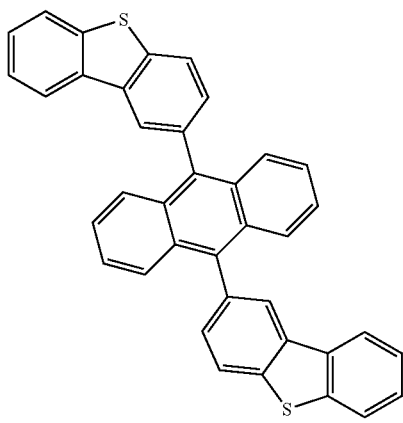

-continued
[C40]
2-84
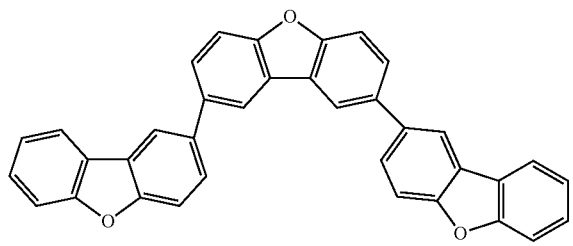
2-85
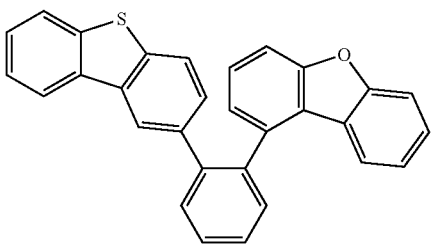
2-86
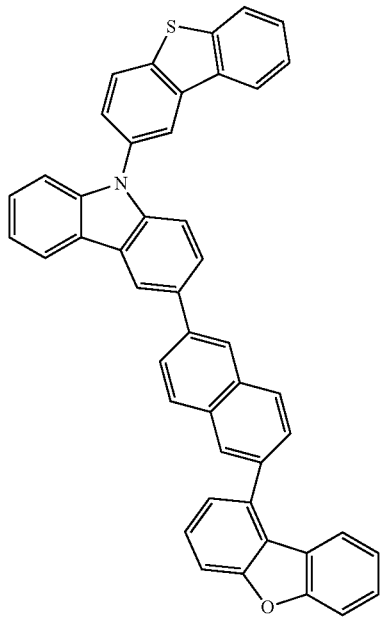
2-87
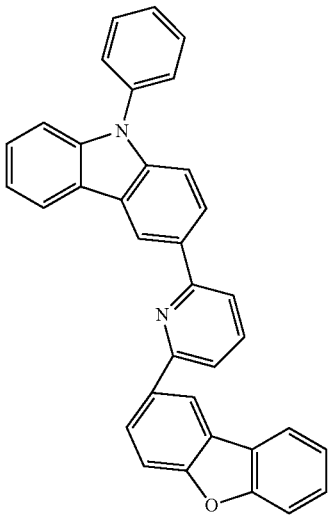
2-88
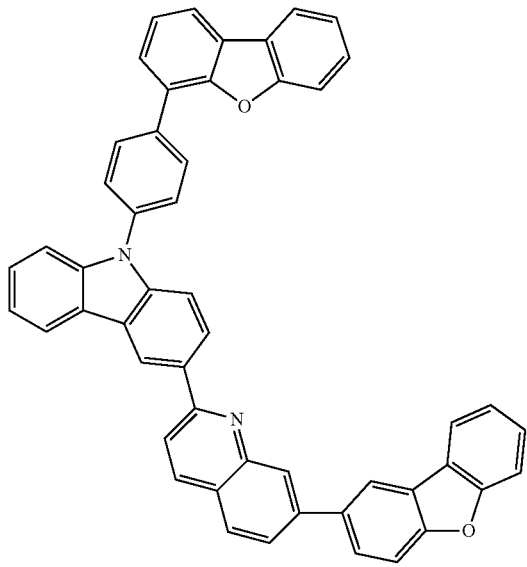
2-89
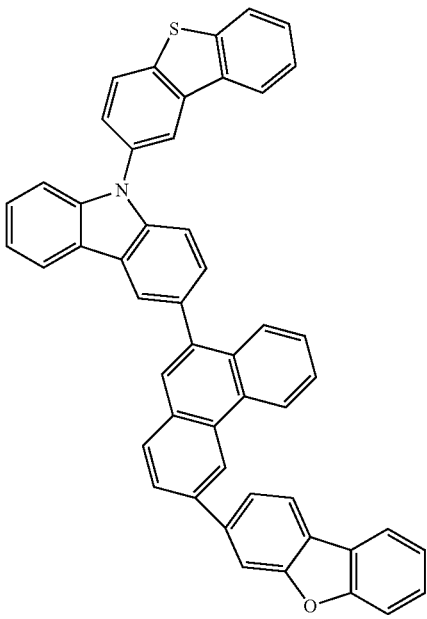

-continued
2-90
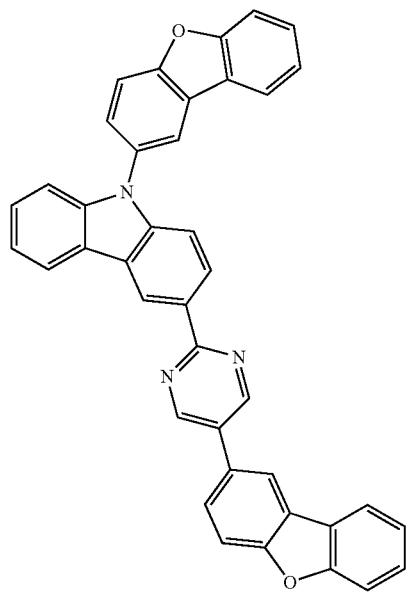
2-91
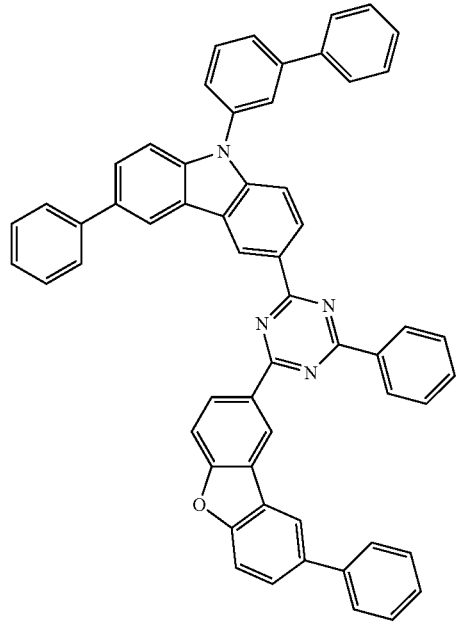
2-92
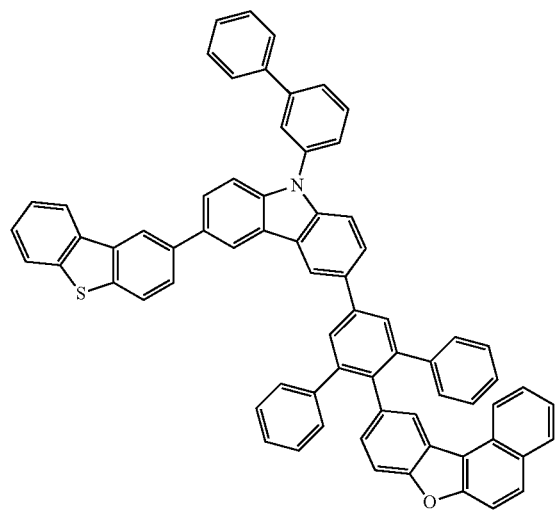
2-93
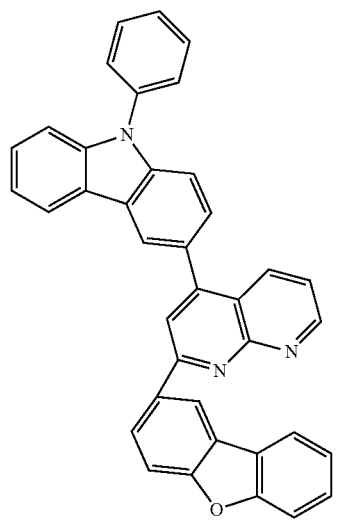

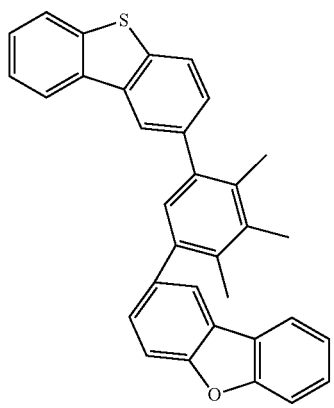

2-94

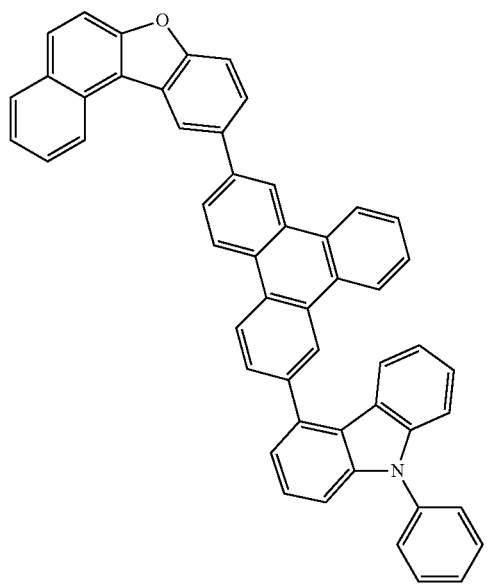

2-95

Next, an explanation is provided of compounds (carborane compounds) represented by general formula (2) and formula (8). Those reference symbols common to general formula (2) and formula (8) have the same meanings.

Ring A represents a $C_2B_{10}H_{10}$ divalent carborane group represented by formula (a1) or formula (b1), and although the plurality of ring A present in a molecule may be the same or different, all of the rings A are preferably carborane groups represented by formula (a1). Although the two bonds possessed by the divalent carborane group may extend from C or B, those bonds connected to $L^1$, $L^2$ and $L^3$ preferably extend from C.

s indicates the number of repeats, represents an integer of 0 to 2, is preferably 0 or 1, and is more preferably 0.

n and m indicate the numbers of substituents, n represents an integer of 1 or 2, m represents an integer of 0 to 4, and preferably n represents 1 and m represents an integer of 0 to 2.

$L^1$ represents a single bond or aromatic group having a valence of n+1. The aromatic group represents a substituted or unsubstituted aromatic hydrocarbon group having 6 to 30 carbon atoms, a substituted or unsubstituted aromatic heterocyclic group having 3 to 30 carbon atoms, or a substituted or unsubstituted linked aromatic group composed by linking 2 to 6 of the aromatic rings thereof. $L^1$ preferably represents a single bond, substituted or unsubstituted aromatic hydrocarbon group having 6 to 18 carbon atoms, substituted or unsubstituted aromatic heterocyclic group having 3 to 17 carbon atoms or substituted or unsubstituted linked aromatic group composed by linking two to five of the aromatic rings thereof. However, in the case n=1 and s=1, $L^1$ represents a single bond, aromatic heterocyclic group or linked aromatic group containing at least one aromatic heterocyclic group.

$L^2$ independently represents a single bond or divalent aromatic group. The divalent aromatic group represents a substituted or unsubstituted aromatic hydrocarbon group having 6 to 30 carbon atoms, a substituted or unsubstituted aromatic heterocyclic group having 3 to 30 carbon atoms, or a substituted or unsubstituted linked aromatic group composed by linking 2 to 6 of the aromatic rings thereof. $L^2$ preferably represents a single bond, substituted or unsubstituted aromatic hydrocarbon group having 6 to 18 carbon atoms, substituted or unsubstituted aromatic heterocyclic group having 3 to 17 carbon atoms, or substituted or unsubstituted linked aromatic group composed by linking two to five of the aromatic rings thereof.

$L^3$ represents an unsubstituted aromatic hydrocarbon group or unsubstituted aromatic heterocyclic group having a valence of m+1. The aromatic hydrocarbon group has 6 to 30 carbon atoms and preferably 6 to 18 carbon atoms, and the aromatic heterocyclic group has 3 to 30 carbon atoms and preferably 3 to 17 carbon atoms.

In formula (8), Z represents $NR^{10}$, $PR^{11}$, O, S, Se, $CR^{12}R^{13}$ or $SiR^{14}R^{15}$, and preferably represents $NR^{10}$, O or S. Here, $R^{10}$ to $R^{15}$ independently represent a substituted or unsubstituted aromatic hydrocarbon group having 6 to 30 carbon atoms and preferably 6 to 18 carbon atoms, a substituted or unsubstituted aromatic heterocyclic group having 3 to 30 carbon atoms and preferably 3 to 17 carbon atoms, or a substituted or unsubstituted linked aromatic group obtained by linking 2 to 6 of the aromatic rings thereof.

In general formula (2) and formula (8), the aromatic hydrocarbon group, aromatic heterocyclic group and linked aromatic group have the same meanings as the aromatic hydrocarbon group, aromatic heterocyclic group and linked aromatic group explained for $R^1$ to $R^6$ in the above-mentioned general formula (1) and formulas (3) to (7) with the exception of $L^1$ having a valence of n+1, $L^2$ having a valence of 2 and $L^3$ having a valence of m+1. However, in the case $L^3$ is not a linked aromatic group, n=1 and s=1, $L^1$ represents a single bond, aromatic hydrocarbon heterocyclic group or linked aromatic group containing at least one aromatic heterocyclic group. In addition, in the case n=0, the aromatic groups directly bonded to ring A are preferably the same and more preferably such that $L^1-(H)_n=L^3-(R^9)_m$.

In general formula (2) and formula (8), $R^9$ has the same meaning as $R^7$ and $R^8$ in the above-mentioned general formula (1).

Although the following indicates preferable specific examples of compounds represented by the above-mentioned general formula (2), these compounds are not limited thereto.

[C41]
3-1
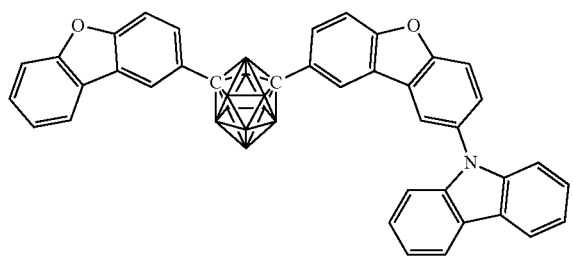
3-2
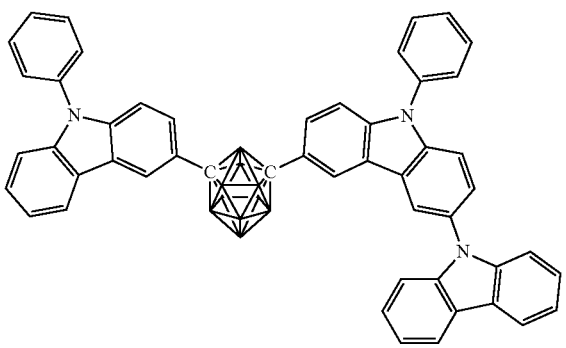
3-3
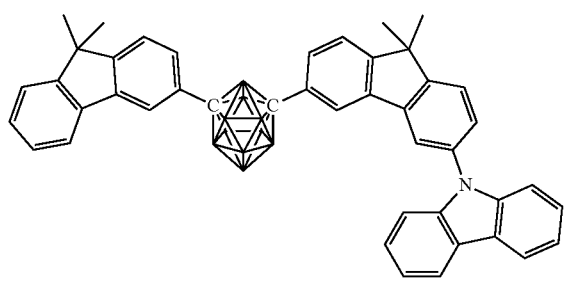
3-4
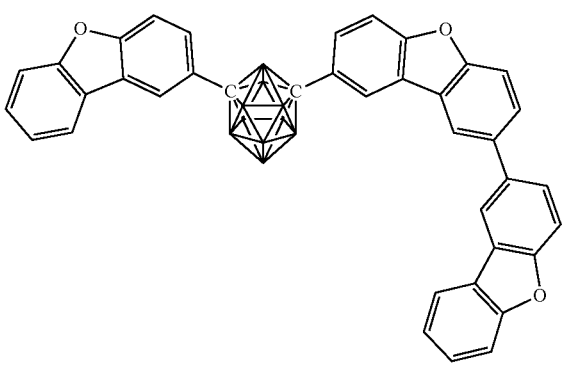
3-5
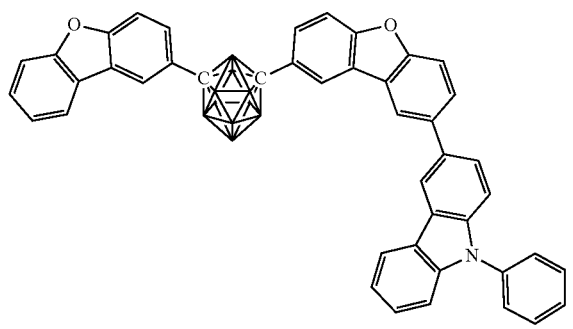
3-6
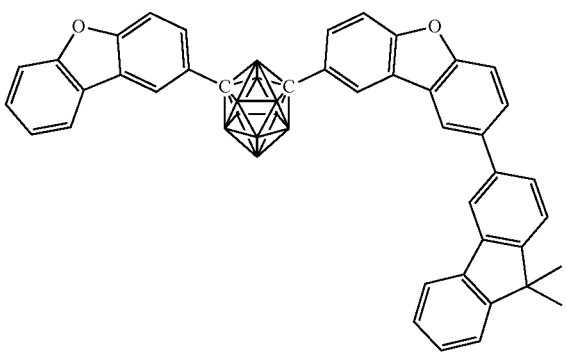
3-7
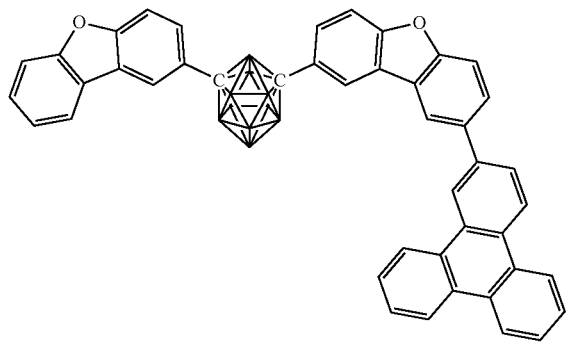
3-8
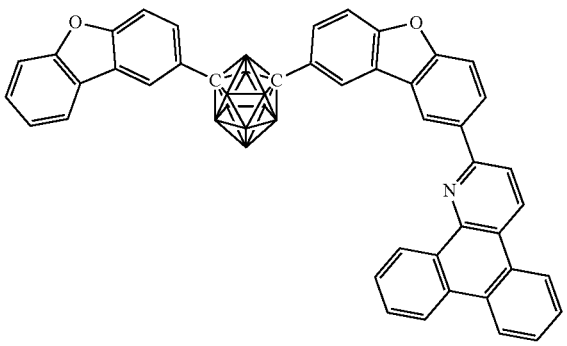

-continued
3-9
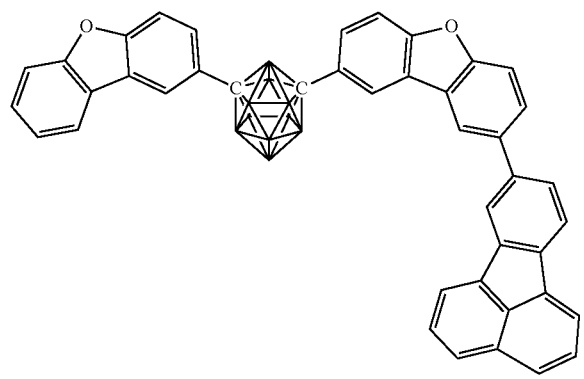
3-10
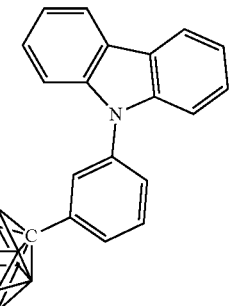
3-11
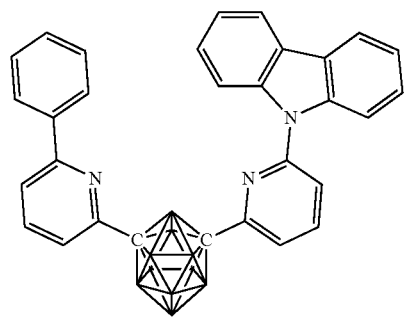
3-12
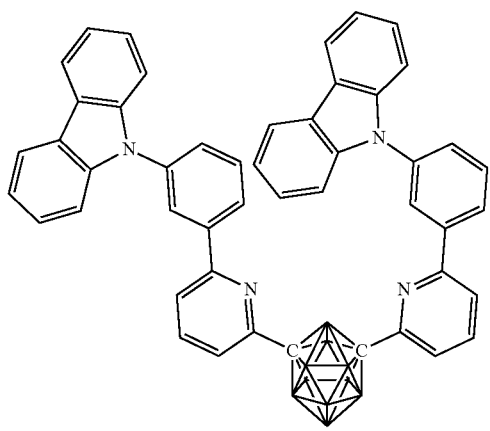
3-13
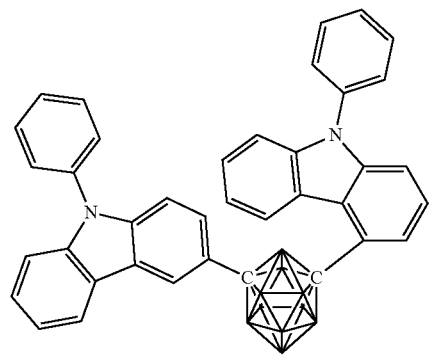
3-14
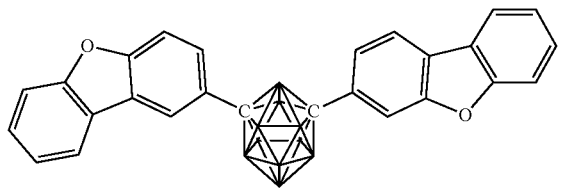
3-15
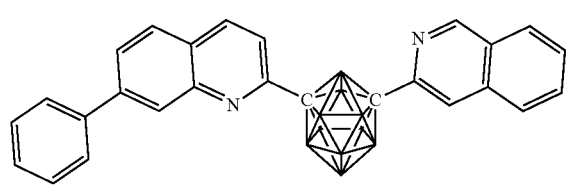

-continued
[C42]
3-16
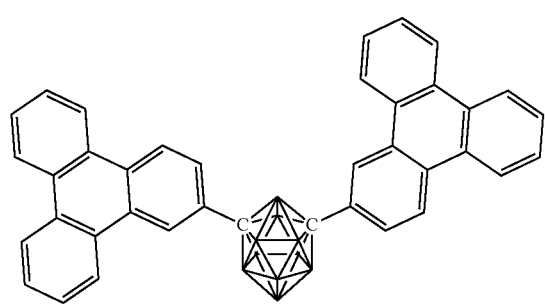
3-17
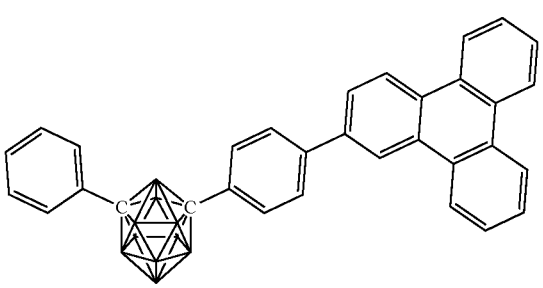
3-18
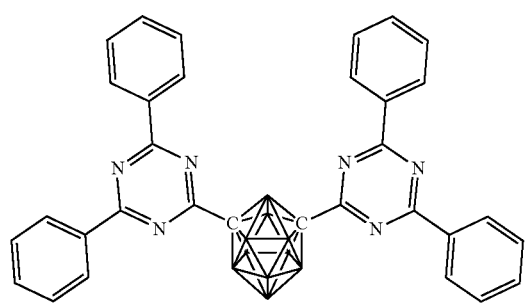
3-19
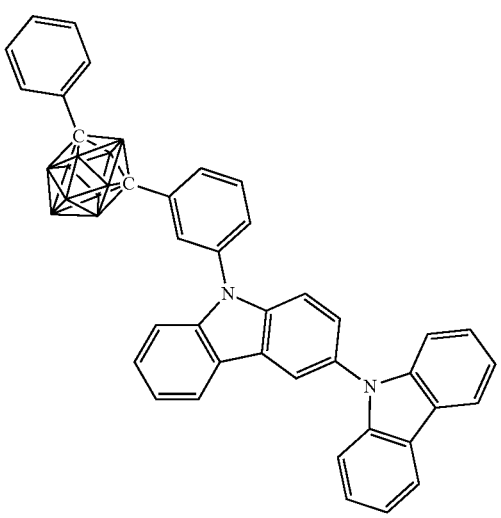
3-20
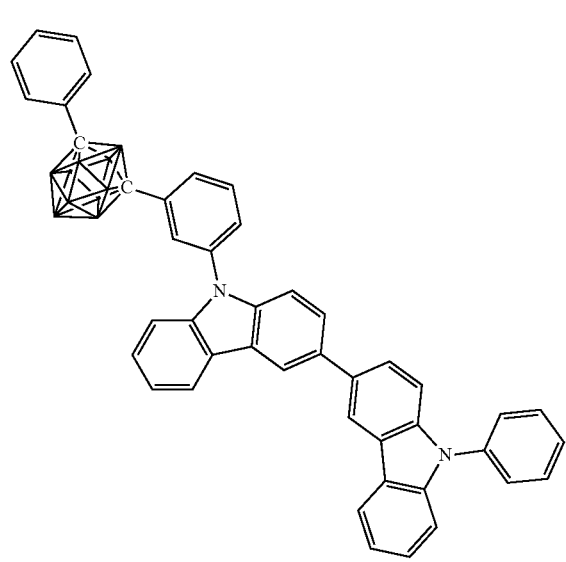
3-21
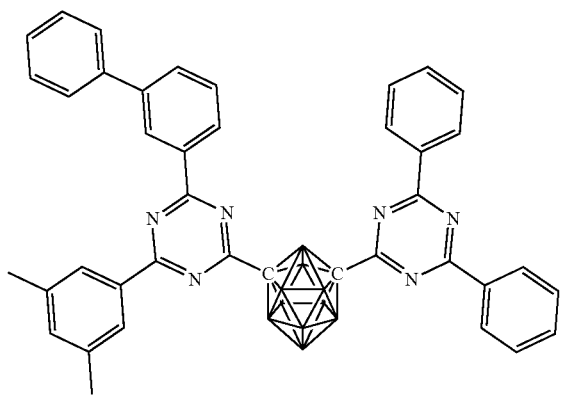

-continued
3-22
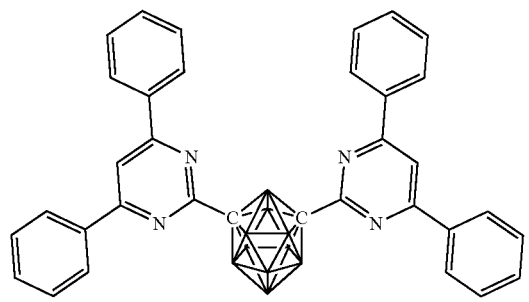
3-23
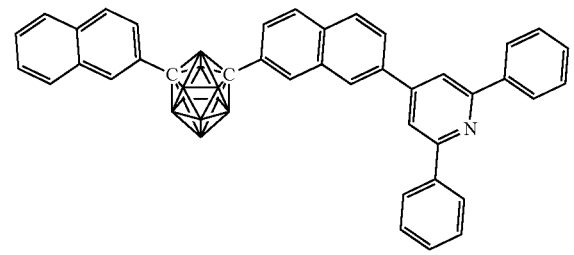
3-24
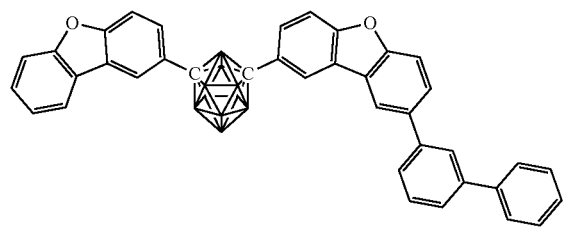
3-25
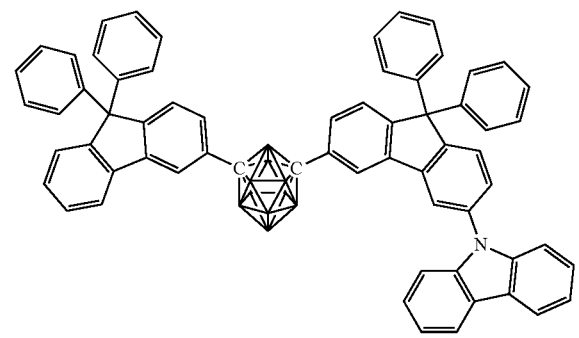
3-26
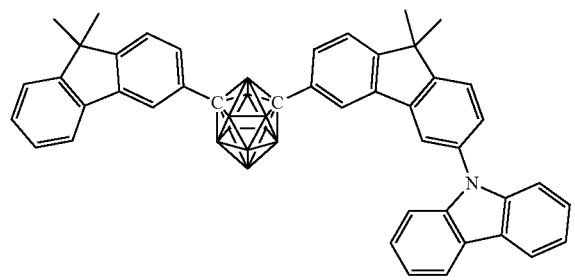
3-27
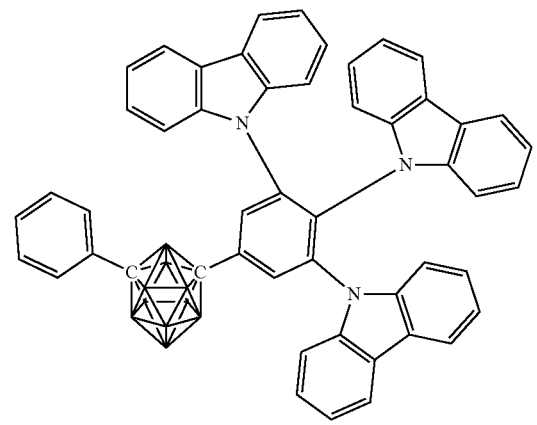
3-28
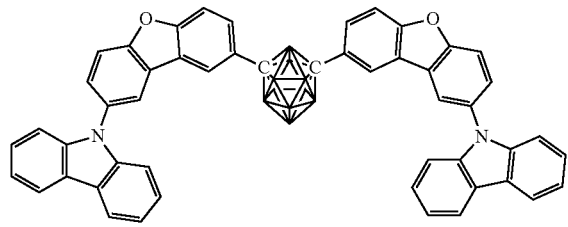
3-29
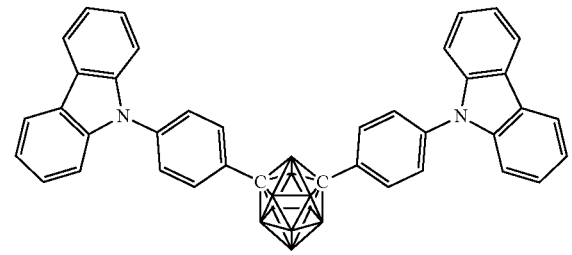

[43]
3-30
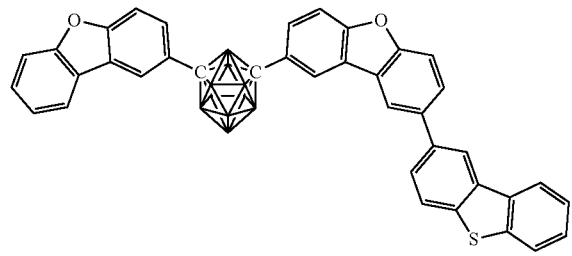
3-31
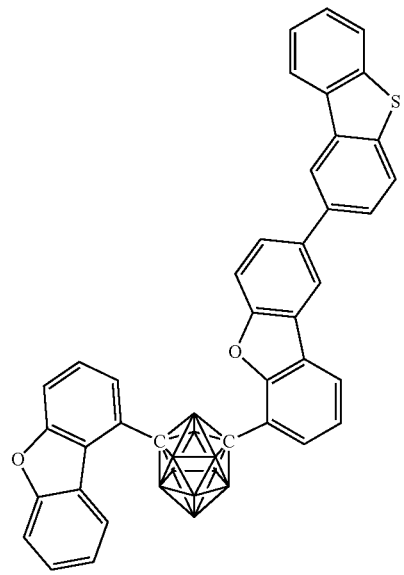
3-32
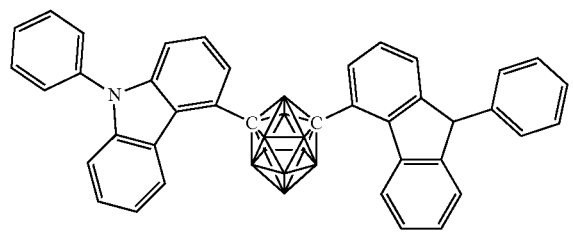
3-33
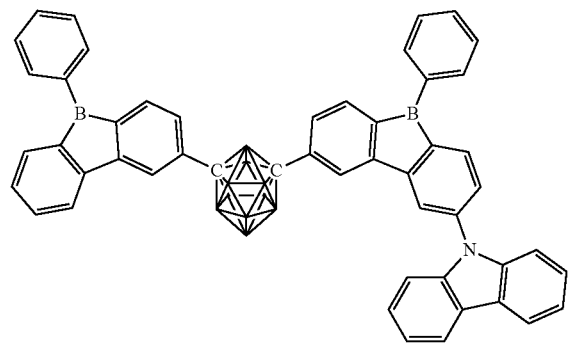
3-34
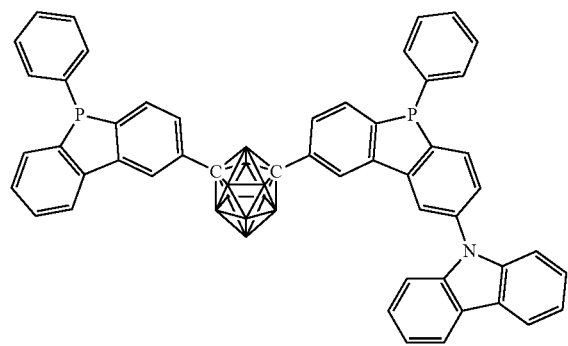
3-35
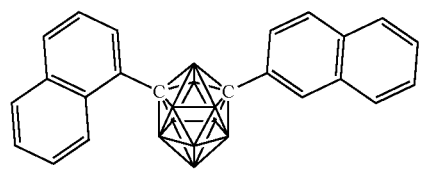

-continued
3-36
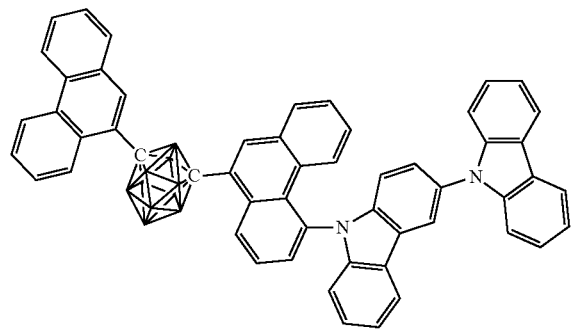
3-37
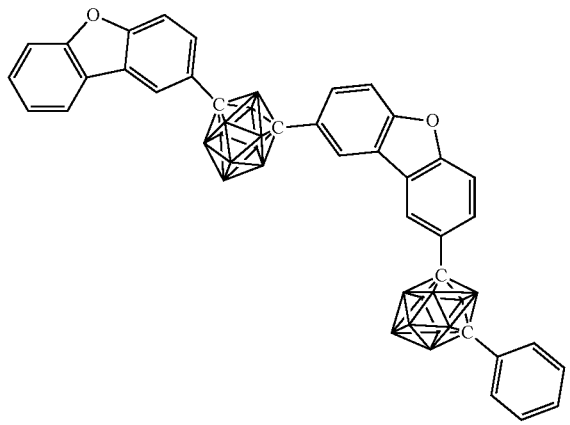
3-38
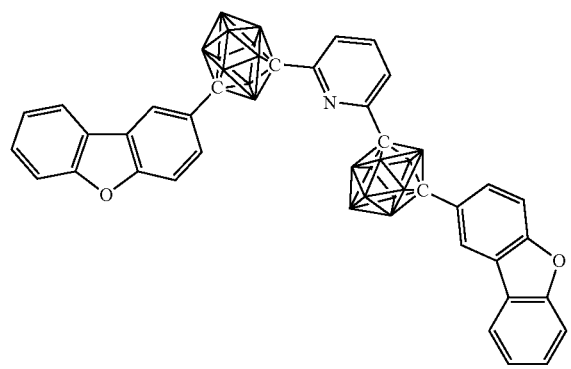
3-39
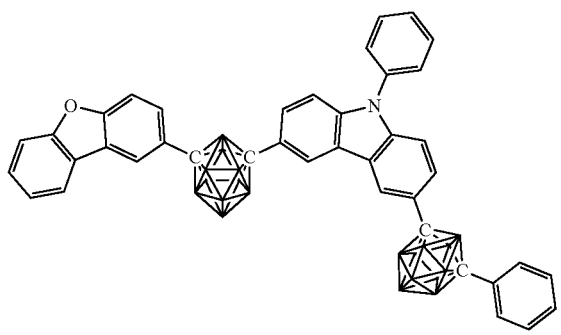
[C44]
3-40
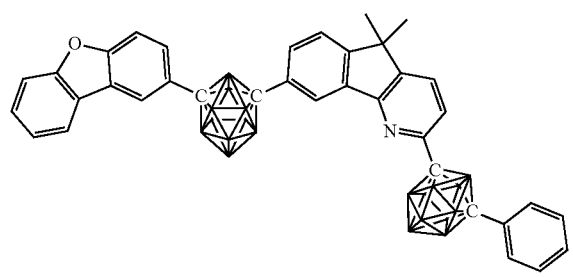
3-41
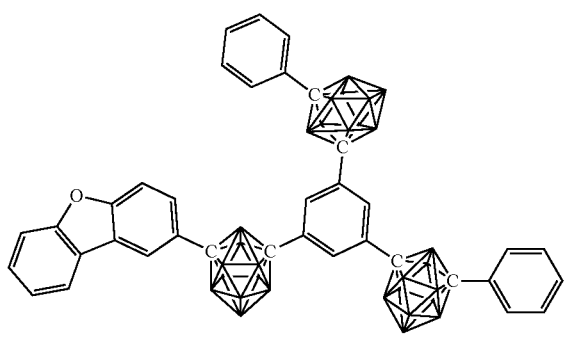
3-42
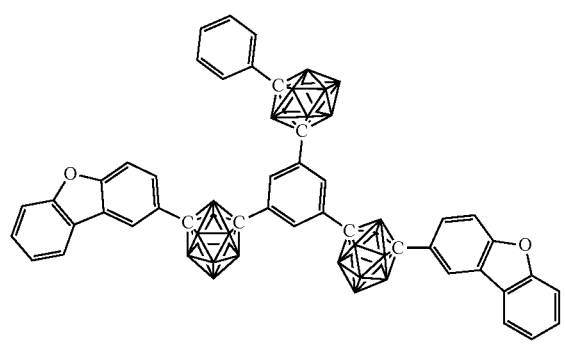
3-43
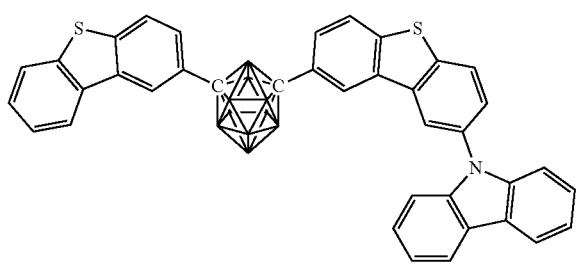

-continued
3-44
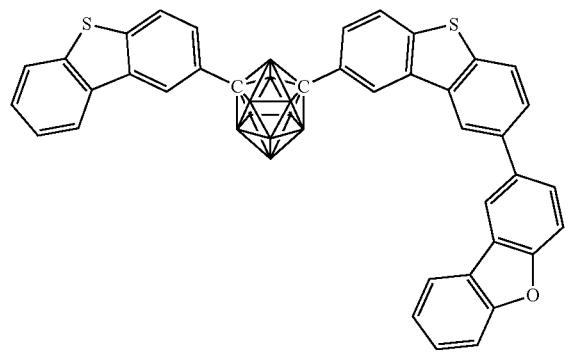
3-45
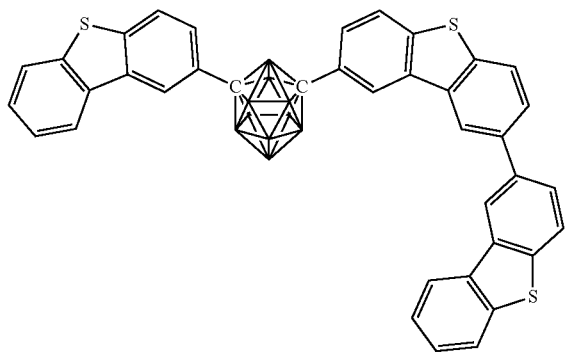
3-46
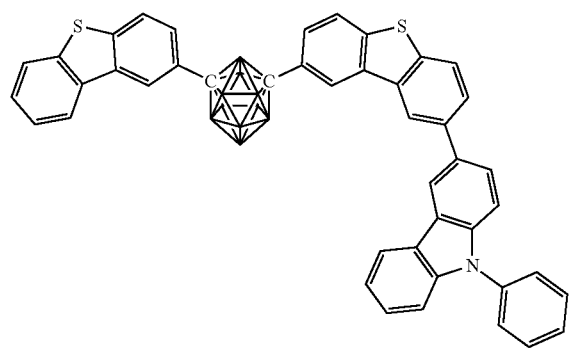
3-47
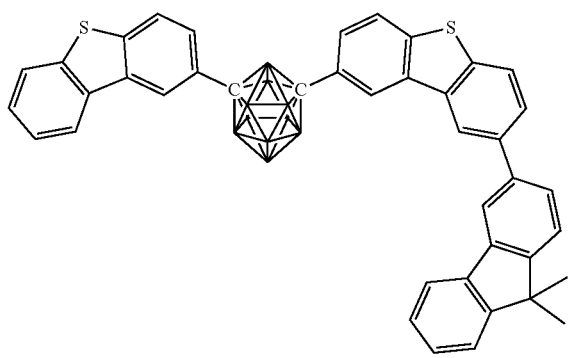
[C45]
3-48
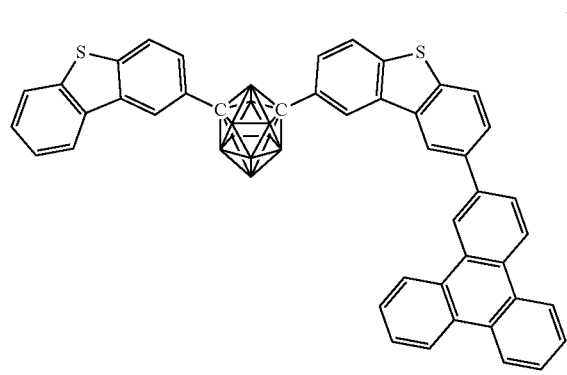
3-49
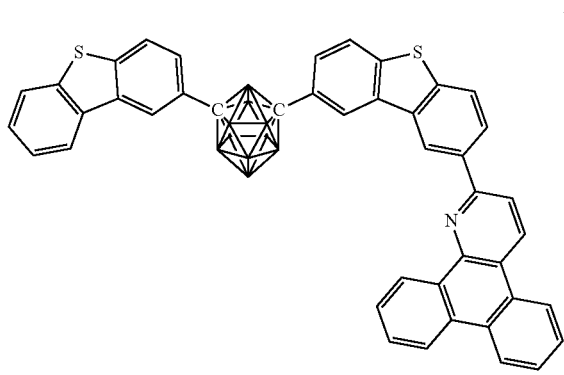
3-50
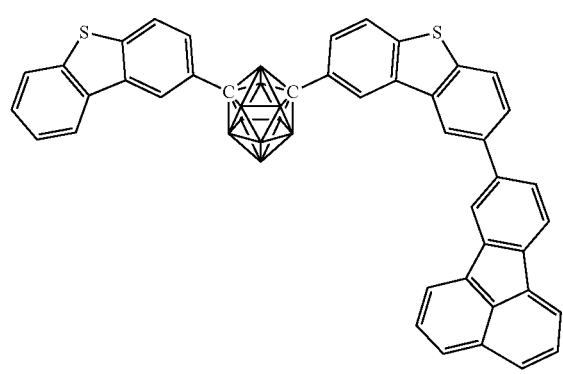
3-51
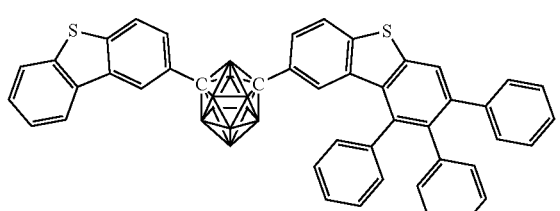

-continued
3-52
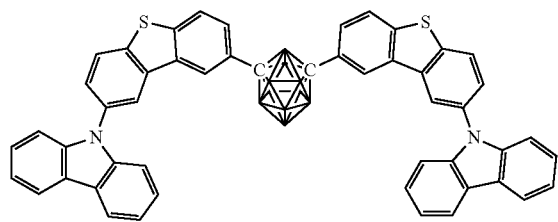
3-53
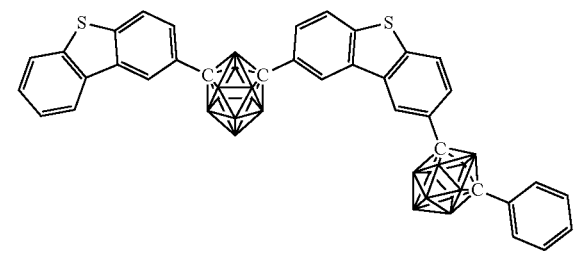
3-54
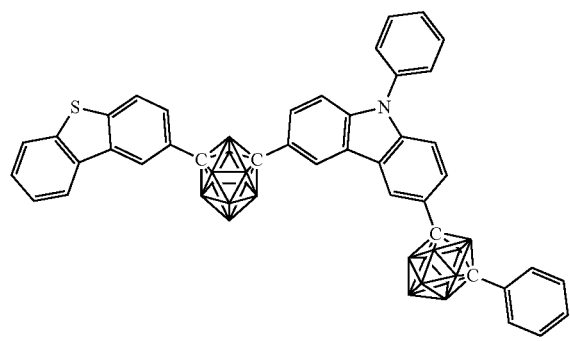
3-55
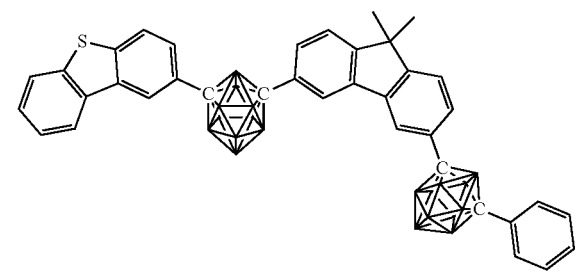
3-56
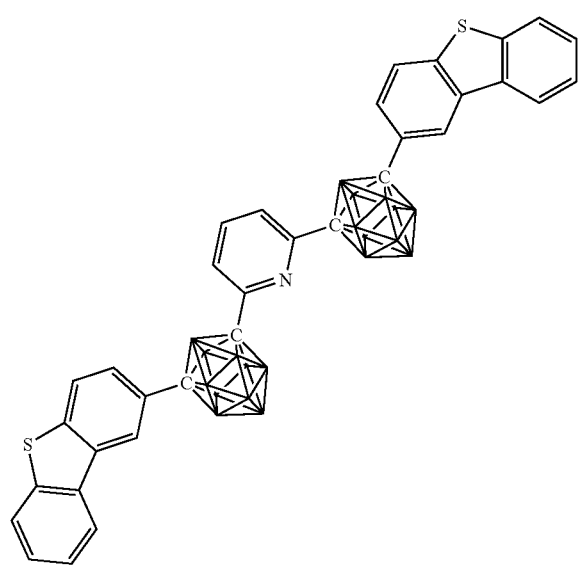

[C46]
3-57
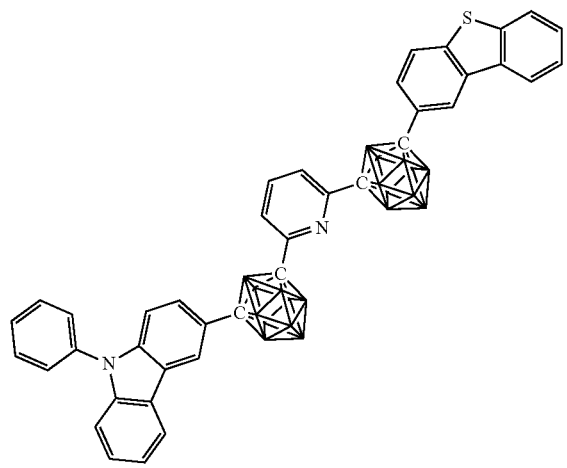
3-58
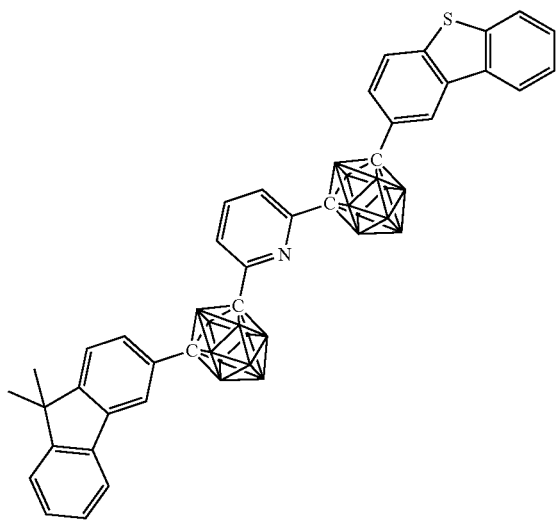
3-59
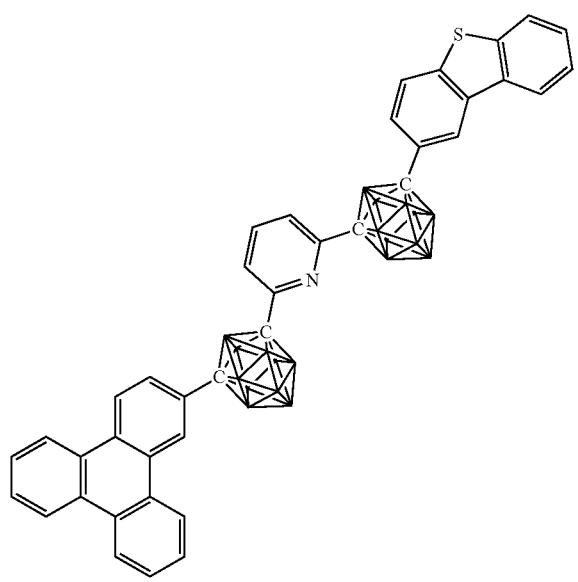
3-60
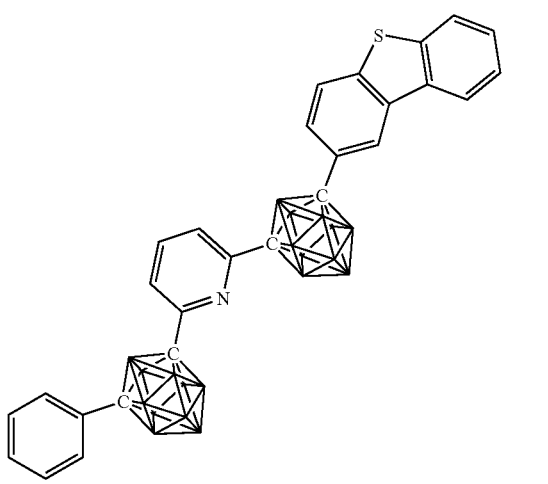

-continued
3-61
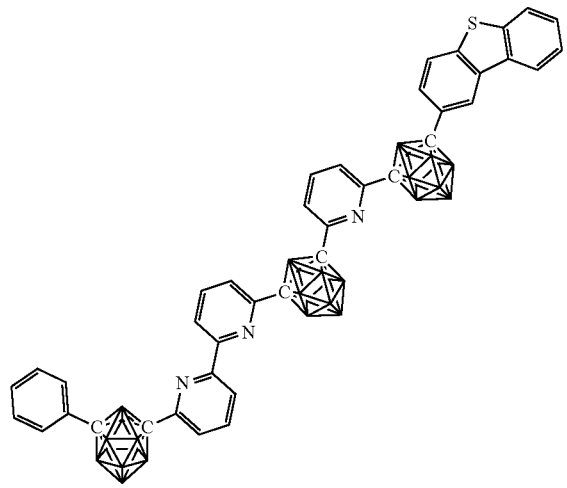
3-62
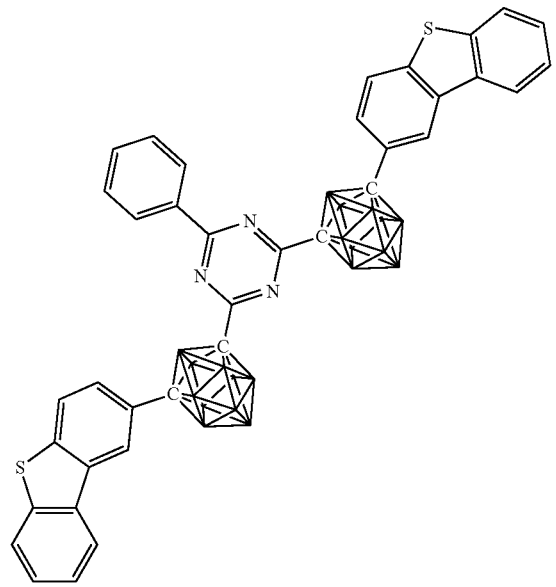
3-63
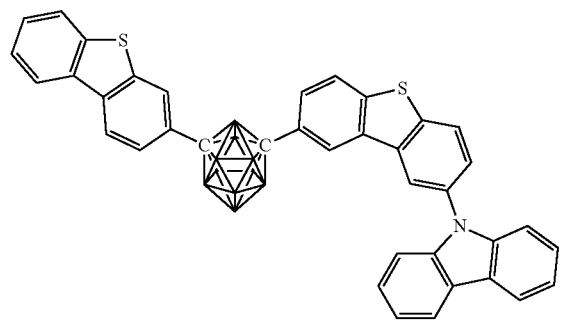
3-64
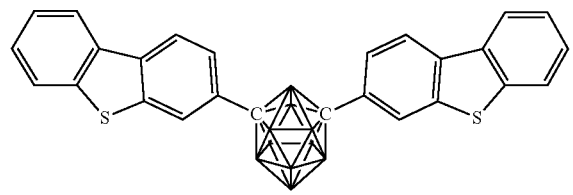
3-65
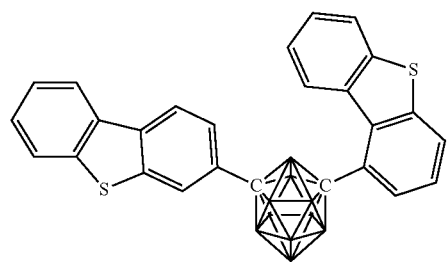
3-66
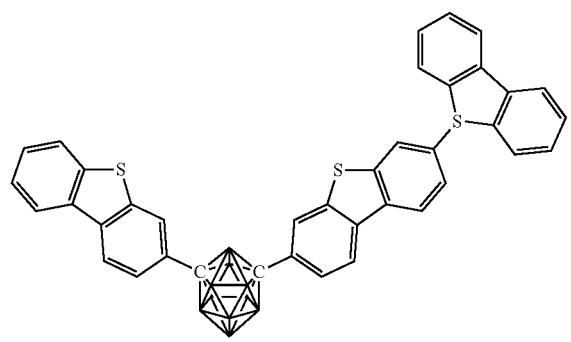

-continued
3-67
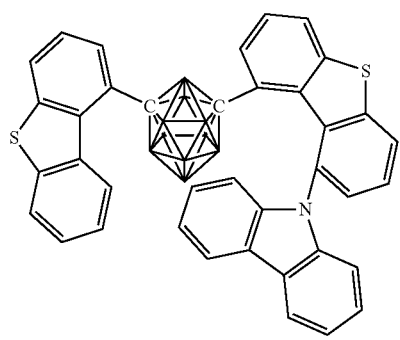
3-68
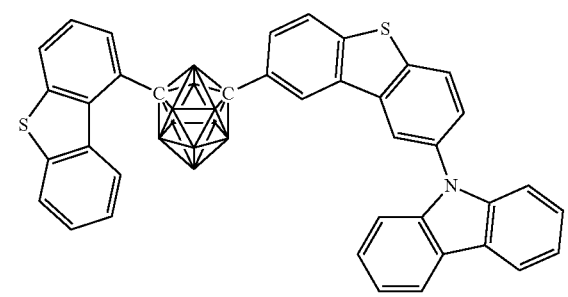
3-69
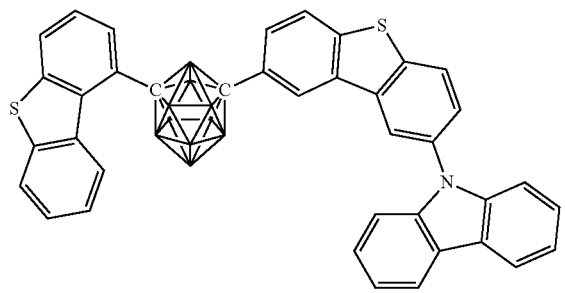
3-70
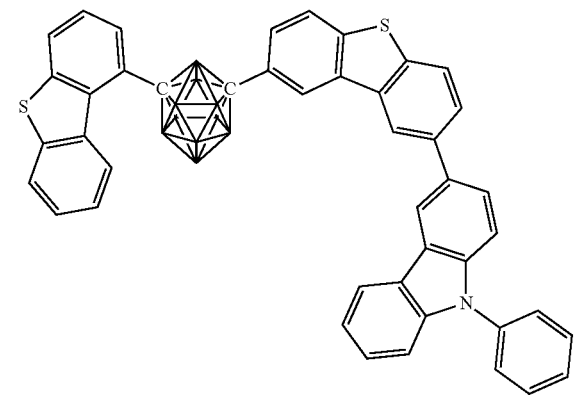
3-71
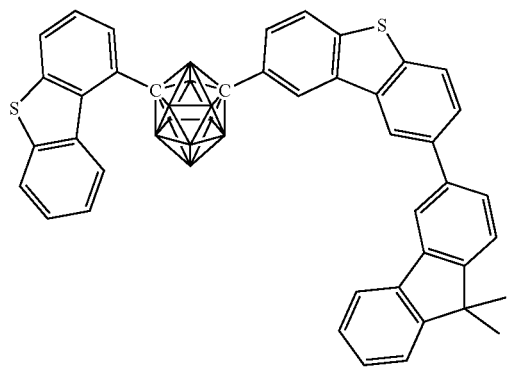
3-72
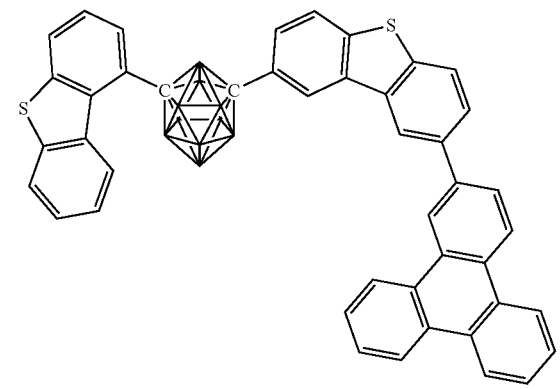
3-73
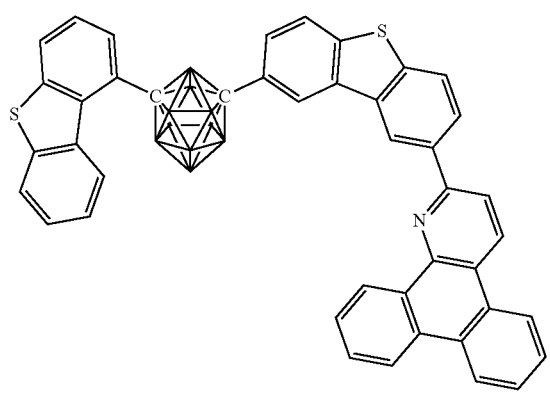
3-74
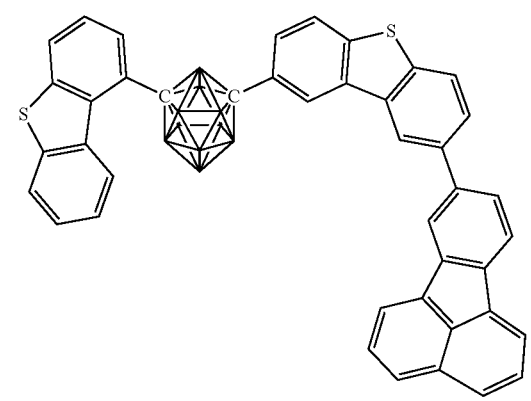

-continued
3-75
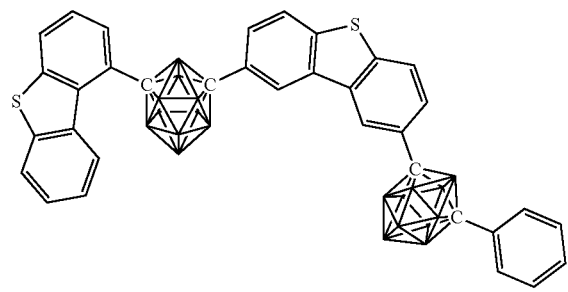
3-76
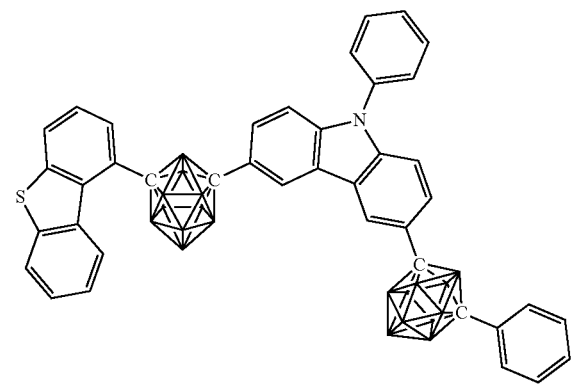
3-77
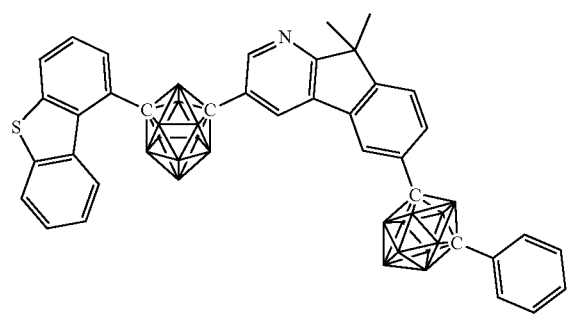
3-78
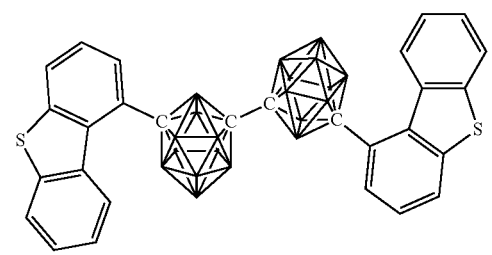
3-79
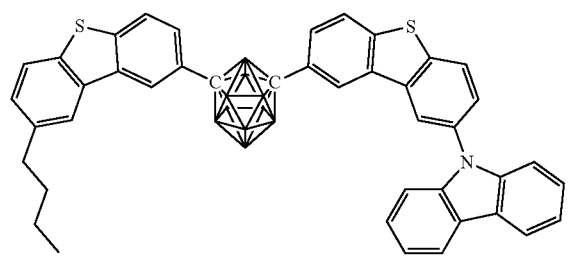
3-80
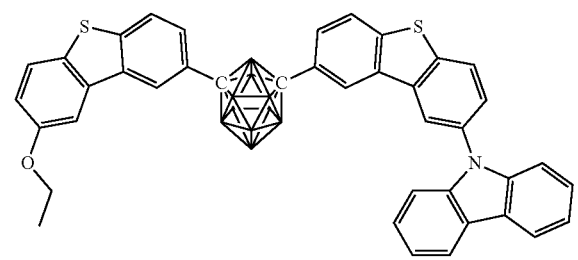
3-81
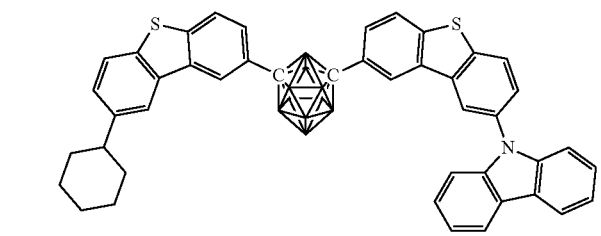
3-82
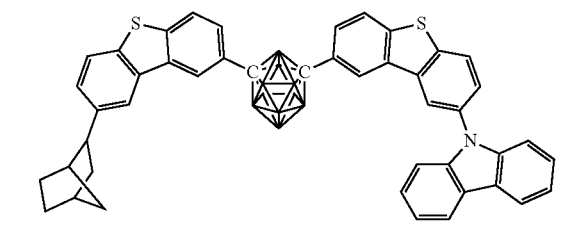

-continued
3-83
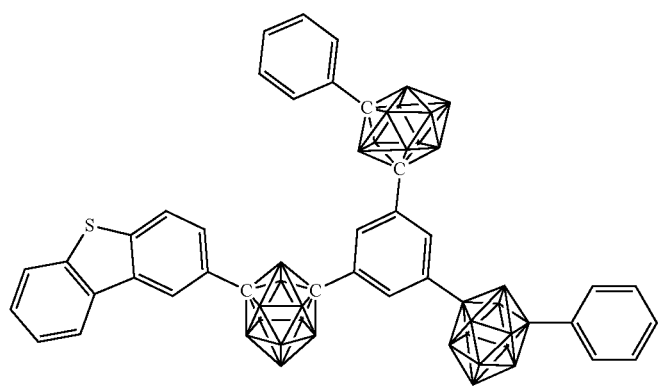
3-84
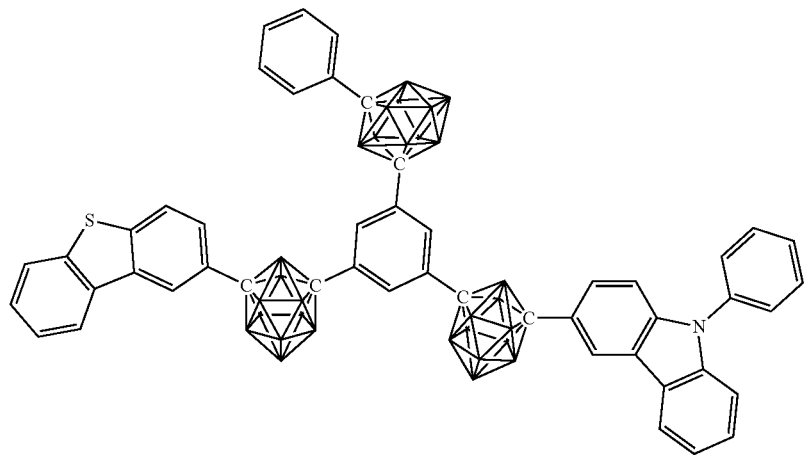
3-85
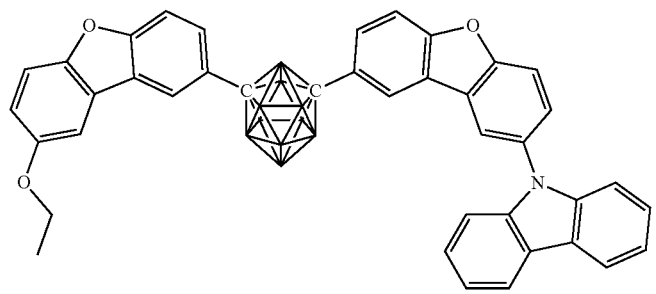
3-86
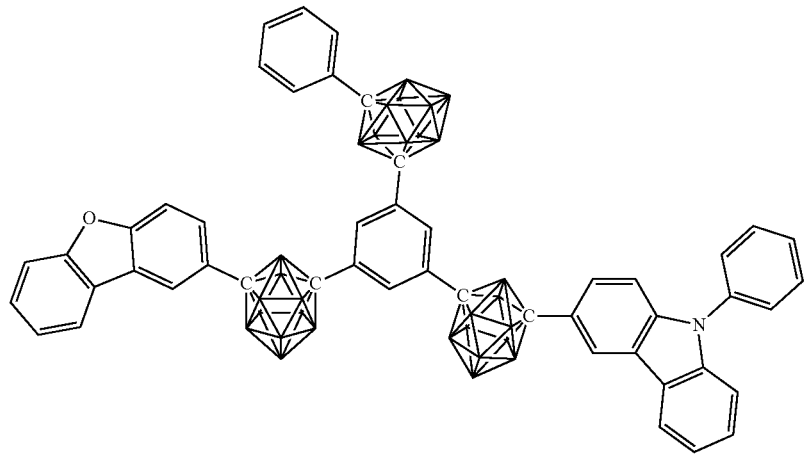

-continued
225
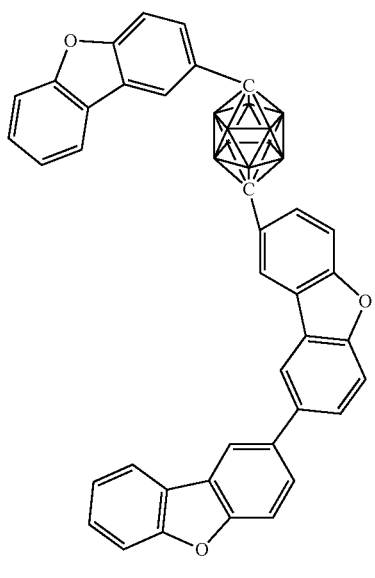
226
3-87
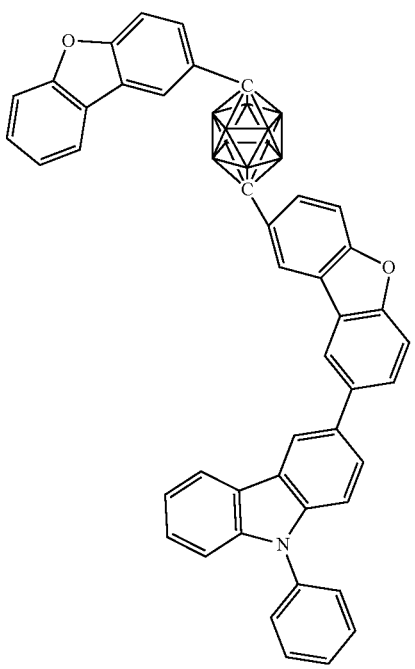
3-88
3-89
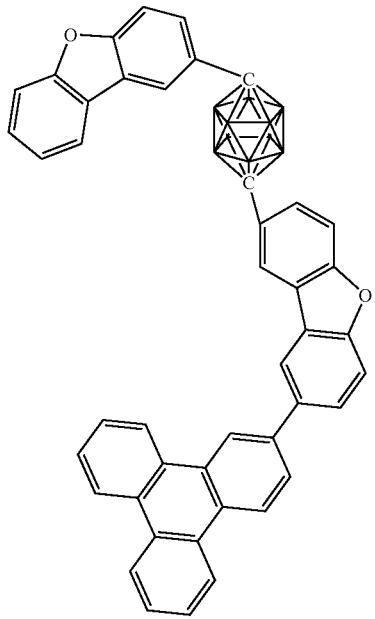
3-90
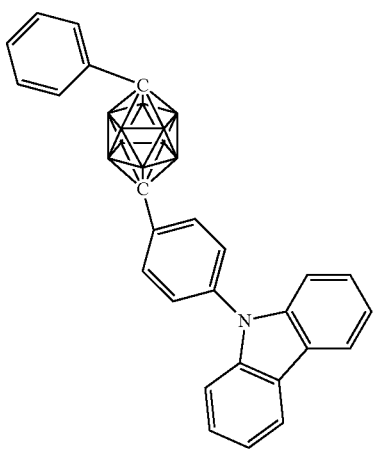

3-91
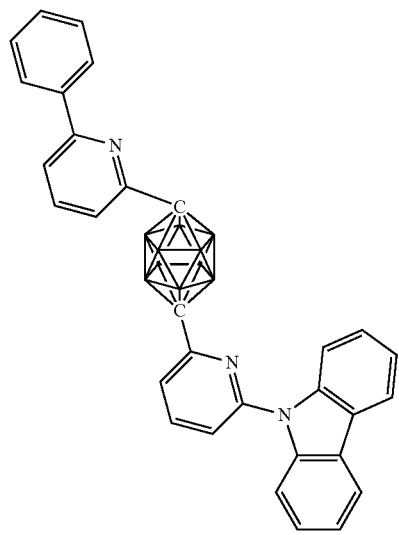
3-92
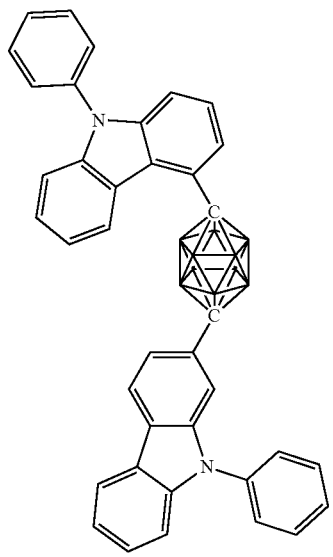
3-93
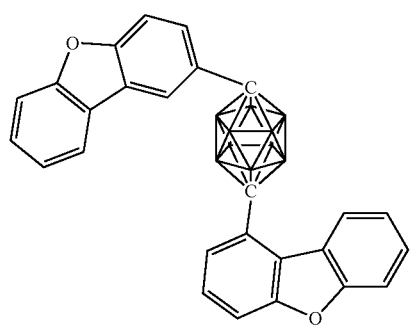
[C49]
3-94
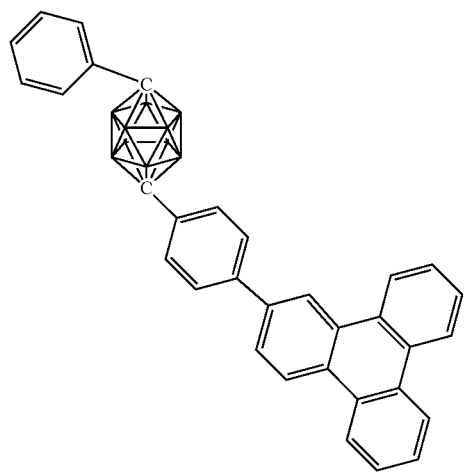
3-95
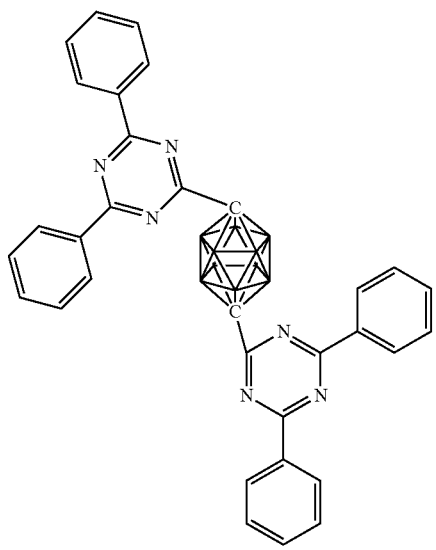

-continued
3-96
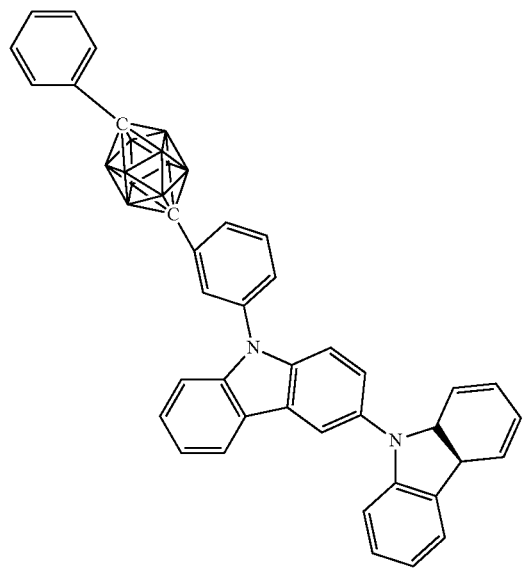
3-97
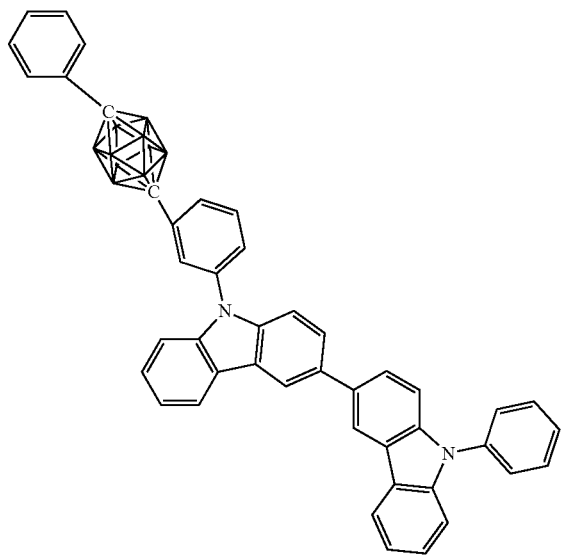
3-98
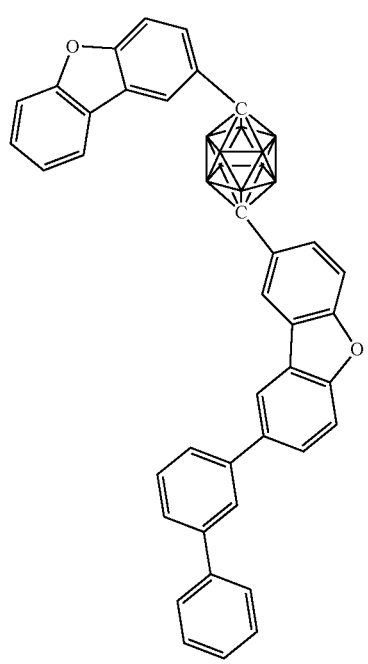
3-99
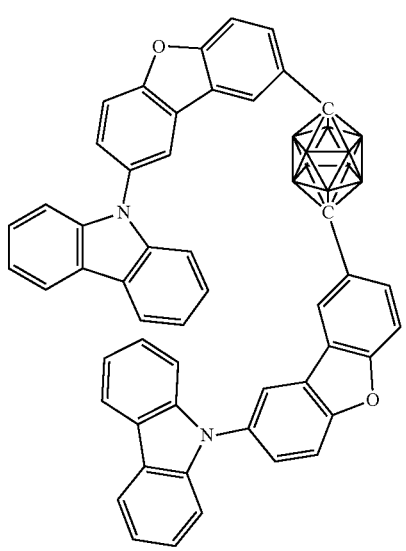

3-100
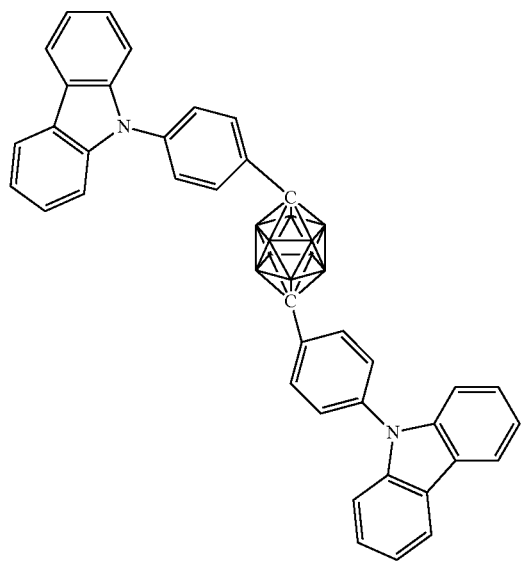
3-101
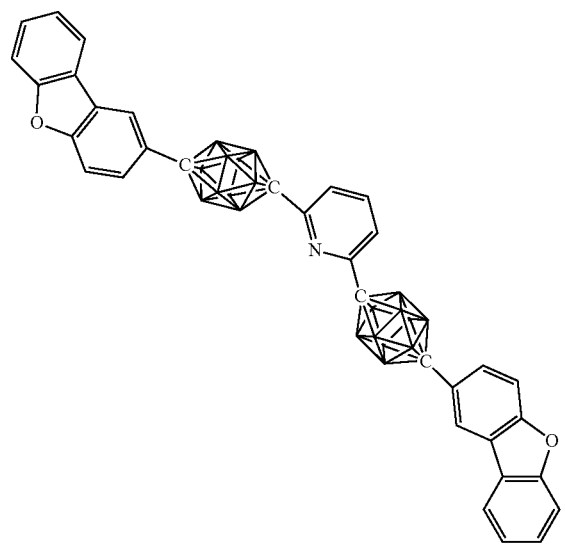
3-102
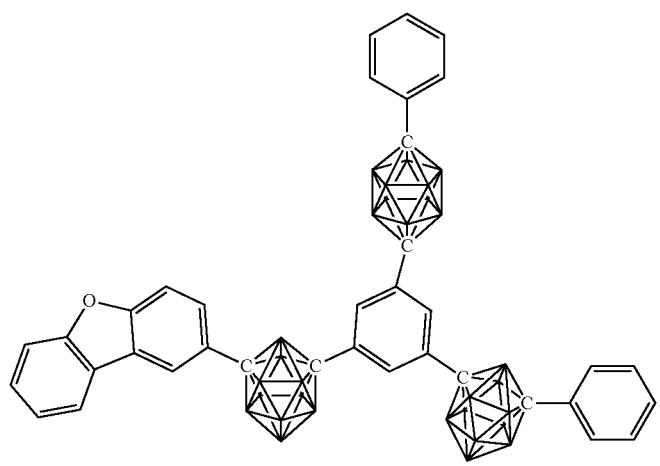

[C50]
3-103
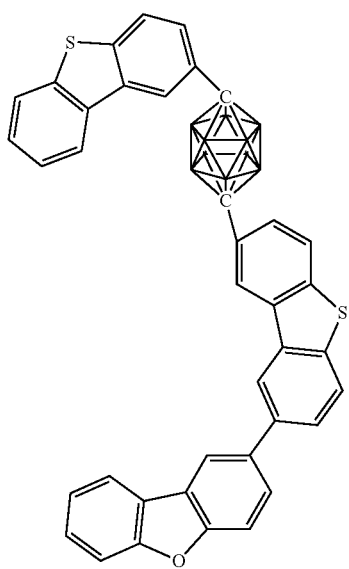
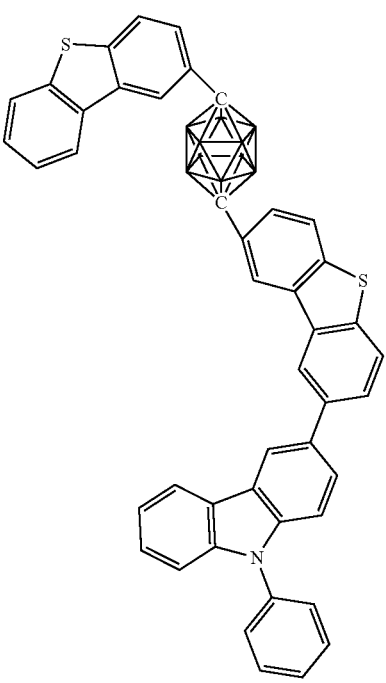
3-104
3-105
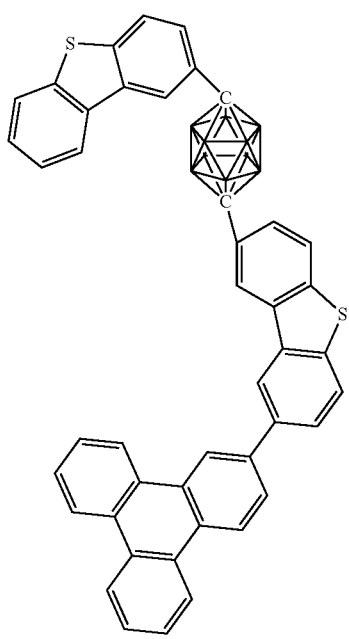
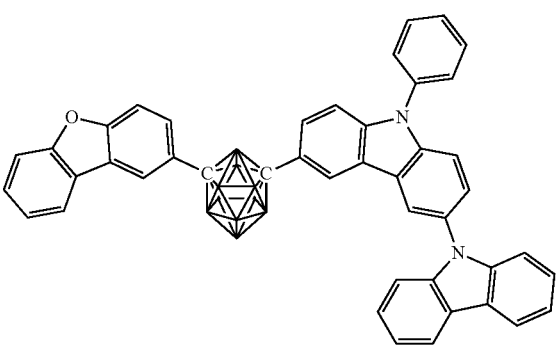
3-106

3-107
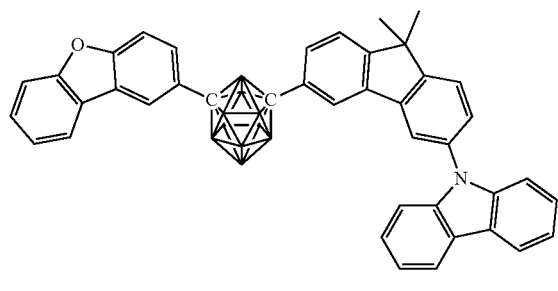
3-108
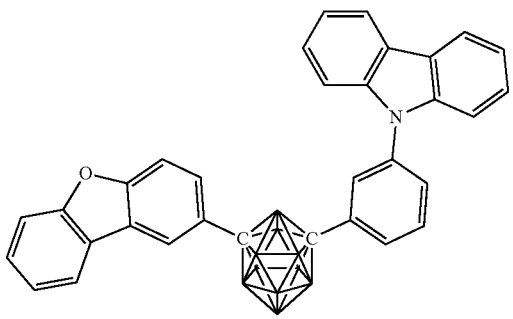
3-109
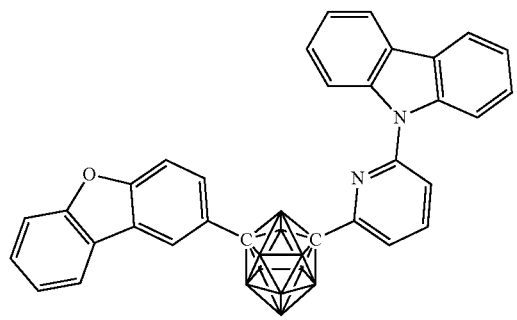
3-110
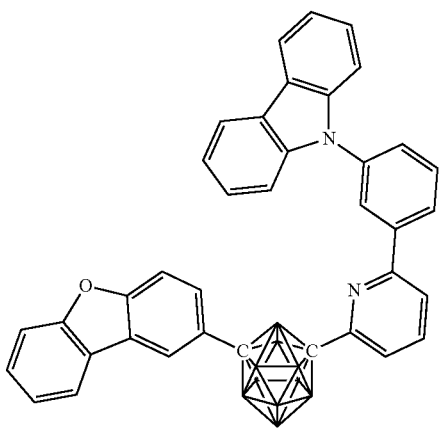
3-111
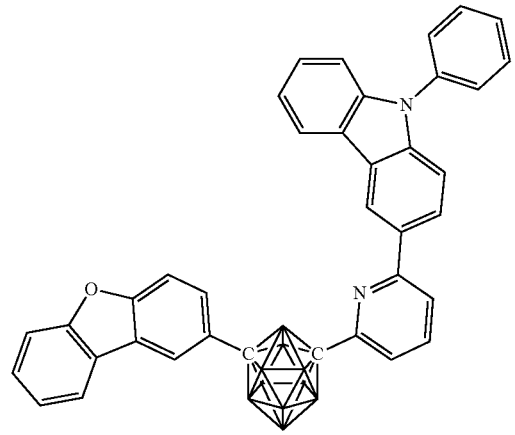
3-112
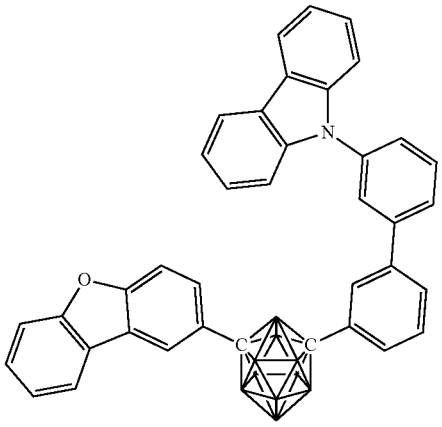

-continued
3-113
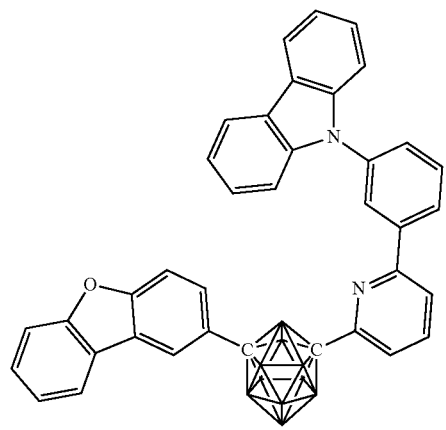
[C51]
3-114
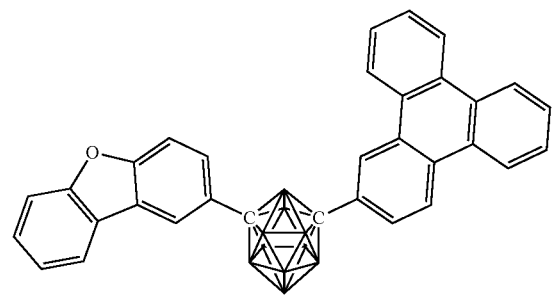
3-115
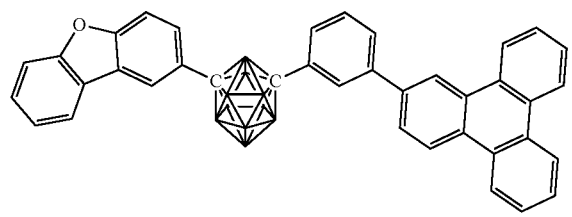
3-116
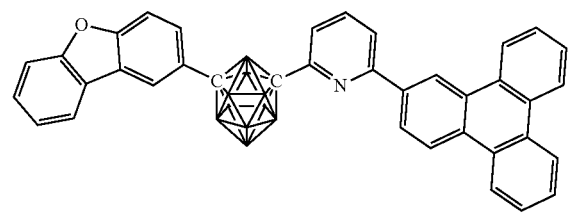
3-117
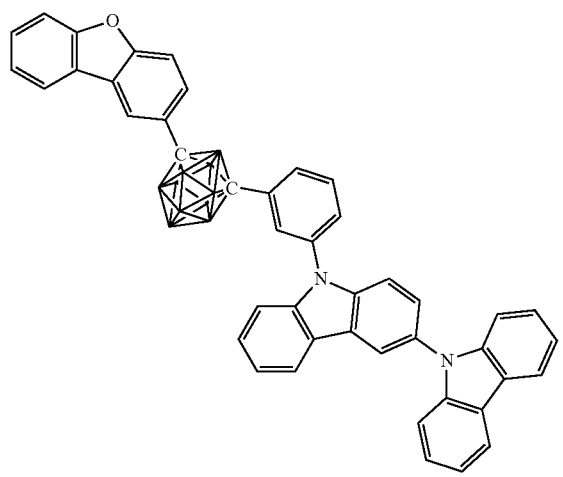
3-118
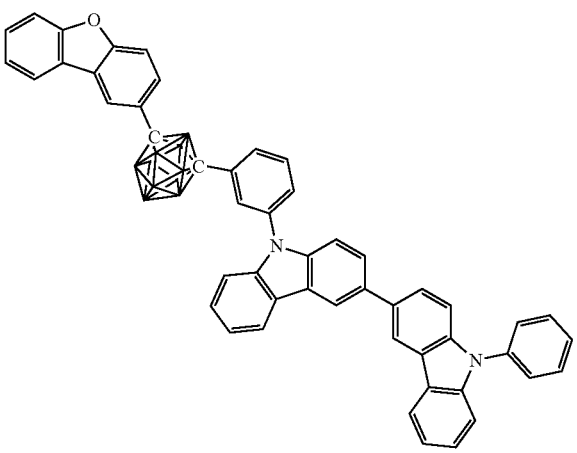
3-119
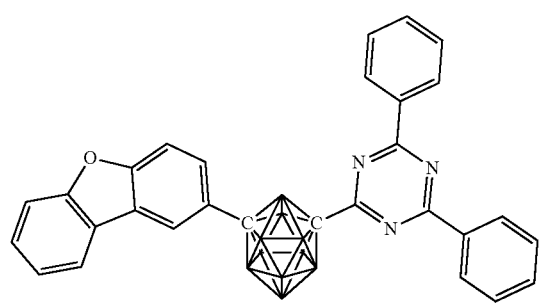
3-120
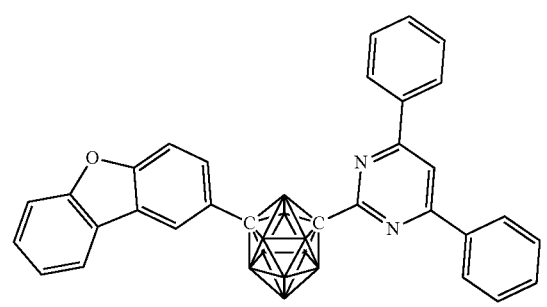

-continued
3-121
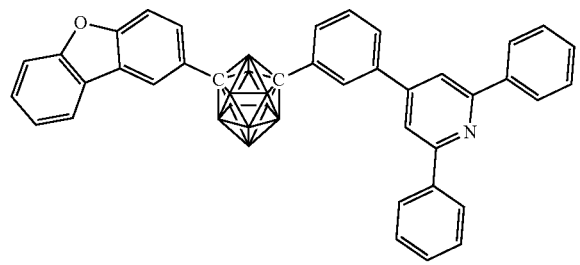
3-122
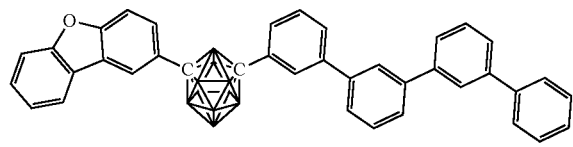
3-123
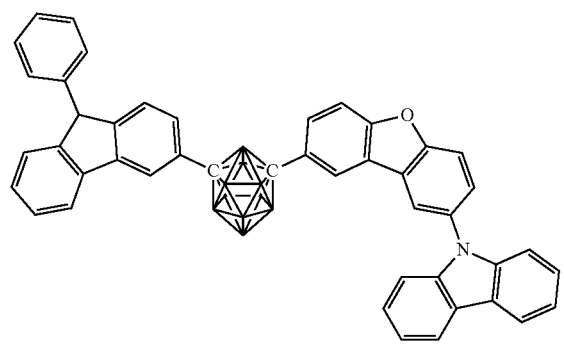
3-124
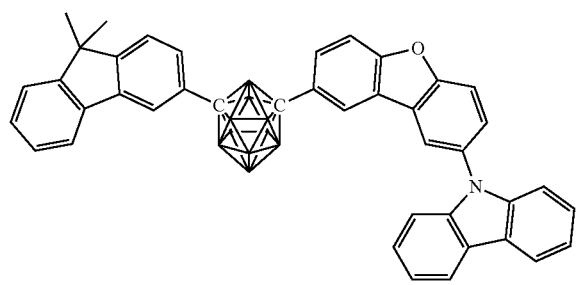
3-125
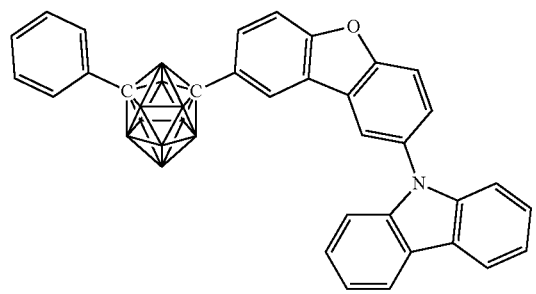
3-126
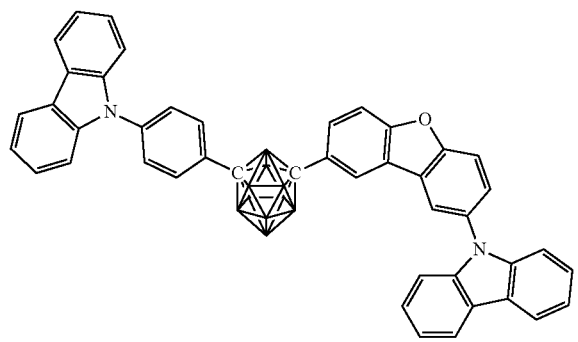
3-127
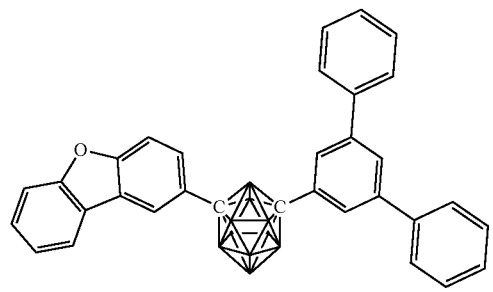
3-128
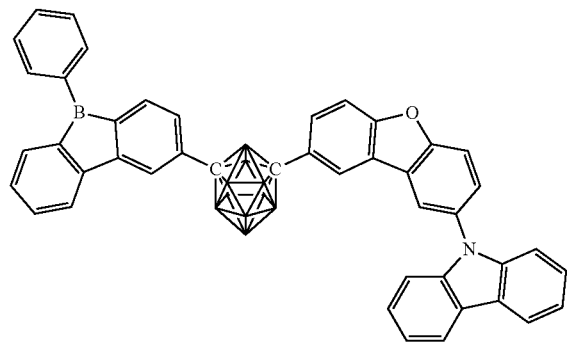

-continued
[52]
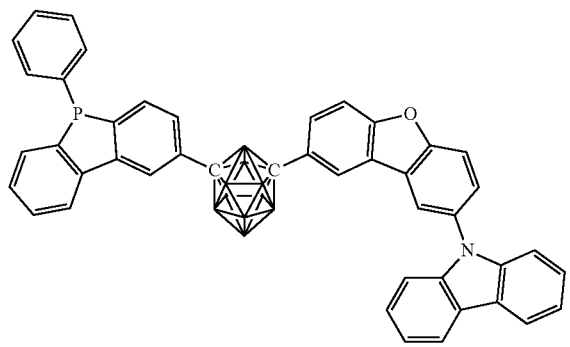
3-129
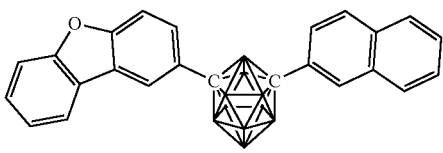
3-130
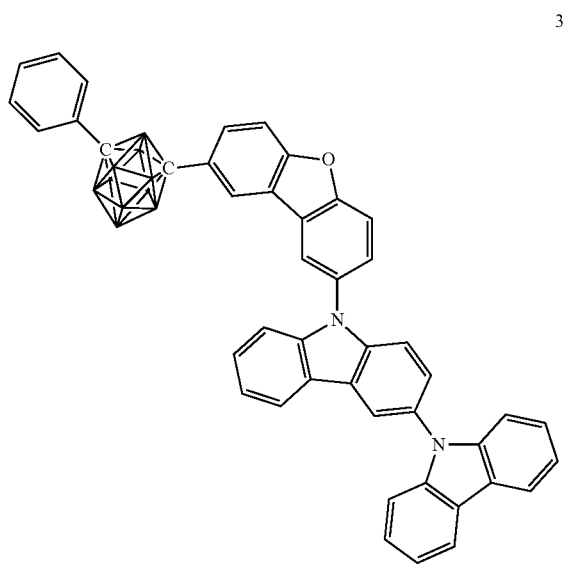
3-131
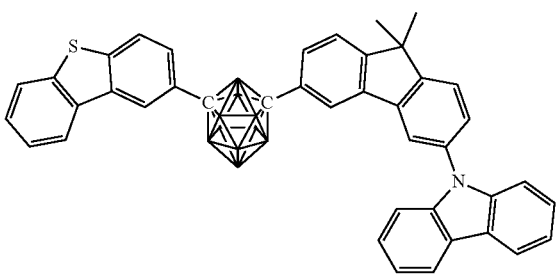
3-132
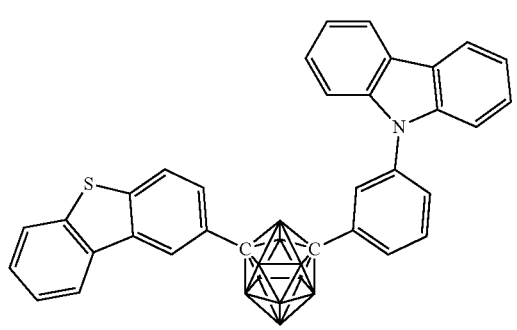
3-133
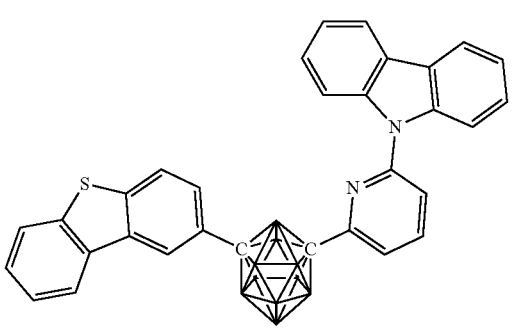
3-134

-continued
3-135
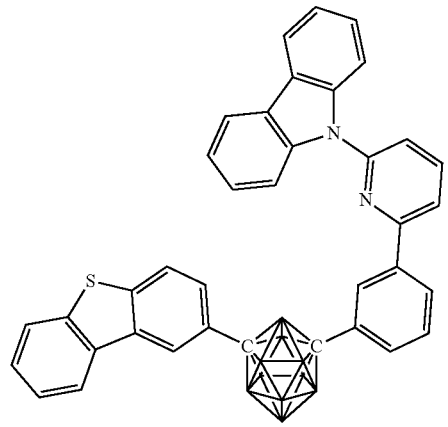
3-136
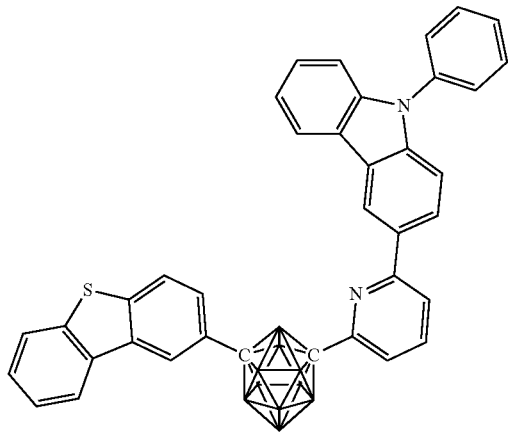
3-137
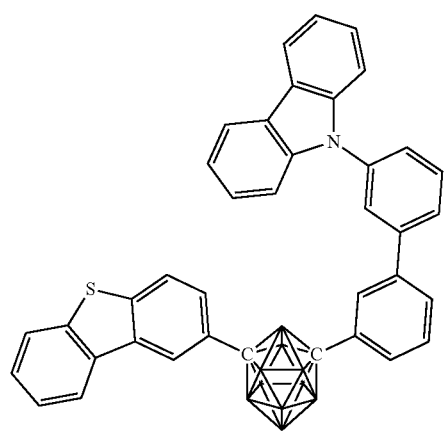
3-138
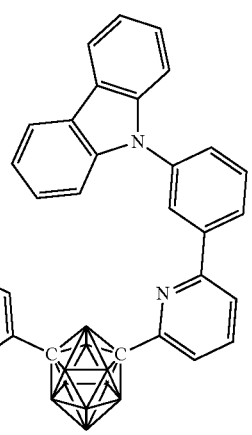
3-139
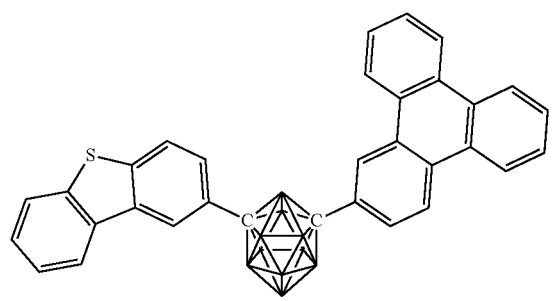
3-140
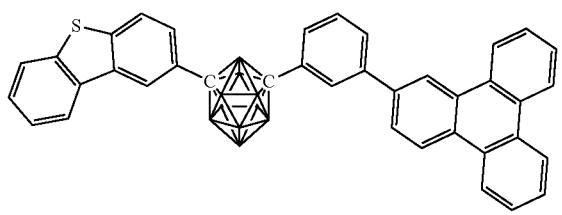
3-141
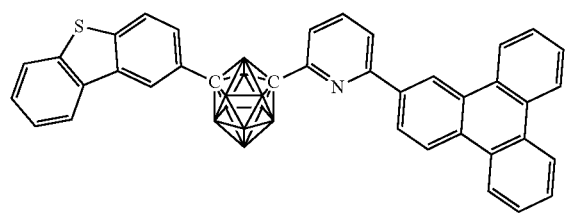
3-142
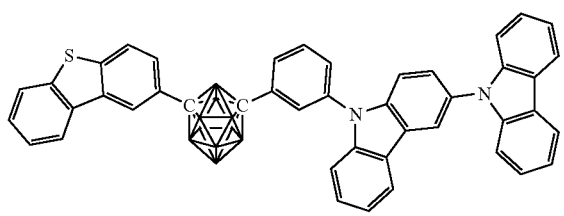

-continued
3-143
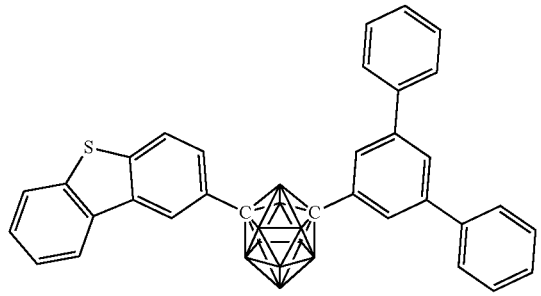
[C53]
3-144
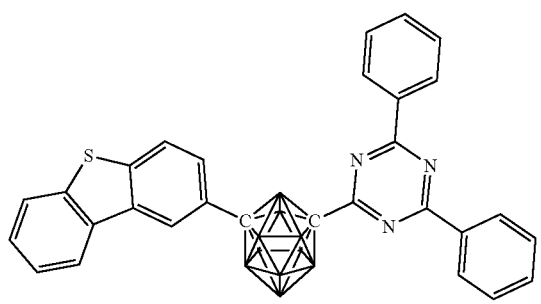
3-145
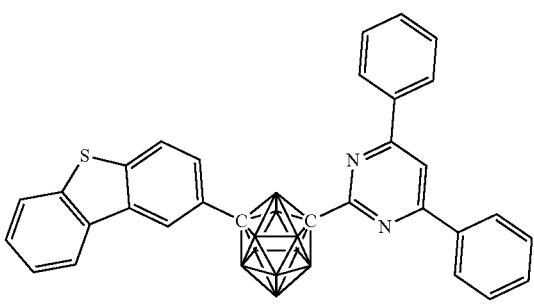
3-146
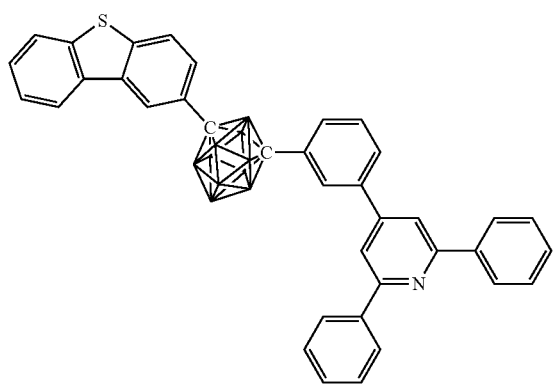
3-147
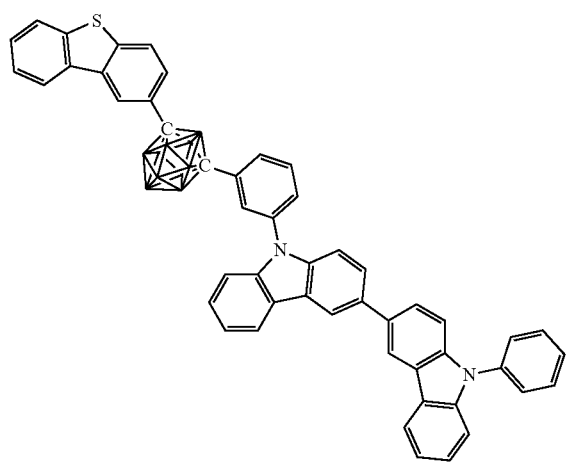
3-148
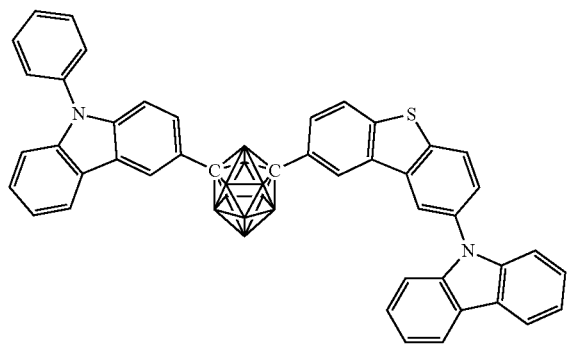
3-149
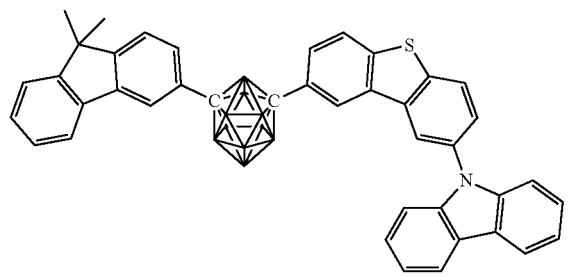

-continued
3-150
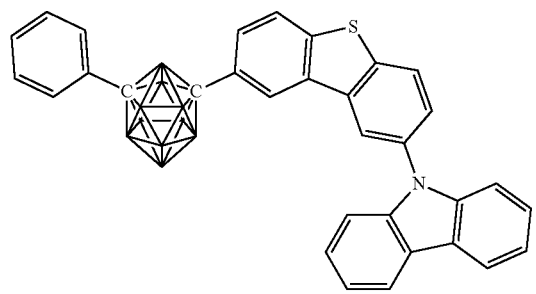
3-151
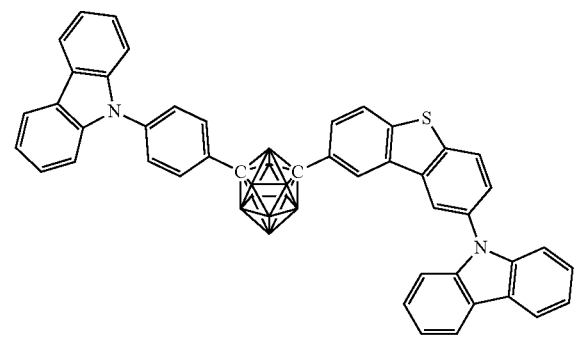
3-151
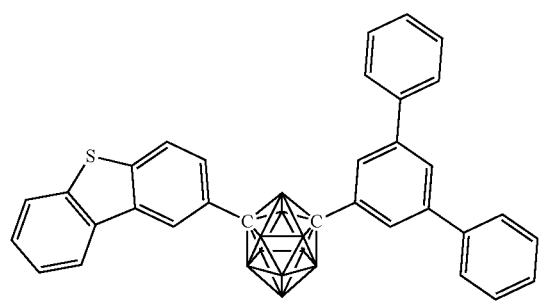
3-152
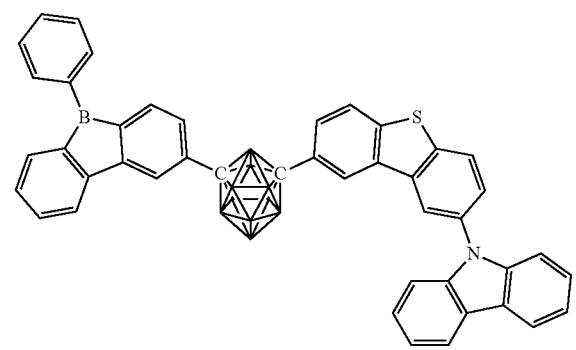
3-153
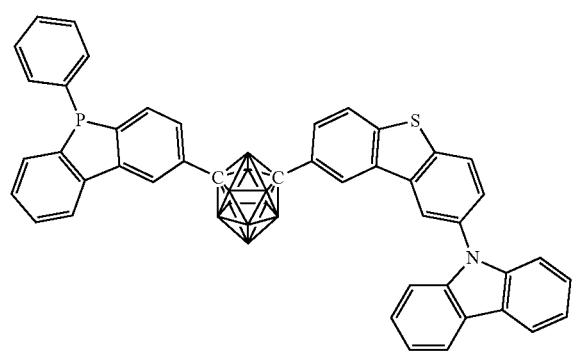
[C54]
3-154
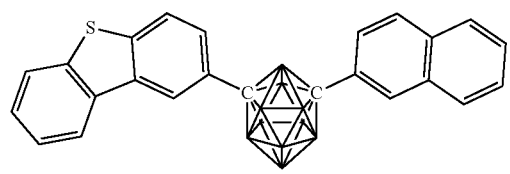
3-155
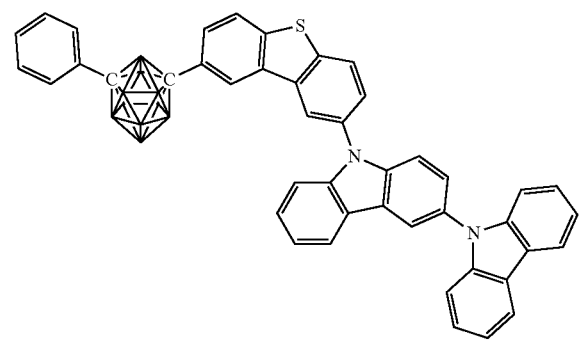

-continued
3-156
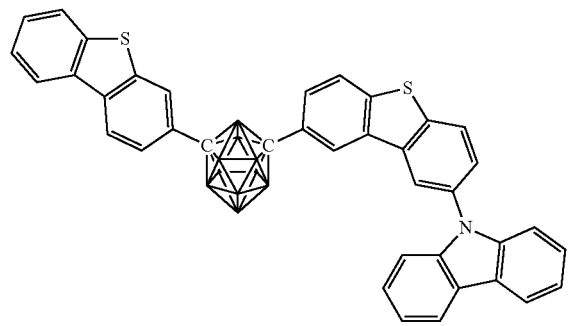
3-157
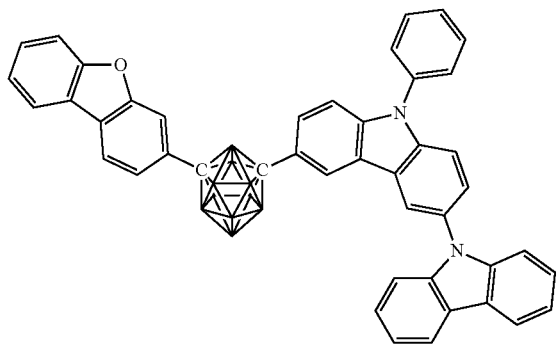
3-158
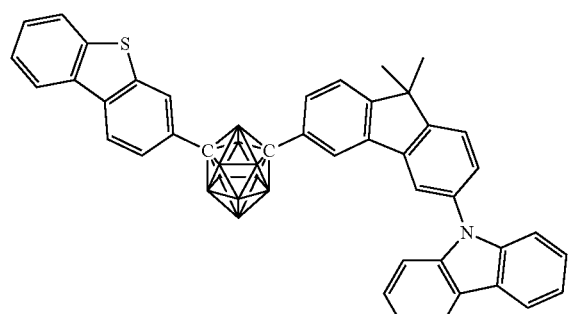
3-159
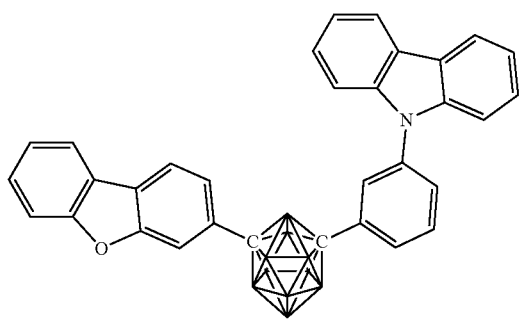
3-160
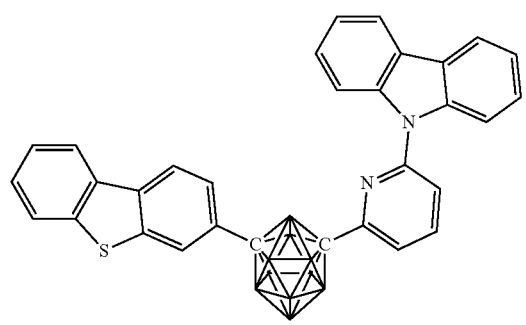
3-161
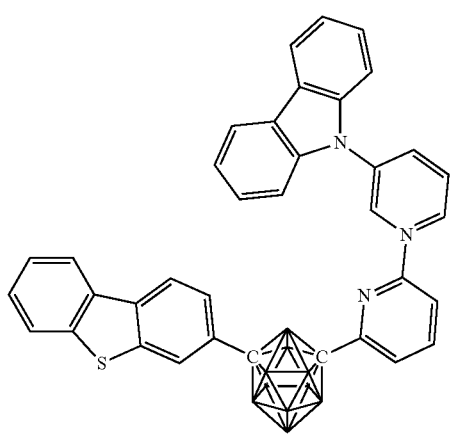
3-162
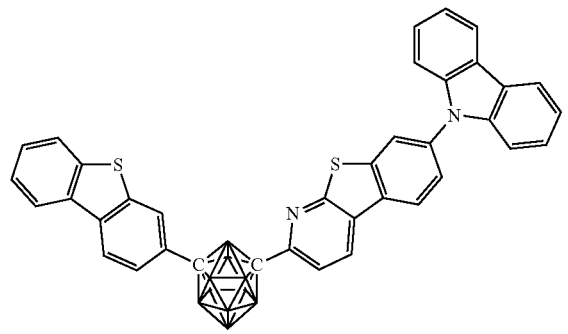
3-163
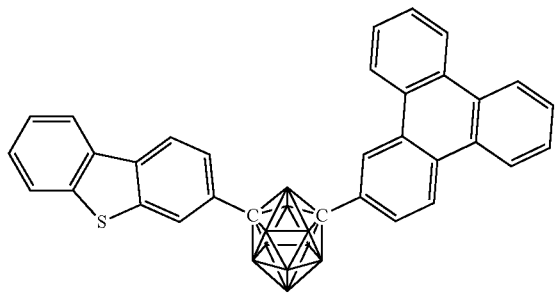

3-164
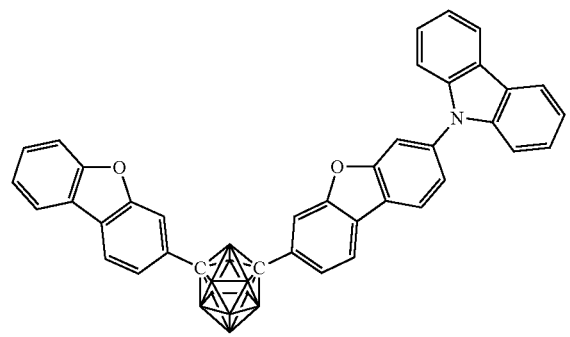
3-165
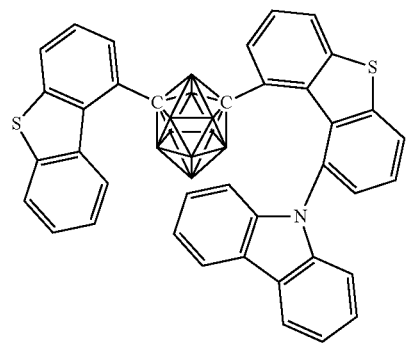
3-166
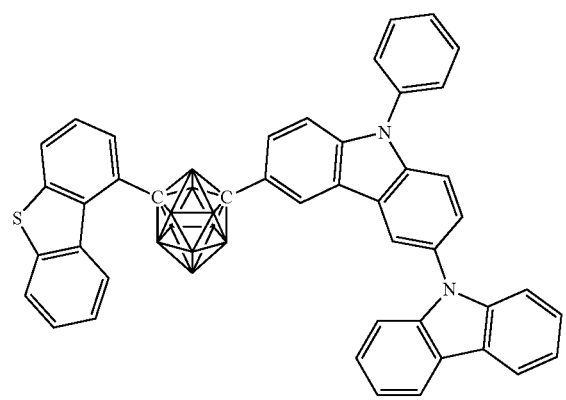
3-167
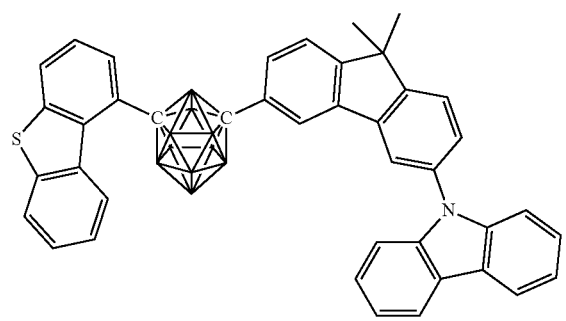
[C55]
3-168
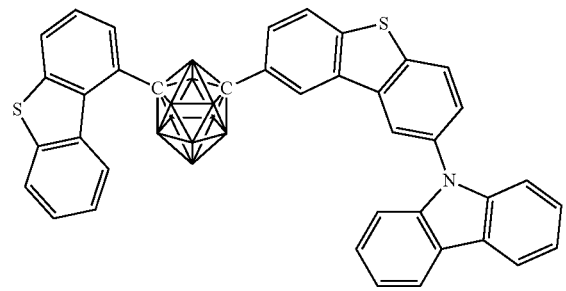
3-169
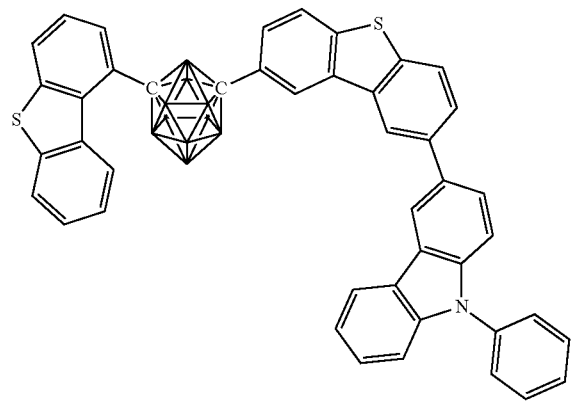
3-170
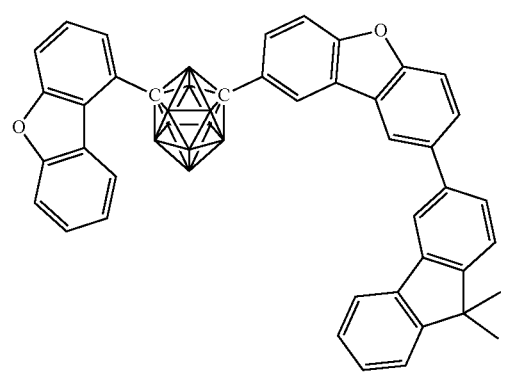
3-171
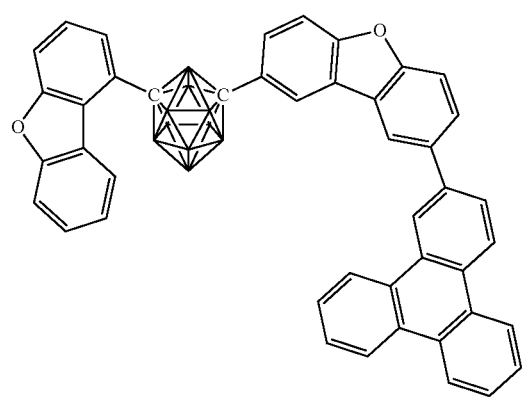

-continued
3-172
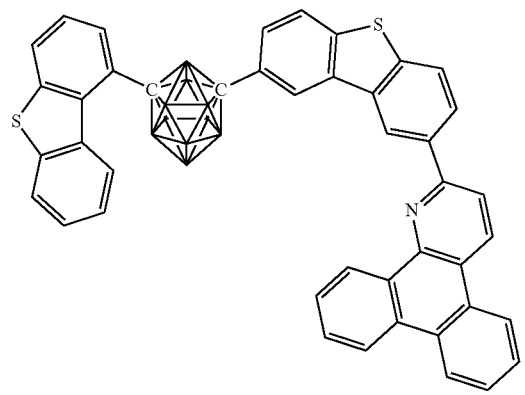
3-173
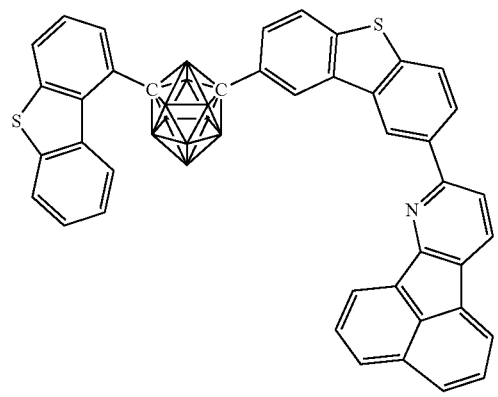
3-174
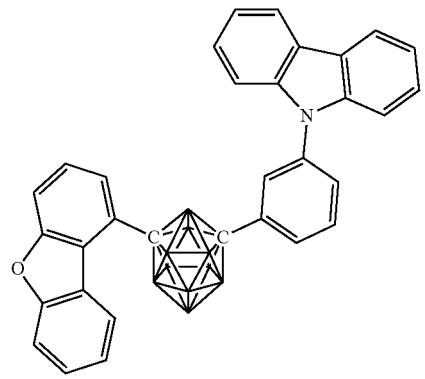
3-175
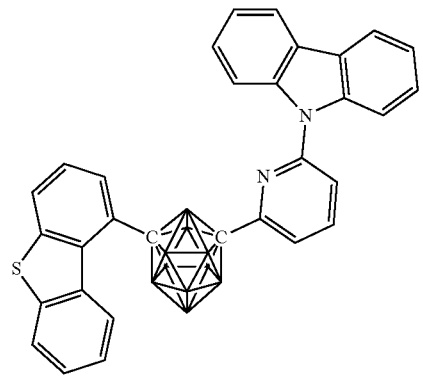
3-176
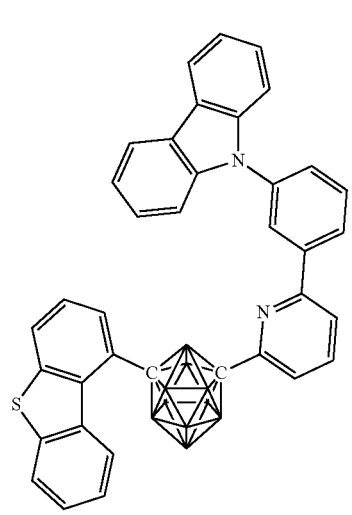
3-177
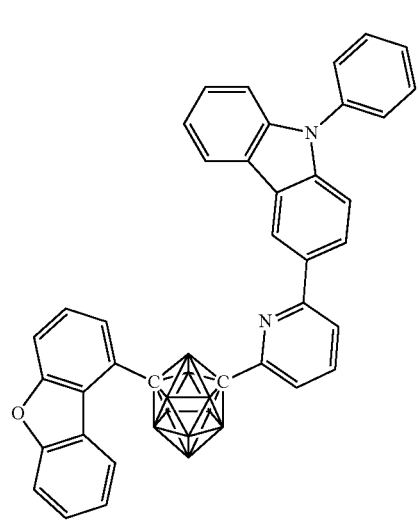

-continued
3-178
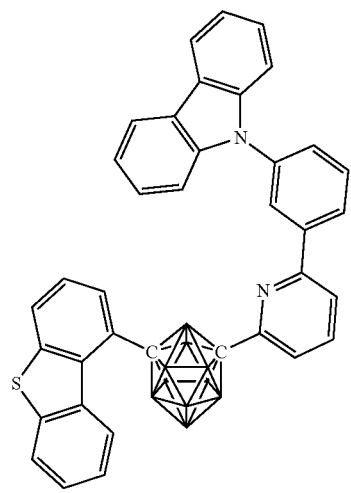
3-179
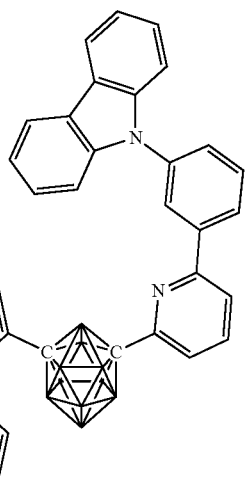
3-180
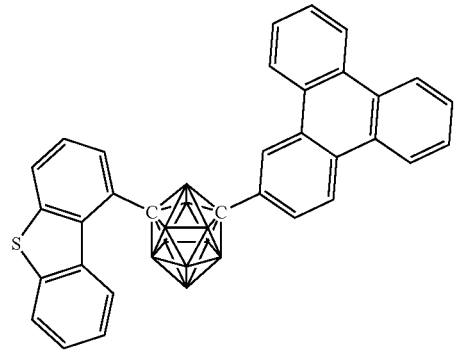
3-181
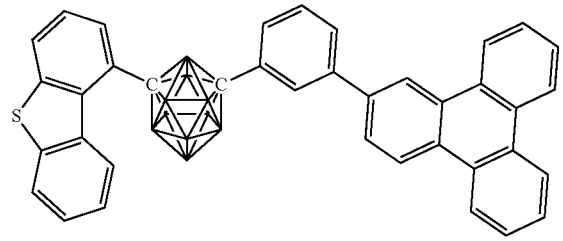
3-182
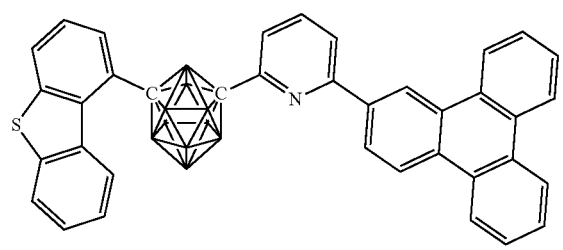
[C56]
3-183
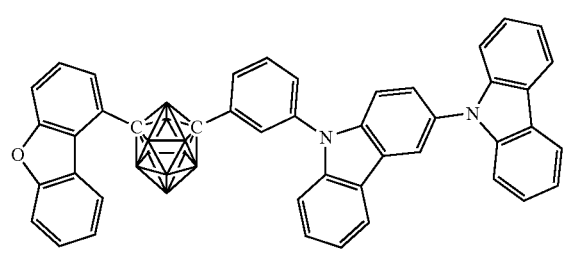
3-184
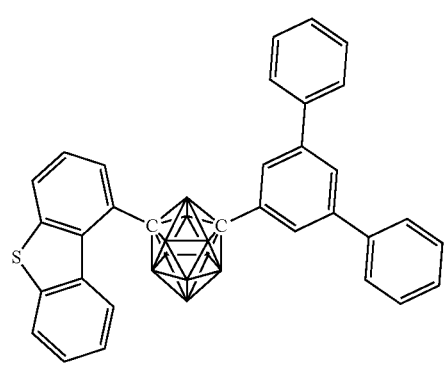

-continued 3-185

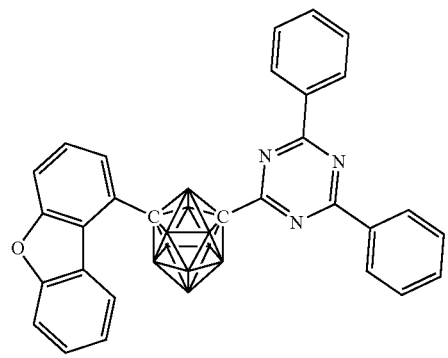

3-186

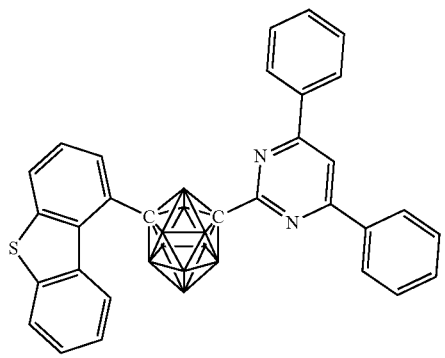

3-187

3-188

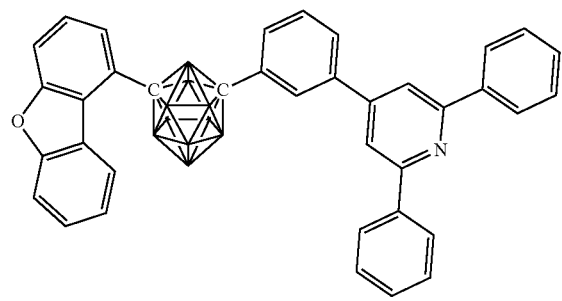

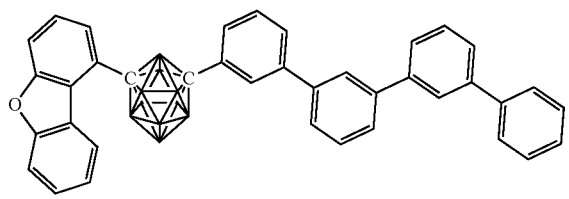

3-189

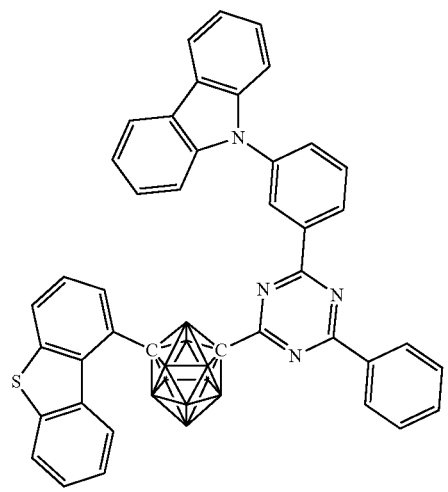

The organic EL device of the present invention contains a mixture of a compound represented by general formula (1) and a compound represented by general formula (2) in at least one organic layer of the organic EL device. Although this mixture may be used in any organic layer since it has superior durability with respect to a charge, it is preferably contained in any of a light emitting layer, electron transport layer and hole blocking layer, and is particularly preferably contained in a light emitting layer.

In the case using in a light emitting layer, although the above-mentioned mixture may also be used as a luminescent dopant material, other phosphorescent dopant materials, fluorescent dopant materials or thermally activated delayed fluorescent dopant materials are preferably used for the luminescent dopant material, and a mixture thereof is preferably used for the host material. In particular, an organic metal complex containing at least one metal selected from ruthenium, rhodium, palladium, silver, rhenium, osmium, iridium, platinum and gold is a preferable aspect thereof.

The above-mentioned mixture containing at least two compounds may be vapor-deposited using a single deposition source by mixing prior to production of the device, or may be mixed at the time of producing the device by a procedure such as co-depositing using a plurality of deposition sources.

In addition, the aforementioned mixture may be used by depositing on a substrate and the like using a wet process such as spin coating or ink jet printing instead of using a dry process using a deposition source.

Next, although an explanation is provided of the structure of the organic EL device of the present invention with reference to the drawing, the structure of the organic EL device of the present invention is not limited to that shown in the drawing.

(1) Configuration of Organic EL Device

FIG. 1 is a cross-sectional view schematically indicating an example of the structure of an ordinary organic EL device, and reference symbol 1 indicates a substrate, reference symbol 2 an anode, reference symbol 3 a hole injection layer, reference symbol 4 a hole transport layer, reference symbol 5 a light emitting layer, reference symbol 6 an electron transport layer, reference symbol 7 an electron injection layer and reference symbol 8 a cathode. Although the organic EL device of the present invention has an anode, light emitting layer, electron transport layer and cathode as essential layers thereof, other layers may be provided as necessary. Although examples of other layers include a hole injection/transport layer, electron blocking layer and hole blocking layer, these other layers are not limited thereto. Furthermore, the hole injection/transport layer refers to a hole injection layer, hole transport layer or both.

(2) Substrate

The substrate 1 serves as a support for the organic electroluminescent device, and a quartz or glass plate, metal plate, metal foil, plastic film or plastic sheet is used. In particular, a glass plate or smooth, clear synthetic resin sheet such as polyester, polymethacrylate, polycarbonate or polysulfone is preferable. In the case of using a synthetic resin sheet, it is necessary to pay attention gas impermeability. If a gas impermeability of the substrate is excessively low, the organic electroluminescent device may be deteriorated by outside air that has passed over the substrate, thereby making this undesirable. Consequently, one method preferably used to ensure gas impermeability consists of providing a dense silicon oxide film on at least one side of the synthetic resin sheet.

(3) Anode

The anode 2 is provided on the substrate 1 and fulfills the role of injecting holes into the hole transport layer. This anode is normally composed of a metal such as aluminum, gold, silver, nickel, palladium or platinum, indium and/or tin oxide, a metal oxide such as an oxide of indium and/or zinc, a metal halide such as copper iodide, carbon black, or an electrically conductive polymer such as poly(3-methylthiophene), polypyrrole or polyaniline. Formation of the anode is normally frequently carried out by a method such as sputtering or vacuum deposition. In addition, in the case of fine particles of a metal such as silver, fine particles of copper iodide, carbon black, fine particles of an electrically conductive metal oxide or fine particles of an electrically conductive polymer, the anode can be formed by dispersing in a suitable binder resin solution and coating onto a substrate. Moreover, in the case of an electrically conductive polymer, an anode can be formed by forming a thin film directly on a substrate by electrolytic polymerization or by coating an electrically conductive polymer on the substrate 1. The anode can also be formed by laminating different substances. The thickness of the anode varies according to the required transparency. In cases in which transparency is required, transmittance of visible light is normally 60% or more and preferably 80% or more, and in this case, thickness is normally about 5 nm to 1000 nm and preferably about 10 nm to 500 nm. In the case an opaque anode is acceptable, the anode may be identical to the substrate. In addition, different electrically conductive materials can be further laminated onto the above-mentioned anode.

(4) Hole Transport Layer

The hole transport layer 4 is provided on the anode 2. The hole injection layer 3 can also be provided between the two. Conditions required of the material of the hole transport layer consist of the use of a material that is highly efficient in injection holes from the anode and is able to efficiently transport the injected holes. In order to accomplish this, the material is required to have a small ionization potential, have high transparency with respect to visible light, have large hole mobility, superior stability, and be resistant to the generation of impurities serving as traps during production and use. In addition, the material is also required to quench light emitted from the light emitting layer in order to contact the light emitting layer 5 as well as not cause a decrease in efficiency by the formation of an exciplex between the material and the light emitting layer. In addition to above-mentioned typical requirements, the device is also required to demonstrate heat resistance in the case of considering applications for vehicle-mounted displays. Thus, a material having a Tg value of 85° C. or higher is preferable.

The hole transport material may use a mixture of a compound represented by general formula (1) and a compound represented by general formula (2) or a known compound conventionally used in this layer can be used. Examples of known compounds include aromatic diamines containing two or more tertiary amines in which two or more condensed aromatic rings are substituted with nitrogen atoms, aromatic amine compounds having a starburst structure such as 4,4',4"-tris(1-naphthylphenylamino)triphenylamine, an aromatic amine compound composed of a tetramer of a triphenylamine, and a spiro compound such as 2,2',7,7'-tetrakis(diphenylamino)-9,9'-spirobifluorene.

These compounds may be used alone or may each be mixed prior to use as necessary.

In addition, additional examples other than the above-mentioned compounds include polymer materials such as polyarylene ether sulfones containing polyvinylcarbazole, polyvinyltriphenylamine or tetraphenylbenzidine.

In the case the hole transport layer is formed by a coating method, one type or two or more types of hole transport materials and an additive such as a binder resin, which does not trap holes, or coatability improver and the like, are added as necessary and dissolved to prepare a coating solution followed by applying the coating solution to the anode by a method such as spin coating and drying to form a hole transport layer. Examples of binder resin include polycarbonate, polyarylate and polyester. Since the binder resin causes a decrease in hole mobility if the added amount thereof is excessively large, a small amount is preferable and is normally 50% by weight or less.

In the case of forming by vacuum deposition, the hole transport material is placed in a crucible installed inside a vacuum chamber, and after evacuating the inside of the vacuum chamber to about $10^{-4}$ Pa with a suitable vacuum pump, the crucible is heated to evaporate the hole transport material to form a hole transport layer on a substrate having an anode formed thereon placed in opposition to the crucible. The film thickness of the hole transport layer is normally 1 nm to 300 nm and preferably 5 nm to 100 nm. The vacuum deposition method is typically frequently used to uniformly form a thin film in this manner.

(5) Hole Injection Layer

The hole injection layer 3 is inserted between the hole transport layer 4 and the anode 2 for the purpose of further improving the efficiency of hole injection and improving the adhesive force of the entire organic layer to the anode. As a result of inserting the hole injection layer, simultaneous to lowering the voltage at which the device is initially driven, there is also the effect of inhibiting voltage increases when the device is continuously driven at a constant current. Conditions required of the material used for the hole injection layer consist of allowing the formation of a uniform thin film that makes favorable contact with the anode, thermal stability, or in other words, a high glass transition temperature, with a temperature of 100° C. or higher being required for the glass transition temperature. Moreover, other examples of requirements include a low ionization potential, ease of injection of holes from the anode and high hole mobility.

In order to achieve this objective, a mixture of compounds represented by general formula (1) and general formula (2) may be used, or a known phthalocyanine compound such as copper phthalocyanine, an organic compound such as polyaniline or polythiophene, a sputtered carbon film, a metal oxide such as vanadium oxide, ruthenium oxide or molybdenum oxide, or a P-type organic material such as naphthalene-1,4,5,8-tetracarboxylic dianhydride (NTCDA) or hexaazatriphenylene hexanitrile (HAT) may be used alone or may be used as a mixture thereof as necessary. In the case of the hole injection layer as well, although a thin film can be formed in the same manner as the hole transport layer, in the case of an inorganic material, sputtering, electron beam deposition or plasma CVD and the like are also used. The film thickness of a hole injection layer formed in the manner described above is normally 1 nm to 300 nm and preferably 5 nm to 100 nm.

(6) Light Emitting Layer

The light emitting layer 5 is provided on the hole transport layer 4. The light emitting layer may be formed from a single light emitting layer or may be composed by laminating a plurality of light emitting layers so as to be in direct contact. The light emitting layer is composed of a host material and luminescent dopant, and the luminescent dopant may be a fluorescent material, delayed fluorescence material or phosphorescent material. A mixture of compounds represented by general formula (1) and general formula (2) may be used as a host material or may be used as a luminescent dopant, it is preferably used as a host material.

In the case of a fluorescent organic EL device, examples of fluorescent materials added to the host material that can be used include condensed ring derivatives such as perylene or rubrene, quinacridone derivatives, phenoxazone 660, DCM1, perinone, coumarin derivatives, pyrromethene (diazaindacene) derivatives and cyanine dyes.

In the case of a delayed fluorescence organic EL device, examples of delayed fluorescence materials used in the light emitting layer include carborane derivatives, tin complexes, indolocarbazole derivatives, copper complexes and carbazole derivatives. More specifically, examples of delayed fluorescence materials include, but are not limited to, compounds described in the following non-patent literature and patent literature.

1) Adv. Mater. 2009, 21, 4802-4806, 2) Appl. Phys. Lett. 98, 083302 (2011), 3) Japanese Patent Application Publication No. 2011-213643, and 4) J. Am. Chem. Soc. 2012, 134, 14706-14709.

Although the following indicates specific examples of delayed fluorescence materials, these materials are not limited to the following compounds.

[C57]

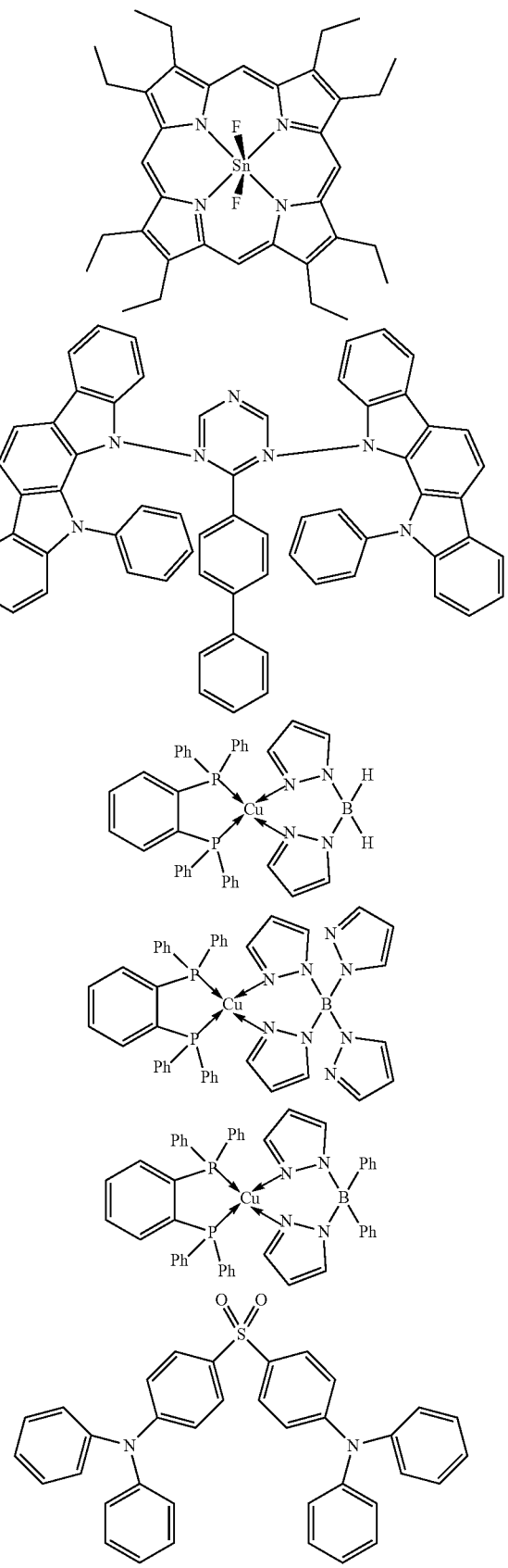

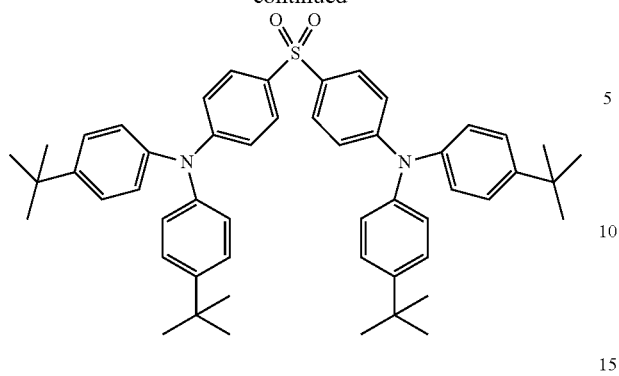

In the case of using the above-mentioned delayed fluorescence materials as a delayed fluorescent dopant and containing as a host material, the amount of delay fluorescent dopant contained in the light emitting layer is within the range of 0.01% by weight to 50% by weight, preferably within the range of 0.1% by weight to 20% by weight, and more preferably within the range of 0.01% by weight to 10% by weight.

In the case of a phosphorescent organic EL device, an organic metal complex is contained that contains at least one metal selected from ruthenium, rhodium, palladium, silver, rhenium, osmium, iridium, platinum and gold as a phosphorescent dopant. More specifically, examples thereof include, but are not limited to, compounds described in the following non-patent literature and patent literature.

WO 2009/073245 A1, WO 2009/046266 A1, WO 2007/095118 A1, WO 2008/156879 A1, WO 2008/140657 A1, US 2008/261076, JP 2008-542203 A, WO 2008/054584 A1, JP2008-505925 A, JP 2007-522126 A, JP 2004-506305 A, JP 2006-513278 A, JP 2006-50596 A, WO 2006/046980 A1, WO 2005/113704 A1, US 2005/260449 A1, US 2005/2260448 A1, US 2005/214576 A1, and WO 2005/076380 A1.

Preferable examples of phosphorescent dopants include complexes such as Ir (ppy)$_3$ having a precious metal element such as Ir as a central metal, complexes such as Ir (bt) 2.acac3, and complexes such as PtOEt3. Although the following indicates specific examples of these complexes, these complexes are not limited to the following compounds.

[C58]

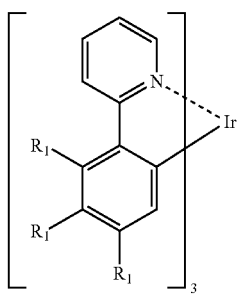

R$_1$: H' CH$_3$' CF$_3$' F

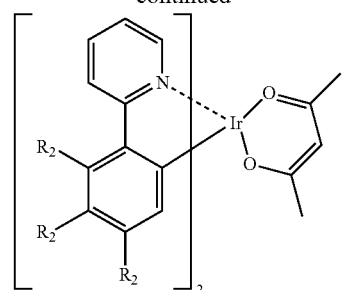

R$_2$: H' F

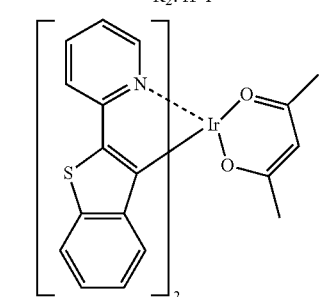

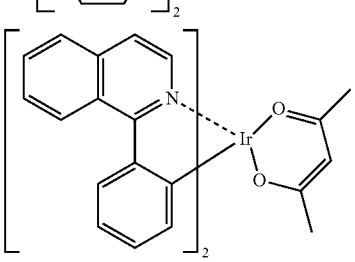

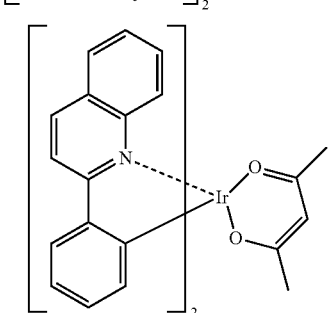

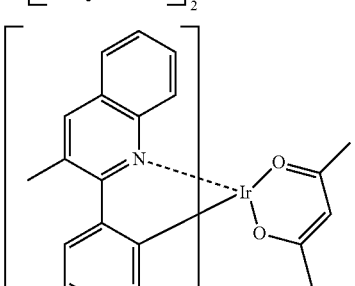

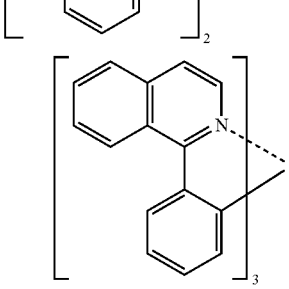

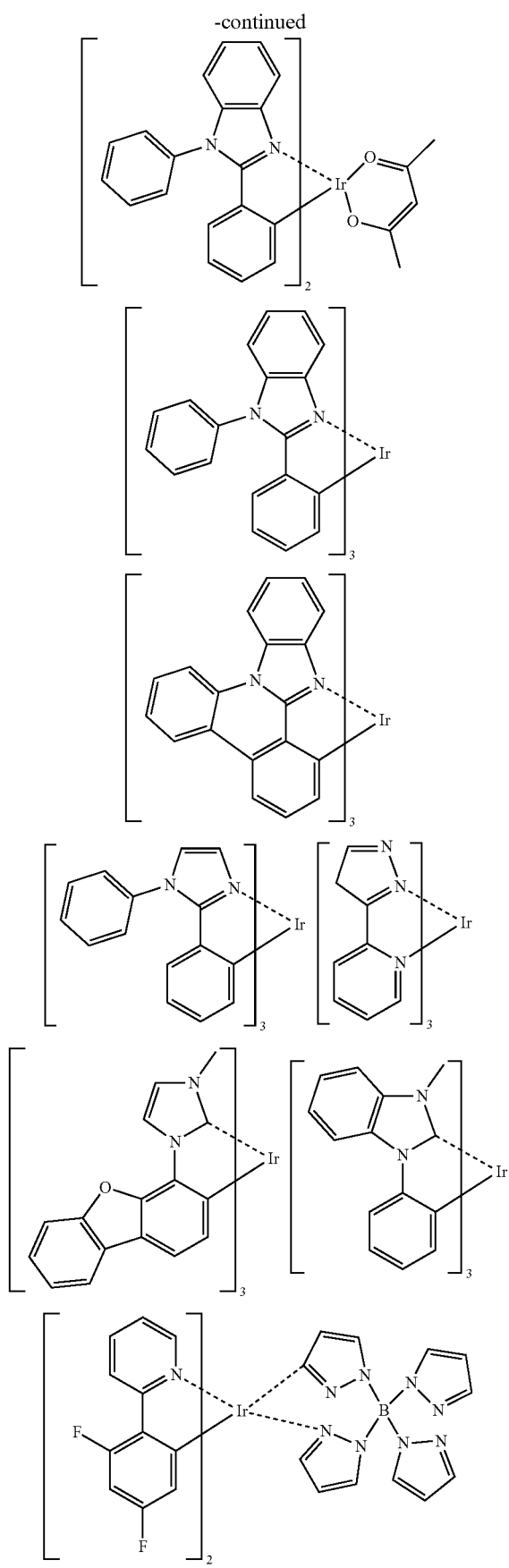
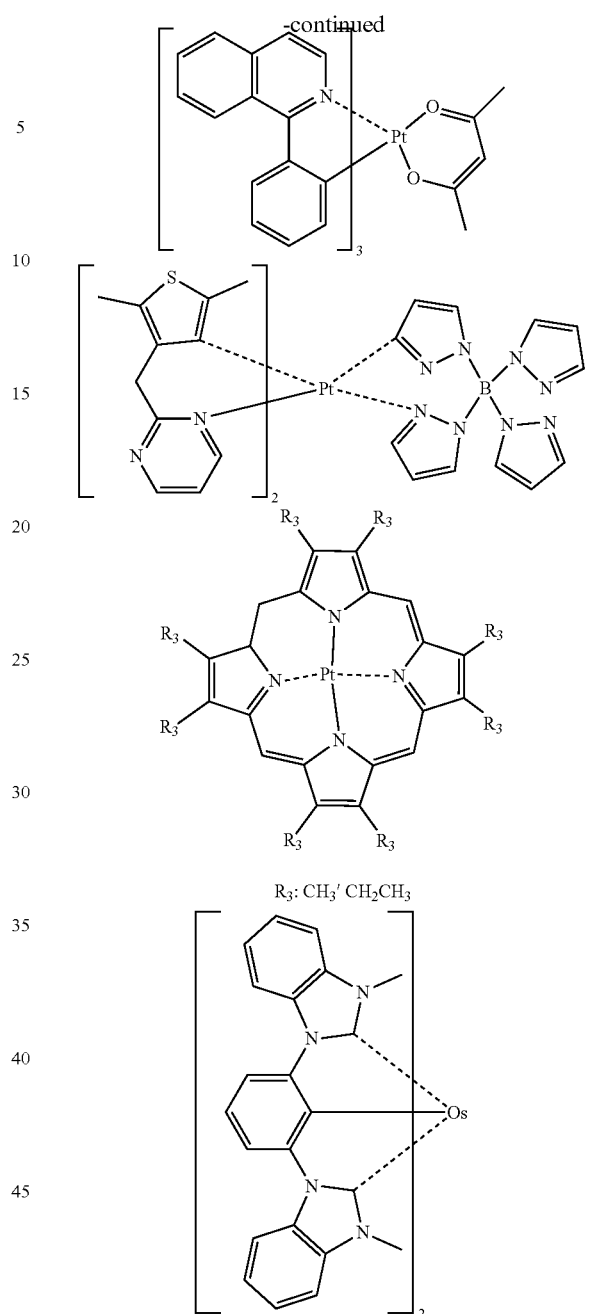

The amount of the above-mentioned phosphorescent dopant contained in the light emitting layer is within the range of 2% by weight to 40% by weight and preferably within the range of 5% by weight to 30% by weight.

Although there are no particular limitations thereon, the film thickness of the light emitting layer is normally 1 nm to 300 nm and preferably 5 nm to 100 nm, and a thin film thereof is formed in the same manner as the hole transport layer.

—Blocking Layers—

A blocking layer is able to block the diffusion of charge (electrons or holes) and/or excitons present in the light emitting layer outside the light emitting layer. The electron blocking layer can be arranged between the light emitting layer and the hole transport layer and blocks the passage of electrons through the light emitting layer in the direction of the hole transport layer. Similarly, the hole blocking layer can be arranged between the light emitting layer and the electron transport layer and blocks the passage of holes through the light emitting layer in the direction of the electron transport layer. Blocking layers can also be used to block diffusion of excitons outside the light emitting layer. Namely, the electron blocking layer and hole blocking layer are each provided with the function of an exciton blocking layer. The electron blocking layer and hole blocking layer as referred to in the present description are used in the sense of containing a layer having the function of a charge (electron or hole) blocking layer and exciton blocking layer in a single layer.

—Hole Blocking Layer—

The hole blocking layer has the function of an electron transport layer in the broad sense. The hole blocking layer has the role of transporting electrons while preventing holes from reaching the electron transport layer, and as a result thereof, is able to improve the probability of electrons and holes recombining in the light emitting layer.

A mixture of compounds represented by general formula (1) and general formula (2) is preferably used for the material of the hole blocking layer and materials of the electron transport layer to be subsequently described can also be used. The film thickness of the hole blocking layer according to the present invention is preferably 3 nm to 100 nm and more preferably 5 nm to 30 nm.

—Electron Blocking Layer—

The electron blocking layer refers to a layer having the function of transporting holes in the broad sense. The electron blocking layer has the role of transporting holes while preventing electrons from reaching the hole transport layer, and as a result thereof, is able to improve the probability of electrons and holes recombining in the light emitting layer.

A mixture of compounds represented by general formula (1) and general formula (2) is preferably used for the material of the electron blocking layer and materials of the hole transport layer to be subsequently described can also be used. The film thickness of the electron blocking layer according to the present invention is preferably 3 nm to 100 nm and more preferably 5 nm to 30 nm.

—Exciton Blocking Layers—

The exciton blocking layers refer to layers for preventing excitons, which have formed as a result of holes and electrons recombining in the light emitting layer, from diffusing in the charge transport layers, and the insertion of these layers makes it possible to efficiently trap excitons in the light emitting layer, thereby making it possible to improve luminous efficiency of the device. The exciton blocking layers can be inserted on either the anode side or cathode side adjacent to the light emitting layer, and both can be inserted simultaneously. Namely, in the case of having an exciton blocking layer on the anode side, this layer can be inserted adjacent to the light emitting layer between hole transport layer and the light emitting layer, while in the case of inserting on the cathode side, this layer can be inserted adjacent to the light emitting layer between the light emitting layer and the cathode. In addition, a layer such as the hole injection layer or electron blocking layer can be present between the anode and the exciton blocking layer adjacent to the light emitting layer on the anode side, and a layer such as the electron injection layer, electron transport layer or hole blocking layer can be present between the cathode and the exciton blocking layer adjacent to the light emitting layer on the cathode side.

A mixture of compounds represented by general formula (1) and general formula (2) is preferably used for the material of the exciton blocking layer and any ordinarily used material can be used.

Examples of known exciton blocking layer materials that can be used include 1,3-dicarbazolylbenzene (mCP) and bis(2-methyl-8-quinolinato)-4-phenylphenylate aluminum (III) (BAlq).

(7) Electron Transport Layer

The electron transport layer 6 is provided between the light emitting layer 5 and the cathode 8 for the purpose of further improving luminous efficiency of the device. An electron transport material capable of smoothly injecting electrons from the cathode is preferable for the electron transport layer, and a mixture of compounds represented by general formula (1) and general formula (2) may be used or any ordinarily used material can be used. Examples of electron transport materials satisfying such conditions include metal complexes such as $Alq_3$, metal complexes such as 10-hydroxybenzo[h]quinoline, oxadiazole derivatives, distyrylbiphenyl derivatives, silole derivatives, 3- or 5-hydroxyflavone metal complexes, benzoxazole metal complexes, benzothiazole metal complexes, tris-benzimidazolylbenzene, quinoxaline compounds, phenanthroline derivatives, 2-t-butyl-9,10-N,N'-dicyanoanthraquinone diimine, n-type amorphous silicon carbide hydride, n-type zinc selenide, and n-type zinc selenide.

The film thickness of the electron transport layer is normally 1 nm to 300 nm and preferably 5 nm to 100 nm. The electron transport layer is formed by laminating on the light emitting layer by a coating method or vacuum deposition in the same manner as the hole transport layer. Normally, vacuum deposition is used.

(8) Cathode

The cathode 8 fulfills the role of injecting electrons into the electron transport layer 6. Although a material used for the above-mentioned anode 2 can be used for the material used for the cathode, in order to inject electrons efficiently, a metal having a low work function is preferable, and examples thereof that are used include a suitable metal such as tin, magnesium, indium, calcium, aluminum or silver, or an alloy thereof. Specific examples include alloy electrode having a low work function such as magnesium-silver alloy, magnesium-indium alloy or aluminum-lithium alloy.

The film thickness of the cathode is the same as that of the anode. The additional lamination of a metal layer having a high work function and is stable in air on the cathode for the purpose of protecting the cathode from metal having a low work function increases stability of the device. A metal such as aluminum, silver, copper, nickel, chromium, gold or platinum is used for this purpose.

Moreover, insertion of an ultrathin insulating film (0.1 nm to 5 nm) such as LiF, $MgF_2$ or $Li_2O$ between the cathode 8 and the electron transport layer 6 for use as the electron injection layer 7 is also an effective method for improving device efficiency.

Furthermore, a structure opposite from that shown in FIG. 1, namely a structure in which the cathode 8, electron injection layer 7, electron transport layer 6, light emitting layer 5, hole transport layer 4, hole injection layer 3 and anode 2 are laminated on the substrate 1 in that order, can also be employed, and the organic EL device of the present invention can be provided between two substrates, at least one of which has high transparency, as previously described. In this case as well, layers can be added or omitted as necessary.

The organic EL device of the present invention can be in the form of a single device, a device composed of a structure in which the organic EL device is arranged in the form of an array, or a device employing a structure in which the cathode and anode are arranged in the form of an X-Y matrix. According to the organic EL device of the present invention, by using the two compounds of the present invention in at least one organic layer, and using as a mixed host material of the light emitting layer in particular, a device can be obtained that demonstrates high luminous efficiency and stability when driven even at a low voltage, and makes it possible to demonstrate superior performance when applying to full color or multicolor panels.

Although the following provides a more detailed explanation of the present invention through examples thereof, the present invention is not limited to these examples, but rather can be worked in various forms provided the gist thereof is not exceeded. Furthermore, the first host and the first component refer to a compound represented by general formula (1), while the second host and the second component refer to a compound represented by general formula (2).

EXAMPLES

Example 1

Various thin films were laminated on a glass substrate having an anode, composed of indium tin oxide (ITO) formed thereon at a film thickness of 70 nm, by vacuum deposition at a degree of vacuum of $2.0 \times 10^{-5}$ Pa. First, a hole injection layer in the form of copper phthalocyanine (CuPC) was formed to a thickness of 30 nm on the ITO. Next, a hole transport layer in the form of 4,4-bis[N-(1-naphthyl)-N-phenylamino]biphenyl (NPB) was formed to a thickness of 15 nm. Next, a first host in the form of Compound 1-25, a second host in the form of Compound 3-1, and a light emitting layer guest in the form of an indium complex serving as a blue phosphorescent material [iridium (III) bis(4,6-difluorophenyl)-pyridinate-N, C2']picolinate (FIrpic), were co-deposited from different deposition sources to form a light emitting layer having a thickness of 30 nm. At this time, the ratio of the deposition rates (weight ratio) of the first host to the second host to the FIrpic was 47:47:6. Next, an electron transport layer in the form of $Alq_3$ was formed to a thickness of 25 nm. Moreover, an electron injection layer in the form of lithium fluoride (LiF) was formed to a thickness of 1.0 nm on the electron transport layer. Finally, an electrode in the form of aluminum (Al) was formed to a thickness of 70 nm on the electron injection layer. The resulting organic EL device had a layer having an electron injection layer added thereto between the cathode and the electron transport layer in the organic EL device shown in FIG. 1.

Examples 2 to 18

Organic EL devices were produced in the same manner as Example 1 with the exception of using the compounds described in Table 1 as the first host of the light emitting layer instead of the compound used in Example 1 (Examples 2 to 9).

In addition, organic EL devices were produced in the same manner as Example 1 with the exception of using Compound 3-43 as the second host and using the compounds described in Table 1 as the first host of the light emitting layer instead of the compounds used in Example 1 (Examples 10 to 18).

When an external power supply was connected to the resulting organic EL devices and a direct current voltage was applied thereto, emission spectra having a maximum wavelength of 475 nm were observed to be emitted from each of the organic EL devices, and emission of light was determined to be obtained from FIrpic. Characteristics of the organic EL devices produced are shown in Table 1.

Comparative Examples 1 to 11

Organic EL devices were produced in the same manner as Example 1 with the exception of using only the compounds described in Table 2 for the light emitting layer host instead of the compound used in Example 1. Furthermore, the amount of host was made to be equal to the total amount of the first host and second host in Example 1, and the amount of the guest was the same. When a power supply was connected to the resulting organic EL devices and a direct current voltage was applied thereto, emission spectra having a maximum wavelength of 475 nm were observed to be emitted from each of the organic EL devices, and emission of light was determined to be obtained from FIrpic. The characteristics of the organic EL devices produced are shown in Table 2.

In Tables 1 and 2, luminance, voltage and luminous efficiency indicate values obtained when the devices were driven at a current of 2.5 $mA/cm^2$, and luminance half-life is the value at an initial luminance of 1000 $cd/m^2$. Compound no. indicates the number assigned in the previously listed chemical formulas.

TABLE 1

| Ex. | 1st host compd. No. | 2nd host compd. No. | Luminance ($cd/m^2$) | Voltage (V) | Luminous efficiency (lm/W) | Luminance half-life (h) |
|---|---|---|---|---|---|---|
| 1 | 1-25 | 3-1 | 510 | 5.4 | 11.9 | 2100 |
| 2 | 1-56 |  | 520 | 5.5 | 11.9 | 1900 |
| 3 | 1-61 |  | 500 | 4.5 | 13.7 | 1700 |
| 4 | 1-101 |  | 500 | 4.5 | 13.9 | 1500 |
| 5 | 1-222 |  | 510 | 5.0 | 12.8 | 1600 |
| 6 | 1-226 |  | 510 | 5.1 | 12.5 | 2000 |
| 7 | 1-268 |  | 540 | 5.8 | 11.7 | 2000 |
| 8 | 2-29 |  | 530 | 4.9 | 13.5 | 2100 |
| 9 | 2-42 |  | 510 | 4.9 | 13.0 | 1900 |
| 10 | 1-25 | 3-43 | 490 | 5.5 | 11.3 | 2100 |
| 11 | 1-56 |  | 500 | 4.5 | 13.9 | 1900 |
| 12 | 1-61 |  | 480 | 4.5 | 13.3 | 1700 |
| 13 | 1-101 |  | 480 | 4.5 | 13.4 | 1500 |
| 14 | 1-222 |  | 490 | 5.0 | 12.3 | 1600 |
| 15 | 1-226 |  | 490 | 5.1 | 12.1 | 2000 |
| 16 | 1-268 |  | 520 | 5.8 | 11.3 | 2000 |
| 17 | 2-29 |  | 510 | 4.9 | 13.0 | 2100 |
| 18 | 2-42 |  | 490 | 4.9 | 12.6 | 1900 |

TABLE 2

| Comp. Ex. | 1st host compd. No. | 2nd host compd. No. | Luminance ($cd/m^2$) | Voltage (V) | Luminous efficiency (lm/W) | Luminance half-life (h) |
|---|---|---|---|---|---|---|
| 1 | — | 3-1 | 410 | 5.9 | 8.7 | 700 |
| 2 | — | 3-43 | 400 | 5.9 | 8.6 | 620 |
| 3 | 1-25 | — | 400 | 6.5 | 7.7 | 710 |
| 4 | 1-56 | — | 390 | 6.4 | 7.7 | 620 |
| 5 | 1-61 | — | 410 | 7.7 | 6.7 | 570 |
| 6 | 1-101 | — | 400 | 7.7 | 6.6 | 500 |
| 7 | 1-222 | — | 400 | 7.0 | 7.2 | 550 |

TABLE 2-continued

| Comp. Ex. | 1st host compd. No. | 2nd host compd. No. | Luminance (cd/m²) | Voltage (V) | Luminous efficiency (lm/W) | Luminance half-life (h) |
|---|---|---|---|---|---|---|
| 8 | 1-226 | — | 400 | 6.9 | 7.3 | 660 |
| 9 | 1-268 | — | 380 | 6.1 | 7.8 | 670 |
| 10 | 2-29 | — | 380 | 7.1 | 6.8 | 680 |
| 11 | 2-42 | — | 400 | 7.1 | 7.0 | 630 |

Example 19

Various thin films were laminated on a glass substrate having an anode, composed of ITO formed thereon at a film thickness of 150 nm, by vacuum deposition at a degree of vacuum of $4.0 \times 10^{-4}$ Pa. First, a hole injection layer in the form of CuPC was formed to a thickness of 20 nm on the ITO, after which an electron transport layer in the form of NPB was formed to a thickness of 20 nm. Next, a first host in the form of Compound 1-25, a second host in the form of Compound 3-1, and a light emitting layer guest in the form of tris(2-phenylpyridinato)iridium (III) (Ir(PPy)$_3$) were co-deposited from different deposition sources to form a light emitting layer having a thickness of 30 nm. At this time, the ratio of the deposition rates of the first host to the second host to the Ir(PPy)$_3$ was 47:47:6. Next, a hole blocking layer in the form of bis(2-methyl-8-quinolinato)-4-phenylphenylate aluminum (III) (BAlq) was formed to a thickness of 10 nm. Next, an electron transport layer in the form of Alq$_3$ was formed to a thickness of 40 nm. Moreover, an electron injection layer in the form of LiF was formed at a thickness of 0.5 nm on the electron transport layer. Finally, a cathode in the form of Al was formed at a thickness of 100 nm on the electron injection layer to produce an organic EL device.

When an external power supply was connected to the resulting organic EL device and a direct current voltage was applied thereto, an emission spectrum having a maximum wavelength of 517 nm was observed, and emission of light was determined to be obtained from Ir(PPy)$_3$. The characteristics of the resulting organic EL device (luminance, voltage, external quantum efficiency and luminance half-life) are shown in Table 3.

Examples 20 to 36

Organic EL devices were produced in the same manner as Example 19 with the exception of using the compounds described in Table 3 for the first host of the light emitting layer instead of the compound used in Example 19 (Examples 20 to 27).

In addition, organic EL devices were produced in the same manner as Example 19 with the exception of using Compound 3-43 for the second host and using the compounds described in Table 3 for the first host of the light emitting layer (Examples 28 to 36).

When an external power supply was connected to the resulting organic EL devices and a direct current voltage was applied thereto, emission spectra having a maximum wavelength of 517 nm were observed to be emitted from each of the organic EL devices, and emission of light was determined to be obtained from Ir (PPy)$_3$. Characteristics of the resulting organic EL devices are shown in Table 3.

Comparative Examples 12 to 22

Organic EL devices were produced in the same manner as Example 19 with the exception of using only the compounds described in Table 4 for the light emitting layer host instead of the compound used in Example 19. Furthermore, the amount of host was made to be equal to the total amount of the first host and second host in Example 19, and the amount of the guest was the same. When a power supply was connected to the resulting organic EL devices and a direct current voltage was applied thereto, emission spectra having a maximum wavelength of 517 nm were observed to be emitted from each of the organic EL devices, and emission of light was determined to be obtained from Ir (PPy)$_3$. The characteristics of the organic EL devices produced are shown in Table 4.

In Tables 3 and 4, luminance, voltage and luminous efficiency indicate values obtained when the devices were driven at a current of 20 mA/cm², and luminance half-life is the value at an initial luminance of 1000 cd/m².

TABLE 3

| Ex. | 1st host compd. No. | 2nd host compd. No. | Luminance (cd/m²) | Voltage (V) | Luminous efficiency (lm/W) | Luminance half-life (h) |
|---|---|---|---|---|---|---|
| 19 | 1-25 | 3-1 | 8400 | 4.4 | 30.1 | 20000 |
| 20 | 1-56 | | 8300 | 4.5 | 29.3 | 16000 |
| 21 | 1-61 | | 8700 | 3.8 | 36.3 | 16000 |
| 22 | 1-101 | | 8600 | 3.7 | 36.0 | 14000 |
| 23 | 1-222 | | 8500 | 4.1 | 32.7 | 16000 |
| 24 | 1-226 | | 8500 | 4.2 | 32.1 | 19000 |
| 25 | 1-268 | | 8000 | 4.4 | 28.6 | 19000 |
| 26 | 2-29 | | 8200 | 4.0 | 31.8 | 20000 |
| 27 | 2-42 | | 8300 | 4.0 | 32.3 | 18000 |
| 28 | 1-25 | 3-43 | 8200 | 4.5 | 28.8 | 17000 |
| 29 | 1-56 | | 8000 | 3.8 | 33.6 | 15000 |
| 30 | 1-61 | | 8400 | 3.8 | 35.1 | 14000 |
| 31 | 1-101 | | 8300 | 3.8 | 34.8 | 12000 |
| 32 | 1-122 | | 8200 | 4.1 | 31.6 | 13000 |
| 33 | 1-226 | | 8200 | 4.2 | 31.1 | 16000 |
| 34 | 1-268 | | 7800 | 4.4 | 28.0 | 16000 |
| 35 | 2-29 | | 8000 | 4.0 | 31.1 | 16000 |
| 36 | 2-42 | | 8200 | 4.0 | 32.0 | 15000 |

TABLE 4

| Comp. Ex. | 1st host compd. No. | 2nd host compd. No. | Luminance (cd/m²) | Voltage (V) | Luminous efficiency (lm/W) | Luminance half-life (h) |
|---|---|---|---|---|---|---|
| 12 | — | 3-1 | 8100 | 4.5 | 28.3 | 3000 |
| 13 | — | 3-43 | 7900 | 4.5 | 27.7 | 2600 |
| 14 | 1-25 | — | 7800 | 4.9 | 24.9 | 4000 |
| 15 | 1-56 | — | 7700 | 4.9 | 24.8 | 3500 |
| 16 | 1-61 | — | 8000 | 5.9 | 21.6 | 3200 |
| 17 | 1-101 | — | 8000 | 5.9 | 21.3 | 2800 |
| 18 | 1-222 | — | 7900 | 5.3 | 23.2 | 3100 |
| 19 | 1-226 | — | 7900 | 5.2 | 23.6 | 3700 |
| 20 | 1-268 | — | 7400 | 4.6 | 25.2 | 3800 |
| 21 | 2-29 | — | 7600 | 5.4 | 21.9 | 3800 |
| 22 | 2-42 | — | 7900 | 5.4 | 22.8 | 3500 |

A comparison of Table 3 and Table 4 reveals that Example 19 to 36 demonstrate improved luminance and service life characteristics and exhibit favorable characteristics.

Example 37

Various thin films were laminated on a glass substrate having an anode, composed of indium tin oxide (ITO) formed thereon at a film thickness of 70 nm, by vacuum deposition at a degree of vacuum of $2.0 \times 10^{-5}$ Pa. First, a hole injection layer in the form of copper phthalocyanine (CuPC) was formed to a thickness of 30 nm on the ITO. Next, an electron transport layer in the form of diphenylnaphthyldiamine (NPD) was formed to a thickness of 15 nm. Next, a light emitting layer host material in the form of mCBP and a dopant in the form of FIrpic were co-deposited on the hole transport layer from different deposition sources to form a light emitting layer at a thickness of 30 nm. At this time, the ratio of the deposition rates of mCBP to FIrpic was 94:6. Next, a first component of a hole blocking layer in the form of Compound 1-61 and a second component in the form of Compound 3-1 were used to form a layer having a thickness of 5 nm on the light emitting layer. At this time, the ratio of the deposition rates of Compound 3-1 to Compound 1-61 was 50:50. Next, an electron transport layer in the form of $Alq_3$ was formed to a thickness of 20 nm. Moreover, an electron injection layer in the form of lithium fluoride (LiF) was formed to a thickness of 1.0 nm on the electron transport layer. Finally, an electrode in the form of aluminum (Al) was formed to thickness of 70 nm on the electron injection layer. The resulting organic EL device had a layer configuration consisting of an electron injection layer between the cathode and electron transport layer and a hole blocking layer between the light emitting layer and electron transport layer in the organic EL device shown in FIG. 1.

When an external power supply was connected to the resulting organic EL device and a direct current voltage was applied thereto, the resulting organic EL device was confirmed to have emission characteristics as shown in Tables. In Table 5, luminance, voltage and luminous efficiency indicate values obtained when the device was driven at a current of 2.5 mA/cm$^2$ (initial characteristics). The maximum wavelength of the device emission spectrum was 475 nm and emission of light from FIrpic was determined to be obtained.

Examples 38 to 46

Organic EL devices were produced in the same manner as Example 37 with the exception of using the compounds described in Table 5 for the first component of the hole blocking layer instead of the compound used in Example 37 (Examples 38 to 41).

In addition, organic EL devices were produced in the same manner as Example 37 with the exception of using Compound 3-43 for the second component and using the compound described in Table 5 for the first component of the hole blocking layer (Examples 42 to 46).

When an external power supply was connected to the resulting organic EL devices and a direct current voltage was applied thereto, emission spectra having a maximum wavelength of 475 nm were observed to be emitted from each of the organic EL devices, and emission of light was determined to be obtained from FIrpic. The characteristics of the organic EL devices produced are shown in Table 5.

Comparative Example 23

An organic EL device was produced in the same manner as Example 37 with the exception of changing the film thickness of the $Alq_3$ used for the electron transport layer in Example 37 to 25 nm and not providing a hole blocking layer.

When the organic EL devices obtained in Examples 38 to 46 and Comparative Example 23 were evaluated in the same manner as Example 37, the organic EL devices were confirmed to have the emission characteristics shown in Table 5. Furthermore, the maximum wavelength of the emission spectra of the organic EL devices obtained in Examples 37 to 46 and Comparative Example 23 was 475 nm, and emission of light was identified as being obtained from FIrpic.

TABLE 5

| Ex. | 1st component compd. No. | 2nd component compd. No. | Luminance (cd/m$^2$) | Voltage (V) | Luminous efficiency (lm/W) | Luminance half-life (h) |
|---|---|---|---|---|---|---|
| 37 | 1-61 | 3-1 | 790 | 9.2 | 10.7 | 1600 |
| 38 | 1-101 | | 790 | 9.2 | 10.8 | 1500 |
| 39 | 1-222 | | 640 | 9.9 | 8.1 | 1600 |
| 40 | 1-226 | | 640 | 10.1 | 8.0 | 1500 |
| 41 | 2-42 | | 640 | 9.8 | 8.2 | 1500 |
| 42 | 1-61 | 3-43 | 780 | 9.2 | 10.6 | 1200 |
| 43 | 1-101 | | 780 | 9.2 | 10.7 | 1200 |
| 44 | 1-222 | | 630 | 9.9 | 8.0 | 1200 |
| 45 | 1-226 | | 630 | 10.1 | 7.9 | 1300 |
| 46 | 2-42 | | 630 | 9.8 | 8.1 | 1300 |
| Comp. Ex. 23 | — | — | 520 | 9.4 | 7.0 | 300 |

According to Table 5, Examples 37 to 45 demonstrated more favorable characteristics in comparison with Comparative Example 23 that did not use a hole blocking material.

INDUSTRIAL APPLICABILITY

The organic EL device of the present invention is able to achieve high efficiency and a long service life even at a low voltage.

REFERENCE SIGNS LIST

1 Substrate
2 Anode
3 Hole injection layer
4 Hole transport layer
5 Light emitting layer
6 Electron transport layer
7 Electron injection layer
8 Cathode

The invention claimed is:
1. An organic electroluminescence device obtained by laminating an anode, organic layers and a cathode electrode on a substrate, wherein (i) a compound represented by general formula (1) below and (ii) a compound represented by general formula (2) below are contained in at least one of the organic layers:

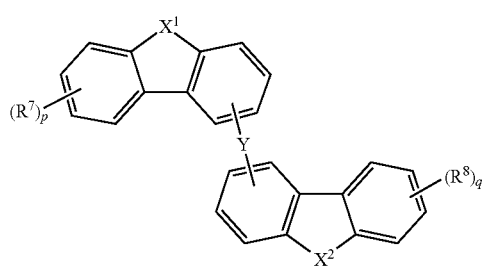

(1)

wherein, $X^1$ and $X^2$ represent $NR^1$, $PR^2$, O, S, Se, $CR^3R^4$ or $SiR^5R^6$ and may mutually be the same or different, Y represents a single bond or a divalent substituted or unsubstituted aromatic hydrocarbon group having 6 to 30 carbons, a substituted or unsubstituted aromatic heterocyclic group having 3 to 17 carbon atoms, excluding a carbazole group, or a substituted or unsubstituted linked aromatic group obtained by linking 2 to 6 of the aromatic rings of the aromatic hydrocarbon group or aromatic heterocyclic group, $R^1$ to $R^6$ independently represent a substituted or unsubstituted aromatic hydrocarbon group having 6 to 30 carbon atoms, a substituted or unsubstituted aromatic heterocyclic group having 3 to 17 carbon atoms, or a substituted or unsubstituted linked aromatic group obtained by linking 2 to 6 of the aromatic groups of the aromatic hydrocarbon group or aromatic heterocyclic group, $R^7$ and $R^8$ independently represent a substituted or unsubstituted aromatic hydrocarbon group having 6 to 30 carbon atoms, a substituted or unsubstituted aromatic heterocyclic group having 3 to 17 carbon atoms, a substituted or unsubstituted linked aromatic group obtained by linking 2 to 6 of the aromatic rings of the aromatic hydrocarbon group or aromatic heterocyclic group, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a diaralkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, a cyano group, a nitro group, a fluoro group or a tosyl group, and p and q indicate the numbers of substituents and independently represent an integer of 0 to 7; and,

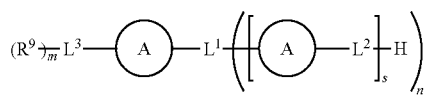

(2)

(a1)

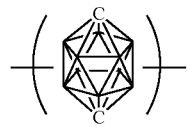

(b1)

wherein, ring A represents a $C_2B_{10}H_{10}$ divalent carborane group represented by formula (a1) or formula (b1), and may be the same or different in the case a plurality of ring A are present within a molecule, s indicates the number of repeats and is an integer of 0 to 2, n and m indicate the number of substituents, n represents an integer of 1 or 2 and m represents an integer of 0 to 4, $L^1$ represents a single bond or a substituted or unsubstituted aromatic hydrocarbon group having 6 to 30 carbon atoms and having a valence of n+1, a substituted or unsubstituted aromatic heterocyclic group having 3 to 30 carbon atoms and a valence of n+1, or a substituted or unsubstituted linked aromatic group having a valence of n+1 obtained by linking 2 to 6 of the aromatic rings of the aromatic hydrocarbon group or aromatic heterocyclic group, provided that, in the case n=1 and s=1, $L^1$ represents a single bond, aromatic heterocyclic group or linked aromatic group containing at least one aromatic heterocyclic group, $L^2$ independently represents a single bond or a divalent substituted or unsubstituted aromatic hydrocarbon group having 6 to 30 carbon atoms, a divalent substituted or unsubstituted aromatic heterocyclic group having 3 to 30 carbon atoms, or a divalent substituted or unsubstituted linked aromatic group obtained by linking 2 to 6 of the aromatic rings of the aromatic hydrocarbon group or aromatic heterocyclic group, $L^3$ represents an unsubstituted aromatic hydrocarbon group having 6 to 30 carbon atoms and a valence of m+1, or an unsubstituted aromatic heterocyclic group having 3 to 30 carbon atoms and valence of m+1, and $R^9$ independently represents a group selected from a substituted or unsubstituted aromatic hydrocarbon group having 6 to 30 carbon atoms, a substituted or unsubstituted aromatic heterocyclic group having 3 to 30 carbon atoms, a substituted or unsubstituted linked aromatic group obtained by linking 2 to 6 of the aromatic rings of the aromatic hydrocarbon group or aromatic heterocyclic group, an alkyl group having 1 to 20 carbon atoms, an aralkyl group having 7 to 38 carbon atoms, an alkenyl group having 2 to 20 carbon atoms, an alkynyl group having 2 to 20 carbon atoms, a dialkylamino group having 2 to 40 carbon atoms, a diarylamino group having 12 to 44 carbon atoms, a diaralkylamino group having 14 to 76 carbon atoms, an acyl group having 2 to 20 carbon atoms, an acyloxy group having 2 to 20 carbon atoms, an alkoxy group having 1 to 20 carbon atoms, an alkoxycarbonyl group having 2 to 20 carbon atoms, an alkoxycarbonyloxy group having 2 to 20 carbon atoms, an alkylsulfonyl group having 1 to 20 carbon atoms, a cyano group, a nitro group, a fluoro group or a tosyl group, and may further have substituents in the case of being a group other than a cyano group, a nitro group, a fluoro group or a tosyl group.

2. The organic electroluminescent device according to claim 1, wherein the substituted or unsubstituted aromatic heterocyclic group having 3 to 17 carbon atoms represented by Y, $R^1$ to $R^6$ and $R^7$ to $R^8$ in general formula (1) is a group formed by removing one or more hydrogen atoms from an aromatic heterocyclic compound selected from the group consisting of furan, benzofuran, isobenzofuran, xanthene, oxathrene, dibenzofuran, perioxanthenoxanthene, thiophene, thioxanthene, thianthrene, phenoxathiin, thionaphthene, isothianaphthene, thiobutene, thiophenanthrene, dibenzothiophene, pyrrole, pyrazole, tellurazole, selanazole, thiazole, isothiazole, oxazole, furazan, pyridine, pyrazine, pyrimidine, pyridazine, triazine, indolizine, indole, isoindole, indazole, purine, quinolidine, isoquinoline, carbazole, imidazole, naphthyridine, phthalazine, quinazoline, azepine, benzodiazepine, tribenzoazepine, quinoxaline, cinnoline, quinoline, pteridine, phenanthridine, acridine, perymidine, phenanthroline, phenazine, carboline, phenotellurazine, phenoselanazin, phenothiazine, phenoxazine, anthyridine, benzothiazole, benzoimidazole, benzoxazole, benzoisoxazole, benzoisothiazole, dibenzophosphole and dibenzoborole.

3. The organic electroluminescent device according to claim 2, wherein $X^1$ and $X^2$ in general formula (1) independently represent NR1, O or S, and p and q independently represent an integer of 0 to 3.

4. The organic electroluminescent device according to claim 1, wherein general formula (1) is represented by any of the following formulas (3) to (7):

(3)
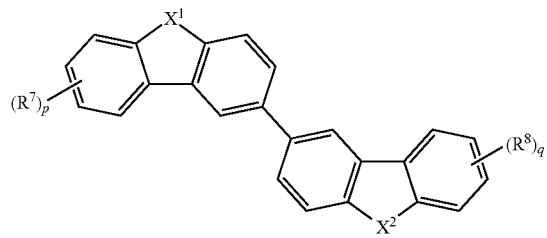

(4)
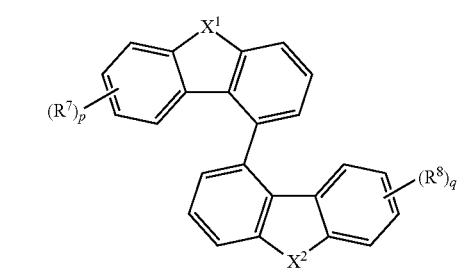

(5)
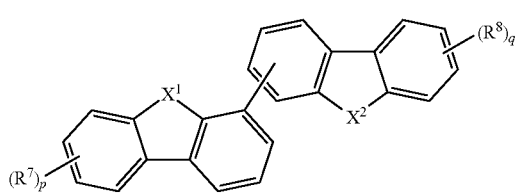

(6)
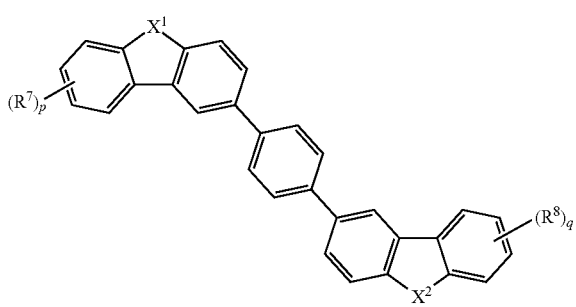

(7)
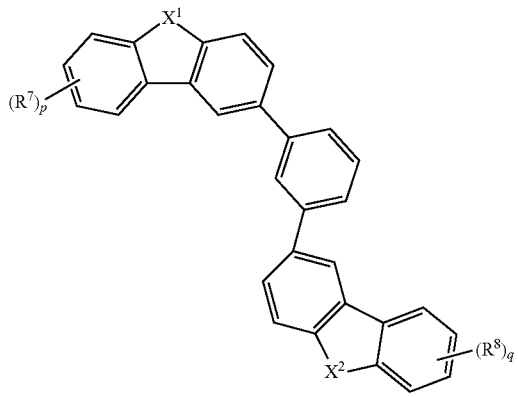

wherein, $X^1$, $X^2$, $R^7$, $R^8$, p and q have the same meanings as $X^1$, $X^2$, $R^7$, $R^8$, p and q defined in general formula (1).

5. The organic electroluminescent device according to claim 1, wherein the aromatic rings directly bonded to ring A of $L^1$ and $L^3$ in general formula (2) are the same.

6. The organic electroluminescent device according to claim 1, wherein general formula (2) is represented by the following formula (8):

(8)
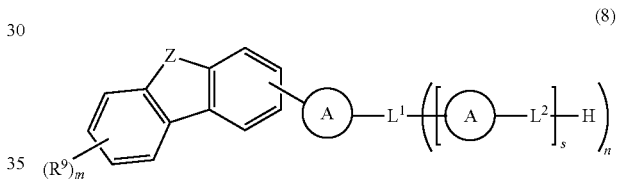

wherein, Z represents $NR^{10}$, $PR^{11}$, O, S, Se, $CR^{12}R^{13}$ or $SiR^{14}R^{15}$, $R^{10}$ to $R^{15}$ independently represent a substituted or unsubstituted aromatic hydrocarbon group having 6 to 30 carbon atoms, a substituted or unsubstituted aromatic heterocyclic group having 3 to 30 carbon atoms, or a substituted or unsubstituted linked aromatic group obtained by linking 6 to 6 of the aromatic rings of the aromatic hydrocarbon group or aromatic heterocyclic group, and ring A, $R^9$, $L^1$, $L^2$, s, m and n have the same meaning as defined in general formula (2).

7. The organic electroluminescent device according to claim 1, wherein ring A of general formula (2) is a $C_2B_{10}H_{10}$ divalent carborane group represented by formula (a1).

8. The organic electroluminescent device according to claim 1, wherein the organic layers containing a compound represented by general formula (1) and a compound represented by general formula (2) consist of at least one layer selected from the group consisting of a light emitting layer containing a luminescent dopant, an electron blocking layer and a hole blocking layer.

9. The organic electroluminescent device according to claim 8, wherein the organic layers are light emitting layers containing a luminescent dopant, and contain a compound represented by general formula (1) and a compound represented by general formula (2) as host materials.

10. The organic electroluminescent device according to claim 9, wherein the luminescent dopant is a delayed fluorescent dopant.

11. The organic electroluminescent device according to claim 9, wherein the luminescent dopant is an organic metal complex containing at least one metal selected from ruthenium, rhodium, palladium, silver, rhenium, osmium, iridium, platinum and gold.

12. The organic electroluminescent device according to claim 4, wherein the organic layers containing a compound represented by general formula (1) and a compound represented by general formula (2) consist of at least one layer selected from the group consisting of a light emitting layer containing a luminescent dopant, an electron blocking layer and a hole blocking layer.

13. The organic electroluminescent device according to claim 1, wherein $X^1$ is $NR^1$, O or S, and $X^2$ is $NR^1$, O or S.

14. The organic electroluminescent device according to claim 1, wherein Y is a single bond.

15. The organic electroluminescent device according to claim 1, wherein Y is a phenylene.

16. The organic electroluminescent device according to claim 1, wherein s is 0 or 1.

17. The organic electroluminescent device according to claim 4, wherein $X^1$ is $NR^1$, and $X^2$ is $NR^1$.

18. The organic electroluminescent device according to claim 4, wherein $X^1$ is $NR^1$, and $X^2$ is O or S.

19. The organic electroluminescent device according to claim 4, wherein $X^1$ is O or S, and $X^2$ is O or S.

* * * * *